US007846673B2

(12) United States Patent
Pastorek et al.

(10) Patent No.: US 7,846,673 B2
(45) Date of Patent: Dec. 7, 2010

(54) SOLUBLE FORM OF CARBONIC ANHYDRASE IX (S-CA IX), ASSAYS TO DETECT S-CA IX, CA IX'S COEXPRESSION WITH HER-2/NEU/C-ERBB-2, AND CA IX-SPECIFIC MONOCLONAL ANTIBODIES TO NON-IMMUNODOMINANT EPITOPES

(75) Inventors: Jaromir Pastorek, Bratislava (SK); Silvia Pastorekova, Bratislava (SK); Miriam Zatovicova, Bratislava (SK); Jan Zavada, Prague (CZ); Marta Ortova Gut, Prague (CZ); Zuzanna Zavadova, Prague (CZ)

(73) Assignee: Institute of Virology of the Slovak Academy of Sciences, Bratislava (SK)

( * ) Notice: Subject to any disclaimer, the term of this patent is extended or adjusted under 35 U.S.C. 154(b) by 1073 days.

(21) Appl. No.: 10/921,590

(22) Filed: Aug. 19, 2004

(65) Prior Publication Data
US 2005/0031623 A1    Feb. 10, 2005

Related U.S. Application Data

(63) Continuation of application No. PCT/US03/05136, filed on Feb. 21, 2003.

(60) Provisional application No. 60/358,824, filed on Feb. 21, 2002, provisional application No. 60/383,068, filed on May 23, 2002, provisional application No. 60/431,499, filed on Dec. 5, 2002.

(51) Int. Cl.
G01N 33/53    (2006.01)

(52) U.S. Cl. .................. 435/7.1; 435/7.92; 435/183; 435/337; 435/338; 435/344; 530/350; 530/387.1; 530/387.7; 530/388.25; 530/388.26; 436/64

(58) Field of Classification Search .................. 435/7.1, 435/7.92, 183, 337, 338, 344; 530/387.1, 530/387.7, 388.25, 388.26, 350; 436/64, 436/501; 536/23.5
See application file for complete search history.

(56) References Cited

U.S. PATENT DOCUMENTS

| 4,968,603 | A | 11/1990 | Slamon et al. ................. 435/6 |
|---|---|---|---|
| 5,387,676 | A | 2/1995 | Zavada et al. ............. 536/23.5 |
| 5,401,638 | A | 3/1995 | Carney et al. ............. 435/7.23 |
| 5,955,075 | A | 9/1999 | Zavada et al. ............ 424/138.1 |
| 5,972,353 | A | 10/1999 | Zavada et al. ............ 424/277.1 |
| 5,981,711 | A | 11/1999 | Zavada et al. ............ 530/387.7 |
| 5,989,838 | A | 11/1999 | Zavada et al. ............ 435/7.23 |
| 6,004,535 | A | 12/1999 | Zavada et al. ............ 424/9.34 |
| 6,027,887 | A | 2/2000 | Zavada et al. ................. 435/6 |
| 6,051,226 | A | 4/2000 | Zavada et al. ............ 424/138.1 |
| 6,069,242 | A | 5/2000 | Zavada et al. ............ 536/24.31 |
| 6,093,548 | A | 7/2000 | Zavada et al. ............... 435/7.1 |
| 6,204,370 | B1 | 3/2001 | Zavada et al. ............ 536/23.1 |
| 6,297,041 | B1 | 10/2001 | Zavada et al. ............... 435/232 |
| 6,297,051 | B1 | 10/2001 | Zavada et al. ............... 435/375 |
| 6,770,438 | B2 | 8/2004 | Zavada et al. ................. 435/6 |
| 6,774,117 | B1 | 8/2004 | Zavada et al. ................. 514/44 |

FOREIGN PATENT DOCUMENTS

| WO | WO 93/18152 | 9/1993 |
|---|---|---|
| WO | WO 95/34650 | 12/1995 |
| WO | WO 00/24913 | 5/2000 |
| WO | WO 2004/017923 | 3/2004 |
| WO | WO 2008/103327 A2 | 8/2008 |

OTHER PUBLICATIONS

Barathova et al. (Br. J. Cancer. Jan. 15, 2008; 98 (1):129-136).*
Banks et al. (Eur. J. Biochem. 1976; 71: 469-473).*
Zavadora et al. (Oncol. Rep. May 2005; 13 (5): 977-982).*
Holotnakova et al. (Pflugers Arch. May 2008; 456 (2): 323-337).*
Vordermark et al. (Int. J. Radiat. Oncol. Biol. Phys. Mar. 15, 2005; 61 (4): 1197-1207).*
Zavada et al. (Br. J. Cancer. Sep. 15, 2003; 89 (6): 1067-1071).*
Roessler et al. (Mol. Cell. Prot. 2006; 5 (11): 2092-2101).*
Roessler et al. (Clin. Can. Res. 2005; 11 (18): 6550-6557).*
Zolg et al. (Mol. Cell. Prot. 2004; 3 (4): 345-354).*
Rae et al. (International Journal of Cancer 2000; 88: 726-732).*
Ward (Developmental Oncology 1985; 21: 91-106).*
Critchfield (Disease Markers 1999; 15: 108-111).*
Sidransky (Science 1997; 278: 1054-1058).*
Tockman et al. (Cancer Research 1992; 52: 2711s-2718s).*
Leibovich et al. (J. Clin. Oncol. Oct. 20, 2007; 25 (3): 4757-4764).*
Chia et al. (J. Clin. Oncol. Aug. 15, 2001; 19 (16): 3660-3668).*
Watson et al. (Br. J. Cancer. 2003; 88: 1065-1070).*
Brewer et al. (Gynecol. Oncol. Dec. 1996; 63 (3): 337-344).*
Eriksen et al. (Radiother. Oncol. 2007; 83: 383-388).*

(Continued)

Primary Examiner—Stephen L Rawlings
(74) Attorney, Agent, or Firm—Leona L. Lauder; Joan C. Harland; Barbara A. Shimei

(57) ABSTRACT

Disclosed herein is the discovery of a soluble MN/CA IX (s-CA IX) found in body fluids, such as, urine and serum. Soluble CA IX comprises the extracellular domain of CA IX or portions thereof. The predominant s-CA IX species is the extracellular domain comprising a proteoglycan-like (PG) domain and carbonic anhydrase (CA) domain, and having a molecular weight of about 50/54 kilodaltons. Diagnostic/prognostic methods for precancer/cancer that detect or detect and quantitate s-CA IX in body fluids, are described. Also disclosed is the coexpression of CA IX and HER-2 that provides potentially synergistic diagnostic/prognostic and therapeutic strategies for precancer/cancer. Further disclosed are new MN/CA IX-specific antibodies generated from MN/CA IX-deficient mice, useful diagnostically/prognostically and therapeutically for cancer/precancer. Preferred are new antibodies, specific for non-immunodominant epitopes of MN/CA IX, are useful to detect soluble CA IX (s-CA IX) in body fluids, preferably in combination with antibodies specific to immunodominant epitopes of MN/CA IX.

34 Claims, 20 Drawing Sheets

OTHER PUBLICATIONS

De Schutter et al. (BMC Cancer. Apr. 25, 2005; 5: 42; published on the Internet; pp. 1-11).*

Sekine et al. (J. Clin. Oncol. Oct. 1985; 3 (10): 1355-1363).*

Diotti et al (Int. J. Biol. Markers. Sep.-Dec. 1987; 2 (3): 161-168).*

Griffiths et al. (Acta Derm. Venereol. Jan. 1996; 76 (1): 12-5).*

Saga et al (Acta Obstet. Gynecol. Scand. 1990; 69 (2): 175-181).*

Zavada et al. (Br. J. Cancer. Sep. 2003; 89 (15): 1067-71).*

Hyrsl et al. (Neoplasma. 2009; 56 (4): 298-302).*

Li et al. (Biochem. Biophys. Res. Commun. Aug. 28, 2009; 386 (3): 488-92).*

Zhou et al. (Urology. Feb. 2010; 75 (2): 257-61).*

Airley et al., "Glucose Transporter Glut-1 Expression Correlates with Tumor Hypoxia and Predicts Metastasis-free Survival in Advanced Carcinoma on the Cervix," *Clinical Cancer Research*, 7: 928-934 (Apr. 2001).

Bander et al., "Renal cancer imaging with monoclonal antibody G250," *J. Urol.*, 155 (5 Suppl.): 583A (Abstract 1088).

Chia et al., "Prognostic significance of a novel hypoxia- regulated marker, carbonic anhydrase IX, in invasive breast carcinoma," *J. Clin. Oncol.*, 19(16): 3660-3668 (Aug. 15, 2001).

Giatromanolaki et al., "Expression of Hypoxia-inducible Carbonic Anhydrase-9 Relates to Angiogenic Pathways and Independently to Poor Outcome in Non-Small Cell Lung Cancer," *Cancer Research*, 61(21): 7992-7998 (Nov. 1, 2001).

Griffiths et al., "The macrophate—a novel system to deliver gene therapy to pathological hypoxia," *Gene Therapy*, 7: 255-262 (2000).

Horton, J., "Trastuzumab Use in Breast Cancer: Clinical Issues," *Cancer Control*, 9(6): 499-507 (2002).

Ivanov et al., "Expression of Hypoxia-Inducible Cell-Surface Transmembrane Carbonic Anhydrases in Human Cancer," *American Journal of Pathology*, 158(3): 905-919 (Mar. 2001).

Kaluz et al., "Lowered Oxygen Tension Induces Expression of the Hypoxia Marker MN/Carbonic Anhydrase IX in the Absence of Hypoxia-inducible Factor 1 Stabilization: A Role for Phosphatidylinositol 3'-Kinase," *Cancer Research*, 62: 4469-4477 (Aug. 1, 2002).

Kivela et al., "Expression of transmembrane carbonic anhydrase isoenzymes IX and XII in normal human pancreas and pancreatic tumours," *Histochemistry and Cell Biology*, 114(3): 197-204 (2000).

Kuter, I., "Breast Cancer," *The Oncologist*, 6: 338-346 (2001).

Lieskovska et al., "Study of in vitro conditions modulating expression of MN/CA IX protein in human cell lines derived from cervical carcinoma," *Neoplasma*, 46(1): 17-24 (1999).

Loncaster et al., "Carbonic Anhydrase (CA IX) Expression, a Potential New Intrinsic Marker of Hypoxia: Correlations with Tumor Oxygen Measurements and Prognosis in Locally Advanced Carcinoma of the Cervix," *Caner Res*, 61(17): 6394-6399 (Sep. 1, 2001).

Oosterwijk and Debruyne, "Radiolabeled monoclonal antibody G250 in renal-cell carcinoma," *World Journal of Urology*, 13: 186-190 (1995).

Opavsky et al., "Human MN/CA9 Gene a Novel Member of the Carbonic Anhydrase Family: Structure and Exon to Protein Domain Relationships," *Genomics*, 33: 480-487 (1996).

Parkkila et al., "Carbonic anhydrase inhibitor suppresses invasion of renal cancer cells in vitro," *PNAS (USA)*, 97(5): 2220-2224 (Feb. 29, 2000).

Pastorek et al., "Cloning and characterization of MN, a human tumor-associated protein with a domain homologous to carbonic anhydrase and a putative helix-loop-helix DNA binding segment," *Oncogene*, 9: 2877-2888 (1994).

Pastorekova et al., "A Novel Quasi-viral Agent, MaTu, Is a Two-Component System," *Virology*, 187: 620-626 (1992).

Pastorekova et al., "Carbonic Anhydrase IX, MN/CA IX: Analysis of Stomach Complementary DNA Sequence and Expression in Human and Rat Alimentary Tracts," *Gastroenterology*, 112: 398-408 (1997).

Revillion et al., "*ERBB2* Oncogene in Human Breast Cancer and its Clinical Significance," *Euro J. Cancer*, 34: 791-808 (1998).

Steffens et al., "Targeting of Renal Cell Carcinoma with Iodine-131-Labeled Chimeric Monoclonal Antibody G250," *Journal of Clinical Oncology*, 15(4): 1529-1537 (Apr. 1997).

Steffens et al., "Radioimmunotherapy with 131I-cG250 Monoclonal antibody in Patients with Metastasized RCC, Phase I/II Study," *Journal of Urology*, 159 (5 Suppl.): Abstract No. 562 (May 1998).

Teicher et al., "A Carbonic Anhydrase Inhibitor as a Potential Modulator of Cancer Therapies," *Anticancer Research*, 13: 1549-1556 (1993).

Trikha et al., "Monoclonal antibodies as therapeutics in oncology," *Current Opinion in Biotechnoogy*, 13(6): 609-614 (2002).

Turner et al., "MN Antigen Expression in Normal, Preneoplastic, and Neoplastic Esophagus: a Clinicopathogical Study of a New Cancer-Associated Biomarker," *Hum. Pathol.*, 28(6): 740-744 (Jun. 1997).

Uemura et al., "MN/CA IX/G250 as a potential target for immunotherapy of renal call carcinomas," *Br. J. Cancer*, 81(4):741-746 (Oct. 1999).

Uemura et al., "MN Target Immunotherapy for Renal Cell Carcinoma," *Journal of Urology*, 159 (5 Suppl.): 188, Abstract No. 724 (May 1998).

Vaupel and Hoeckel, "Predictive Power of the Tumor Oxygenation Status," *Adv. Exp. Med. Biol.*, 471: 533-539 (1999).

Von Mehren et al., "Monoclonal Antibody Therapy for Cancer," *Annu. Rev. Med.*, 54: 343-369 (2003).

Watson et al., "Carbonic anhydrase XII is a marker of good prognosis in invasive breast carcinoma," *Br. J. Cancer*, 88(7):1065-1070 (2003).

Wingo et al., "The Catalytic Properties of Human Carbonic Anhydrase IX," *Biochemical and Biophysical Research Communications*, 288: 666-669 (2001).

Wykoff et al., "Hypoxia-inducible Expression of Tumor-associated Carbonic Anhydrases," *Cancer Research*, 60:7075-7083 (Dec. 15, 2000).

Wykoff et al., "Expression of the hypoxia-inducible and tumor-associated carbonic anhydrases in ductal carcinoma in situ of the breast," *Am. J. Pathol.*, 158(3): 1011-1019 (Mar. 2001).

Zavada et al., "Expression of MaTu-MN Protein in Human Tumor Cultures and in Clinical Specimens," *Int. J. Cancer*, 54: 268-274 (1993).

Zavada et al., "Human tumour-associated cell adhesion protein MN/CA IX: identification of M75 epitope and of the region mediating cell adhesion," *British Journal of Cancer*, 82(11): 1808-1813 (2000).

Belozerov and Van Meir, "Inhibitors of hypoxia-inducible factor-1 signaling," Curr Opin Investig Drugs, 7(12): 1067-1076 (Dec. 2006) Abstract.

Bui et al, "Carbonic Anhydrase IX Is an Independent Predictor of Survival in Advanced Renal Clear Cell Carcinoma: Implications for Prognosis and Therapy," *Clinical Cancer Research*, 9: 802-811 (Feb. 2003).

Cui et al., "Computational prediction of human proteins that can be secreted into the bloodstream," *Bioinformatics*, 24(20): 2370-2375 (Oct. 15, 2008) Abstract.

Hui et al, "Coexpression of Hypoxia-inducible Factors Factor 1 and 2, Carbonic Anhydrase IX, and Vascular Endothelial Growth in Nasopharyngeal Carcinoma and Relationship to Survival," *Clinical Cancer Research*, 8: 2595-2604 (Aug. 2002).

Koukourakis et al., "Hypoxia-regulated Carbonic Anhydrase-9 (CA9) Relates to Poor Vascularization and Resistance of Squamous Cell Head and Neck Cancer to Chemoradiotherapy," *Clinical Cancer Research*, 7(11): 3399-3403 (Nov. 2001).

Pastorekova and Zavada, "Carbonic anhydrase IX (CA IX) as a potential target for cancer therapy," *Cancer Therapy*, 2: 245-262 (2004).

Potter and Harris, "Hypoxia Inducible Carbonic Anhydrase IX, marker of Tumor Hypoxia, Survival Pathway and Therapy Target," *Cell Cycle*, 3(2): 164-167 (Feb. 2004).

Rafajova et al., "Induction by Hypoxia Combined with Low Glucose or Low Bicarbonate and High Posttranslational Stability Upon Reoxygenation Contribute to Carbonic Anhydrase IX Expression in Cancer Cells," *International Journal of Oncology*, 24(4): 995-1004 (Apr. 2004).

Sorensen et al., "Influence of oxygen concentration and pH on expression of hypoxia induced genes," *Radiotherapy and Oncology*, 76(2): 187-193 (Aug. 2005).

Soyupak et al., "CA9 Expression as a Prognostic Factor in Renal Clear Cell Carcinoma," *Urol Int*, 74(1): 68-73 (2005).

Swinson et al., "Carbonic Anhydrase IX Expression, a Novel Surrogate Marker of Tumor Hypoxia, is Associated With a Poor Prognosis in Non-Small-Cell Lung Cancer," *Journal of Clinical Oncology*, 21(3): 473-482 (Feb. 1, 2003).

Tatum et al., "Hypoxia: Importance in Tumor Biology, Noninvasive Measurement by Imaging, and Value of its Measurement in the Management of Cancer Therapy," *International Journal of Radiation Biology*, 82(10): 699-757 (Oct. 2006).

Carney, W.P., "Circulating oncoproteins HER2/neu, EGFR and CAIX (MN) as novel cancer biomarkers," *Expert Rev. Mol. Diagn.*, 7(3): 309-319 (2007).

Hulick et al.,"Blood Levels of Carbonic Anhydrase 9 Correlate with Clear Cell Renal Cell Carcinoma Activity, " *Clinical Proteomics*, 1542-6416 (Print) 1559-0275 (Online) [DOI 10,1007/s12014-008-9012-1; Jul. 12, 20081.

Li et al., "MN/CA9 as a novel molecular marker for the detection of cancer," *Expert Opin Med Diagn.*, 1(1): 91-97 (2007).

Li et al., "Serum Carbonic Anhydrase 9 Level is Associated With Postoperative Recurrence of Conventional Renal Cell Cancer," *J Urol.*, 180(2): 510-514 (2008).

Sivendran et al., *Proc. Am. Assoc. Cancer Res.*, 48: 636 (Abstract 2666) (2007) [AACR Meeting Abstracts *Abstract* 2666 ((AACR Annual Proceedings, [Apr. 20071, Los Angeles, CA; Philadelphia, PA)].

* cited by examiner

FIG._1A

| | | | | | | | | | | | | | | | |
|---|---|---|---|---|---|---|---|---|---|---|---|---|---|---|---|
| T | V | S | R | M | A | P | L | C | P | S | P | W | L | P | L |
| ACA | GTC | AGC | CGC | ATG | GCT | CCC | CTG | TGC | CCC | AGC | CCC | TGG | CTC | CCT | CTG |
| L | I | P | A | P | L | M | P | V | H | P | Q | V | L | L | S |
| TTG | ATC | CCG | GCC | CCT | CTG | ATG | CCT | GTC | CAT | CCC | CAA | GTG | CTG | CTG | TCA |
| L | L | L | L | L | M | P | G | P | H | G | G | S | Q | R | M | Q |
| CTG | CTG | CTT | CTG | ATG | CCT | GGA | CCA | GGC | CAT | GGC | GGC | AGG | CAG | AGG | ATG | CAG |
| E | D | S | P | G | L | G | S | E | E | G | P | L | P | D | P | L |
| GAG | GAT | TCC | CCC | GGA | TTG | GGA | AGT | GAA | GAA | GGA | CCT | TTG | CCC | GAC | CCA | CTG |
| G | E | E | D | P | E | S | E | E | G | R | E | E | E | D |
| GGC | GAG | GAG | GAT | CCC | GAG | TCA | GAG | GAG | GGA | AGA | GAG | GAG | GAG | GAT |
| P | G | E | L | E | P | K | S | P | R | L | E | E | G | E |
| CCA | GGA | GAG | CTA | GAA | CCT | AAA | TCA | CCC | AGA | CTA | GAG | GAG | GGA | GAG |
| E | D | L | P | V | K | P | T | V | E | A | K | S | Q | E |
| GAG | GAT | CTA | CCT | GAA | AAG | CCT | ACT | GTT | GAG | GCT | AAA | TCC | CAA | GAA |
| K | L | E | D | L | P | H | R | D | K | E | G | D | D | H |
| AAG | TTA | GAG | GAT | CTA | CCT | CAC | AGG | GAC | AAA | GAA | GGG | GAT | GAT | CAT |
| P | Q | N | N | A | H | R | D | P | P | W | R | V | P | Q | S |
| CCC | CAG | AAT | AAT | GCC | CAC | AGG | GAC | CCG | CCC | TGG | CGG | GTG | CCA | CAG | AGT |
| W | R | Y | G | G | D | P | P | W | P | R | V | S | P | A | C |
| TGG | CGC | TAT | GGA | GGC | GAC | CCC | CCC | TGG | CCC | CGG | GTG | TCC | CCA | GCC | TGC |
| A | G | R | F | Q | N | G | D | P | V | D | I | R | P | Q | L | A |
| GCG | GGC | CGC | TTC | CAG | AAT | GGA | GAC | CCG | GTG | GAT | ATC | CGC | CCC | CAG | CTC | GCC |

FIG._1B

| F | C | P | A | L | R | P | L | E | L | L | G | F | Q | L | P |
|---|---|---|---|---|---|---|---|---|---|---|---|---|---|---|---|
| TTC | TGC | CCG | GCC | CTG | CGC | CCC | CTG | GAA | CTC | CTG | GGC | TTC | CAG | CTC | CCG |

| P | L | P | E | P | L | R | L | R | M | N | G | H | S | V | Q | L |
|---|---|---|---|---|---|---|---|---|---|---|---|---|---|---|---|---|
| CCG | CTC | CCA | GAA | CCT | CTG | CGC | CTG | CGC | ATG | AAT | GGC | CAC | AGT | GTG | CAA | CTG |

| T | L | Q | P | L | E | M | A | L | G | H | R | G | E | Y |
|---|---|---|---|---|---|---|---|---|---|---|---|---|---|---|
| ACC | CTG | CAG | CCT | CTA | GAG | ATG | GCT | CTG | GGC | CAC | AGT | GGG | GAG | TAC |

| R | A | L | Q | L | H | L | H | W | G | P | A | G | R | G |
|---|---|---|---|---|---|---|---|---|---|---|---|---|---|---|
| CGG | GCT | CTG | CAG | CTG | CAT | CTG | CAC | TGG | GGG | CCC | GCA | GGT | CGT | GGC |

| S | E | H | T | V | E | G | H | R | F | P | A | E | I | H | V |
|---|---|---|---|---|---|---|---|---|---|---|---|---|---|---|---|
| TCG | GAG | CAC | ACT | GTG | GAA | GGC | CAC | CGT | TTC | CCT | GCC | GAG | ATC | CAC | GTG |

| V | H | L | S | T | A | F | A | R | V | D | E | A | L | G | R |
|---|---|---|---|---|---|---|---|---|---|---|---|---|---|---|---|
| GTT | CAC | CTC | AGC | ACC | GCC | TTT | GCC | AGA | GTT | GAC | GAG | GCC | TTG | GGG | CGC |

| P | G | G | L | A | V | L | A | A | F | L | E | E | G | P | E |
|---|---|---|---|---|---|---|---|---|---|---|---|---|---|---|---|
| CCG | GGA | GGC | CTG | GCC | GTG | TTG | GCC | GCC | TTT | CTG | GAG | GAG | GGC | CCG | GAA |

| E | N | S | A | Y | E | Q | L | V | P | Q | L | S | R | L | E | I | A |
|---|---|---|---|---|---|---|---|---|---|---|---|---|---|---|---|---|---|
| GAA | AAC | AGT | GCC | TAT | GAG | CAG | CTG | GTG | CCA | CAG | CTG | TCT | CGC | TTG | GAA | ATC | GCT |

| E | G | S | E | T | Q | G | L | D | I | G | L | A | L |
|---|---|---|---|---|---|---|---|---|---|---|---|---|---|
| GAG | GGC | TCA | GAG | ACT | CAG | GGA | CTG | GAC | ATA | GGG | CTG | GCA | CTC |

| L | P | S | D | F | S | R | Y | F | Q | Y | E | G | S | L | T |
|---|---|---|---|---|---|---|---|---|---|---|---|---|---|---|---|
| CTG | CCC | TCT | GAC | TTC | AGC | CGC | TAC | TTC | CAA | TAT | GAG | GGG | TCT | CTG | ACT |

| T | P | P | C | A | Q | G | V | I | W | T | V | F | N | Q | T |
|---|---|---|---|---|---|---|---|---|---|---|---|---|---|---|---|
| ACA | CCG | CCC | TGT | GCC | CAG | GGT | GTC | ATC | TGG | ACT | GTG | TTT | AAC | CAG | ACA |

| V | M | L | S | A | K | Q | L | H | T | L | S | D | T | L | W |
|---|---|---|---|---|---|---|---|---|---|---|---|---|---|---|---|
| GTG | ATG | CTG | AGT | GCT | AAG | CAG | CTC | CAC | ACC | CTC | TCT | GAC | ACC | CTG | TGG |

| G | P | G | D | S | R | L | Q | L | N | F | R | A | T | Q | P |
|---|---|---|---|---|---|---|---|---|---|---|---|---|---|---|---|
| GGA | CCT | GGT | GAC | TCT | CGG | CTA | CAG | CTG | AAC | TTC | CGA | GCG | ACG | CAG | CCT |

| L | N | G | R | V | I | E | A | S | F | P | A | G | V | D | S |
|---|---|---|---|---|---|---|---|---|---|---|---|---|---|---|---|
| TTG | AAT | GGG | CGA | GTG | ATT | GAG | GCC | TCC | TTC | CCT | GCT | GGA | GTG | GAC | AGC |

| S | P | R | A | A | E | P | V | Q | L | N | S | C | L | A | A |
|---|---|---|---|---|---|---|---|---|---|---|---|---|---|---|---|
| AGT | CCT | CGG | GCT | GCT | GAG | CCA | GTC | CAG | CTG | AAT | TCC | TGC | CTG | GCT | GCT |

| G | D | I | L | A | L | V | F | G | L | F | A | V | T | S |
|---|---|---|---|---|---|---|---|---|---|---|---|---|---|---|
| GGT | GAC | ATC | CTA | GCC | CTG | GTT | TTT | GGC | CTC | TTT | GCT | GTC | ACC | AGC |

| V | A | F | L | V | Q | M | R | R | Q | H | R | R | G | T | K |
|---|---|---|---|---|---|---|---|---|---|---|---|---|---|---|---|
| GTC | GCG | TTC | CTT | GTG | CAG | ATG | AGA | AGA | CAG | CAC | AGA | AGG | GGA | ACC | AAA |

| G | G | V | S | Y | R | P | A | E | V | A | E | T | G | A | * |
|---|---|---|---|---|---|---|---|---|---|---|---|---|---|---|---|
| GGG | GGT | GTG | AGC | TAC | CGC | CCA | GCA | GAG | GTA | GCC | GAG | ACT | GGA | GCC | TAG |

AGG CTG GAT CTT GGA GAA TGT CCT GTC CTG CTC ATT ATG CCA CTT CCT GGG

GGA GCC GGT AAC TGT TCC GAG AAG CCA GAG AGA GGC ATC TGA GCC TTT AAC

TGC CAA GAA ATT TTT TAA AAT AAA TAT TTA TAA T

```
ggatcctgtt gactcgtgac cttaccccca accctgtgct ctctgaaaca tgagctgtgt
ccactcaggg ttaaatggat taagggcggt gcaagatgtg ctttgttaaa cagatgcttg
aagcagcat gctcgttaag agtcatcacc aatccctaat ctcaagtaat cagggacaca
aacactgcgg aaggccgcag ggtcctctgc ctagaaaaac cagagaccct tgttcacttg
tttatctgac cttccctcca ctattgtcca tgaccctgcc aatcccccct ctgtgagaaa
cacccaagaa ttatcaataa aaaaataaat ttaaaaaaaa aatacaaaaa aaaaaaaaaa
aaaaaaaaaa gacttacgaa tagttattga taaatgaata gctattggta aagccaagta
aatgatcata ttcaaaacca gacggccatc atcacagctc aagtctacct gatttgatct
ctttatcatt gtcattcttt ggattcacta gattagtcat catcctcaaa attctccccc
aagtctaat tacgttccaa acattaggg gttacatgaa gcttgaacct actaccttct
ttgctttga gccatgagtt gtaggaatga tgagtttaca cctacatgc tgggattaa
tttaaacttt acctctaagt cagttgggta gcctttggct tatttttgta gctaattttg
tagttaatgg atgcactgtg aatcttgcta tgatagtttt cctccacact ttgccactag
gggtaggtag gtactcagtt ttcagtaatt gcttacctaa gaccctaagc cctattctc
ttgtactggc ctttatctgt aatatggca tatttaatac aatataattt ttggagtttt
tttgttgtt tgttttgttg ttttttttgag acggagtctt acgagtgtca tgcccaggct
ggagtagcag tggtgccatc tcggctcact gcaagctcca cctcccgagt tcacgccatt
tcctgcctc agcctcccga gtagctggga ctacaggcgc ccgccaccat gccggctaa
ttttttgtat tttggtaga gacggggttt caccgtgtta gccagaatgg tctcgatctc
ctgacttcgt gatccacccg cctcggcctc ccaaagttct gggattacag gtgtgagcca
ccgcacctgg ccaatttttt gagtcttta aagtaaaaat atgtcttgta agctggtaac
tatggtacat ttcctttat taatgtggtg ctgacggtca cattacattt ttctctcttc tttgagtttg
gcatgcatat gctactttt gcagtccttt ggcttttcct cattttccag cttttccag atttgaagag
catgtatat cttttagctt cacttggctt aaaaggttct aaaggttct tccatatttc aggaatgttt
tcattgttt taccacttgg atcataagtg gaaaaacagt caagaaattg ctacctgagg
cttgttgta agggggatga ttcaggtgaa tctgacacta agaaactccc ctacctgagg
tctgagattc ctctgacatt gctgtatata ggcttttcct ttgacagcct gtgactgcgg
actatttttc ttaagcaaga tatgctaaag tttgtgagc ctttttccag agagaggtct
catatctgca tcaagtgaga acatataatg tctgcatgtt tccatatttc aggaatgttt
gcttgtttt tatgctttta tatagacagg gaaactgttt cctcagtgac ccaaaagagg
tgggaattgt tattggatat catcattggc ccacgctttc tgaccttgga aacaattaag
ggtcataat ctcaattctg tcagaattgg tacaagaaat agctgctatg tttcttgaca
ttccacttgg taggaaataa gaatgtgaaa ctcttcagtt ggtgtgtc cct?gttttt
```

```
ttgcaatttc ctccttactg tgttaaaaaa aagtatgatc ttgctctgag agtgaggca
ttcttaatca tgatctttaa agatcaataa tataatcctt tcaaggatta tgtctttatt
ataataaaga taatttgtct ttaacagaat caataatata atcccttaaa ggattatatc
tttgctgggc gcagtggctc acacctgtaa tcccagcact ttgggtggcc aaggtggaag
gatcaaattt gcctacttct atattatcct ctaaagcaga attcatctct cttccctcaa
tatgatgata ttgacagggt ttgccctcac tcactagatt gtgagctcct gctcagggca
ggtagcgttt tttgttttg tttttgtttt tcttttttga gacagggtct tgctctgtca
ccaggccag agtgcaatgg tacagtctca gctcactgca gcctcaaccg cctcggctca
aaccatcatc ccattcagc ctcctgagta gctggacta caggcacatg ccattacacc
tggctaattt ttttgtattt ctagtagaga caggttttgg ccatgttgcc cgggctggtc
tcgaactcct ggactcaagc aatccaccca cctcagcctc ccaaaatgag ggaccgtgtc
ttattcattt ccatgtccct agtccatagc agttttgtct cccacatacc acctatggta gtactaaata
aatatttgtt gaatgcaata gtaaatagca tttcaggag caagaactag attaacaaag
gtggtaaaag gtttggagaa aaaaataata gtttaatttg gctagagtat gagggagagt
agtaggagac aagatgaa gtctcttgg gcaaggtttt gaaggaagtt ggaagtcaga
agtacacaat gtgcatatcg tgcaggcag tgggagcca atgaaggctt ttgagcagga
gagtaatgtg ttgaaaaata aatataggtt aaacctatca gagcccctct gacacataca
cttgcttttc attcaagctc aagtttgtct cccacatacc cattacttaa ctcaccctcg
ggctcccta gcagcctgcc ctacctcttt acctgcttcc tggtggagtc aggatgtat
acatgagctg ctttcccctct cagccagagg acatgggggg ccccagctcc cctgcctttc
cccttctgtg cctggagctg ggaagcaggc caggttagc caggctggc tgcaagcag
ctgggtggtg ccaggagag cctgcatagt gccaggtggt gccttgggtt ccaagctagt
ccatggcccc gataaccttc tgcctgtgca cacacctgcc cctcactcca ccccatcct
agctttggta tgggggagag ggcacagggc cagacaaacc tgtgagactt tgctccatc
tctgcaaaag ggcgctctgt gagtcagct gctcccctcc agctgtctc ctccccacc
cagctctcgt ttccaatgca cgtacagcc gtacacaccg tgtgctggga caccACCAG
TCAGCCGCAT GGCTCCCCTG TGCCCCAGCC CCTGGCTCCC CACTGCTCCC CCGGCCCCTG
CTCCAGGCCT CACTGTGCAA CTGCTGCTGT CACTGCTGCT TCTGGTGCCT GTCCATCCCC
AGAGGTTGCC CCGGAGATT GAGGATTCC CCTTGGAGG AGGCTCTTCT GGGAAGATG
ACCCACTGGG CGAGGAGGAT CTGCCCAGTG AAGAGGATTC ACCCAGAGAG GAGGATCCAC
CCGGAGGAGA GGATCTACCT GGAGAGGAGG ATCTACCTGG AGAGGAGGAT CTACCTGAAG
TTAAGCCTAA ATCAGAAGAA GAGGGCTCCC TGAAGTTAGA GGATCTACCT ACTGTTGAGG
CTCCTGGAGA TCCTCAAGAA CCCCAGAATA ATGCCCACAG GGACAAAGAA Ggtaagtggt
```

*FIG. 2B*

```
catcaatctc caaatccagg ttccaggagg ttcatgactc cctcccata cccagccta
ggctctgttc actcaggaa ggaggggaga ctgtactccc cacagaagcc cttccagagg
tcccatacca atatcccat ccccactctc ggaggtagaa agggacagat gtggagagaa
aataaaaagg gtgcaaaagg agagaggtga gctggatgag atgggagaga aggggaggc
tggagagag aagggatga gaactgcaga tgagagagtt aatgtgcaga cagagaaaa
aatataggtg agaaggagag tcagagagtt tgagggaag agaaaggaa agcttgggag
gtgaagtggg taccagagac aagcaagaag agctggtaga agtcatctca tcttaggcta
caatgaggaa ttgagaccta acacagcagg tagagaaacg tggcttcttg
actcccaagc caggaatttg ttgagacca tacaaggcag agggatgagt
ggggagaaga aagaagggag aaagaaaga tggtgtactc actcatttgg gactcaggac
tgaagtgccc actcacttt tttttttttt ttttgagac aaactttcac tttgttgcc
caggctggag tgcaatgcg cgatctcggc tcactgcaac ctccacctcc cgggttcaag
tgattctcct gcctcagcct ctagccaagt agctgcgatt acaggcatgc gccaccacgc
ccggctaatt tttgtatttt tagtagagac gggtttcgc catgttggtc agctggtct
cgaactcctg atctcaggtg atccaaccac cctgcctcc caaagtgctg ggattatagg
cgtgagccac agcgcctggc ctgaagcagc cactcacttt tacagaccct aagacaatga
ttgcaagctg gtaggattgc tgtttggccc accagctgc ggtgttgagt ttgggtgcgg
tctcctgtgc tttgcacctg gcccgcttaa ggcatttgtt acccgtaatg ctcctgtaag
gcatctgcgt ttgtgacatc gttttggtcg ccaggaaggg attgggctc taagcttgag
cggttcatcc ttttcattta tacagGGGAT GACCAGAGTC ATTGGCGCTA TGGAGgtgag
acaccaccc gctgcacaga cccaatctgg gaacccagct ctgtgatct ccctacagc
cgtcccctgaa cactgtgtcc gggcgtccca cccgcgccc accgtccac ccctcacct
tttctaccg ggttccctaa gttcctgacc taggcgtcag acttcctcac tatactctcc
caccccagGC GACCCGCCT GGCCCCGCCT GTCCCCAGCC TGCGCGGGCC GCTTCCAGTC
CCCGGTGAT ATCCGCGCCC AGCTCGCCGC CTTCTGCCCG GCCCTGCGCC CCCTGGAACT
CCTGGGCTTC CAGCTCCCGC CGCTCCCAGA ACTGCGCCTG CGCAACAATG GCCACAGTGG
tgaggggtc tcccgccga gacttgggga tggggcggg cgcagggaag ggaaccgtcg
cgcagtgcct gcccgggggt tgggctggcc ctaccgggcg gggccggtc acttgcctct
ccctacgcag TGCAACTGAC CCTGCCTCCT GGGCTAGAGA TGGCTCTGG TCCCGGCCGG
GAGTACCGGG CTCTGCAGCT GCATCTGCAC TGGGGGGCTG CAGGTCGTCC GGGCTCGGAG
CACACTGTGG AAGGCCACCG TTTCCCTGCC GAGgtgagcg cggactgagc cggaagggc
aaaggagcgg ggcggacggg ggccagagac gtgccctct cctaccctcg tgtcctttc
agATCCACGT GGTTCACCTC AGCACCGCCT TTGCCAGAGT TGACGAGGCC TTGGGGCGCC
```

```
CGGGAGGCCT GGCCGTGTTG GCCGCCCTTTC TGGAGgtacc agatcctgga cacccctac
tcccgcttt cccatcccat gctcctccg gactctatcg tggagccaga gacccatcc
cagcaagctc actcagccc ctggctgaca aactcattca cgcactgttt gttcatttaa
cacccactgt gaaccaggca ccagccccca acaaggattc tgaagctgta ggtccttgcc
tctaaggagc ccacagccag tggggaggc tgacatgaca gacacatagg aaggacatag
taaagatggt ggtcacagag gaggtgacac ttaaagcctt cactggtaga aaagaaaagg
agtgttcat tgcagaggaa acagaatgtg caaagactca gaatatgcc tatttaggga
atgctacat acaccatgat tagaggaggc ccagtaaagg gaagggatgg tgagatgcct
gctaggttca ctcactcact tttattatt tatttatttt tttgacagtc tctctgtcgc
ccaggctgga gtgcagtggt gtgatcttgg gtcactgcaa cttccgcctc ccggttcaa
gggattctcc tgcctcagct tcctgagtag ctggggttac agtgtgtgc caccatgccc
agctaatttt tttttgtatt tttagtagac agggtttcac catgttggtc agctggtct
caaactcctg gcctcaagtg atccgcctga ctcagcctac caaagtgctg attacaagtg
tgagccaccg tgcccagcca cactcactga ttctttaatg ccagccacac agcacaaagt
tcagagaaat gcctccatca tagcatgtca atatgttcat actcttaggt tcatgatgtt
cttaacatta ggttcataag caaaataaga aaaaagaata ataaataaaa gaagtgcat
gtcaggacct cacctgaaaa gccaaacaca gaatcatgaa ggtgaatgca gaggtgacac
caacacaaag gtgtatatat ggtttcctgt ggggagtatg tacggaggca gcagtgagtg
agactgcaaa cgtcagaagg gcacggtca ctgagagcct agtatcctag taaagtgggc
tctctccctc tctctccagc ttgtcattga aaaccagtcc accaagcttg ttggttcgca
cagcaagagt acatagagtt tgaaataata cataggattt taagagggag acactgtctc atgttccctc
taaaaaaaaa aacaacagca acaacaaaaa gcaacaacca ttacaattt gttccgcct
agcattctca gagctgagga atgggagagg actatgggaa cccccttcat gttccgcct
tcagccatgg ccctggatac atgcactcat ctgtcttaca atgtcattcc cccagGAGGG
CCCGGAAGAA AACAGTGCCT ATGAGCAGTT GCTGTCTCGC TTGGAAGAAA TCGCTGAGGA
AGgtcagttt gttggtctgg ccactaatct ctgtggccta gttcataaag aatcaccctt
tggagcttca ggtctgaggc tggagatggg ctcccctccag tgcaggaggg attgaagcat
gagccagcgc tcatcttgat aataaccatg aagctgacag acacagttac ccgcaaacgg
ctgcctacag attgaaaacc agccccggca cgccgggcac gtgctcac gcctgtaatc
ccagcacttt gggaggccaa ggcaggtgga tcacgaggtc aagagatcaa gaccatcctg
gccaacatgg tgaaaccccca tctctactaa aaatacgaaa aaatagccag gcgtggtggc
gggtgcctgt aatcccagct actcgggagg ctgaggcagg agaatggcat gaacccggga
ggcagagagtt gcagtgagcc gagatcgtgc cactgcactc cagcctgggc aacagagcga
```

```
gactcttgtc tcaaaaaaaa aaaaaaaaaa gaaaccaag caaaaaccaa aatgagacaa
aaaaaacaag accaaaaaat ggtgtttgga aattgtcaag gtcaagtctg gagagctaaa
cttttctga gaactgttta tcttctctt gcatcaaata tttaacttt gtaaatactt
ttgttggaaa tcgttctctt cttagtcact cttgggtcat tttaaatctc acttactcta
ctagacctt taggttctg ctagactagg tagaactctg cctttgcatt tcttgtgtct
gtttgtata gttatcaata ttcatattta tttacaagtt attcagatca tttttctt
tcttttttt tttttttt tttttacat ctttagtaga gacaggtttt caccatattg
gccaggctgc tctcaaactc ctgacccttgt ctgaccttgt cctcggcctc ccaaagtgct
gggattcatt tttctttt aatttgctct gggcttaaac ttgtggccca gcactttatg
atggtacaca gagttaagag tgtagactca gacggtcttt ctccttttcct tctcttcctt
cctccttcc ctcccaccct cccttctctc cttcctttct ttcttcctct cttgcttcct
caggcctctt ccagttgctc caaagccctg tacttttttt tgagttaacg tcttatggga
agggcctgca cttagtgaag aagtggtctc agagttgagt taccttggct tctgggaggt
gaaactgtat ccctataccc tgaagcttta aggggtgca atgtagatga gacccaaaca
tagatcctct tcacagGCTC AGAGACTCAG GTCCCAGGAC TGGACATATC TGCACTCCTG
CCCTCTGACT TCAGCCGCTA CTTCCAATAT GAGGGGTCTC TGACTACACC GCCCTGTGCC
CAGGGTGTCA TCTGGACTGT GTTTAACCAG ACAGTGATGC TGAGTGCTAA GCAGgtgggc
ctggggtgtg tgtggacaca gtgggtgcgg gggaaagagg atgtaagatg agatgagaaa
caggagaaga aagaaatcaa ggctgggctc tgtggcttac gcctataatc ccaccacgtt
gggaggctga ggtgggagaa tgtgtttgagc ccaggagttc aagacaaggc gggcaacat
agtgtgaccc catctctacc aaaaaaaacc caacaaaaac aaaaatagcc gggcatggtg
gtatgcggcc tagtcccagc tactcaagga ggctgaggtg ggaagatcgc ttgattccag
gagtttgaga ctgcagtgag ctatgatccc accactgcct accatctta ggatacatttt
atttatttat aaaagaaatc aagaggctgg atgggaata caggagctgg agggtggagc
cctgagtgc tggttgtgag ctgcctggg accctgttt ctgtcctga tgccaggaga catgaaccca
cccacactgt ccactgacct ccctagCTCC ACACCCTCTC TGACACCCTG TGGGGACCTG
GTGACTCTCG GCTACACAGCTG AACTTCCGAG CGACGCAGCC TTTGAATGGG CGAGTGATTG
AGGCCTTCCTT CCCTGCTGGA GTGGACAGCA GTCCTCGGGC TGCTGAGCCA Ggtacagctt
tgtctgtttt cccccagcc agtagtccct tatcctccca tgtgtgtgcc agtgtctgtc
attggtggtc acagcccgcc tctcacatct cctttttctc ccagtCCAAG CTGAATTCCT
GCCTGGCTGC TGgtgagtct gccccctcctc ttggtcctga tgccaggaga ctcctcagca
ccattcagcc ccaggctgc tcaggaccgc tcctgctccc ctctcctttc tgcagaacag
acccaaccc caatattaga gaggcagatc atggtgggga ttccccatt gtccccagag
```

FIG.—2E

```
gctaattgat  tagaatgaag  cttgagaaat  ctcccagcat  ccctctcgca  aaagaatccc
ccccctttt   tttaaagata  gggtctcact  ctgtttgccc  caggctgggg  tgttgtggca
cgatcatagc  tcactgcagc  ctcgaactcc  taggctcagg  caatccttc   accttagctt
ctcaaagcac  tgggactgta  ggcatgagcc  actgtgcctg  agtcacttca  gcccttttac
ttggcttta   ggaagcaaaa  acgtgctta   tcttacccct  tctcgtgtat  ccacctcat
ccctggctg   gcctcttctg  gagactgagg  cactatgggg  ctgcctgaga  actcggggca
ggggtggtgg  agtgcactga  ggcaggtgtt  gaggaactct  gcagacccct  cttcctccc
aaagcagccc  tctctgctct  ccatcgcagg  ccatcgcagg  TGACATCCTA  GCCCTGGTTT  TTGGCCTCCT
TTTTGCTGTC  ACCAGCGTCG  CGTTCCTTGT  GCAGATGAGA  AGGCAGCACA  Gtattacac
tgaccctttc  ttcaggcaca  agcttccccc  acccttgtgg  agtcacttca  tgcaaagcgc
atgcaaatga  gctgctcctg  ggccagtttt  ctgattagcc  tttcctgttg  tgtacacaca
gAAGGGGAAC  CAAAGGGGGT  GTGAGCTACC  GCCCAGCAGA  GGTAGCCGAG  ACTGGAGCCT
AGAGGGCTGA  TCTTGGAGAA  TGTGAGAAGC  CAGCCAGAGG  CATCTGAGGG  GGAGCCGGTA
ACTGTCCTGT  CCTGCTCATT  ATGCCACTTC  CTTTTAACTG  CCAAGAAATT  TTTTAAAATA
AATATTTATA  ATaaaatatg  tgttagtcac  ctttgttccc  caaatcagaa  ggagtattt
gaatttccta  ttactgttat  tagcaccaat  ttagtggtaa  tgcatttatt  ctattacagt
tcggcctcct  tccacacatc  actccaatgt  gttgctcc
```

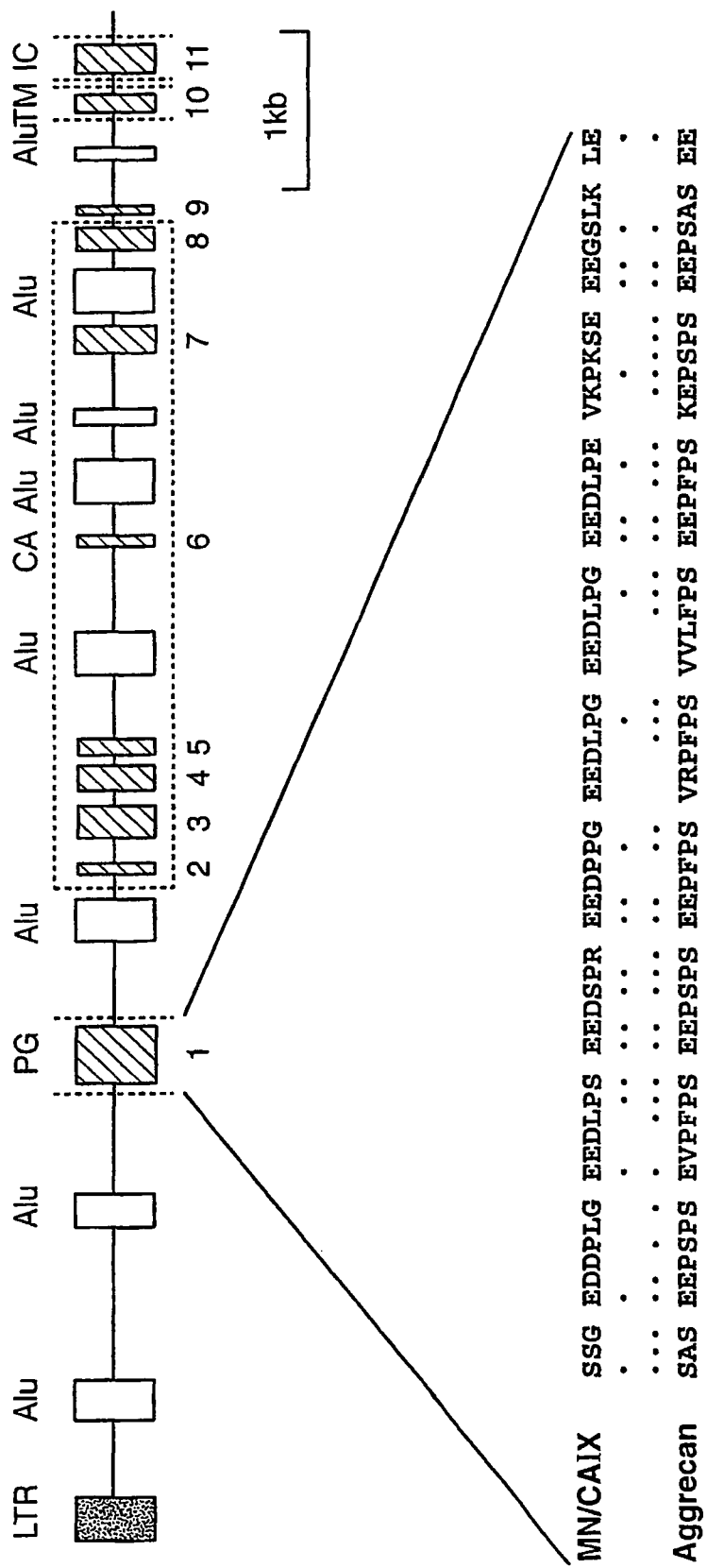
FIG._3

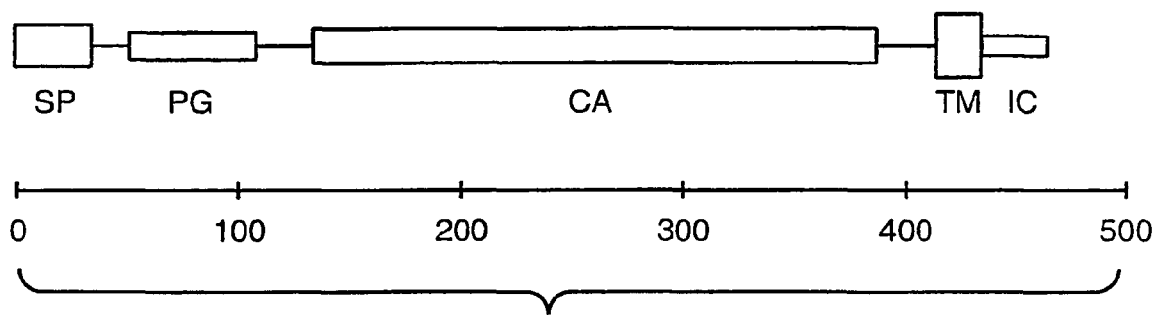
FIG._4

```
              1         10        20        30        40        50      59
HCA IX   MAPLCPSPWLPLLIPAPAPGLTVQLLLSLLLLMPVHPQRLPRMQ-EDSPLGGGSSGEDDP
MCA IX   MASLGPSPWAPLSTPAP----TAQLLLFLLLQVSAQPQGLSGMQGEPS-LGDSSSGEDE- 61        70        80        90       100       110
HCA IX   LGEED-LPSEEDSPREE-DPPGEEDLPGEEDLPGEEDLPEVKPKSE---EEGSLKLEDLP
MCA IX   LGV-DVLPSEEDAP-EEADPP---D--GE-D-P-----PEVN--SEDRMEE-SLGLEDLS 120       130       140       150       160       170
HCA IX   TVEAPGDPQEP-QNNAHRD-KEGDDQSHWRYGGDPPWPRVSPACAGRFQSPVDIRPQLA-
MCA IX   TPEAP-----EHSQGS-HGDEKGGGH-SHWSYGGTLLWPQVSPACAGRFQSPVDIR--LER 180       190       200       210       220       230
HCA IX   -AFCPALRPLELLGFQLPPLPELRLRNNGHSVQLTLPPGLEMALGPGREYRALQLHLHWG
MCA IX   TAFCRTLQPLELLGYELQPLPELSLSNNGHTVQLTLPPGLKMALGPGQEYRALQLHLHWG 240       250       260       270       280       290
HCA IX   AAGRPGSEHTVEGHRFPAEIHVVHLSTAFARVDEALGRPGGLAVLAAFLEEGPEENSAYE
MCA IX   TSDHPGSEHTVNGHRFPAEIHVVHLSTAFSELHEALGRPGGLAVLAAFLQESPEENSAYE 300       310       320       330       340       348
hCA IX   QLLSRLEEIAEEGS--ETQVPGLDISALLPSDFSRYFQYEGSLTTPPCAQGVIWTVFNQT
MCA IX   QLLSHLEEISEEGSKIE--IPGLDVSALLPSDFSRYYRYEGSLTTPPCSQGVIWTVFNET 360       370       380       390       400       408
HCA IX   VMLSAKQLHTLSDTLWGPGDSRLQLNFRATQPLNGRVIEASFPAGVDSSPRAAEPVQLNS
MCA IX   VKLSAKQLHTLSVSLWGPRDSRLQLNFRATQPLNGRTIEASFPAAEDSSP---EPVHVNS 420       430       440       450      459
HCA IX   CLAAGDILALVFGLLFAVTSVAFLVQMRRQHRR--GTKGGVSYRPAEVAETGA
HCA IX   CFTAGDILALVFGLLFAVTSIAFLLQLRRQHRHRSGTKDRVSYSPAEMTETGA
```

*Fig._5A*

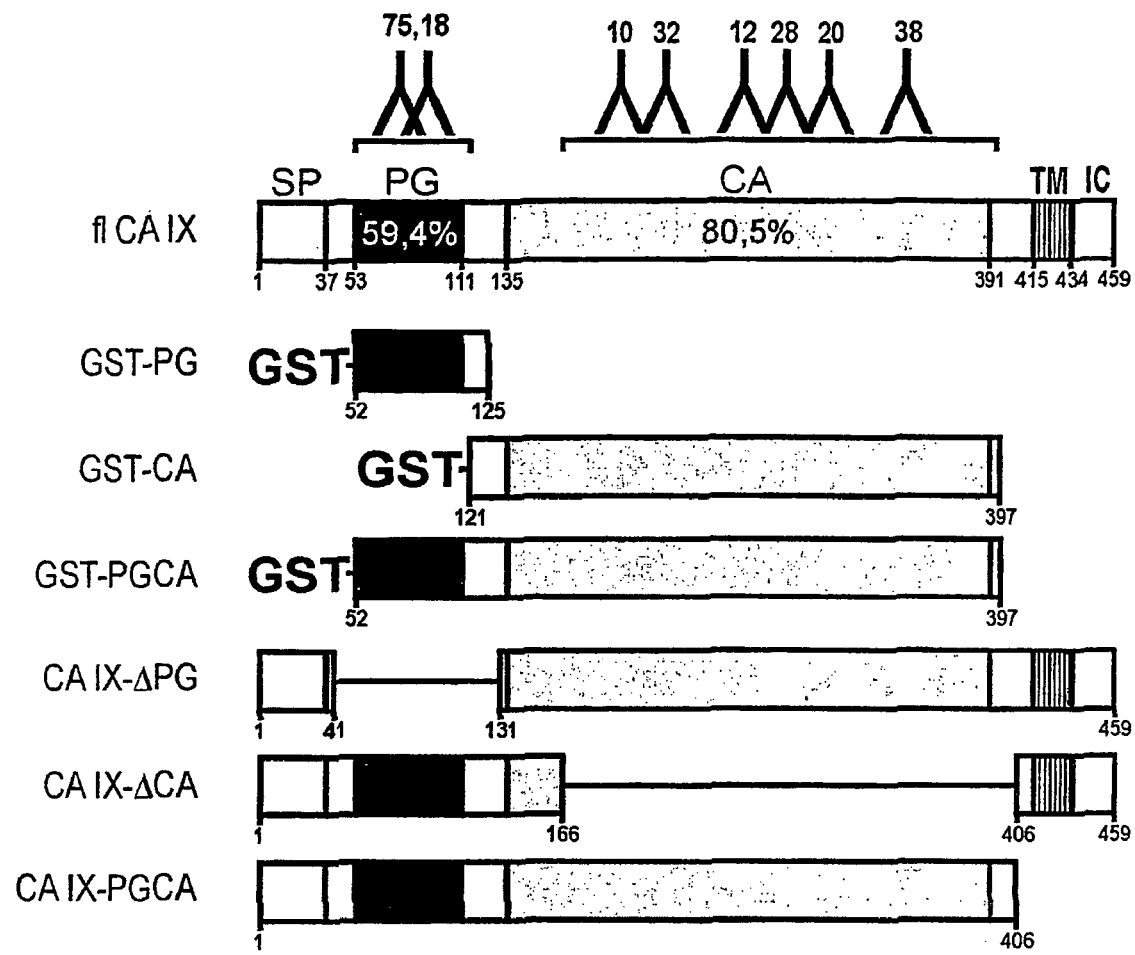
Fig._5B

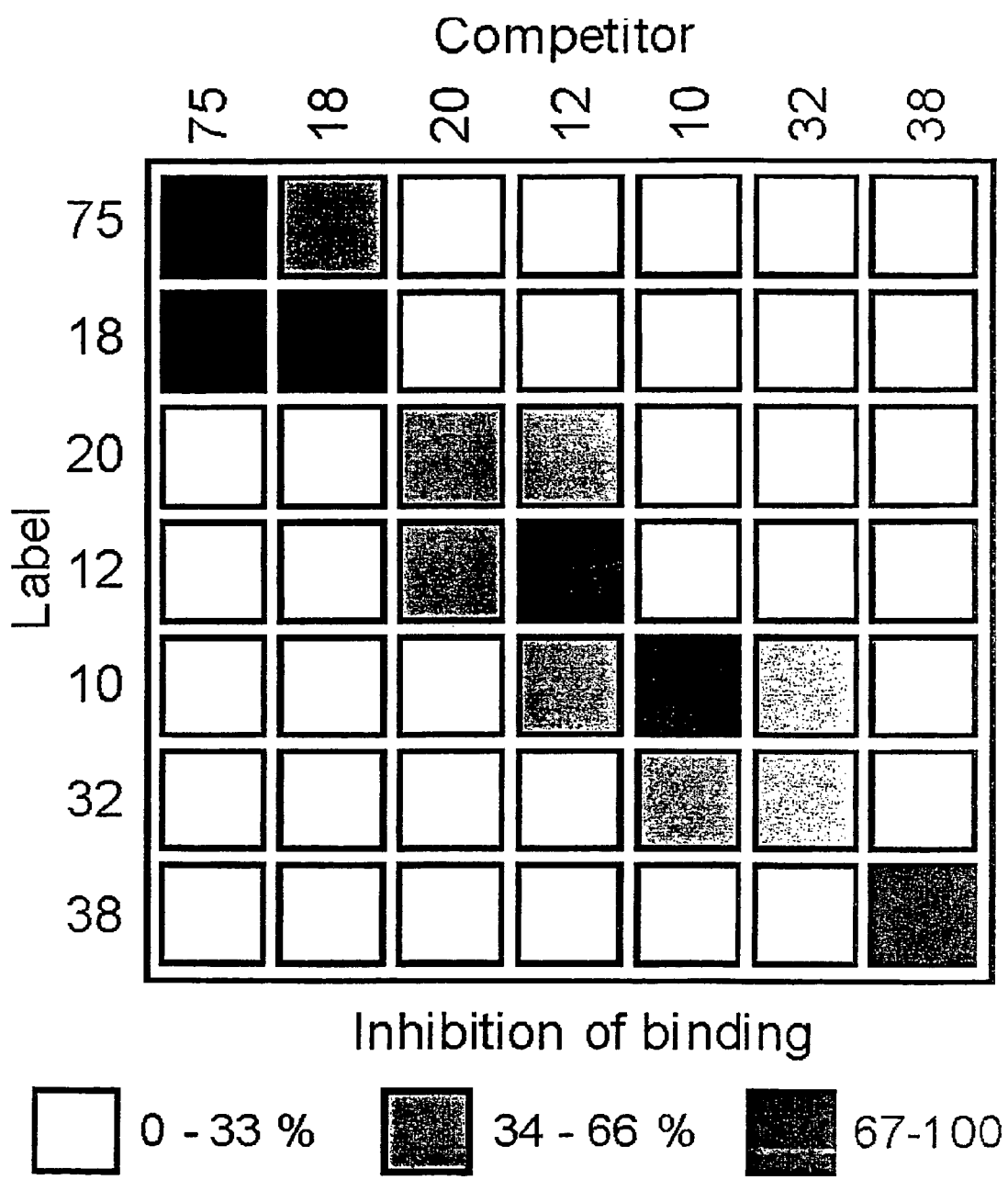
Fig._6

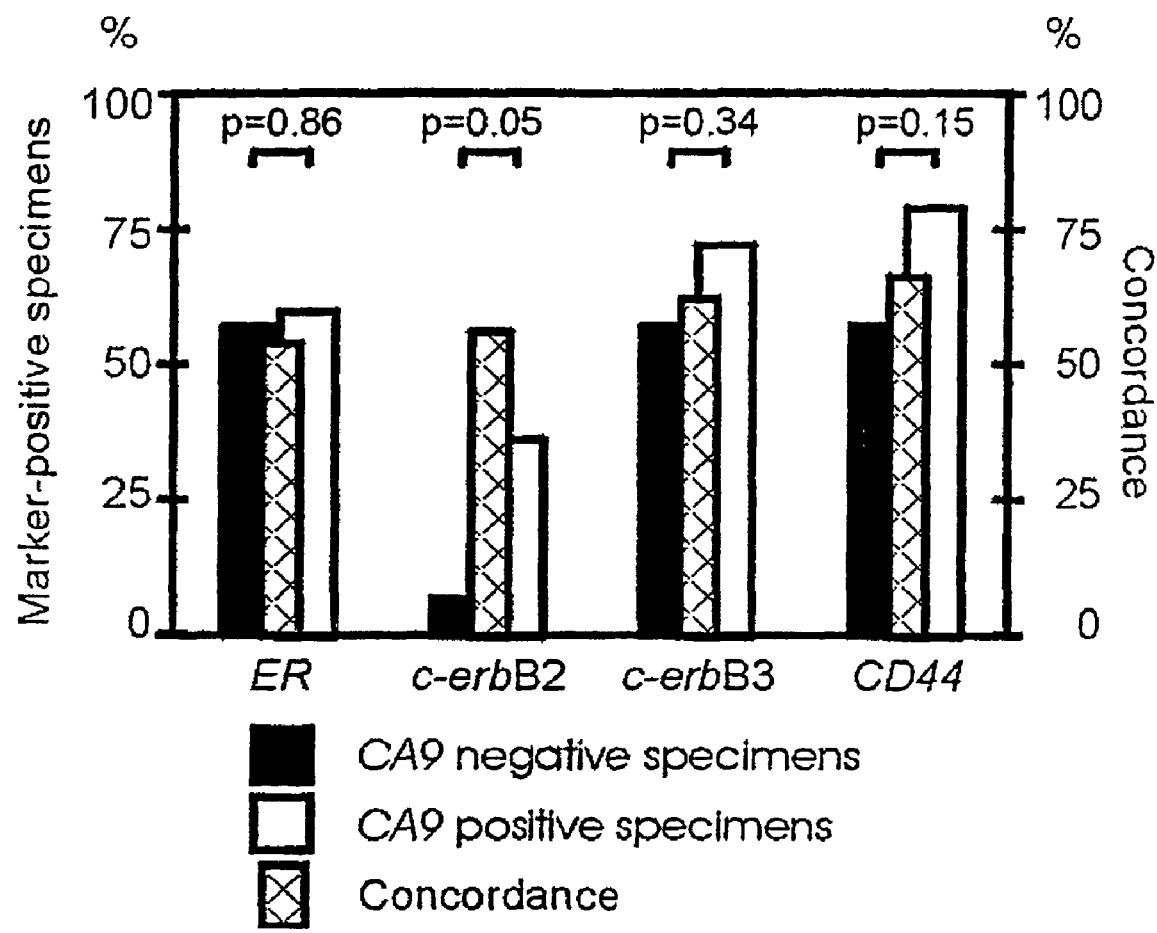
Fig._ 7A

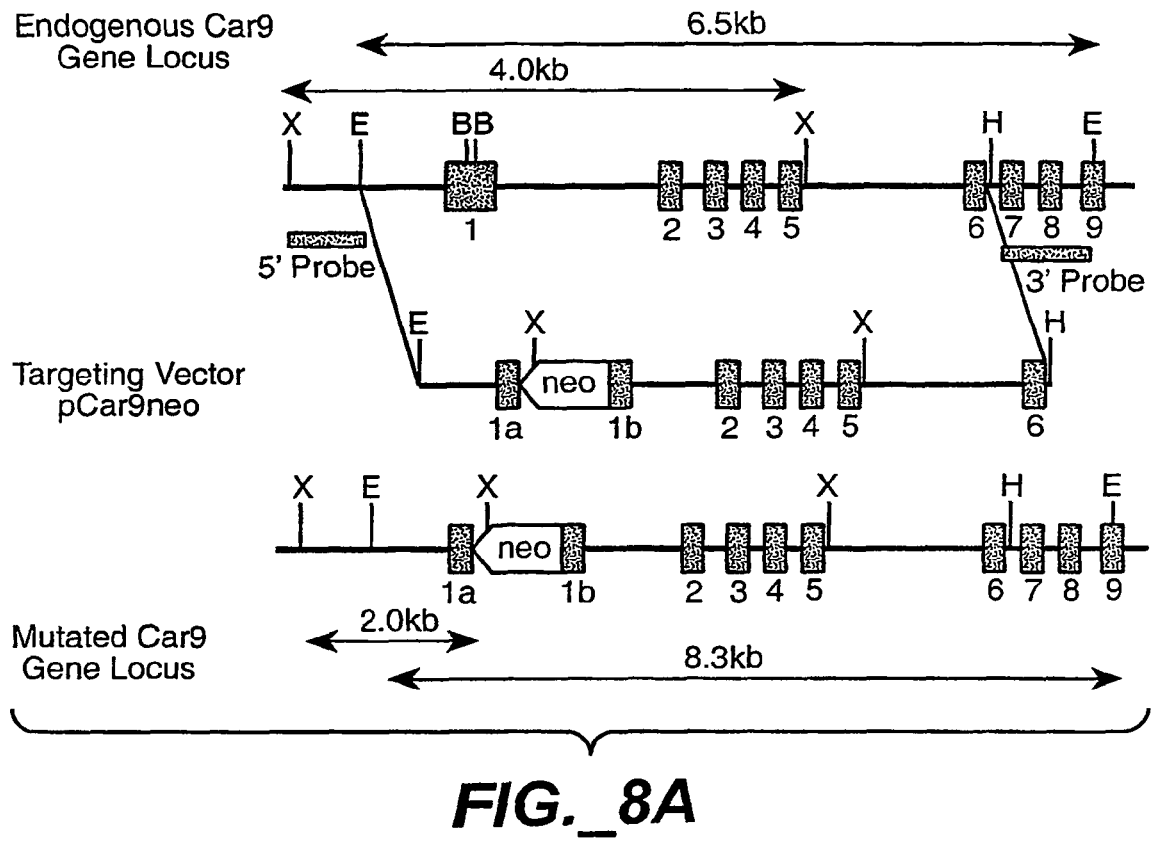
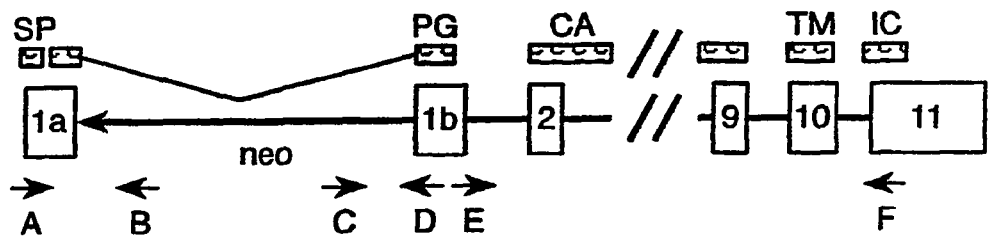
FIG._8A
FIG._8B

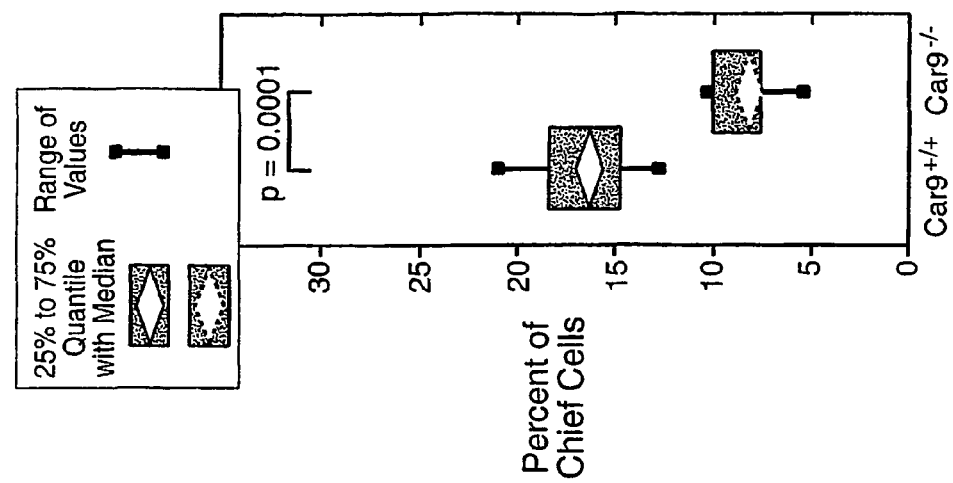
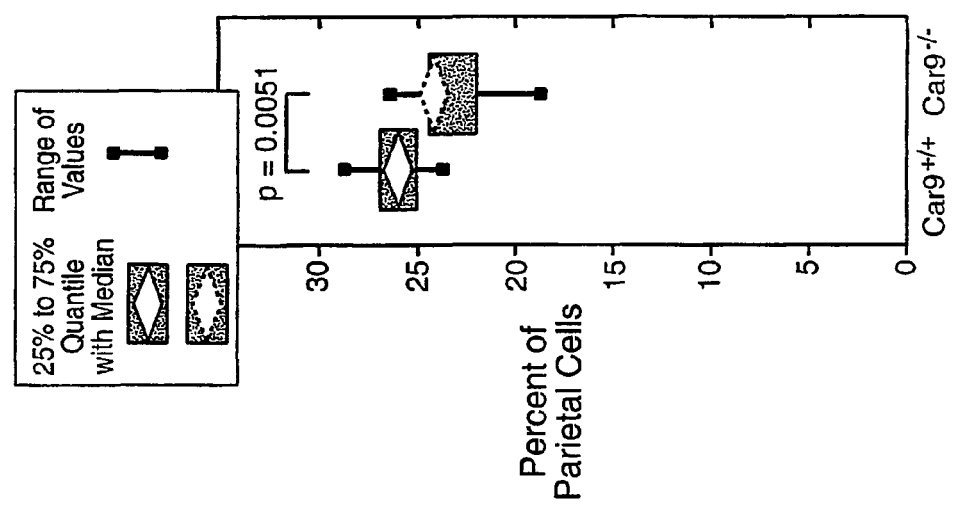
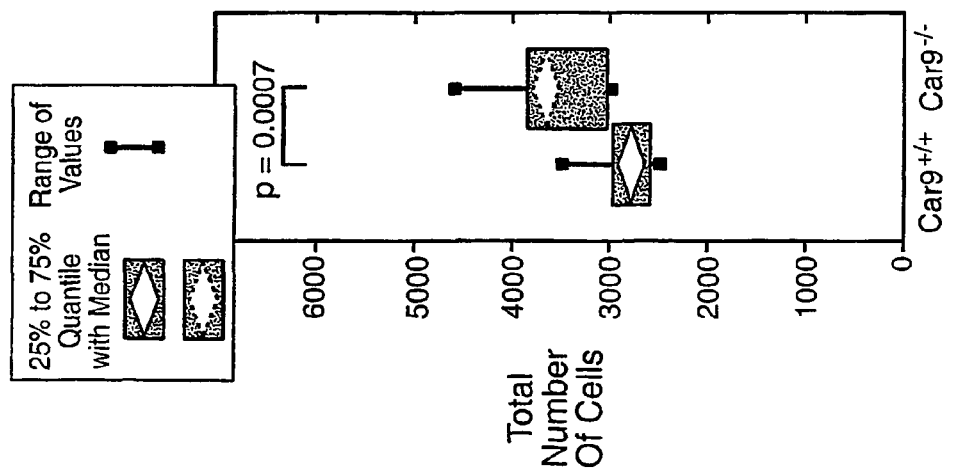
FIG._9C
FIG._9B
FIG._9A

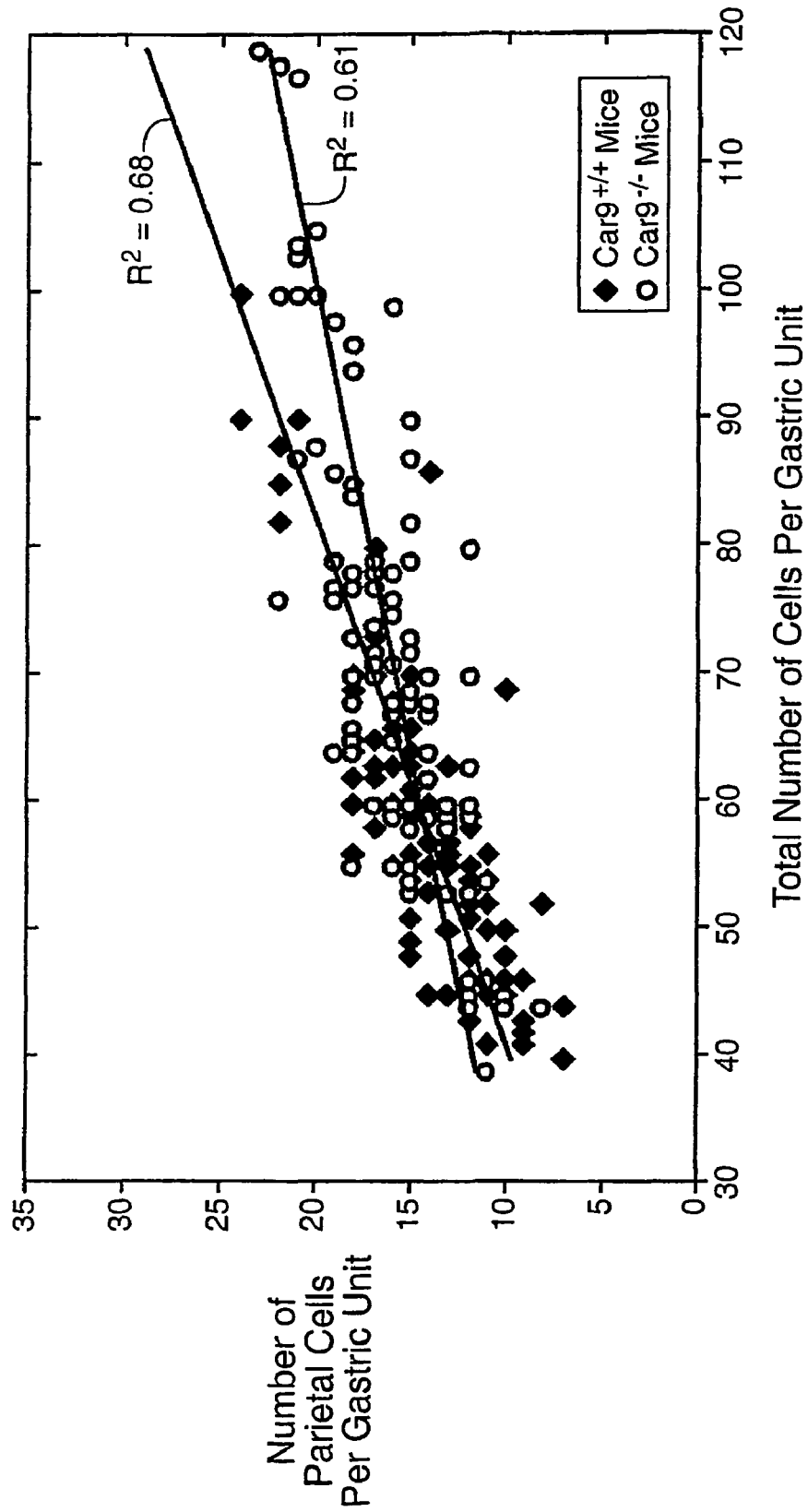
FIG._9D

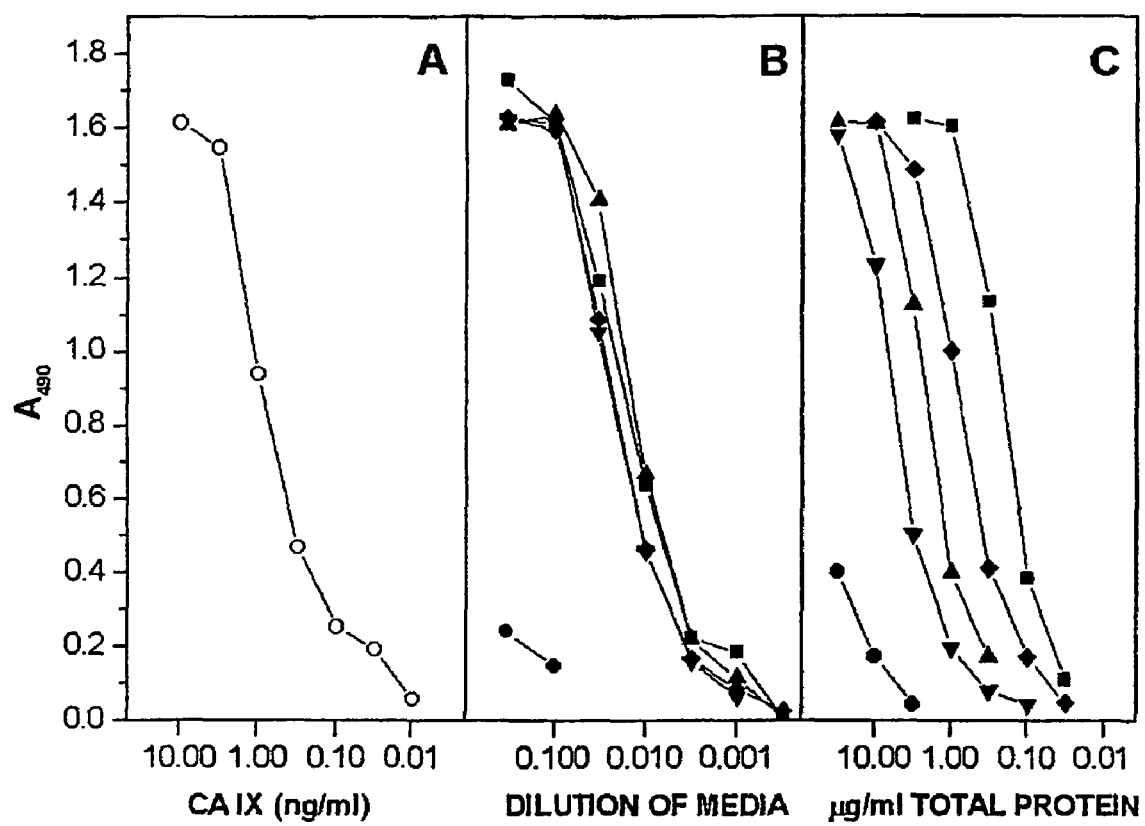
FIG._10

SEQUENCE LISTING

```
<160> NUMBER OF SEQ ID NOS: 118

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1
acagtcagcc gc atg gct ccc ctg tgc ccc agc ccc tgg ctc cct ctg ttg      51
             Met Ala Pro Leu Cys Pro Ser Pro Trp Leu Pro Leu Leu
                 -35                -30                -25
```

| | | |
|---|---|---|
| atc ccg gcc cct gct cca ggc ctc act gtg caa ctg ctg ctg tca ctg<br>Ile Pro Ala Pro Ala Pro Gly Leu Thr Val Gln Leu Leu Leu Ser Leu<br>                 -20                        -15                     -10 | | 99 |
| ctg ctt ctg atg cct gtc cat ccc cag agg ttg ccc gga atg cag gag<br>Leu Leu Leu Met Pro Val His Pro Gln Arg Leu Pro Arg Met Gln Glu<br>        -5                          -1  1                5 | | 147 |
| gat tcc ccc ttg gga gga ggc tct tct ggg gaa gat gac cca ctg ggc<br>Asp Ser Pro Leu Gly Gly Gly Ser Ser Gly Glu Asp Asp Pro Leu Gly<br>    10                      15                      20 | | 195 |
| gag gag gat ctg ccc agt gaa gag gat tca ccc aga gag gag gat cca<br>Glu Glu Asp Leu Pro Ser Glu Glu Asp Ser Pro Arg Glu Glu Asp Pro<br>25                30                      35                      40 | | 243 |
| ccc gga gag gag gat cta cct gga gag gag gat cta cct gga gag gag<br>Pro Gly Glu Glu Asp Leu Pro Gly Glu Glu Asp Leu Pro Gly Glu Glu<br>                    45                      50                      55 | | 291 |
| gat cta cct gaa gtt aag cct aaa tca gaa gaa gag ggc tcc ctg aag<br>Asp Leu Pro Glu Val Lys Pro Lys Ser Glu Glu Glu Gly Ser Leu Lys<br>        60                        65                      70 | | 339 |
| tta gag gat cta cct act gtt gag gct cct gga gat cct caa gaa ccc<br>Leu Glu Asp Leu Pro Thr Val Glu Ala Pro Gly Asp Pro Gln Glu Pro<br>              75                      80                      85 | | 387 |
| cag aat aat gcc cac agg gac aaa gaa ggg gat gac cag agt cat tgg<br>Gln Asn Asn Ala His Arg Asp Lys Glu Gly Asp Asp Gln Ser His Trp<br>90                95                      100 | | 435 |
| cgc tat gga ggc gac ccg ccc tgg ccc cgg gtg tcc cca gcc tgc gcg<br>Arg Tyr Gly Gly Asp Pro Pro Trp Pro Arg Val Ser Pro Ala Cys Ala<br>105                      110                      115                  120 | | 483 |
| ggc cgc ttc cag tcc ccg gtg gat atc cgc ccc cag ctc gcc gcc ttc<br>Gly Arg Phe Gln Ser Pro Val Asp Ile Arg Pro Gln Leu Ala Ala Phe<br>                        125                      130                      135 | | 531 |
| tgc ccg gcc ctg cgc ccc ctg gaa ctc ctg ggc ttc cag ctc ccg ccg<br>Cys Pro Ala Leu Arg Pro Leu Glu Leu Leu Gly Phe Gln Leu Pro Pro<br>                  140                      145                      150 | | 579 |
| ctc cca gaa ctg cgc ctg cgc aac aat ggc cac agt gtg caa ctg acc<br>Leu Pro Glu Leu Arg Leu Arg Asn Asn Gly His Ser Val Gln Leu Thr<br>              155                      160                      165 | | 627 |
| ctg cct cct ggg cta gag atg gct ctg ggt ccc ggg cgg gag tac cgg<br>Leu Pro Pro Gly Leu Glu Met Ala Leu Gly Pro Gly Arg Glu Tyr Arg<br>        170                        175                      180 | | 675 |
| gct ctg cag ctg cat ctg cac tgg ggg gct gca ggt cgt ccg ggc tcg<br>Ala Leu Gln Leu His Leu His Trp Gly Ala Ala Gly Arg Pro Gly Ser<br>185                      190                      195                  200 | | 723 |
| gag cac act gtg gaa ggc cac cgt ttc cct gcc gag atc cac gtg gtt<br>Glu His Thr Val Glu Gly His Arg Phe Pro Ala Glu Ile His Val Val<br>                205                      210                      215 | | 771 |
| cac ctc agc acc gcc ttt gcc aga gtt gac gag gcc ttg ggg cgc ccg<br>His Leu Ser Thr Ala Phe Ala Arg Val Asp Glu Ala Leu Gly Arg Pro<br>              220                      225                      230 | | 819 |
| gga ggc ctg gcc gtg ttg gcc gcc ttt ctg gag gag ggc ccg gaa gaa<br>Gly Gly Leu Ala Val Leu Ala Ala Phe Leu Glu Glu Gly Pro Glu Glu<br>        235                        240                      245 | | 867 |
| aac agt gcc tat gag cag ttg ctg tct cgc ttg gaa gaa atc gct gag<br>Asn Ser Ala Tyr Glu Gln Leu Leu Ser Arg Leu Glu Glu Ile Ala Glu<br>        250                        255                      260 | | 915 |
| gaa ggc tca gag act cag gtc cca gga ctg gac ata tct gca ctc ctg<br>Glu Gly Ser Glu Thr Gln Val Pro Gly Leu Asp Ile Ser Ala Leu Leu<br>265                      270                      275                  280 | | 963 |
| ccc tct gac ttc agc cgc tac ttc caa tat gag ggg tct ctg act aca<br>Pro Ser Asp Phe Ser Arg Tyr Phe Gln Tyr Glu Gly Ser Leu Thr Thr<br>              285                      290                      295 | | 1011 |

```
ccg ccc tgt gcc cag ggt gtc atc tgg act gtg ttt aac cag aca gtg      1059
Pro Pro Cys Ala Gln Gly Val Ile Trp Thr Val Phe Asn Gln Thr Val
        300                 305                 310 atg ctg agt gct aag cag ctc cac acc ctc tct gac acc ctg tgg gga      1107
Met Leu Ser Ala Lys Gln Leu His Thr Leu Ser Asp Thr Leu Trp Gly
        315                 320                 325 cct ggt gac tct cgg cta cag ctg aac ttc cga gcg acg cag cct ttg      1155
Pro Gly Asp Ser Arg Leu Gln Leu Asn Phe Arg Ala Thr Gln Pro Leu
    330                 335                 340 aat ggg cga gtg att gag gcc tcc ttc cct gct gga gtg gac agc agt      1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt      1251
Pro Arg Ala Ala Glu Pro Val Gln Leu Asn Ser Cys Leu Ala Ala Gly
            365                 370                 375 gac atc cta gcc ctg gtt ttt ggc ctc ctt ttt gct gtc acc agc gtc      1299
Asp Ile Leu Ala Leu Val Phe Gly Leu Leu Phe Ala Val Thr Ser Val
        380                 385                 390 gcg ttc ctt gtg cag atg aga agg cag cac aga agg gga acc aaa ggg      1347
Ala Phe Leu Val Gln Met Arg Arg Gln His Arg Arg Gly Thr Lys Gly
        395                 400                 405 ggt gtg agc tac cgc cca gca gag gta gcc gag act gga gcc              1389
Gly Val Ser Tyr Arg Pro Ala Glu Val Ala Glu Thr Gly Ala
    410                 415                 420 tagaggctgg atcttggaga atgtgagaag ccagccagag gcatctgagg gggagccggt    1449
aactgtcctg tcctgctcat tatgccactt ccttttaact gccaagaaat tttttaaaat    1509
aaatatttat aat                                                       1522

<210> SEQ ID NO 2
<211> LENGTH: 459
<212> TYPE: PRT
<213> ORGANISM: Homo sapiens

<400> SEQUENCE: 2

Met Ala Pro Leu Cys Pro Ser Pro Trp Leu Pro Leu Leu Ile Pro Ala
        -35                 -30                 -25

Pro Ala Pro Gly Leu Thr Val Gln Leu Leu Leu Ser Leu Leu Leu Leu
    -20                 -15                 -10

Met Pro Val His Pro Gln Arg Leu Pro Arg Met Gln Glu Asp Ser Pro
-5              -1  1               5                   10

Leu Gly Gly Gly Ser Ser Gly Glu Asp Asp Pro Leu Gly Glu Glu Asp
                15                  20                  25

Leu Pro Ser Glu Glu Asp Ser Pro Arg Glu Glu Asp Pro Pro Gly Glu
            30                  35                  40

Glu Asp Leu Pro Gly Glu Glu Asp Leu Pro Gly Glu Glu Asp Leu Pro
        45                  50                  55

Glu Val Lys Pro Lys Ser Glu Glu Gly Ser Leu Lys Leu Glu Asp
60                  65                  70                  75

Leu Pro Thr Val Glu Ala Pro Gly Asp Pro Gln Glu Pro Gln Asn Asn
                80                  85                  90

Ala His Arg Asp Lys Glu Gly Asp Gln Ser His Trp Arg Tyr Gly
            95                  100                 105

Gly Asp Pro Pro Trp Pro Arg Val Ser Pro Ala Cys Ala Gly Arg Phe
        110                 115                 120

Gln Ser Pro Val Asp Ile Arg Pro Gln Leu Ala Ala Phe Cys Pro Ala
    125                 130                 135
```

```
Leu Arg Pro Leu Glu Leu Leu Gly Phe Gln Leu Pro Leu Pro Glu
140                 145                 150                 155

Leu Arg Leu Arg Asn Asn Gly His Ser Val Gln Leu Thr Leu Pro Pro
                160                 165                 170

Gly Leu Glu Met Ala Leu Gly Pro Gly Arg Glu Tyr Arg Ala Leu Gln
            175                 180                 185

Leu His Leu His Trp Gly Ala Ala Gly Arg Pro Gly Ser Glu His Thr
        190                 195                 200

Val Glu Gly His Arg Phe Pro Ala Glu Ile His Val Val His Leu Ser
205                 210                 215

Thr Ala Phe Ala Arg Val Asp Glu Ala Leu Gly Arg Pro Gly Gly Leu
220                 225                 230                 235

Ala Val Leu Ala Ala Phe Leu Glu Glu Gly Pro Glu Glu Asn Ser Ala
                240                 245                 250

Tyr Glu Gln Leu Leu Ser Arg Leu Glu Glu Ile Ala Glu Glu Gly Ser
            255                 260                 265

Glu Thr Gln Val Pro Gly Leu Asp Ile Ser Ala Leu Leu Pro Ser Asp
        270                 275                 280

Phe Ser Arg Tyr Phe Gln Tyr Glu Gly Ser Leu Thr Thr Pro Pro Cys
285                 290                 295

Ala Gln Gly Val Ile Trp Thr Val Phe Asn Gln Thr Val Met Leu Ser
300                 305                 310                 315

Ala Lys Gln Leu His Thr Leu Ser Asp Thr Leu Trp Gly Pro Gly Asp
                320                 325                 330

Ser Arg Leu Gln Leu Asn Phe Arg Ala Thr Gln Pro Leu Asn Gly Arg
            335                 340                 345

Val Ile Glu Ala Ser Phe Pro Ala Gly Val Asp Ser Ser Pro Arg Ala
        350                 355                 360

Ala Glu Pro Val Gln Leu Asn Ser Cys Leu Ala Ala Gly Asp Ile Leu
365                 370                 375

Ala Leu Val Phe Gly Leu Leu Phe Ala Val Thr Ser Val Ala Phe Leu
380                 385                 390                 395

Val Gln Met Arg Arg Gln His Arg Arg Gly Thr Lys Gly Gly Val Ser
                400                 405                 410

Tyr Arg Pro Ala Glu Val Ala Glu Thr Gly Ala
            415                 420

<210> SEQ ID NO 3
<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3
ggatcctgtt gactcgtgac cttaccccca accctgtgct ctctgaaaca tgagctgtgt      60
ccactcaggg ttaaatggat taagggcggt gcaagatgtg ctttgttaaa cagatgcttg     120
aaggcagcat gctcgttaag agtcatcacc aatcccctaat ctcaagtaat cagggacaca    180
aacactgcgg aaggccgcag ggtcctctgc ctaggaaaac cagagacctt tgttcacttg     240
tttatctgac cttccctcca ctattgtcca tgaccctgcc aaatccccct ctgtgagaaa     300
```

```
cacccaagaa ttatcaataa aaaaataaat ttaaaaaaaa aatacaaaaa aaaaaaaaaa    360
aaaaaaaaaa gacttacgaa tagttattga taaatgaata gctattggta aagccaagta    420
aatgatcata ttcaaaacca gacggccatc atcacagctc aagtctacct gatttgatct    480
ctttatcatt gtcattcttt ggattcacta gattagtcat catcctcaaa attctccccc    540
aagttctaat tacgttccaa acatttaggg gttacatgaa gcttgaacct actaccttct    600
ttgcttttga gccatgagtt gtaggaatga tgagtttaca ccttacatgc tgggattaa     660 tttaaacttt acctctaagt cagttgggta gcctttggct tattttttgta gctaattttg    720 tagttaatgg atgcactgtg aatcttgcta tgatagtttt cctccacact ttgccactag    780
gggtaggtag gtactcagtt ttcagtaatt gcttacctaa gaccctaagc cctatttctc    840
ttgtactggc ctttatctgt aatatgggca tatttaatac aatataattt ttggagtttt    900
tttgtttgtt tgtttgtttg ttttttttgag acggagtctt gcatctgtca tgcccaggct    960
ggagtagcag tggtgccatc tcggctcact gcaagctcca cctcccgagt tcacgccatt   1020
ttcctgcctc agcctcccga gtagctggga ctacaggcgc cgccaccat gcccggctaa    1080 tttttttgtat ttttggtaga gacggggttt caccgtgtta gccagaatgg tctcgatctc   1140
ctgacttcgt gatccacccg cctcggcctc ccaaagttct gggattacag gtgtgagcca   1200
ccgcacctgg ccaatttttt gagtctttta aagtaaaaat atgtcttgta agctggtaac   1260
tatggtacat ttccttttat taatgtggtg ctgacggtca tataggttct tttgagtttg   1320
gcatgcatat gctacttttt gcagtccttt cattacattt ttctctcttc atttgaagag   1380
catgttatat cttttagctt cacttggctt aaaaggttct ctcattagcc taacacagtg   1440
tcattgttgg taccacttgg atcataagtg aaaaacagt caagaaattg cacagtaata    1500
cttgtttgta agagggatga ttcaggtgaa tctgacacta agaaactccc ctacctgagg   1560
tctgagattc ctctgacatt gctgtatata ggcttttcct ttgacagcct gtgactgcgg   1620
actatttttc ttaagcaaga tatgctaaag ttttgtgagc ctttttccag agagaggtct   1680
catatctgca tcaagtgaga acatataatg tctgcatgtt tccatatttc aggaatgttt   1740
gcttgtgttt tatgctttta tatagacagg gaaacttgtt cctcagtgac ccaaaagagg   1800
tgggaattgt tattggatat catcattggc ccacgctttc tgaccttgga aacaattaag   1860
ggttcataat ctcaattctg tcagaattgg tacaagaaat agctgctatg tttcttgaca   1920
ttccacttgg taggaaataa gaatgtgaaa ctcttcagtt ggtgtgtgtc cctngttttt   1980
ttgcaatttc cttcttactg tgttaaaaaa aagtatgatc ttgctctgag aggtgaggca   2040
ttcttaatca tgatctttaa agatcaataa tataatcctt tcaaggatta tgtctttatt   2100
ataataaaga taatttgtct ttaacagaat caataatata atcccttaaa ggattatatc   2160
tttgctgggc gcagtggctc acacctgtaa tcccagcact tgggtggcc aaggtggaag    2220 gatcaaattt gcctacttct atattatctt ctaaagcaga attcatctct cttccctcaa   2280
tatgatgata ttgacagggt ttgccctcac tcactagatt gtgagctcct gctcagggca   2340
ggtagcgttt tttgtttttg ttttgtttt tcttttttga cagggtct tgctctgtca     2400 cccaggccag agtgcaatgg tacagtctca gctcactgca gctcaaccg cctcggctca    2460 aaccatcatc ccatttcagc ctcctgagta gctgggacta caggcacatg ccattacacc   2520
tggctaattt ttttgtattt ctagtagaga cagggtttgg ccatgttgcc cgggctggtc   2580
tcgaactcct ggactcaagc aatccaccca cctcagcctc ccaaaatgag ggaccgtgtc   2640
```

```
ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060
ggctcccta gcagcctgcc ctacctcttt acctgcttcc tggtggagtc agggatgtat    3120
acatgagctg ctttccctct cagccagagg acatgggggg ccccagctcc cctgcctttc    3180
cccttctgtg cctggagctg ggaagcaggc cagggttagc tgaggctggc tggcaagcag    3240
ctgggtggtg ccagggagag cctgcatagt gccaggtggt gccttgggtt ccaagctagt    3300
ccatggcccc gataaccttc tgcctgtgca cacacctgcc cctcactcca cccccatcct    3360
agctttggta tgggggagag ggcacagggc cagacaaacc tgtgagactt tggctccatc    3420
tctgcaaaag ggcgctctgt gagtcagcct gctcccctcc aggcttgctc ctcccccacc    3480
cagctctcgt ttccaatgca cgtacagccc gtacacaccg tgtgctggga cacccacag    3540
tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200
tggagaagag aaagggatga aactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt ttttttttt tttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagacaatga    4920
ttgcaagctg gtaggattgc tgtttggccc acccagctgc ggtgttgagt ttgggtgcgg    4980
tctcctgtgc tttgcacctg gcccgcttaa ggcatttgtt acccgtaatg ctcctgtaag    5040
```

```
gcatctgcgt tgtgacatc gttttggtcg ccaggaaggg attggggctc taagcttgag    5100
cggttcatcc tttcattta tacaggggat gaccagagtc attggcgcta tggaggtgag    5160
acacccaccc gctgcacaga cccaatctgg gaacccagct ctgtggatct cccctacagc    5220
cgtccctgaa cactggtccc gggcgtccca cccgccgccc accgtcccac cccctcacct    5280
tttctacccg ggttccctaa gttcctgacc taggcgtcag acttcctcac tatactctcc    5340
caccccaggc gacccgccct ggccccgggt gtcccagcc tgcgcgggcc gcttccagtc    5400
cccggtggat atccgcccc agctcgccgc cttctgcccg gccctgcgcc cctggaact    5460
cctgggcttc cagctcccgc cgctcccaga actgcgcctg cgcaacaatg ccacagtgg    5520
tgaggggtc tccccgccga gacttgggga tggggcgggg cgcagggaag ggaaccgtcg    5580
cgcagtgcct gcccggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tgggggctg caggtcgtcc gggctcggag    5760
cacactgtgg aaggccaccg tttccctgcc gaggtgagcg cggactggcc gagaaggggc    5820
aaaggagcgg ggcggacggg ggccagagac gtggccctct cctaccctcg tgtcctttc    5880
agatccacgt ggttcacctc agcaccgcct ttgccagagt tgacgaggcc ttggggcgcc    5940
cgggaggcct ggccgtgttg gccgcctttc tggaggtacc agatcctgga caccccctac    6000
tccccgcttt cccatcccat gctcctcccg gactctatcg tggagccaga gaccccatcc    6060
cagcaagctc actcaggccc ctggctgaca aactcattca cgcactgttt gttcatttaa    6120
cacccactgt gaaccaggca ccagccccca acaaggattc tgaagctgta ggtccttgcc    6180
tctaaggagc ccacagccag tggggaggc tgacatgaca gacacatagg aaggacatag    6240
taaagatggt ggtcacagag gaggtgacac ttaaagcctt cactggtaga aaagaaaagg    6300
aggtgttcat tgcagaggaa acagaatgtg caaagactca gaatatgcc tatttaggga    6360
atggctacat acaccatgat tagaggaggc ccagtaaagg gaagggatgg tgagatgcct    6420
gctaggttca ctcactcact ttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt ttttttgtatt tttagtagac agggtttcac catgttggtc aggctggtct    6660
caaactcctg gcctcaagtg atccgcctga ctcagcctac caaagtgctg attacaagtg    6720
tgagccaccg tgcccagcca cactcactga ttctttaatg ccagccacac agcacaaagt    6780
tcagagaaat gcctccatca tagcatgtca atatgttcat actcttaggt tcatgatgtt    6840
cttaacatta ggttcataag caaaataaga aaaagaata ataaataaaa gaagtggcat    6900
gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaaccagtcc accaagcttg ttggttcgca    7140
cagcaagagt acatagagtt tgaaataata cataggattt taagagggag acactgtctc    7200
taaaaaaaaa aacaacagca acaacaaaaa gcaacaacca ttacaatttt atgttccctc    7260
agcattctca gagctgagga atgggagagg actatgggaa ccccttcat gttccggcct    7320
tcagccatgg ccctggatac atgcactcat ctgtcttaca atgtcattcc cccaggaggg    7380
```

```
cccggaagaa aacagtgcct atgagcagtt gctgtctcgc ttggaagaaa tcgctgagga    7440
aggtcagttt gttggtctgg ccactaatct ctgtggccta gttcataaag aatcacccct    7500
tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt gggaggccaa ggcaggtgga tcacgaggtc aagagatcaa gaccatcctg    7740
gccaacatgg tgaaacccca tctctactaa aaatacgaaa aaatagccag gcgtggtggc    7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaaa aaaaaaaaaa gaaaaccaag caaaaaccaa aatgagacaa    7980
aaaaaacaag accaaaaaat ggtgtttgga aattgtcaag gtcaagtctg gagagctaaa    8040
cttttttctga gaactgttta tctttaataa gcatcaaata ttttaacttt gtaaatactt    8100
ttgttggaaa tcgttctctt cttagtcact cttgggtcat tttaaatctc acttactcta    8160
ctagaccttt taggtttctg ctagactagg tagaactctg cctttgcatt tcttgtgtct    8220
gttttgtata gttatcaata ttcatattta tttacaagtt attcagatca ttttttcttt    8280
tcttttttt ttttttttt tttttacat ctttagtaga gacagggttt caccatattg    8340
gccaggctgc tctcaaactc ctgaccttgt gatccaccag cctcggcctc ccaaagtgct    8400
gggattcatt ttttcttttt aatttgctct gggcttaaac ttgtggccca gcactttatg    8460
atggtacaca gagttaagag tgtagactca gacggtcttt cttctttcct tctcttcctt    8520
cctcccttcc ctcccacctt cccttctctc cttccttct ttcttcctct cttgcttcct    8580
caggcctctt ccagttgctc caaagccctg tactttttt tgagttaacg tcttatggga    8640
agggcctgca cttagtgaag aagtggtctc agagttgagt taccttggct tctgggaggt    8700
gaaactgtat ccctataccc tgaagcttta aggggggtgca atgtagatga accccaaca    8760
tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaaagagg atgtaagatg agatgagaaa    9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
agtgtgaccc catctctacc aaaaaaaccc caacaaaacc aaaaatagcc gggcatggtg    9180
gtatgcggcc tagtcccagc tactcaagga ggctgaggtg ggaagatcgc ttgattccag    9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg acccttgttt cctgtcatgc catgaaccca    9420
cccacactgt ccactgacct ccctagctcc acaccctctc tgacaccctg tggggacctg    9480
gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
tgtctggttt cccccagcc agtagtccct tatcctccca tgtgtgtgcc agtgtctgtc    9660
attggtggtc acagcccgcc tctcacatct ccttttctc tccagtccag ctgaattcct    9720
gcctggctgc tggtgagtct gcccctcctc ttggtcctga tgccaggaga ctcctcagca    9780
```

```
ccattcagcc ccagggctgc tcaggaccgc ctctgctccc tctcctttc tgcagaacag    9840 accccaaccc caatattaga gaggcagatc atggtgggga ttcccccatt gtccccagag    9900
gctaattgat tagaatgaag cttgagaaat ctcccagcat ccctctcgca aaagaatccc    9960 ccccccttt tttaaagata gggtctcact ctgtttgccc caggctgggg tgttgtggca   10020
cgatcatagc tcactgcagc ctcgaactcc taggctcagg caatcctttc accttagctt   10080
ctcaaagcac tgggactgta ggcatgagcc actgtgcctg gccccaaacg gccctttac   10140 ttggcttta ggaagcaaaa acggtgctta tcttacccct tctcgtgtat ccaccctcat   10200
cccttggctg gcctcttctg gagactgagg cactatgggg ctgcctgaga actcggggca   10260
ggggtggtgg agtgcactga ggcaggtgtt gaggaactct gcagacccct cttccttccc   10320
aaagcagccc tctctgctct ccatcgcagg tgacatccta gccctggttt ttggcctcct   10380
ttttgctgtc accagcgtcg cgttccttgt gcagatgaga aggcagcaca ggtattacac   10440 tgacccttc ttcaggcaca agcttccccc acccttgtgg agtcacttca tgcaaagcgc   10500
atgcaaatga gctgctcctg ggccagtttt ctgattagcc tttcctgttg tgtacacaca   10560 gaagggggaac caaagggggt gtgagctacc gcccagcaga ggtagccgag actggagcct   10620
agaggctgga tcttggagaa tgtgagaagc cagccagagg catctgaggg ggagccggta   10680
actgtcctgt cctgctcatt atgccacttc cttttaactg ccaagaaatt ttttaaaata   10740 aatattata ataaaatatg tgttagtcac ctttgttccc caaatcagaa ggaggtattt   10800
gaatttccta ttactgttat tagcaccaat ttagtggtaa tgcatttatt ctattacagt   10860
tcggcctcct tccacacatc actccaatgt gttgctcc                          10898
```

<210> SEQ ID NO 4
<211> LENGTH: 37
<212> TYPE: PRT
<213> ORGANISM: Homo sapiens

<400> SEQUENCE: 4

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Met Pro Val His Pro
        35

<210> SEQ ID NO 5
<211> LENGTH: 377
<212> TYPE: PRT
<213> ORGANISM: Homo sapiens

<400> SEQUENCE: 5

Gln Arg Leu Pro Arg Met Gln Glu Asp Ser Pro Leu Gly Gly Gly Ser
1               5                   10                  15

Ser Gly Glu Asp Asp Pro Leu Gly Glu Asp Leu Pro Ser Glu Glu
            20                  25                  30

Asp Ser Pro Arg Glu Glu Asp Pro Gly Glu Glu Asp Leu Pro Gly
        35                  40                  45

Glu Glu Asp Leu Pro Gly Glu Glu Asp Leu Pro Glu Val Lys Pro Lys
    50                  55                  60

Ser Glu Glu Glu Gly Ser Leu Lys Leu Glu Asp Leu Pro Thr Val Glu
65                  70                  75                  80

-continued

```
Ala Pro Gly Asp Pro Gln Glu Pro Gln Asn Asn Ala His Arg Asp Lys
                 85                  90                  95

Glu Gly Asp Asp Gln Ser His Trp Arg Tyr Gly Gly Asp Pro Pro Trp
            100                 105                 110

Pro Arg Val Ser Pro Ala Cys Ala Gly Arg Phe Gln Ser Pro Val Asp
        115                 120                 125

Ile Arg Pro Gln Leu Ala Ala Phe Cys Pro Ala Leu Arg Pro Leu Glu
    130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
        195                 200                 205

Phe Pro Ala Glu Ile His Val Val His Leu Ser Thr Ala Phe Ala Arg
    210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
            260                 265                 270

Gly Leu Asp Ile Ser Ala Leu Leu Pro Ser Asp Phe Ser Arg Tyr Phe
        275                 280                 285

Gln Tyr Glu Gly Ser Leu Thr Thr Pro Pro Cys Ala Gln Gly Val Ile
    290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
            340                 345                 350

Phe Pro Ala Gly Val Asp Ser Ser Pro Arg Ala Ala Glu Pro Val Gln
        355                 360                 365

Leu Asn Ser Cys Leu Ala Ala Gly Asp
    370                 375
```

```
<210> SEQ ID NO 6
<211> LENGTH: 20
<212> TYPE: PRT
<213> ORGANISM: Homo sapiens

<400> SEQUENCE: 6

Ile Leu Ala Leu Val Phe Gly Leu Leu Phe Ala Val Thr Ser Val Ala
1               5                   10                  15

Phe Leu Val Gln
            20

<210> SEQ ID NO 7
<211> LENGTH: 25
<212> TYPE: PRT
<213> ORGANISM: Homo sapiens

<400> SEQUENCE: 7
```

```
Met Arg Arg Gln His Arg Arg Gly Thr Lys Gly Gly Val Ser Tyr Arg
1               5                   10                  15

Pro Ala Glu Val Ala Glu Thr Gly Ala
            20                  25
```

<210> SEQ ID NO 8
<211> LENGTH: 59
<212> TYPE: PRT
<213> ORGANISM: Homo sapiens

<400> SEQUENCE: 8

```
Ser Ser Gly Glu Asp Asp Pro Leu Gly Glu Asp Leu Pro Ser Glu
1               5                   10                  15

Glu Asp Ser Pro Arg Glu Glu Asp Pro Pro Gly Glu Glu Asp Leu Pro
            20                  25                  30

Gly Glu Glu Asp Leu Pro Gly Glu Glu Asp Leu Pro Glu Val Lys Pro
            35                  40                  45

Lys Ser Glu Glu Glu Gly Ser Leu Lys Leu Glu
            50                  55
```

<210> SEQ ID NO 9
<211> LENGTH: 257
<212> TYPE: PRT
<213> ORGANISM: Homo sapiens

<400> SEQUENCE: 9

```
Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30

Arg Pro Gln Leu Ala Ala Phe Cys Pro Ala Leu Arg Pro Leu Glu Leu
            35                  40                  45

Leu Gly Phe Gln Leu Pro Pro Leu Pro Glu Leu Arg Leu Arg Asn Asn
            50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
                100                 105                 110

Pro Ala Glu Ile His Val Val His Leu Ser Thr Ala Phe Ala Arg Val
                115                 120                 125

Asp Glu Ala Leu Gly Arg Pro Gly Gly Leu Ala Val Leu Ala Ala Phe
130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
                180                 185                 190

Tyr Glu Gly Ser Leu Thr Thr Pro Pro Cys Ala Gln Gly Val Ile Trp
                195                 200                 205

Thr Val Phe Asn Gln Thr Val Met Leu Ser Ala Lys Gln Leu His Thr
                210                 215                 220

Leu Ser Asp Thr Leu Trp Gly Pro Gly Asp Ser Arg Leu Gln Leu Asn
225                 230                 235                 240
```

-continued

Phe Arg Ala Thr Gln Pro Leu Asn Gly Arg Val Ile Glu Ala Ser Phe
                245                 250                 255
Pro

<210> SEQ ID NO 10
<211> LENGTH: 59
<212> TYPE: PRT
<213> ORGANISM: Homo sapiens

<400> SEQUENCE: 10

Ser Ala Ser Glu Glu Pro Ser Pro Ser Glu Val Pro Phe Pro Ser Glu
1               5                   10                  15

Glu Pro Ser Pro Ser Glu Glu Pro Phe Pro Ser Val Arg Pro Phe Pro
            20                  25                  30

Ser Val Val Leu Phe Pro Ser Glu Glu Pro Phe Pro Ser Lys Glu Pro
        35                  40                  45

Ser Pro Ser Glu Glu Pro Ser Ala Ser Glu Glu
    50                  55

<210> SEQ ID NO 11
<211> LENGTH: 7
<212> TYPE: PRT
<213> ORGANISM: Homo sapiens

<400> SEQUENCE: 11

Pro Gly Glu Glu Asp Leu Pro
1               5

<210> SEQ ID NO 12
<211> LENGTH: 36
<212> TYPE: PRT
<213> ORGANISM: Homo sapiens

<400> SEQUENCE: 12

Gly Glu Glu Asp Leu Pro Ser Glu Glu Asp Ser Pro Arg Glu Glu Asp
1               5                   10                  15

Pro Pro Gly Glu Glu Asp Leu Pro Gly Glu Glu Asp Leu Pro Gly Glu
            20                  25                  30

Glu Asp Leu Pro
        35

<210> SEQ ID NO 13
<211> LENGTH: 6
<212> TYPE: PRT
<213> ORGANISM: Homo sapiens

<400> SEQUENCE: 13

Gly Glu Glu Asp Leu Pro
1               5

<210> SEQ ID NO 14
<211> LENGTH: 4
<212> TYPE: PRT
<213> ORGANISM: Homo sapiens

<400> SEQUENCE: 14

Glu Glu Asp Leu
1

<210> SEQ ID NO 15
<211> LENGTH: 5
<212> TYPE: PRT

```
<213> ORGANISM: Homo sapiens

<400> SEQUENCE: 15

Glu Glu Asp Leu Pro
1               5

<210> SEQ ID NO 16
<211> LENGTH: 6
<212> TYPE: PRT
<213> ORGANISM: Homo sapiens

<400> SEQUENCE: 16

Glu Asp Leu Pro Ser Glu
1               5

<210> SEQ ID NO 17
<211> LENGTH: 7
<212> TYPE: PRT
<213> ORGANISM: Homo sapiens

<400> SEQUENCE: 17

Glu Glu Asp Leu Pro Ser Glu
1               5

<210> SEQ ID NO 18
<211> LENGTH: 6
<212> TYPE: PRT
<213> ORGANISM: Homo sapiens

<400> SEQUENCE: 18

Asp Leu Pro Gly Glu Glu
1               5

<210> SEQ ID NO 19
<211> LENGTH: 6
<212> TYPE: PRT
<213> ORGANISM: Homo sapiens

<400> SEQUENCE: 19

Glu Glu Asp Leu Pro Ser
1               5

<210> SEQ ID NO 20
<211> LENGTH: 6
<212> TYPE: PRT
<213> ORGANISM: Homo sapiens

<400> SEQUENCE: 20

Gly Glu Asp Asp Pro Leu
1               5

<210> SEQ ID NO 21
<211> LENGTH: 16
<212> TYPE: PRT
<213> ORGANISM: Homo sapiens

<400> SEQUENCE: 21

His Pro Gln Arg Leu Pro Arg Met Gln Glu Asp Ser Pro Leu Gly Gly
1               5                   10                  15

<210> SEQ ID NO 22
<211> LENGTH: 24
<212> TYPE: PRT
<213> ORGANISM: Homo sapiens
```

<400> SEQUENCE: 22

Glu Glu Asp Ser Pro Arg Glu Glu Asp Pro Gly Glu Glu Asp Leu
1               5                   10                  15

Pro Gly Glu Glu Asp Leu Pro Gly
            20

<210> SEQ ID NO 23
<211> LENGTH: 21
<212> TYPE: PRT
<213> ORGANISM: Homo sapiens

<400> SEQUENCE: 23

Asn Asn Ala His Arg Asp Lys Glu Gly Asp Asp Gln Ser His Trp Arg
1               5                   10                  15

Tyr Gly Gly Asp Pro
            20

<210> SEQ ID NO 24
<211> LENGTH: 540
<212> TYPE: DNA
<213> ORGANISM: Homo sapiens
<220> FEATURE:
<221> NAME/KEY: promoter
<222> LOCATION: (1)..(540)

<400> SEQUENCE: 24

```
cttgcttttc attcaagctc aagtttgtct cccacatacc cattacttaa ctcaccctcg    60
ggctccccta gcagcctgcc ctacctcttt acctgcttcc tggtggagtc agggatgtat   120
acatgagctg ctttccctct cagccagagg acatgggggg ccccagctcc cctgcctttc   180
cccttctgtg cctggagctg ggaagcaggc cagggttagc tgaggctggc tggcaagcag   240
ctgggtggtg ccagggagag cctgcatagt gccaggtggt gccttgggtt ccaagctagt   300
ccatggcccc gataaccttc tgcctgtgca cacacctgcc cctcactcca cccccatcct   360
agctttggta tggggagag ggcacagggc cagacaaacc tgtgagactt tggctccatc   420
tctgcaaaag ggcgctctgt gagtcagcct gctcccctcc aggcttgctc ctcccccacc   480
cagctctcgt ttccaatgca cgtacagccc gtacacaccg tgtgctggga caccccacag   540
```

<210> SEQ ID NO 25
<211> LENGTH: 445
<212> TYPE: DNA
<213> ORGANISM: Homo sapiens

<400> SEQUENCE: 25

```
gcccgtacac accgtgtgct gggacacccc acagtcagcc gcatggctcc cctgtgcccc    60
agccctggc tccctctgtt gatcccggcc cctgctccag gcctcactgt gcaactgctg   120
ctgtcactgc tgcttctggt gcctgtccat ccccagaggt tgcccggat gcaggaggat   180
tccccttgg gaggaggctc ttctggggaa gatgaccac tgggcgagga ggatctgccc   240
agtgaagagg attcacccag agaggaggat ccaccggag aggaggatct acctggagag   300
gaggatctac ctggagagga ggatctacct gaagttaagc ctaaatcaga agaagagggc   360
tccctgaagt tagaggatct acctactgtt gaggctcctg gagatcctca agaaccccag   420
aataatgccc acaggacaa agaag                                          445
```

<210> SEQ ID NO 26
<211> LENGTH: 30
<212> TYPE: DNA

<213> ORGANISM: Homo sapiens

<400> SEQUENCE: 26
gggatgacca gagtcattgg cgctatggag           30

<210> SEQ ID NO 27
<211> LENGTH: 171
<212> TYPE: DNA
<213> ORGANISM: Homo sapiens

<400> SEQUENCE: 27
gcgacccgcc ctggcccggg gtgtccccag cctgcgcggg ccgcttccag tccccggtgg           60
atatccgccc ccagctcgcc gccttctgcc cggccctgcg ccccctggaa ctcctgggct          120
tccagctccc gccgctccca gaactgcgcc tgcgcaacaa tggccacagt g                  171

<210> SEQ ID NO 28
<211> LENGTH: 143
<212> TYPE: DNA
<213> ORGANISM: Homo sapiens

<400> SEQUENCE: 28
tgcaactgac cctgcctcct gggctagaga tggctctggg tcccgggcgg gagtaccggg           60
ctctgcagct gcatctgcac tgggggctg caggtcgtcc gggctcggag cacactgtgg          120
aaggccaccg tttccctgcc gag                                                 143

<210> SEQ ID NO 29
<211> LENGTH: 93
<212> TYPE: DNA
<213> ORGANISM: Homo sapiens

<400> SEQUENCE: 29
atccacgtgg ttcacctcag caccgccttt gccagagttg acgaggcctt ggggcgcccg           60
ggaggcctgg ccgtgttggc cgcctttctg gag                                       93

<210> SEQ ID NO 30
<211> LENGTH: 67
<212> TYPE: DNA
<213> ORGANISM: Homo sapiens

<400> SEQUENCE: 30
gagggcccgg aagaaaacag tgcctatgag cagttgctgt ctcgcttgga agaaatcgct           60
gaggaag                                                                    67

<210> SEQ ID NO 31
<211> LENGTH: 158
<212> TYPE: DNA
<213> ORGANISM: Homo sapiens

<400> SEQUENCE: 31
gctcagagac tcaggtccca ggactggaca tatctgcact cctgccctct gacttcagcc           60
gctacttcca atatgagggg tctctgacta caccgccctg tgcccagggt gtcatctgga          120
ctgtgtttaa ccagacagtg atgctgagtg ctaagcag                                 158

<210> SEQ ID NO 32
<211> LENGTH: 145
<212> TYPE: DNA
<213> ORGANISM: Homo sapiens

<400> SEQUENCE: 32
ctccacaccc tctctgacac cctgtgggga cctggtgact ctcggctaca gctgaacttc    60
cgagcgacgc agcctttgaa tgggcgagtg attgaggcct ccttccctgc tggagtggac   120
agcagtcctc gggctgctga gccag                                        145

<210> SEQ ID NO 33
<211> LENGTH: 27
<212> TYPE: DNA
<213> ORGANISM: Homo sapiens

<400> SEQUENCE: 33
tccagctgaa ttcctgcctg gctgctg                                       27

<210> SEQ ID NO 34
<211> LENGTH: 82
<212> TYPE: DNA
<213> ORGANISM: Homo sapiens

<400> SEQUENCE: 34
gtgacatcct agccctggtt tttggcctcc tttttgctgt caccagcgtc gcgttccttg    60
tgcagatgag aaggcagcac ag                                            82

<210> SEQ ID NO 35
<211> LENGTH: 191
<212> TYPE: DNA
<213> ORGANISM: Homo sapiens

<400> SEQUENCE: 35
aaggggaacc aaaggggtg tgagctaccg cccagcagag gtagccgaga ctggagccta    60
gaggctggat cttggagaat gtgagaagcc agccagaggc atctgagggg agccggtaa   120 ctgtcctgtc ctgctcatta tgccacttcc ttttaactgc caagaaattt tttaaaataa   180
atatttataa t                                                       191

<210> SEQ ID NO 36
<211> LENGTH: 1174
<212> TYPE: DNA
<213> ORGANISM: Homo sapiens

<400> SEQUENCE: 36
gtaagtggtc atcaatctcc aaatccaggt tccaggaggt tcatgactcc cctcccatac    60
cccagcctag gctctgttca ctcagggaag gaggggagac tgtactcccc acagaagccc   120
ttccagaggt cccataccaa tatccccatc cccactctcg gaggtagaaa gggacagatg   180
tggagagaaa ataaaagggg tgcaaaagga gagaggtgag ctggatgaga tgggagagaa   240
gggggaggct ggagaagaga aagggatgag aactgcagat gagagaaaaa atgtgcagac   300
agaggaaaaa aataggtgga gaaggagagt cagagagttt gaggggaaga gaaaaggaaa   360
gcttgggagg tgaagtgggt accagagaca agcaagaaga gctggtagaa gtcatctcat   420
cttaggctac aatgaggaat tgagacctag gaagaaggga cacagcaggt agagaaacgt   480
ggcttcttga ctcccaagcc aggaatttgg ggaaaggggt tggagaccat acaaggcaga   540
gggatgagtg gggagaagaa agaagggaga aggaaagat ggtgtactca ctcatttggg   600
actcaggact gaagtgccca ctcactttt ttttttttt tttgagaca aactttcact   660 tttgttgccc aggctggagt gcaatggcgc gatctcggct cactgcaacc tccacctccc   720
gggttcaagt gattctcctg cctcagcctc tagccaagta gctgcgatta caggcatgcg   780

```
ccaccacgcc cggctaattt ttgtattttt agtagagacg gggtttcgcc atgttggtca      840
ggctggtctc gaactcctga tctcaggtga tccaaccacc ctggcctccc aaagtgctgg      900
gattataggc gtgagccaca cgcctggcc tgaagcagcc actcactttt acagaccta       960 agacaatgat tgcaagctgg taggattgct gtttggccca cccagctgcg gtgttgagtt    1020
tgggtgcggt ctcctgtgct ttgcacctgg cccgcttaag gcatttgtta cccgtaatgc    1080
tcctgtaagg catctgcgtt tgtgacatcg ttttggtcgc caggaaggga ttggggctct    1140
aagcttgagc ggttcatcct tttcatttat acag                                1174
```

```
<210> SEQ ID NO 37
<211> LENGTH: 193
<212> TYPE: DNA
<213> ORGANISM: Homo sapiens

<400> SEQUENCE: 37
gtgagacacc cacccgctgc acagacccaa tctgggaacc cagctctgtg gatctcccct     60
acagccgtcc ctgaacactg gtcccgggcg tcccaccgc cgcccaccgt cccacccct     120 cacctttct acccggttc cctaagttcc tgacctaggc gtcagacttc ctcactatac     180
tctcccaccc cag                                                       193
```

```
<210> SEQ ID NO 38
<211> LENGTH: 131
<212> TYPE: DNA
<213> ORGANISM: Homo sapiens

<400> SEQUENCE: 38 gtgaggggt ctccccgccg agacttgggg atgggcggg gcgcagggaa gggaaccgtc      60
gcgcagtgcc tgcccgggg ttgggctggc cctaccgggc ggggccggct cacttgcctc    120
tccctacgca g                                                        131
```

```
<210> SEQ ID NO 39
<211> LENGTH: 89
<212> TYPE: DNA
<213> ORGANISM: Homo sapiens

<400> SEQUENCE: 39
gtgagcgcgg actggccgag aaggggcaaa ggagcggggc ggacggggc cagagacgtg     60 gccctctcct accctcgtgt ccttttcag                                      89
```

```
<210> SEQ ID NO 40
<211> LENGTH: 1400
<212> TYPE: DNA
<213> ORGANISM: Homo sapiens

<400> SEQUENCE: 40
gtaccagatc ctggacaccc cctactcccc gctttcccat cccatgctcc tcccggactc     60
tatcgtggag ccagagaccc catcccagca agctcactca ggcccctggc tgacaaactc    120
attcacgcac tgtttgttca tttaacaccc actgtgaacc aggcaccagc ccccaacaag    180
gattctgaag ctgtaggtcc ttgcctctaa ggagcccaca gccagtgggg gaggctgaca    240
tgacagacac ataggaagga catagtaaag atggtggtca cagaggaggt gacacttaaa    300
gccttcactg gtagaaaaga aaaggaggtg ttcattgcag aggaaacaga atgtgcaaag    360
actcagaata tggcctattt agggaatggc tacatacacc atgattagag gaggcccagt    420
aaagggaagg gatggtgaga tgcctgctag gttcactcac tcacttttat ttatttattt    480
```

```
attttttttga cagtctctct gtcgcccagg ctggagtgca gtggtgtgat cttgggtcac     540
tgcaacttcc gcctcccggg ttcaagggat tctcctgcct cagcttcctg agtagctggg     600
gttacaggtg tgtgccacca tgcccagcta attttttttt gtattttag tagacagggt     660 ttcaccatgt tggtcaggct ggtctcaaac tcctggcctc aagtgatccg cctgactcag     720
cctaccaaag tgctgattac aagtgtgagc caccgtgccc agccacactc actgattctt     780
taatgccagc cacacagcac aaagttcaga gaaatgcctc catcatagca tgtcaatatg     840
ttcatactct taggttcatg atgttcttaa cattaggttc ataagcaaaa taagaaaaaa     900
gaataataaa taaagaagt ggcatgtcag gacctcacct gaaaagccaa acacagaatc      960
atgaaggtga atgcagaggt gacaccaaca caaaggtgta tatatggttt cctgtgggga    1020
gtatgtacgg aggcagcagt gagtgagact gcaaacgtca aagggcacg ggtcactgag     1080 agcctagtat cctagtaaag tgggctctct ccctctctct ccagcttgtc attgaaaacc    1140
agtccaccaa gcttgttggt tcgcacagca agagtacata gagtttgaaa taatacatag    1200
gattttaaga gggagacact gtctctaaaa aaaaaacaa cagcaacaac aaaaagcaac     1260
aaccattaca attttatgtt ccctcagcat tctcagagct gaggaatggg agaggactat    1320
gggaaccccc ttcatgttcc ggccttcagc catggccctg gatacatgca ctcatctgtc    1380
ttacaatgtc attcccccag                                                1400

<210> SEQ ID NO 41
<211> LENGTH: 1334
<212> TYPE: DNA
<213> ORGANISM: Homo sapiens

<400> SEQUENCE: 41
gtcagtttgt tggtctggcc actaatctct gtggcctagt tcataaagaa tcacccttg       60 gagcttcagg tctgaggctg agatgggct ccctccagtg caggagggat tgaagcatga      120
gccagcgctc atcttgataa taaccatgaa gctgacagac acagttaccc gcaaacggct     180
gcctacagat tgaaaaccaa gcaaaaaccg ccgggcacgg tggctcacgc ctgtaatccc     240
agcactttgg gaggccaagg caggtggatc acgaggtcaa gagatcaaga ccatcctggc     300
caacatggtg aaaccccatc tctactaaaa atacgaaaaa atagccaggc gtggtggcgg     360
gtgcctgtaa tcccagctac tcgggaggct gaggcaggag aatggcatga acccgggagg     420
cagaagttgc agtgagccga atcgtgcca ctgcactcca gcctgggcaa cagagcgaga     480
ctcttgtctc aaaaaaaaaa aaaaaaaga aaccaagca aaaccaaaa tgagacaaaa        540 aaacaagac caaaaatgg tgtttggaaa ttgtcaaggt caagtctgga gagctaaact      600
ttttctgaga actgtttatc tttaataagc atcaaatatt ttaactttgt aaatactttt    660
gttggaaatc gttctcttct tagtcactct tgggtcattt taaatctcac ttactctact   720 agaccttta ggtttctgct agactaggta gaactctgcc tttgcatttc ttgtgtctgt    780
tttgtatagt tatcaatatt catatttatt tacaagttat tcagatcatt ttttcttttc   840
tttttttttt ttttttttt ttttacatct ttagtagaga cagggtttca ccatattggc   900
caggctgctc tcaaactcct gaccttgtga tccaccagcc tcggcctccc aaagtgctgg    960
gattcatttt ttcttttaa tttgctctgg gcttaaactt gtggcccagc actttatgat   1020
ggtacacaga gttaagagtg tagactcaga cggtctttct tctttccttc tcttccttcc   1080
tcccttccct cccaccttcc cttctctcct tcctttcttt cttcctctct tgcttcctca   1140
```

```
ggcctcttcc agttgctcca aagccctgta cttttttttg agttaacgtc ttatgggaag    1200
ggcctgcact tagtgaagaa gtggtctcag agttgagtta ccttggcttc tgggaggtga    1260
aactgtatcc ctatccctg aagctttaag ggggtgcaat gtagatgaga ccccaacata    1320
gatcctcttc acag                                                     1334

<210> SEQ ID NO 42
<211> LENGTH: 512
<212> TYPE: DNA
<213> ORGANISM: Homo sapiens

<400> SEQUENCE: 42
gtgggcctgg ggtgtgtgtg gacacagtgg gtgcggggga aagaggatgt aagatgagat      60
gagaaacagg agaagaaaga aatcaaggct gggctctgtg gcttacgcct ataatcccac     120
cacgttggga ggctgaggtg ggagaatggt ttgagcccag gagttcaaga caaggcgggg    180
caacatagtg tgaccccatc tctaccaaaa aaacccaac aaaaccaaaa atagccgggc     240
atggtggtat gcggcctagt cccagctact caaggaggct gaggtgggaa gatcgcttga    300
ttccaggagt ttgagactgc agtgagctat gatcccacca ctgcctacca tctttaggat    360
acatttattt atttataaaa gaaatcaaga ggctggatgg ggaatacagg agctggaggg    420
tggagccctg aggtgctggt tgtgagctgg cctgggaccc ttgtttcctg tcatgccatg    480
aacccaccca cactgtccac tgacctccct ag                                  512

<210> SEQ ID NO 43
<211> LENGTH: 114
<212> TYPE: DNA
<213> ORGANISM: Homo sapiens

<400> SEQUENCE: 43
gtacagcttt gtctggtttc cccccagcca gtagtcccctt atcctcccat gtgtgtgcca     60
gtgtctgtca ttggtggtca cagcccgcct ctcacatctc cttttctct ccag            114

<210> SEQ ID NO 44
<211> LENGTH: 617
<212> TYPE: DNA
<213> ORGANISM: Homo sapiens

<400> SEQUENCE: 44
gtgagtctgc ccctcctctt ggtcctgatg ccaggagact cctcagcacc attcagcccc      60
agggctgctc aggaccgcct ctgctcctc tcctttctg cagaacagac cccaacccca      120
atattagaga ggcagatcat ggtgggggatt cccccattgt ccccagaggc taattgatta    180
gaatgaagct tgagaaatct cccagcatcc ctctcgcaaa agaatccccc ccctttttt     240 taaagatagg gtctcactct gtttgccca ggctggggtg ttgtggcacg atcatagctc     300
actgcagcct cgaactccta ggctcaggca atcctttcac cttagcttct caaagcactg    360
ggactgtagg catgagccac tgtgcctggc cccaaacggc cctttactt ggcttttagg    420 aagcaaaaac ggtgcttatc ttacccttc tcgtgtatcc accctcatcc cttggctggc    480
ctcttctgga gactgaggca ctatgggct gcctgagaac tcgggcagg ggtggtggag     540 tgcactgagg caggtgttga ggaactctgc agacccctct tccttcccaa agcagccctc    600
tctgctctcc atcgcag                                                   617

<210> SEQ ID NO 45
<211> LENGTH: 130
```

```
<210> SEQ ID NO 45
<211> LENGTH: 130
<212> TYPE: DNA
<213> ORGANISM: Homo sapiens

<400> SEQUENCE: 45
gtattacact gacccttct tcaggcacaa gcttccccca cccttgtgga gtcacttcat      60
gcaaagcgca tgcaaatgag ctgctcctgg gccagttttc tgattagcct ttcctgttgt    120
gtacacacag                                                          130

<210> SEQ ID NO 46
<211> LENGTH: 11
<212> TYPE: DNA
<213> ORGANISM: Homo sapiens

<400> SEQUENCE: 46
agaaggtaag t                                                         11

<210> SEQ ID NO 47
<211> LENGTH: 11
<212> TYPE: DNA
<213> ORGANISM: Homo sapiens

<400> SEQUENCE: 47
tggaggtgag a                                                         11

<210> SEQ ID NO 48
<211> LENGTH: 11
<212> TYPE: DNA
<213> ORGANISM: Homo sapiens

<400> SEQUENCE: 48
cagtcgtgag g                                                         11

<210> SEQ ID NO 49
<211> LENGTH: 11
<212> TYPE: DNA
<213> ORGANISM: Homo sapiens

<400> SEQUENCE: 49
ccgaggtgag c                                                         11

<210> SEQ ID NO 50
<211> LENGTH: 11
<212> TYPE: DNA
<213> ORGANISM: Homo sapiens

<400> SEQUENCE: 50
tggaggtacc a                                                         11

<210> SEQ ID NO 51
<211> LENGTH: 11
<212> TYPE: DNA
<213> ORGANISM: Homo sapiens

<400> SEQUENCE: 51
ggaaggtcag t                                                         11

<210> SEQ ID NO 52
<211> LENGTH: 11
<212> TYPE: DNA
<213> ORGANISM: Homo sapiens

<400> SEQUENCE: 52
```

-continued agcaggtggg c                    11

<210> SEQ ID NO 53
<211> LENGTH: 11
<212> TYPE: DNA
<213> ORGANISM: Homo sapiens

<400> SEQUENCE: 53
gccaggtaca g                    11

<210> SEQ ID NO 54
<211> LENGTH: 11
<212> TYPE: DNA
<213> ORGANISM: Homo sapiens

<400> SEQUENCE: 54
tgctggtgag t                    11

<210> SEQ ID NO 55
<211> LENGTH: 11
<212> TYPE: DNA
<213> ORGANISM: Homo sapiens

<400> SEQUENCE: 55
cacaggtatt a                    11

<210> SEQ ID NO 56
<211> LENGTH: 11
<212> TYPE: DNA
<213> ORGANISM: Homo sapiens

<400> SEQUENCE: 56
atacagggga t                    11

<210> SEQ ID NO 57
<211> LENGTH: 11
<212> TYPE: DNA
<213> ORGANISM: Homo sapiens

<400> SEQUENCE: 57
ccccaggcga c                    11

<210> SEQ ID NO 58
<211> LENGTH: 11
<212> TYPE: DNA
<213> ORGANISM: Homo sapiens

<400> SEQUENCE: 58
acgcagtgca a                    11

<210> SEQ ID NO 59
<211> LENGTH: 11
<212> TYPE: DNA
<213> ORGANISM: Homo sapiens

<400> SEQUENCE: 59
tttcagatcc a                    11

<210> SEQ ID NO 60
<211> LENGTH: 11
<212> TYPE: DNA
<213> ORGANISM: Homo sapiens

<400> SEQUENCE: 60

```
ccccaggagg g                                                              11

<210> SEQ ID NO 61
<211> LENGTH: 11
<212> TYPE: DNA
<213> ORGANISM: Homo sapiens

<400> SEQUENCE: 61
tcacaggctc a                                                              11

<210> SEQ ID NO 62
<211> LENGTH: 11
<212> TYPE: DNA
<213> ORGANISM: Homo sapiens

<400> SEQUENCE: 62
ccctagctcc a                                                              11

<210> SEQ ID NO 63
<211> LENGTH: 11
<212> TYPE: DNA
<213> ORGANISM: Homo sapiens

<400> SEQUENCE: 63
ctccagtcca g                                                              11

<210> SEQ ID NO 64
<211> LENGTH: 12
<212> TYPE: DNA
<213> ORGANISM: Homo sapiens

<400> SEQUENCE: 64
tcgcaggtga ca                                                             12

<210> SEQ ID NO 65
<211> LENGTH: 11
<212> TYPE: DNA
<213> ORGANISM: Homo sapiens

<400> SEQUENCE: 65
acacagaagg g                                                              11

<210> SEQ ID NO 66
<211> LENGTH: 470
<212> TYPE: RNA
<213> ORGANISM: Homo sapiens

<400> SEQUENCE: 66
cauggccccg auaaccuucu gccugugcac acaccugccc cucacuccac ccccauccua         60
gcuuugguau gggggagagg gcacagggcc agacaaaccu gugagacuuu ggcuccaucu        120
cugcaaaagg gcgcucugug agucagccug cuccccucca ggcuugcucc uccccaccc         180 agcucucguu uccaaugcac guacagcccg uacacaccgu gugcgggac accccacagu         240 cagccgcaug gcuccccugu gccccagccc cuggcucccu cguugaucc cggcccugc          300 uccaggccuc acugugcaac ugcugcuguc acugcugcuu cuggugccug uccauccca         360 gagguugccc cggaugcagg aggauucccc cuuggagga ggcucuucug gggaagauga        420
cccacugggc gaggaggauc ugcccaguga agaggauuca cccagagagg                   470

<210> SEQ ID NO 67
```

```
<211> LENGTH: 13
<212> TYPE: PRT
<213> ORGANISM: Homo sapiens

<400> SEQUENCE: 67

Leu Glu Glu Gly Pro Glu Glu Asn Ser Ala Tyr Glu Gln
1               5                   10

<210> SEQ ID NO 68
<211> LENGTH: 16
<212> TYPE: PRT
<213> ORGANISM: Homo sapiens

<400> SEQUENCE: 68

Met Arg Arg Gln His Arg Gly Thr Lys Gly Gly Val Ser Tyr Arg
1               5                   10                  15

<210> SEQ ID NO 69
<211> LENGTH: 232
<212> TYPE: PRT
<213> ORGANISM: Homo sapiens

<400> SEQUENCE: 69

Ile Arg Pro Gln Leu Ala Ala Phe Cys Pro Ala Leu Arg Pro Leu Glu
1               5                   10                  15

Leu Leu Gly Phe Gln Leu Pro Leu Pro Glu Leu Arg Leu Arg Asn
            20                  25                  30

Asn Gly His Ser Val Gln Leu Thr Leu Pro Pro Gly Leu Glu Met Ala
            35                  40                  45

Leu Gly Pro Gly Arg Glu Tyr Arg Ala Leu Gln Leu His Leu His Trp
    50                  55                  60

Gly Ala Ala Gly Arg Pro Gly Ser Glu His Thr Val Glu Gly His Arg
65                  70                  75                  80

Phe Pro Ala Glu Ile His Val Val His Leu Ser Thr Ala Phe Ala Arg
                85                  90                  95

Val Asp Glu Ala Leu Gly Arg Pro Gly Gly Leu Ala Val Leu Ala Ala
            100                 105                 110

Phe Leu Glu Glu Gly Pro Glu Glu Asn Ser Ala Tyr Glu Gln Leu Leu
        115                 120                 125

Ser Arg Leu Glu Glu Ile Ala Glu Glu Gly Ser Glu Thr Gln Val Pro
    130                 135                 140

Gly Leu Asp Ile Ser Ala Leu Leu Pro Ser Asp Phe Ser Arg Tyr Phe
145                 150                 155                 160

Gln Tyr Glu Gly Ser Leu Thr Thr Pro Pro Cys Ala Gln Gly Val Ile
                165                 170                 175

Trp Thr Val Phe Asn Gln Thr Val Met Leu Ser Ala Lys Gln Leu His
            180                 185                 190

Thr Leu Ser Asp Thr Leu Trp Gly Pro Gly Asp Ser Arg Leu Gln Leu
        195                 200                 205

Asn Phe Arg Ala Thr Gln Pro Leu Asn Gly Arg Val Ile Glu Ala Ser
    210                 215                 220

Phe Pro Ala Gly Val Asp Ser Ser
225                 230

<210> SEQ ID NO 70
<211> LENGTH: 1552
<212> TYPE: DNA
<213> ORGANISM: Homo sapiens
<300> PUBLICATION INFORMATION:
```

<308> DATABASE ACCESSION NUMBER: EMBL Accession No. X66839
<309> DATABASE ENTRY DATE: 1995-10-10
<313> RELEVANT RESIDUES: (1)..(1552)

<400> SEQUENCE: 70

```
gcccgtacac accgtgtgct gggacacccc acagtcagcc gcatggctcc cctgtgcccc      60
agcccctggc tccctctgtt gatcccggcc cctgctccag gcctcactgt gcaactgctg     120
ctgtcactgc tgcttctgat gcctgtccat ccccagaggt tgccccggat gcaggaggat     180
tccccttgg gaggaggctc ttctggggaa gatgacccac tgggcgagga ggatctgccc      240
agtgaagagg attcacccag agaggaggat ccacccggag aggaggatct acctggagag     300
gaggatctac ctggagagga ggatctacct gaagttaagc ctaaatcaga agaagagggc     360
tccctgaagt tagaggatct acctactgtt gaggctcctg agatcctcag aaccccag      420
aataatgccc acagggacaa agaagggat gaccagagtc attggcgcta tggaggcgac     480
ccgcctggc cccgggtgtc cccagcctgc gcgggccgct tccagtcccc ggtggatatc     540
cgcccccagc tcgccgcctt ctgccggcc ctgcgcccc tggaactcct gggcttccag      600
ctcccgccgc tccagaact gcgcctgcgc aacaatggcc acagtgtgca actgaccctg     660
cctcctgggc tagagatggc tctgggtccc gggcgggagt accgggctct gcagctgcat     720
ctgcactggg gggctgcagg tcgtccggc tcggagcaca ctgtggaagg ccaccgtttc      780
cctgccgaga tccacgtggt tcacctcagc accgcctttg ccagagttga cgaggccttg     840
gggcgcccgg gaggcctggc cgtgttggcc gcctttctgg aggagggccc ggaagaaaac      900
agtgcctatg agcagttgct gtctcgcttg gaagaaatcg ctgaggaagg ctcagagact     960
caggtcccag gactggacat atctgcactc ctgccctctg acttcagccg ctacttccaa    1020
tatgagggt ctctgactac accgccctgt gcccagggtg tcatctggac tgtgtttaac     1080
cagacagtga tgctgagtgc taagcagctc acacccctct ctgacaccct gtggggacct    1140
ggtgactctc ggctacagct gaacttccga gcgacgcagc ctttgaatgg gcgagtgatt    1200
gaggcctcct tccctgctgg agtggacagc agtcctcggg ctgctgagcc agtccagctg    1260
aattcctgcc tggctgctgg tgacatccta gccctggttt ttggcctcct ttttgctgtc    1320
accagcgtcg cgttccttgt gcagatgaga aggcagcaca gaaggggaac caaaggggt    1380
gtgagctacc gcccagcaga ggtagccgag actggagcct agaggctgga tcttggagaa    1440
tgtgagaagc cagccagagg catctgaggg ggagccggta actgtcctgt cctgctcatt    1500
atgccacttc cttttaactg ccaagaaatt ttaaaata aatatttata at             1552
```

<210> SEQ ID NO 71
<211> LENGTH: 20
<212> TYPE: DNA
<213> ORGANISM: Homo sapiens

<400> SEQUENCE: 71

```
atccacgtgg ttcacctcag                                                   20
```

<210> SEQ ID NO 72
<211> LENGTH: 20
<212> TYPE: DNA
<213> ORGANISM: Homo sapiens

<400> SEQUENCE: 72

```
ctttggttcc ccttctgtgc                                                   20
```

```
<210> SEQ ID NO 73
<211> LENGTH: 586
<212> TYPE: DNA
<213> ORGANISM: Homo sapiens

<400> SEQUENCE: 73
atccacgtgg ttcacctcag caccgccttt gccagagttg acgaggcctt ggggcgcccg      60
ggaggcctgg ccgtgttggc cgcctttctg gaggagggcc cggaagaaaa cagtgcctat     120
gagcagttgc tgtctcgctt ggaagaaatc gctgaggaag gctcagagac tcaggtccca     180
ggactggaca tatctgcact cctgccctct gacttcagcc gctacttcca atatgagggg     240
tctctgacta caccgccctg tgcccagggt gtcatctgga ctgtgtttaa ccagacagtg     300
atgctgagtg ctaagcagct ccacaccctc tctgacaccc tgtggggacc tggtgactct     360
cggctacagc tgaacttccg agcgacgcag cctttgaatg ggcgagtgat tgaggcctcc     420
ttccctgctg gagtggacag cagtcctcgg gctgctgagc cagtccagct gaattcctgc     480
ctggctgctg gtgacatcct agccctggtt tttggcctcc tttttgctgt caccagcgtc     540
gcgttccttg tgcagatgag aaggcagcac agaaggggaa ccaaag                    586

<210> SEQ ID NO 74
<211> LENGTH: 20
<212> TYPE: DNA
<213> ORGANISM: Homo sapiens

<400> SEQUENCE: 74
caggagagcc cagaagaaaa                                                  20

<210> SEQ ID NO 75
<211> LENGTH: 20
<212> TYPE: DNA
<213> ORGANISM: Homo sapiens

<400> SEQUENCE: 75
tgaagggtct ctgaccacac                                                  20

<210> SEQ ID NO 76
<211> LENGTH: 20
<212> TYPE: DNA
<213> ORGANISM: Homo sapiens

<400> SEQUENCE: 76
agctgtagga ggaaggcgat                                                  20

<210> SEQ ID NO 77
<211> LENGTH: 20
<212> TYPE: DNA
<213> ORGANISM: Homo sapiens

<400> SEQUENCE: 77
tgacagcaaa gagaaggcca                                                  20

<210> SEQ ID NO 78
<211> LENGTH: 20
<212> TYPE: DNA
<213> ORGANISM: Homo sapiens

<400> SEQUENCE: 78
cagggaagga agcctcaatc                                                  20

<210> SEQ ID NO 79
```

<211> LENGTH: 1965
<212> TYPE: DNA
<213> ORGANISM: Mus musculus

<400> SEQUENCE: 79

```
acagtgtgtc ctgggacacc ccagtcagct gcatggcctc cctgggcccc agccctggg       60
cccctttgtc gacccagcc cctactgcac agctgctgct gttcctgctg ctccaagtgt      120
ctgctcagcc ccagggcctg tccgggatgc agggggagcc ctccttggga gacagttcat      180
ctggggagga tgagctgggc gtggatgttc tgcccagtga agaggatgca cctgaagagg      240
cggatccacc cgatggggag gatccacctg aagttaattc tgaagacagg atggaggagt      300
cccttgggtt agaggatcta tcgactcccg aggctcctga gcacagtcaa ggttcccacg      360
gggatgaaaa agggggtggc cacagtcatt ggagctatgg aggcacccta ctctggcccc      420
aggtgtcccc agcctgtgct ggccgctttc agtccccggt agacatccgc ctggagcgca      480
ccgcattctg ccgcactctg caaccctgg aacttctggg ttatgagctc cagcctctcc       540
cggaactgag cctatccaac aatggccaca cggtacagct gactctgccg ccggggctga      600
agatggctct gggacctggg caggaatacc gggccttgca gttgcatcta cactggggaa      660
cttcagatca cccaggctca gaacacacag tcaatggtca ccgtttccct gctgagatcc      720
acgtggtgca cctcagtact gctttctccg aacttcatga agccttgggc cgcccaggag      780
gcctggcagt tttggctgcc tttctgcagg agagcccaga agaaaacagt gcttacgaac      840
agttgctgtc ccatttggaa gaaatctcgg aggaaggctc caagattgag atcccaggtt      900
tggatgtatc tgcactgttg ccctcggacc tcagccgcta ctaccgatat gaagggtctc      960
tgaccacacc tccctgcagc caggggtca tctggactgt gttcaatgag acagtgaaac     1020
tgagcgctaa gcagctccat actctctccg tttccttgtg gggacctcgt gattctcggc     1080
tacaactgaa cttccgagcc acgcaaccct tgaatgggcg aacgattgag gcttccttcc     1140
ctgctgcaga ggatagcagc cctgagccag tccatgtgaa ttcctgcttc actgctggtg     1200
acatcctagc cttggtgttt ggccttctct ttgctgtcac cagcatcgcc ttcctcctac     1260
agctgaggag gcagcacagg cacagaagtg ggaccaaaga tagagttagc tacagtccgg     1320
cagagatgac agaaactgga gcctaataag gagaaaccag ctaaaggaat ctggaaacct     1380
tgtcctgtcc tgcctgttat acagcctcct ttttaaccac tacgaaatca tttccatctt     1440
tttaactttc ttctttcctt aaagtactgt gataggagct aaccgtgaaa aacaagatt     1500
gggctcaatt cttgctgggt tttgatggtt ttgaagacag ggtttctctg tgtagccctg     1560
gctgtcctgg gactcactct gtagcctagg ctggccttga actcagagat ccgattgcct     1620
ctgccttctt agtgccagga ctgagggtat gtaccactac caccgccacc ccgcaattct     1680
tgcttttatt ctgcagtcaa atgctccacc actgagctac acaccctcc atcttactat      1740
gcaggcagac tggccttgca ttgtgtatgt atggtgatgg agtttgaagc cagggtctta     1800
cctactaggc aagcgttcta tcactgacct aagcctctct agtcccttct cttgaaccct     1860
ctattctcct gtcccagcct cttgaatgct gggattacag gaatgcacca tcatgcttgg     1920
tcatcccaat tatttaaaaa aaatatataa atcttcctag taaaa                     1965
```

<210> SEQ ID NO 80
<211> LENGTH: 8725
<212> TYPE: DNA
<213> ORGANISM: Mus musculus
<220> FEATURE:
<221> NAME/KEY: misc_feature -continued

```
<222> LOCATION: (1434)..(1434)
<223> OTHER INFORMATION: n is a, c, g, or t
<220> FEATURE:
<221> NAME/KEY: misc_feature
<222> LOCATION: (1470)..(1470)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1634)..(1634)
<223> OTHER INFORMATION: n is a, c, g, or t
<220> FEATURE:
<221> NAME/KEY: misc_feature
<222> LOCATION: (1655)..(1655)
<223> OTHER INFORMATION: n is a, c, g, or t
<220> FEATURE:
<221> NAME/KEY: misc_feature
<222> LOCATION: (1734)..(1734)
<223> OTHER INFORMATION: n is a, c, g, or t
<220> FEATURE:
<221> NAME/KEY: misc_feature
<222> LOCATION: (1752)..(1752)
<223> OTHER INFORMATION: n is a, c, g, or t
<220> FEATURE:
<221> NAME/KEY: misc_feature
<222> LOCATION: (3057)..(3057)
<223> OTHER INFORMATION: n is a, c, g, or t
<220> FEATURE:
<221> NAME/KEY: misc_feature
<222> LOCATION: (3499)..(3499)
<223> OTHER INFORMATION: n is a, c, g, or t
<220> FEATURE:
<221> NAME/KEY: misc_feature
<222> LOCATION: (3781)..(3781)
<223> OTHER INFORMATION: n is a, c, g, or t
<220> FEATURE:
<221> NAME/KEY: misc_feature
<222> LOCATION: (4535)..(4535)
<223> OTHER INFORMATION: n is a, c, g, or t
<220> FEATURE:
<221> NAME/KEY: misc_feature
<222> LOCATION: (6708)..(6708)
<223> OTHER INFORMATION: n is a, c, g, or t
<220> FEATURE:
<221> NAME/KEY: misc_feature
<222> LOCATION: (6923)..(6923)
<223> OTHER INFORMATION: n is a, c, g, or t
<220> FEATURE:
<221> NAME/KEY: misc_feature
<222> LOCATION: (7020)..(7020)
<223> OTHER INFORMATION: n is a, c, g, or t
<220> FEATURE:
<221> NAME/KEY: misc_feature
<222> LOCATION: (7087)..(7087)
<223> OTHER INFORMATION: n is a, c, g, or t
<300> PUBLICATION INFORMATION:
<308> DATABASE ACCESSION NUMBER: EMBL Accession No. AY049077
<309> DATABASE ENTRY DATE: 2002-12-19
<313> RELEVANT RESIDUES: (1)..(8725)

<400> SEQUENCE: 80
aaatataatg caggcaaaac agcaatgcac atgaaataaa ataaccaag tttaaacctg      60 gttaggtccc tcaaataaag ttccttggac ccttctgtat agatactacc ttttatttag    120
atcaggaatc atctagaagg ctctcaaaga gaagatggga tagcagggtt acctagagcc    180
atgggatgta gctgtatgtg tccaggaata aaaataactc aatgcattca attaacctag    240
acacccacac tggtggatgc tcgttgcatc attttagata cctggatgaa acgacccttat  300 tcttttatag ttgctgaggc tatgggaatc tcctgggaat gggagctgca gagcttaagg    360
ctgtctgcta ttctgtgctg cgtgcctgga gacaccagca gagtcaagga cactgggaga   420
```

```
ggcttggtac atggtcacta gatggacaga ttgggagctc catccgttct cactctgtcc    480
tgattcataa agaatcaggc tgcctgtgaa atccacactc atagttgtct tccacatggc    540
ctgatgtaag aactggtctc tgtcacgctc ttcaaaagac tttattttac atctatttgg    600
tgtatgtgtg tgtgtgtgca catgcatgtg ccatggcaca cacaggggc agagggcaac    660 ttgtagtaca ggttctctct ttccaccatg tcgattttgg ggttccacct cagatcatca    720
gattcggtgg caagtgtctt tacccactaa gcctctgacc agtctctatt caaaatggtc    780
catgtctctt ctttgtccag aattccaatc tctttactgt gattattaac caaccctcc    840 ccgtggggct tctacctctg cttcaaagat gggaacagat tttacccaca tccatagttc    900
cttgaggcag aattatgaca tctgtcctca ctcgctggag cgagagcttc tcagatagga    960
gccttcgttt tcatttccgc atccctagtc cacagcccag tgcctaacat accgtaggta   1020
ttaaacaaat acggcgtgca acatgaatg gcattctggg caacaagacg gagattcaca   1080
aaggcagtgc agagtttgga gagacgaatg aatagtttag ctctgggagc aaagctcaag   1140
tgaaagaatg cttgcatggc acccatggcc ccctggaatc agtctccagc actgaaaaag   1200
aaacaaacaa acaaagcaaa aaatgcatgc gcgcaggagc acacacacac aaattatctg   1260
accagaacat taggtggaag agcaagagac aagactggtt tcttgggtga ggttttgaag   1320
acctggaagt cgggaaataa aatgatcaga ctttggcagg cagtgggggg gggggggtaa   1380
ccattagagt ctcatatgta gattcaaata atcatgctca aatttgcctt ttanttagct   1440
gtgagcccct ccacctattc acccctaggn tcctccaggg tnttaacctg cccccttacc   1500
caagacctga ctgggccagg atacatgcat ggatttcttg cctcctcagc ccaactccac   1560
gggggcccag cttctttctt tccctgccc tgccagggcc gggaagcagg ccaggcttag   1620
cagaggccag gagntgggtg gtgccaggga gaacntatac agtgccaggt ggtgccttgg   1680
gttccaagct gagctggtga tcctgataac cttctttctg cctatgaaca cacntgcccc   1740 tcacccaac cntacccatt accgcaccaa tgtccaggct ttgatatcgg ggaggggca    1800 tagggccaga cagaacctgt gggactttgg ctccatctct acaaaagggc actgtgagtc   1860
agcctgctcc cctcaaggct tgctcctccc ctacccagct cctatttccg atgcacgtac   1920
agcccgtcca cagtgtgtcc tgggacaccc cagtcagctg catggcctcc ctgggcccca   1980 gccctgggc ccctttgtcg accccagccc ctactgcaca gctgctgctg ttcctgctgc   2040
tccaagtgtc tgctcagccc cagggcctgt ccgggatgca ggggagccc tccttgggag   2100 acagttcatc tggggaggat gagctgggcg tggatgttct gcccagtgaa gaggatgcac   2160
ctgaagaggc ggatccaccc gatggggagg atccacctga agttaattct gaagacagga   2220
tggaggagtc ccttgggtta gaggatctat cgactcccga ggctcctgag cacagtcaag   2280
gttcccacgg ggatgaaaaa ggtaagtggt cattaacttc caaatctagg ctcaggtaag   2340
tttatgcctt gtcctccccc actcccctct cttccccgaa atgctagctg agagcattcg   2400
gcaattatac tctaataggt agtctttccc ccctaaaagg agagaagaaa aaaaagccg   2460 agaataggg gaaattaaag aggaaataga actgggaatg gacagagggg gaaataagt   2520 gtgtgtgtgt gtgtgtgtgt gtgtgtgtgt gaagagaggg aggtagagag aatgagagac   2580
agacagacag agacagacac agagagacag agacagagag atgaaagggg aagagaaggg   2640
ggctcctgga agacacacaa ggagctcaca gccgttactc acctatgatt tgcggtgtgg   2700
gaaaagacag gtgaggaac tttggtttgc tctgggggcg gaggatgaga taaggtctta   2760
ttgtgtagat cggattggcc ttgaactagt tctgcccttt accttcttct tcctccgagt   2820
```

```
tctgggattt caggtgtgtg cgccaccgtg cttggctcta agccaggaac tttagacagg    2880
aaagagagat gagtgggaag gtgggtgagt aagggaaaaa gaacgatgat ttggatctca    2940
aactgaagcc gtgcctacag accctagttt gcaaactatc ggtagggcta ctgatggctc    3000
ctgcagtgat ggttgcggtg ggcggaattc ccagctggtg gttaatccac ttgtgcntca    3060
caccaaccct ggctacattc cctttctatt acgtgcaaca ctcttgtaag acatccgggg    3120
ctgtgaggcc cctgccaga gcgggaggga atattttttt attctgggca ctgggaaggg    3180
actgggctgt aagagtgggc ttattaattc ttctcattta tgcaggcggt ggccacagtc    3240
attggagcta tggaggtaag acacggccgg ctacacagac ccaatctggg agcccagccc    3300
tggtgatctg ccgcaccaac attcccagta gtagccctag actggaccca ggtcctactc    3360
tatggccccc ctcccgcgcc ccgcactccc ccacgccagt ccctggagcg ccccccttc    3420 ctcccaaccc caagcgtcct gattccaacc cttcatttat cctaacggtt cttgtccaaa    3480
tcgctagatt tcttgcacnt tttctttttca tcccaggcac cctactctgg ccccaggtgt    3540
ccccagcctg tgctggccgc tttcagtccc cggtagacat ccgcctggag cgcaccgcat    3600
tctgccgcac tctgcaaccc ctggaacttc tgggttatga gctccagcct ctcccggaac    3660
tgagcctatc caacaatggc cacacgggtg aggtgtctgg ggcgggacct atggagggga    3720
gtggcaatca acgtgtgcac ttaggagttc tgctggtgct cacgctcacg tgtgggtaga    3780
nttctcactt gccactcccc acgcagtaca gctgactctg ccgccggggc tgaagatggc    3840
tctgggacct gggcaggaat accgggcctt gcagttgcat ctacactggg gaacttcaga    3900
tcacccaggc tcagaacaca cagtcaatgg tcaccgtttc cctgctgagg tggggactgg    3960
gctgtcccaa gaagaagcaa gagggtatga tcagaggtct ggccactatc tgatccttcc    4020
atcctctcta gatccacgtg gtgcacctca gtactgcttt ctccgaactt catgaagcct    4080
tgggccgccc aggaggcctg gcagttttgg ctgccttttct gcaggtaccc tatttgacat    4140
tcacgtcctg tgggttcatg catctggcta gcagagacac cattccaagc acaagcgcaa    4200
gctggtcaat tagctctcag ccccattcac tcctttgttc attcactcag caccagcagg    4260
gaaccaggag cagactaaca caaggcttcc tttaggagga aggctgtctt gacagtcata    4320
agtgacgaac acgaaaaaaa taatggccac agaggaggcg aaacttaaat ctttcactga    4380
tgggaaacca aggaggaata ctgcacagag agaggtcagc gtgagcaagg ctggagtatg    4440
gaccagttag ggagtgccac agcaacaagc attgccctgg gaagagccat ttctctgctg    4500
cttctgtggc ccctcacttc ccctttcatga agtanaagta ttcaagtgac ctctttgtac    4560
ctgtaataat caagaacgta cactccaagg tgggaggaag ccaggaagtg aggacgccta    4620
tgagacttac cagtgtgaca ttcacagcac aaagttcagg gaagttcctc aggagcaggc    4680
gggcaggcgt agttattaaa gtgaacgcaa aggcagtaca agtataacat acatgatggt    4740
ttttttcagg aaaccacggc gtgtgtgtgt gtgtgtgtgt gtgtgtgtgt gcgagagaga    4800
gagagagaga gagagagaga gagagagaga gagagagaga gagagtgtaa atagtgatga    4860
gtgaaacgat ggacctagat cttgagggcc aggcagcctg ggaaactttc tccccttcag    4920
tttgccattg ctaattcatt tgcaaagcaa gagtaataga acttgaataa gattgtatat    4980
tccccagcat ccttagaggt gaggaacggg gaaagactat gggaaccca tcccatgccc    5040 aggcttccag ctgtagtcct agaaatgggg atcaattggc cttgtactat atcccgtgtt    5100 caccctgca ggagagccca gaagaaaaca gtgcttacga acagttgctg tcccatttgg    5160
```

```
aagaaatctc ggaggaaggt tggtggcttg cccagtgaac aatgaacata gatggaggga   5220
gctgagggtg aactggctct gactggtgat agctaaactg atgagaaaca caggggatag   5280
ggaaactact gtccacaggc ttgacaatta gaatcaaagc caaacagaaa ataacattag   5340
agaaaacaag caaagctgag tctggccgtg gtggcctccc tggtctatag agtgagttcc   5400
aggccggtca gggttacaca gtaagacctg gcctcaaaca caaacaaaac aaaaagcaaa   5460
atagagaaaa caagccaaag aaaatgttta aatttataa gactgagtat ggaaagctaa    5520 acttttttg tttgagaact gtctatcatt tatacatatc aaatatttat atattttttc    5580
ttattttggt ttttcgagac agggttttc tgtgtagccc tggctggcct ggaacttact    5640
ctgtagtcca ggctggcctc gaactcagaa atccgcctgc ctctgcctcc caagtgctgg   5700
gattaaaggc gtggccacca cgcccagctg atgaatgatt ttgagcaggt catggaagag   5760
catgctgata ataccaacgt ttgggaggtt ggctactcac caagccagcc taggttacct   5820
gaaatcataa agactagggc tagggctgaa gagagaaggc tcaggggtta agagcactga   5880
ctgctctccc agaggtccaa agtttaattc ccaaccacat ggtggctcac aaccatctgt   5940
aatgagacct gatgccctct tctggtgtgt ccgaagacag ctacagtgta ctcatataca   6000
ttaaatagat agtatttgga agaaaaaaaa aaaaaggcta gggctatagc tctgagtaga   6060
gcaagaacat agcatgcatg aagccttagg tccagagctg caaaaacact ttagtcaaaa   6120
agcttgttcc cttccatgac tgagccattt taaacctcac tctactagac tttttaggtg   6180
ttttgataaa ctggaactca tagaactttt gtgtctgttt cttatcgttg caaatattac   6240
atgtatttac aagttattct acttgtctat ctgtgtatcc acgggaatgt gctcagtaga   6300
tagaataacc ccccaccccc ccacccccag taccctcct cccgagcta cattccaatt     6360 ccgctttatt ccagtctggg gttaaccgcg gtccccccct tccccacccc ccgcacccct   6420
cctccccgag ctacattcca attccgcttt attccagtct ggggttaagt tagcagttgt   6480
gtattcagat gattgaaggt accacaggag ggcttatgag cttttggctt gaggctggaa   6540
agatggctca gcagtacaag gcctcctcta actgcccgaa gccctttact tccttttgga   6600
ttatccacac atagtaagaa gcattgaaac tatgcttgtc ccgaaagctt ccaagggca    6660 gcagtggggg gggggggggg ggaacgggcc cgaggaggca gggtgatnta ggtgagactt   6720
cacacaatcc caatccgtag gctccaagat tgagatccca ggtttggatg tatctgcact   6780
gttgccctcg gacctcagcc gctactaccg atatgaaggg tctctgacca cacctccctg   6840
cagccagggg gtcatctgga ctgtgttcaa tgagacagtg aaactgagcg ctaagcaggt   6900
tagaatgggg cgtggtattg acntggggtg ttggaaaatg ggaatgtggg aaaaaggag   6960 gaaggggtca tgcagtaaag atagacagag ggttggggtc cccttgtttc tttttgtctn   7020
gagcctgtac tatccatcga cccccacttc cccagctcca tactctctcc gtttccttgt   7080
ggggacntcg tgattctcgg ctacaactga acttccgagc cacgcaaccc ttgaatgggc   7140
gaacgattga ggcttccttc cctgctgcag aggatagcag ccctgagcca ggtgccagt    7200 tatctgatag cccacgttga catatcccca gtcaggggtc ctgcctcttc ctgtgtcttc   7260
atttgtacca gcctgtccca ggtactcatg ggccctggtt ctaatgtctc cttttatctc   7320
ttcagtccat gtgaattcct gcttcactgc tggtgagtct gggtcccttg ttcctggtgc   7380
cagtggcggg aggggccac accctttag tatttcagcc caggagctag tctttacttt     7440
ttctgtagaa taaacttgat ccccaaatcg atgtgatcgg tcaagtaaga gacctgtacc   7500
tctggcttag ttgtctgaat gaggctccag aaatctcctg tgagacccc tccccaagg     7560
```

-continued

```
cacctttcac ctagctgctg aagggagaa gagtgcttta cccttctcac tatctgcctc    7620
cattctccag atggcctgtt ctgccgaccg aggccctggg ggctgcctga acactcactg    7680
gggaaagggt caggcaggag tatgggaagc cagcttgcag ggaatcccct ggcatcccca    7740
gaagcagctg cctctcccct tccaggtgac atcctagcct tggtgtttgg ccttctcttt    7800
gctgtcacca gcatcgcctt cctcctacag ctgaggaggc agcacaggta tctatgaccc    7860
tccttggcat agcattcttg tataacccag aattcccgga ctgcaaatga gctctcatgc    7920
ggagtcggct ttctgattct cgttccttgt tctataggca cagaagtggg accaaagata    7980
gagttagcta cagtccggca gagatgacag aaactggagc ctaataagga gaaaccagct    8040
aaaggaatct ggaaaccttg tcctgtcctg cctgttatac agcctccttt ttaaccacta    8100
cgaaatcatt tccatctttt taactttctt ctttccttaa agtactgtga taggagctaa    8160
ccgtgaaaaa acaagattgg gctcaattct tgctgggttt tgatggtttt gaagacaggg    8220
tttctctgtg tagccctggc tgtcctggga ctcactctgt agcctaggct ggccttgaac    8280
tcagagatcc gattgcctct gccttcttag tgccaggact gagggtatgt accactacca    8340
ccgccacccc gcaattcttg cttttattct gcagtcaaat gctccaccac tgagctacac    8400 accccctccat cttactatgc aggcagactg gccttgcatt gtgtatgtat ggtgatggag    8460
tttgaagcca gggtcttacc tactaggcaa gcgttctatc actgacctaa gcctctctag    8520
tcccttctct tgaaccctct attctcctgt cccagcctct tgaatgctgg gattacagga    8580
atgcaccatc atgcttggtc atcccaatta tttaaaaaaa atatataaat cttcctagta    8640
aaactcgtgt atttgccttt attcctcaca tcaagggat attatattaa tttcttatgt    8700
ttgccgggaa aacaaagcaa cttcc                                         8725
```

<210> SEQ ID NO 81
<211> LENGTH: 25
<212> TYPE: DNA
<213> ORGANISM: Mus musculus

<400> SEQUENCE: 81

```
gatacatcca aacctgggat ctcaa                                          25
```

<210> SEQ ID NO 82
<211> LENGTH: 25
<212> TYPE: DNA
<213> ORGANISM: Mus musculus

<400> SEQUENCE: 82

```
tcctgcagaa aggcagccaa aactg                                          25
```

<210> SEQ ID NO 83
<211> LENGTH: 25
<212> TYPE: DNA
<213> ORGANISM: Mus musculus

<400> SEQUENCE: 83

```
cagggaaacg gtgaccattg actgt                                          25
```

<210> SEQ ID NO 84
<211> LENGTH: 25
<212> TYPE: DNA
<213> ORGANISM: Mus musculus

<400> SEQUENCE: 84

```
gacaccccag tcagctgcat ggcct                                              25

<210> SEQ ID NO 85
<211> LENGTH: 26
<212> TYPE: DNA
<213> ORGANISM: Mus musculus

<400> SEQUENCE: 85
cattctcagt attgttttgc caagtt                                             26

<210> SEQ ID NO 86
<211> LENGTH: 25
<212> TYPE: DNA
<213> ORGANISM: Mus musculus

<400> SEQUENCE: 86
cgaaggagca aagctgctat tggcc                                              25

<210> SEQ ID NO 87
<211> LENGTH: 25
<212> TYPE: DNA
<213> ORGANISM: Mus musculus

<400> SEQUENCE: 87
tgtgctcagg agcctcggga gtcga                                              25

<210> SEQ ID NO 88
<211> LENGTH: 24
<212> TYPE: DNA
<213> ORGANISM: Mus musculus

<400> SEQUENCE: 88
agtcaaggtt cccacgggga tgaa                                               24

<210> SEQ ID NO 89
<211> LENGTH: 25
<212> TYPE: DNA
<213> ORGANISM: Mus musculus

<400> SEQUENCE: 89
aaggaggctg tataacaggc aggac                                              25

<210> SEQ ID NO 90
<211> LENGTH: 437
<212> TYPE: PRT
<213> ORGANISM: Mus musculus
<300> PUBLICATION INFORMATION:
<308> DATABASE ACCESSION NUMBER: EMBL Accession Nos. AJ245857;
      CAC80975.1
<309> DATABASE ENTRY DATE: 2003-02-01
<313> RELEVANT RESIDUES: (1)..(437)

<400> SEQUENCE: 90

Met Ala Ser Leu Gly Pro Ser Pro Trp Ala Pro Leu Ser Thr Pro Ala
1               5                   10                  15

Pro Thr Ala Gln Leu Leu Leu Phe Leu Leu Leu Gln Val Ser Ala Gln
            20                  25                  30

Pro Gln Gly Leu Ser Gly Met Gln Gly Glu Pro Ser Leu Gly Asp Ser
        35                  40                  45

Ser Ser Gly Glu Asp Glu Leu Gly Val Asp Val Leu Pro Ser Glu Glu
    50                  55                  60

Asp Ala Pro Glu Glu Ala Asp Pro Pro Asp Gly Glu Asp Pro Pro Glu
65                  70                  75                  80
```

```
Val Asn Ser Glu Asp Arg Met Glu Glu Ser Leu Gly Leu Asp Leu
                85                  90                  95

Ser Thr Pro Glu Ala Pro Glu His Ser Gln Gly Ser His Gly Asp Glu
            100                 105                 110

Lys Gly Gly Gly His Ser His Trp Ser Tyr Gly Gly Thr Leu Leu Trp
            115                 120                 125

Pro Gln Val Ser Pro Ala Cys Ala Gly Arg Phe Gln Ser Pro Val Asp
        130                 135                 140

Ile Arg Leu Glu Arg Thr Ala Phe Cys Arg Thr Leu Gln Pro Leu Glu
145                 150                 155                 160

Leu Leu Gly Tyr Glu Leu Gln Pro Leu Pro Glu Leu Ser Leu Ser Asn
                165                 170                 175

Asn Gly His Thr Val Gln Leu Thr Leu Pro Pro Gly Leu Lys Met Ala
            180                 185                 190

Leu Gly Pro Gly Gln Glu Tyr Arg Ala Leu Gln Leu His Leu His Trp
        195                 200                 205

Gly Thr Ser Asp His Pro Gly Ser Glu His Thr Val Asn Gly His Arg
    210                 215                 220

Phe Pro Ala Glu Ile His Val Val His Leu Ser Thr Ala Phe Ser Glu
225                 230                 235                 240

Leu His Glu Ala Leu Gly Arg Pro Gly Gly Leu Ala Val Leu Ala Ala
                245                 250                 255

Phe Leu Gln Glu Ser Pro Glu Glu Asn Ser Ala Tyr Glu Gln Leu Leu
            260                 265                 270

Ser His Leu Glu Glu Ile Ser Glu Glu Gly Ser Lys Ile Glu Ile Pro
        275                 280                 285

Gly Leu Asp Val Ser Ala Leu Leu Pro Ser Asp Leu Ser Arg Tyr Tyr
    290                 295                 300

Arg Tyr Glu Gly Ser Leu Thr Thr Pro Pro Cys Ser Gln Gly Val Ile
305                 310                 315                 320

Trp Thr Val Phe Asn Glu Thr Val Lys Leu Ser Ala Lys Gln Leu His
                325                 330                 335

Thr Leu Ser Val Ser Leu Trp Gly Pro Arg Asp Ser Arg Leu Gln Leu
            340                 345                 350

Asn Phe Arg Ala Thr Gln Pro Leu Asn Gly Arg Thr Ile Glu Ala Ser
        355                 360                 365

Phe Pro Ala Ala Glu Asp Ser Ser Pro Glu Pro Val His Val Asn Ser
    370                 375                 380

Cys Phe Thr Ala Gly Asp Ile Leu Ala Leu Val Phe Gly Leu Leu Phe
385                 390                 395                 400

Ala Val Thr Ser Ile Ala Phe Leu Leu Gln Leu Arg Arg Gln His Arg
                405                 410                 415

His Arg Ser Gly Thr Lys Asp Arg Val Ser Tyr Ser Pro Ala Glu Met
            420                 425                 430

Thr Glu Thr Gly Ala
        435

<210> SEQ ID NO 91
<211> LENGTH: 31
<212> TYPE: PRT
<213> ORGANISM: Mus musculus

<400> SEQUENCE: 91

Met Ala Ser Leu Gly Pro Ser Pro Trp Ala Pro Leu Ser Thr Pro Ala
```

```
                1               5                   10                  15
Pro Thr Ala Gln Leu Leu Leu Phe Leu Leu Gln Val Ser Ala
                20                  25                  30

<210> SEQ ID NO 92
<211> LENGTH: 358
<212> TYPE: PRT
<213> ORGANISM: Mus musculus

<400> SEQUENCE: 92

Gln Pro Gln Gly Leu Ser Gly Met Gln Gly Glu Pro Ser Leu Gly Asp
1               5                   10                  15

Ser Ser Ser Gly Glu Asp Glu Leu Gly Val Asp Val Leu Pro Ser Glu
                20                  25                  30

Glu Asp Ala Pro Glu Glu Ala Asp Pro Pro Asp Gly Glu Asp Pro Pro
            35                  40                  45

Glu Val Asn Ser Glu Asp Arg Met Glu Glu Ser Leu Gly Leu Glu Asp
        50                  55                  60

Leu Ser Thr Pro Glu Ala Pro Glu His Ser Gln Gly Ser His Gly Asp
65                  70                  75                  80

Glu Lys Gly Gly Gly His Ser His Trp Ser Tyr Gly Gly Thr Leu Leu
                85                  90                  95

Trp Pro Gln Val Ser Pro Ala Cys Ala Gly Arg Phe Gln Ser Pro Val
                100                 105                 110

Asp Ile Arg Leu Glu Arg Thr Ala Phe Cys Arg Thr Leu Gln Pro Leu
            115                 120                 125

Glu Leu Leu Gly Tyr Glu Leu Gln Pro Leu Pro Glu Leu Ser Leu Ser
        130                 135                 140

Asn Asn Gly His Thr Val Gln Leu Thr Leu Pro Pro Gly Leu Lys Met
145                 150                 155                 160

Ala Leu Gly Pro Gly Gln Glu Tyr Arg Ala Leu Gln Leu His Leu His
                165                 170                 175

Trp Gly Thr Ser Asp His Pro Gly Ser Glu His Thr Val Asn Gly His
                180                 185                 190

Arg Phe Pro Ala Glu Ile His Val Val His Leu Ser Thr Ala Phe Ser
            195                 200                 205

Glu Leu His Glu Ala Leu Gly Arg Pro Gly Gly Leu Ala Val Leu Ala
        210                 215                 220

Ala Phe Leu Gln Glu Ser Pro Glu Glu Asn Ser Ala Tyr Glu Gln Leu
225                 230                 235                 240

Leu Ser His Leu Glu Glu Ile Ser Glu Glu Gly Ser Lys Ile Glu Ile
                245                 250                 255

Pro Gly Leu Asp Val Ser Ala Leu Leu Pro Ser Asp Leu Ser Arg Tyr
                260                 265                 270

Tyr Arg Tyr Glu Gly Ser Leu Thr Thr Pro Pro Cys Ser Gln Gly Val
            275                 280                 285

Ile Trp Thr Val Phe Asn Glu Thr Val Lys Leu Ser Ala Lys Gln Leu
        290                 295                 300

His Thr Leu Ser Val Ser Leu Trp Gly Pro Arg Asp Ser Arg Leu Gln
305                 310                 315                 320

Leu Asn Phe Arg Ala Thr Gln Pro Leu Asn Gly Arg Thr Ile Glu Ala
                325                 330                 335

Ser Phe Pro Ala Ala Glu Asp Ser Ser Pro Glu Pro Val His Val Asn
            340                 345                 350
```

```
Ser Cys Phe Thr Ala Gly
        355
```

<210> SEQ ID NO 93
<211> LENGTH: 60
<212> TYPE: PRT
<213> ORGANISM: Mus musculus

<400> SEQUENCE: 93

```
Ser Ser Ser Gly Glu Asp Glu Leu Gly Val Asp Val Leu Pro Ser Glu
1               5                   10                  15
Glu Asp Ala Pro Glu Glu Ala Asp Pro Pro Gly Glu Asp Pro Pro
            20                  25                  30
Glu Val Asn Ser Glu Asp Arg Met Glu Glu Ser Leu Gly Leu Glu Asp
            35                  40                  45
Leu Ser Thr Pro Glu Ala Pro Glu His Ser Gln Gly
            50                  55                  60
```

<210> SEQ ID NO 94
<211> LENGTH: 258
<212> TYPE: PRT
<213> ORGANISM: Mus musculus

<400> SEQUENCE: 94

```
Glu Lys Gly Gly Gly His Ser His Trp Ser Tyr Gly Gly Thr Leu Leu
1               5                   10                  15
Trp Pro Gln Val Ser Pro Ala Cys Ala Gly Arg Phe Gln Ser Pro Val
            20                  25                  30
Asp Ile Arg Leu Glu Arg Thr Ala Phe Cys Arg Thr Leu Gln Pro Leu
            35                  40                  45
Glu Leu Leu Gly Tyr Glu Leu Gln Pro Leu Pro Glu Leu Ser Leu Ser
            50                  55                  60
Asn Asn Gly His Thr Val Gln Leu Thr Leu Pro Pro Gly Leu Lys Met
65                  70                  75                  80
Ala Leu Gly Pro Gly Gln Glu Tyr Arg Ala Leu Gln Leu His Leu His
                85                  90                  95
Trp Gly Thr Ser Asp His Pro Gly Ser Glu His Thr Val Asn Gly His
                100                 105                 110
Arg Phe Pro Ala Glu Ile His Val Val His Leu Ser Thr Ala Phe Ser
                115                 120                 125
Glu Leu His Glu Ala Leu Gly Arg Pro Gly Gly Leu Ala Val Leu Ala
            130                 135                 140
Ala Phe Leu Gln Glu Ser Pro Glu Glu Asn Ser Ala Tyr Glu Gln Leu
145                 150                 155                 160
Leu Ser His Leu Glu Glu Ile Ser Glu Glu Gly Ser Lys Ile Glu Ile
                165                 170                 175
Pro Gly Leu Asp Val Ser Ala Leu Leu Pro Ser Asp Leu Ser Arg Tyr
                180                 185                 190
Tyr Arg Tyr Glu Gly Ser Leu Thr Thr Pro Pro Cys Ser Gln Gly Val
                195                 200                 205
Ile Trp Thr Val Phe Asn Glu Thr Val Lys Leu Ser Ala Lys Gln Leu
                210                 215                 220
His Thr Leu Ser Val Ser Leu Trp Gly Pro Arg Asp Ser Arg Leu Gln
225                 230                 235                 240
Leu Asn Phe Arg Ala Thr Gln Pro Leu Asn Gly Arg Thr Ile Glu Ala
                245                 250                 255
```

Ser Phe

<210> SEQ ID NO 95
<211> LENGTH: 48
<212> TYPE: PRT
<213> ORGANISM: Mus musculus

<400> SEQUENCE: 95

Asp Ile Leu Ala Leu Val Phe Gly Leu Leu Phe Ala Val Thr Ser Ile
1               5                   10                  15

Ala Phe Leu Leu Gln Leu Arg Arg Gln His Arg His Arg Ser Gly Thr
            20                  25                  30

Lys Asp Arg Val Ser Tyr Ser Pro Ala Glu Met Thr Glu Thr Gly Ala
        35                  40                  45

<210> SEQ ID NO 96
<211> LENGTH: 22
<212> TYPE: PRT
<213> ORGANISM: Mus musculus

<400> SEQUENCE: 96

Asp Ile Leu Ala Leu Val Phe Gly Leu Leu Phe Ala Val Thr Ser Ile
1               5                   10                  15

Ala Phe Leu Leu Gln Leu
            20

<210> SEQ ID NO 97
<211> LENGTH: 26
<212> TYPE: PRT
<213> ORGANISM: Mus musculus

<400> SEQUENCE: 97

Arg Arg Gln His Arg His Arg Ser Gly Thr Lys Asp Arg Val Ser Tyr
1               5                   10                  15

Ser Pro Ala Glu Met Thr Glu Thr Gly Ala
            20                  25

<210> SEQ ID NO 98
<211> LENGTH: 74
<212> TYPE: PRT
<213> ORGANISM: Homo sapiens

<400> SEQUENCE: 98

Gly Ser Ser Gly Glu Asp Asp Pro Leu Gly Glu Glu Asp Leu Pro Ser
1               5                   10                  15

Glu Glu Asp Ser Pro Arg Glu Glu Asp Pro Pro Gly Glu Glu Asp Leu
            20                  25                  30

Pro Gly Glu Glu Asp Leu Pro Gly Glu Glu Asp Leu Pro Glu Val Lys
        35                  40                  45

Pro Lys Ser Glu Glu Gly Ser Leu Lys Leu Glu Asp Leu Pro Thr
    50                  55                  60

Val Glu Ala Pro Gly Asp Pro Gln Glu Pro
65                  70

<210> SEQ ID NO 99
<211> LENGTH: 26
<212> TYPE: DNA
<213> ORGANISM: Homo sapiens

<400> SEQUENCE: 99
tagaattcgg ctcttctggg gaagat                                        26

<210> SEQ ID NO 100
<211> LENGTH: 27
<212> TYPE: DNA
<213> ORGANISM: Homo sapiens

<400> SEQUENCE: 100
atactcgagg ggttcttgag gatctcc    27

<210> SEQ ID NO 101
<211> LENGTH: 277
<212> TYPE: PRT
<213> ORGANISM: Homo sapiens

<400> SEQUENCE: 101

```
Asp Pro Gln Glu Pro Gln Asn Asn Ala His Arg Asp Lys Glu Gly Asp
1               5                   10                  15

Asp Gln Ser His Trp Arg Tyr Gly Gly Asp Pro Pro Trp Pro Arg Val
            20                  25                  30

Ser Pro Ala Cys Ala Gly Arg Phe Gln Ser Pro Val Asp Ile Arg Pro
        35                  40                  45

Gln Leu Ala Ala Phe Cys Pro Ala Leu Arg Pro Leu Glu Leu Leu Gly
    50                  55                  60

Phe Gln Leu Pro Pro Leu Pro Glu Leu Arg Leu Arg Asn Asn Gly His
65                  70                  75                  80

Ser Val Gln Leu Thr Leu Pro Pro Gly Leu Glu Met Ala Leu Gly Pro
                85                  90                  95

Gly Arg Glu Tyr Arg Ala Leu Gln Leu His Leu His Trp Gly Ala Ala
            100                 105                 110

Gly Arg Pro Gly Ser Glu His Thr Val Glu Gly His Arg Phe Pro Ala
        115                 120                 125

Glu Ile His Val Val His Leu Ser Thr Ala Phe Ala Arg Val Asp Glu
    130                 135                 140

Ala Leu Gly Arg Pro Gly Gly Leu Ala Val Leu Ala Ala Phe Leu Glu
145                 150                 155                 160

Glu Gly Pro Glu Glu Asn Ser Ala Tyr Glu Gln Leu Leu Ser Arg Leu
                165                 170                 175

Glu Glu Ile Ala Glu Gly Ser Glu Thr Gln Val Pro Gly Leu Asp
            180                 185                 190

Ile Ser Ala Leu Leu Pro Ser Asp Phe Ser Arg Tyr Phe Gln Tyr Glu
        195                 200                 205

Gly Ser Leu Thr Thr Pro Pro Cys Ala Gln Gly Val Ile Trp Thr Val
    210                 215                 220

Phe Asn Gln Thr Val Met Leu Ser Ala Lys Gln Leu His Thr Leu Ser
225                 230                 235                 240

Asp Thr Leu Trp Gly Pro Gly Asp Ser Arg Leu Gln Leu Asn Phe Arg
                245                 250                 255

Ala Thr Gln Pro Leu Asn Gly Arg Val Ile Glu Ala Ser Phe Pro Ala
            260                 265                 270

Gly Val Asp Ser Ser
        275
```

<210> SEQ ID NO 102
<211> LENGTH: 26
<212> TYPE: DNA
<213> ORGANISM: Homo sapiens

<400> SEQUENCE: 102
tagaattcga tcctcaagaa ccccag                                          26

<210> SEQ ID NO 103
<211> LENGTH: 27
<212> TYPE: DNA
<213> ORGANISM: Homo sapiens

<400> SEQUENCE: 103
aatctcgaga ctgctgtcca ctccagc                                         27

<210> SEQ ID NO 104
<211> LENGTH: 346
<212> TYPE: PRT
<213> ORGANISM: Homo sapiens

<400> SEQUENCE: 104

Gly Ser Ser Gly Glu Asp Pro Leu Gly Glu Glu Asp Leu Pro Ser
1               5                   10                  15

Glu Glu Asp Ser Pro Arg Glu Glu Asp Pro Pro Gly Glu Glu Asp Leu
            20                  25                  30

Pro Gly Glu Glu Asp Leu Pro Gly Glu Glu Asp Leu Pro Glu Val Lys
        35                  40                  45

Pro Lys Ser Glu Glu Gly Ser Leu Lys Leu Glu Asp Leu Pro Thr
    50                  55                  60

Val Glu Ala Pro Gly Asp Pro Gln Glu Pro Gln Asn Asn Ala His Arg
65                  70                  75                  80

Asp Lys Glu Gly Asp Asp Gln Ser His Trp Arg Tyr Gly Gly Asp Pro
                85                  90                  95

Pro Trp Pro Arg Val Ser Pro Ala Cys Ala Gly Arg Phe Gln Ser Pro
            100                 105                 110

Val Asp Ile Arg Pro Gln Leu Ala Ala Phe Cys Pro Ala Leu Arg Pro
        115                 120                 125

Leu Glu Leu Leu Gly Phe Gln Leu Pro Pro Leu Pro Glu Leu Arg Leu
    130                 135                 140

Arg Asn Asn Gly His Ser Val Gln Leu Thr Leu Pro Pro Gly Leu Glu
145                 150                 155                 160

Met Ala Leu Gly Pro Gly Arg Glu Tyr Arg Ala Leu Gln Leu His Leu
                165                 170                 175

His Trp Gly Ala Ala Gly Arg Pro Gly Ser Glu His Thr Val Glu Gly
            180                 185                 190

His Arg Phe Pro Ala Glu Ile His Val Val His Leu Ser Thr Ala Phe
        195                 200                 205

Ala Arg Val Asp Glu Ala Leu Gly Arg Pro Gly Gly Leu Ala Val Leu
    210                 215                 220

Ala Ala Phe Leu Glu Glu Gly Pro Glu Glu Asn Ser Ala Tyr Glu Gln
225                 230                 235                 240

Leu Leu Ser Arg Leu Glu Glu Ile Ala Glu Glu Gly Ser Glu Thr Gln
                245                 250                 255

Val Pro Gly Leu Asp Ile Ser Ala Leu Leu Pro Ser Asp Phe Ser Arg
            260                 265                 270

Tyr Phe Gln Tyr Glu Gly Ser Leu Thr Thr Pro Pro Cys Ala Gln Gly
        275                 280                 285

Val Ile Trp Thr Val Phe Asn Gln Thr Val Met Leu Ser Ala Lys Gln
    290                 295                 300

```
Leu His Thr Leu Ser Asp Thr Leu Trp Gly Pro Gly Asp Ser Arg Leu
305                 310                 315                 320

Gln Leu Asn Phe Arg Ala Thr Gln Pro Leu Asn Gly Arg Val Ile Glu
            325                 330                 335

Ala Ser Phe Pro Ala Gly Val Asp Ser Ser
            340                 345

<210> SEQ ID NO 105
<211> LENGTH: 232
<212> TYPE: PRT
<213> ORGANISM: Homo sapiens

<400> SEQUENCE: 105

Ile Arg Pro Gln Leu Ala Ala Phe Cys Pro Ala Leu Arg Pro Leu Glu
1               5                   10                  15

Leu Leu Gly Phe Gln Leu Pro Pro Leu Pro Glu Leu Arg Leu Arg Asn
            20                  25                  30

Asn Gly His Ser Val Gln Leu Thr Leu Pro Pro Gly Leu Glu Met Ala
        35                  40                  45

Leu Gly Pro Gly Arg Glu Tyr Arg Ala Leu Gln Leu His Leu His Trp
    50                  55                  60

Gly Ala Ala Gly Arg Pro Gly Ser Glu His Thr Val Glu Gly His Arg
65                  70                  75                  80

Phe Pro Ala Glu Ile His Val Val His Leu Ser Thr Ala Phe Ala Arg
                85                  90                  95

Val Asp Glu Ala Leu Gly Arg Pro Gly Gly Leu Ala Val Leu Ala Ala
            100                 105                 110

Phe Leu Glu Glu Gly Pro Glu Glu Asn Ser Ala Tyr Glu Gln Leu Leu
        115                 120                 125

Ser Arg Leu Glu Glu Ile Ala Glu Glu Gly Ser Glu Thr Gln Val Pro
    130                 135                 140

Gly Leu Asp Ile Ser Ala Leu Leu Pro Ser Asp Phe Ser Arg Tyr Phe
145                 150                 155                 160

Gln Tyr Glu Gly Ser Leu Thr Thr Pro Pro Cys Ala Gln Gly Val Ile
                165                 170                 175

Trp Thr Val Phe Asn Gln Thr Val Met Leu Ser Ala Lys Gln Leu His
            180                 185                 190

Thr Leu Ser Asp Thr Leu Trp Gly Pro Gly Asp Ser Arg Leu Gln Leu
        195                 200                 205

Asn Phe Arg Ala Thr Gln Pro Leu Asn Gly Arg Val Ile Glu Ala Ser
    210                 215                 220

Phe Pro Ala Gly Val Asp Ser Ser
225                 230

<210> SEQ ID NO 106
<211> LENGTH: 32
<212> TYPE: PRT
<213> ORGANISM: Homo sapiens

<400> SEQUENCE: 106

Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30

<210> SEQ ID NO 107
<211> LENGTH: 20
```

```
<212> TYPE: DNA
<213> ORGANISM: Homo sapiens

<400> SEQUENCE: 107
ccgagcgacg cagcctttga                                              20

<210> SEQ ID NO 108
<211> LENGTH: 30
<212> TYPE: DNA
<213> ORGANISM: Homo sapiens

<400> SEQUENCE: 108
tagtcgacta ggctccagtc tcggctacct                                   30

<210> SEQ ID NO 109
<211> LENGTH: 20
<212> TYPE: DNA
<213> ORGANISM: Homo sapiens

<400> SEQUENCE: 109
catccagcgt actccaaaga                                              20

<210> SEQ ID NO 110
<211> LENGTH: 20
<212> TYPE: DNA
<213> ORGANISM: Homo sapiens

<400> SEQUENCE: 110
gacaagtctg aatgctccac                                              20

<210> SEQ ID NO 111
<211> LENGTH: 25
<212> TYPE: DNA
<213> ORGANISM: Homo sapiens

<400> SEQUENCE: 111
actcgctact gtgcagtgtg caatg                                        25

<210> SEQ ID NO 112
<211> LENGTH: 25
<212> TYPE: DNA
<213> ORGANISM: Homo sapiens

<400> SEQUENCE: 112
cctcttcggt cttttcgtat cccac                                        25

<210> SEQ ID NO 113
<211> LENGTH: 27
<212> TYPE: DNA
<213> ORGANISM: Homo sapiens

<400> SEQUENCE: 113
agtttccaga tgaggagggc gcatgcc                                      27

<210> SEQ ID NO 114
<211> LENGTH: 27
<212> TYPE: DNA
<213> ORGANISM: Homo sapiens

<400> SEQUENCE: 114
ttctccccat cagggatcca gatgccc                                      27

<210> SEQ ID NO 115
```

-continued

```
<211> LENGTH: 26
<212> TYPE: DNA
<213> ORGANISM: Homo sapiens
<300> PUBLICATION INFORMATION:
<308> DATABASE ACCESSION NUMBER: M34309
<309> DATABASE ENTRY DATE: 1999-07-02
<313> RELEVANT RESIDUES: (222)..(247)

<400> SEQUENCE: 115
ggtgctgggc ttgcttttca gcctgg                                        26

<210> SEQ ID NO 116
<211> LENGTH: 26
<212> TYPE: DNA
<213> ORGANISM: Homo sapiens

<400> SEQUENCE: 116
accacgcgga ggttgggcaa tggtag                                        26

<210> SEQ ID NO 117
<211> LENGTH: 24
<212> TYPE: DNA
<213> ORGANISM: Homo sapiens

<400> SEQUENCE: 117
gggtcccata ccactcatgg atct                                          24

<210> SEQ ID NO 118
<211> LENGTH: 24
<212> TYPE: DNA
<213> ORGANISM: Homo sapiens

<400> SEQUENCE: 118
gggaaaggtt ggcgatcagg aata                                          24
```

SOLUBLE FORM OF CARBONIC ANHYDRASE IX (S-CA IX), ASSAYS TO DETECT S-CA IX, CA IX'S COEXPRESSION WITH HER-2/NEU/C-ERBB-2, AND CA IX-SPECIFIC MONOCLONAL ANTIBODIES TO NON-IMMUNODOMINANT EPITOPES

This application is a continuation of International Application No. PCT/US03/05136, with an international filing date of Feb. 21, 2003, now pending. This application declares priority under 35 USC §§120 and 365(c) from PCT/US03/05136 and co-pending PCT/US03/05137, and from the following three now abandoned U.S. provisional patent applications: 60/358,824 (filed Feb. 21, 2002), 60/383,068 (filed May 23, 2002) and 60/431,499 (filed Dec. 5, 2002).

FIELD OF THE INVENTION

The present invention is in the general area of medical genetics and in the fields of biochemical engineering, immunochemistry and oncology. More specifically, it relates to the MN gene—a cellular gene considered to be an oncogene, known alternatively as MN/CA9, CA9, or carbonic anhydrase 9, which gene encodes the oncoprotein now known alternatively as the MN protein, the MN/CA IX isoenzyme, MN/CA IX, carbonic anhydrase IX, CA IX or the MN/G250 protein.

More specifically, the instant invention is directed to new MN/CA IX-specific antibodies prepared in MN/CA IX-deficient mice (knock out mice) and to uses of those new antibodies. Significantly, some of the new MN/CA IX-specific antibodies, preferably monoclonal antibodies and immunoreactive fragments thereof are directed to non-immunodominant epitopes on CA IX proteins and polypeptides, rendering such antibodies and immunoreactive fragments, among many diagnostic/prognostic and therapeutic uses, useful in highly specific double antibody sandwich assays to detect MN/CA IX antigen, particularly soluble MN/CA IX antigen (s-CA IX) found in body fluids.

This invention is also directed to the soluble MN/CA IX antigen (s-CA IX) itself, and assays to detect or to detect and quantify it. Further this invention concerns the coexpression of CA IX and HER-2/neu/c-erbB-2 ("HER-2"), and diagnostic/prognostic and therapeutic methods in parallel with and/or alternative to those targeting HER-2. Particularly preferred are assays to detect both the HER-2 ectodomain ("p100") and the CA IX extracellular domain (50/54 kilodaltons) in the same body fluid sample from a cancer patient. Backup therapeutic methods targeting CA IX can be used for patients not responding to HER-2 therapy. Such integrated diagnostic/prognostic and therapeutic methods with HER-2 and CA IX as targets can provide clinicians with more comprehensive resources to help cancer patients, such as, metastatic breast cancer patients.

BACKGROUND OF THE INVENTION

As indicated above, the MN gene and protein are known by a number of alternative names, which names are used herein interchangeably. The MN protein was found to bind zinc and have carbonic anhydrase (CA) activity and is now considered to be the ninth carbonic anhydrase isoenzyme—MN/CA IX or CA IX [Opavsky et al. 1996]. According to the carbonic anhydrase nomenclature, human CA isoenzymes are written in capital roman letters and numbers, while their genes are written in italic letters and arabic numbers. Alternatively, "MN" is used herein to refer either to carbonic anhydrase isoenzyme IX (CA IX) proteins/polypeptides, or carbonic anhydrase isoenzyme 9 (CA9) gene, nucleic acids, cDNA, mRNA etc. as indicated by the context.

The MN protein has also been identified with the G250 antigen. Uemura et al., "Expression of Tumor-Associated Antigen MN/G250 in Urologic Carcinoma: Potential Therapeutic Target," *J. Urol.*, 154 (4 Suppl.): 377 (Abstract 1475; 1997) states: "Sequence analysis and database searching revealed that G250 antigen is identical to MN, a human tumor-associated antigen identified in cervical carcinoma (Pastorek et al., 1994)."

CA IX is a cancer-related carbonic anhydrase identified by Zavada, Pastorekova, Pastorek (U.S. Pat. No. 5,387,676) using the M75 monoclonal antibody first described by Pastorekova et al. [*Virology* 187: 620-626 (1992)]. That antibody was employed in cloning of cDNA encoding CA IX [Pastorek et al., *Oncogene*, 9: 2788-2888 (1994)], in assessment of CA IX expression in tumors and normal tissues [Zavada et al., *Int J Cancer,* 54: 268-274, (1993) and many other references], in study of CA IX regulation by cell density [Lieskovska et al., *Neoplasma,* 46: 17-24, (1999), Kaluz et al., *Cancer Research,* 62: 4469-4477, (2002)] as well in demonstration of CA IX induction by hypoxia [Wykoff et al., *Cancer Research,* 60: 7075-7083 (2000), and many other references]. All these studies supported the assumption made in the original U.S. Pat. No. 5,387,676 that CA IX can be used diagnostically and/or prognostically as a preneoplastic/neoplastic tumor marker and therapeutically as a target, and showed that the M75 monoclonal antibody is a valuable CA IX-specific reagent useful for different immunodetection methods and immunotargeting approaches.

Zavada et al., International Publication Number WO 93/18152 (published 16 Sep. 1993) and U.S. Pat. No. 5,387,676 (issued Feb. 7, 1995), describe the discovery and biological and molecular nature of the MN gene and protein. The MN gene was found to be present in the chromosomal DNA of all vertebrates tested, and its expression to be strongly correlated with tumorigenicity.

The MN protein was first identified in HeLa cells, derived from a human carcinoma of cervix uteri. It is found in many types of human carcinomas (notably uterine cervical, ovarian, endometrial, renal, bladder, breast, colorectal, lung, esophageal, and prostate, among others). Very few normal tissues have been found to express MN protein to any significant degree. Those MN-expressing normal tissues include the human gastric mucosa and gallbladder epithelium, and some other normal tissues of the alimentary tract. Paradoxically, MN gene expression has been found to be lost or reduced in carcinomas and other preneoplastic/neoplastic diseases in some tissues that normally express MN, e.g., gastric mucosa.

In general, oncogenesis may be signified by the abnormal expression of MN protein. For example, oncogenesis may be signified: (1) when MN protein is present in a tissue which normally does not express MN protein to any significant degree; (2) when MN protein is absent from a tissue that normally expresses it; (3) when MN gene expression is at a significantly increased level, or at a significantly reduced level from that normally expressed in a tissue; or (4) when MN protein is expressed in an abnormal location within a cell.

Zavada et al., WO 93/18152 and Zavada et al., WO 95/34650 (published 21 Dec. 1995) disclose how the discovery of the MN gene and protein and the strong association of MN gene expression and tumorigenicity led to the creation of methods that are both diagnostic/prognostic and therapeutic for cancer and precancerous conditions. Methods and compositions were provided therein for identifying the onset and presence of neoplastic disease by detecting or detecting and quantitating abnormal MN gene expression in vertebrates. Abnormal MN gene expression can be detected or detected and quantitated by a variety of conventional assays in vertebrate samples, for example, by immunoassays using MN-specific antibodies to detect or detect and quantitate MN antigen, by hybridization assays or by PCR assays, such as RT-PCR, using MN nucleic acids, such as, MN cDNA, to detect or detect and quantitate MN nucleic acids, such as, MN mRNA.

MN/CA IX was first identified in HeLa cells, derived from human carcinoma of cervix uteri, as both a plasma membrane and nuclear protein with an apparent molecular weight of 58 and 54 kilodaltons (kDa) as estimated by Western blotting. It is N-glycosylated with a single 3 kDa carbohydrate chain and under non-reducing conditions forms S—S-linked oligomers [Pastorekova et al., *Virology,* 187: 620-626 (1992); Pastorek et al., *Oncogene,* 9: 2788-2888 (1994)]. MN/CA IX is a transmembrane protein located at the cell surface, although in some cases it has been detected in the nucleus [Zavada et al., *Int. J. Cancer,* 54: 268-274 (1993); Pastorekova et al., supra].

MN is manifested in HeLa cells by a twin protein, p54/58N. Immunoblots using a monoclonal antibody reactive with p54/58N (MAb M75) revealed two bands at 54 kd and 58 kd. Those two bands may correspond to one type of protein that most probably differs by post-translational processing.

Zavada et al., WO 93/18152 and/or WO 95/34650 disclose the MN cDNA sequence (SEQ ID NO: 1) shown herein in FIGS. 1A-1C, the MN amino acid sequence (SEQ ID NO: 2) also shown in FIGS. 1A-1C, and the MN genomic sequence (SEQ ID NO: 3) shown herein in FIGS. 2A-2F. The MN gene is organized into 11 exons and 10 introns. The human MN cDNA sequence of SEQ ID NO: 1 contains 1522 base pairs (bp). The MN cDNA sequence of SEQ ID NO: 70 contains 1552 by [EMBL Acc. No. X66839; Pastorek et al. (1994)].

The first thirty seven amino acids of the MN protein shown in FIGS. 1A-1C (SEQ ID NO: 2) is the putative MN signal peptide [SEQ ID NO: 4]. The MN protein has an extracellular (EC) domain [amino acids (aa) 38-414 of FIGS. 1A-1C (SEQ ID NO: 5)], a transmembrane (TM) domain [aa 415-434 (SEQ ID NO: 6)] and an intracellular (IC) domain [aa 435-459 (SEQ ID NO: 7)]. The extracellular domain contains the proteoglycan-like (PG) domain at about amino acids (aa) 53-111 (SEQ ID NO: 8) or preferably at about aa 52-125 (SEQ ID NO: 98), and the carbonic anhydrase (CA) domain at about aa 135-391 (SEQ ID NO: 9) or preferably, at about aa 121-397 (SEQ ID NO: 101).

Zavada et al, WO 93/18152 and WO 95/34650 describe the production of MN-specific antibodies. A representative and preferred MN-specific antibody, the monoclonal antibody M75 (Mab M75), was deposited at the American Type Culture Collection (ATCC) in Manassus, Va. (USA) under ATCC Number HB 11128. The M75 antibody was used to discover and identify the MN protein and can be used to identify readily MN antigen in Western blots, in radioimmunoassays and immunohistochemically, for example, in tissue samples that are fresh, frozen, or formalin-, alcohol-, acetone- or otherwise fixed and/or paraffin-embedded and deparaffinized. Another representative and preferred MN-specific antibody, Mab MN12, is secreted by the hybridoma MN 12.2.2, which was deposited at the ATCC under the designation HB 11647. Example 1 of Zavada et al., WO 95/34650 provides representative results from immunohistochemical staining of tissues using MAb M75, which results support the designation of the MN gene as an oncogene.

Immunodominant epitopes are considered to be essentially those that are within the PG domain of MN/CA IX, including the repetitive epitopes for the M75 mab, particularly the amino acid sequence PGEEDLP (SEQ ID NO: 11), which is 4× identically repeated in the N-terminal PG region (Zavada et al. 2000). The epitope for the MN12 mab is also immunodominant.

The M75 mab was first reported in Pastorekova et al., *Virology,* 187: 620-626 (1992) and is claimed specifically, as well as generically with all MN/CA IX-specific antibodies, polyclonal and monoclonal as well as fragments thereof, in a number of U.S. and foreign patents, including, for example, Zavada et al., U.S. Pat. No. 5,981,711 and EP 0 637 336 B1. [See also, Zavada et al., U.S. Pat. Nos. 5,387,676; 5,955,075; 5,972,353; 5,989,838; 6,004,535; 6,051,226; 6,069,242; 6,093,548; 6,204,370; 6,204,887; 6,297,041; and 6,297,051; and Zavada et al., AU 669694; CA 2,131,826; DE 69325577.3; and KR 282284.] Those Zavada et al. U.S. and foreign patents are herein incorporated by reference.

CA IX is a highly active member of a carbonic anhydrase family of zinc metalloenzymes that catalyze the reversible conversion between carbon dioxide and bicarbonate [Pastorek et al. (1994); Opaysky et al. (1996); Chegwidden et al. (2000); Wingo et al, (2001)]. It is one of 14 isoforms that exist in mammals and occupy different subcellular positions, including cytoplasm (CA I, II, III, VII), mitochondrion (CA VA, VB), secretory vesicles (CA VI) and plasma membrane (CA IV, IX, XII, XIV). Some of the isozymes are distributed over broad range of tissues (CA I, II, CA IV), others are more restricted to particular organs (CA VI in salivary glands) and two isoforms have been linked to cancer tissues (CA IX, XII) [reviewed in Chegwidden (2000), Pastorek and Pastorekova (2003)]. Enzyme activity and kinetic properties, as well as sensitivity to sulfonamide inhibitors vary from high (CA II, CA IX, CA XII, CA IV) to low (CA III) [Supuran and Scozzafava (2000)]. Several isoforms designated as CA-related proteins (CA-RP VIII, X, XI) are acatalytic due to incompletely conserved active site. This extraordinary variability among the genetically related members of the same family of proteins creates a basis for their employment in diverse physiological and pathological processes. The catalytic activity is of fundamental relevance for the maintenance of acid-base balance and exchange of ions and water in metabolically active tissues. Via this activity, CAs substantially contribute to respiration, production of body fluids (vitreous humor, gastric juice, cerebrospinal fluid), bone resorption, renal acidification etc. (Chegwidden 2000).

CA IX isozyme integrates several properties that make it an important subject of basic as well as clinical research. First of all, expression of CA IX is very tightly associated with a broad variety of human tumors, while it is generally absent from the corresponding normal tissues [Zavada et al. (1993); Liao et al. (1994); Turner et al., 1997; Liao et al., 1997; Saarnio et al., 1998; Vermylen et al., 1999; Ivanov et al. (2001); Bartosova et al. (2002)]. This is principally related to tumor hypoxia that strongly activates transcription of CA9 gene via a hypoxia-inducible transcription factor binding to a hypoxia-response element localized just upstream of transcription initiation site in CA9 promoter [Wykoff et al. (2000)]. Since tumor hypoxia is an important phenomenon with dramatic implications for cancer development and therapy [Hockel and Vaupel (2001)], CA IX bears a significant potential as an intrinsic hypoxic marker with a prognostic/predictive value and as a promising therapeutic target [Wykoff et al. (2000); Wykoff et al. (2001); Beasley et al. (2001); Giatromanolaki et al. (2001); Koukourakis et al. (2001)]. In favor of the proposed clinical applications, CA IX is an integral plasma membrane protein with a large extracellular part exposed at the surface of cancer cells and is thus accessible by the targeting tools, including the specific monoclonal antibodies. Furthermore, CA IX differs from the other CA isozymes by the presence of a unique proteoglycan-related region (PG) that forms an N-terminal extension of the extracellular CA domain and allows for elimination of cross-recognition with other isozymes [Opaysky et al. (1996)]. Moreover, CA IX has been functionally implicated in cell adhesion and due to high catalytic activity it has been proposed to contribute to acidification of extracellular microenvironment [Zavada et al. (2000); Ivanov et al., (1998)]. Therefore, targeting the CA IX protein for abrogation of its function is expected to have therapeutic effects. In addition to potential clinical exploitation of CA IX, there is an increasing interest to resolve many basic molecular and functional aspects of CA IX, because the knowledge on its precise role in cancer cells, on the contribution of different domains/sequence motifs, and concerning its regulation is still fragmentary.

So far, most of the basic CA IX-related studies were performed using a single mouse monoclonal antibody M75 that recognizes the N-terminal PG region of CA IX [Pastorekova (1992), Zavada (2000)]. This antibody proved to be highly specific and perfectly suitable for certain purposes including immunohistochemical analyzes of cancer tissue sections [Liao et al. (1994); Ivanov et al. (2001) and references therein], targeting hypoxic tumor cells in animal models [Chrastina et al. (2003)], CA IX immunodetection in vitro, and molecular characterization [Pastorek et al. (1994); Lieskovska et al. (1999); Kaluz et al. (1999); Kaluz et al. (2002); Olive et al. (2001)]. On the other hand, CA IX-specific monoclonal antibodies with epitope specificity different from that of M75 have not heretofore been available for approaches that are based on capture-detection principle or for study of mutated variants of CA IX. There had been many significant obstacles to producing such antibodies previously. The instant invention solves the problems involved in producing antibodies to the non-immunodominant epitopes of CA IX and discloses a variety of clinical and experimental uses for such antibodies.

SUMMARY OF THE INVENTION

In one aspect, the instant invention concerns new CA IX-specific antibodies generated in CA IX-deficient mice, particularly to monoclonal antibodies and immunoreactive fragments thereof, that are directed to non-immunodominant epitopes on the CA IX extracellular domain. A representative CA IX-specific antibody generated in CA IX-deficient mice as described in Example 2 is the V/10 mab, produced by the V/10-VU, which hybridoma was deposited on Feb. 19, 2003 under the Budapest Treaty at the Belgian Coordinated Collections of Microorganisms (BCCM™) at the Laboratorium Voor Moleculaire Biolojie-Plasmidencollectie (LMBP) in Gent, Belgium.

In view of the protocols specifically detailed herein, the CA IX-specific antibodies generated in the CA IX-deficient mice are directed to the PG or CA domains, ones of skill in the art realize that the analogous methods to those detailed herein alone or in combination with conventional methods known in the art can be used to produce CA IX-specific antibodies or immunoreactive antibody fragments to other domains of CA IX as shown in FIG. 4, for example, the TM or IC domains.

In another aspect, the new CA IX-specific antibodies generated in CA IX-deficient mice and particularly monoclonal antibodies and immunoreactive fragments thereof not directed to immunodominant epitopes of CA IX can be used clinically—diagnostically and/or prognostically to detect precancer and cancer (preneoplastic/neoplastic disease) and therapeutically to treat precancer and cancer (preneoplastic/neoplastic disease). The new CA IX-specific antibodies generated in CA IX-deficient mice to non-immunodominant epitopes can be used diagnostically/prognostically or therapeutically alone or in combination with CA IX-specific antibodies not generated in CA IX-deficient mice, such as the M75 monoclonal antibody. The antibodies of this invention directed to other than the PG domain of CA IX are particularly useful to detect the soluble form of the CA IX antigen (s-CA IX) found in body fluids with CA IX-specific antibodies directed to the PG domain. Preferably such assays include CA IX-specific antibodies directed to the PG and CA domains, but such antibodies directed to other domains, as for example, the IC or TM, in combination with such antibodies to any of the other domains, or as long as such antibodies do not have the same, overlapping and/or closely neighboring epitopes that would cause steric hindrance or blocking of each other's binding could be suitable for such assays. Optimizing assays for different MN target antigens would be within the skill of the art. Double-antibody sandwich assays using the CA-IX-specific antibodies of this invention are particularly preferred for diagnostic/prognostic assays to detect or detect and quantify the soluble form of CA IX (s-CA IX) in body fluids.

The CA IX-specific antibodies generated in CA IX-deficient mice, particularly those not directed to immunodominant epitopes CA IX, alone or in combination with other such CA IX-specific antibodies or with CA IX-specific antibodies directed to immunodominant epitopes, such as the M75 monoclonal antibody, can also be used to detect or detect and quantitate different deletion variants of CA IX protein.

The CA IX-specific antibodies of this invention generated in CA IX-deficient mice, particularly those directed to non-immunodominant epitopes, can be used individually or in combination with other such CA IX-specific antibodies in cancer research, diagnostics/prognostics for precancer/cancer, in making cancer treatment decisions, in the developing new forms of cancer treatment, and in anti-tumor vaccines. For example, the CA IX-specific antibodies generated in CA IX-deficient mice directed to various domains of CA IX, for example, to the CA, TM or IC domains, can be used also to detect and/or identify deletion variants of CA IX. More particularly, for example, the CA IX-specific antibodies generated in CA IX-deficient mice, particularly those not directed to immunodominant epitopes, can be used alone or in combination with CA IX-specific antibodies for many uses, among which are the following.

a) In Basic and Pre-Clinical Research
   Study of the structure-function relationship in CA IX molecule;
   Study of the mechanism of release of soluble CA IX from cancer cells, determination of its biological activity and exploring its possible patho-physiological aspects;
   Study of the signal transduction pathways upstream and downstream of CA IX;
   Study of CA IX role in tumor growth and metabolism;
   Study of CA IX role in response to treatment by drugs, radiation, inhibitors etc.;

b) In Cancer Screening, Detection, Diagnosis and Prognosis
   Detection of CA IX (and its putative variants) in tumor specimens for tumor diagnosis, prediction of treatment outcome and prognosis of disease development;
   Development of sensitive test(s) for detection of soluble CA IX in body fluids;
   Development of screening approaches based on CA IX detection and monitoring of cancer relapse or metastasis after treatment;
   Imaging of tumor and metastases;

c) In Tumor Therapy
   Preparation of humanized antibodies, single-chain fragments, diabodies, minibodies, bispecific antibodies and other form of antibodies for therapeutic purposes;
   Unconjugated antibody-based therapy to hinder cancer expansion and/or progression either by blocking CA IX activity, or by antibody-dependent cell cytotoxicity, or by complement-mediated cytotoxicity;
   Bispecific antibody-based therapy directed to tumor lysis by cytotoxic T cells;
   Therapy by antibody coupled with enzyme converting prodrug to active anticancer drug;
   Radioimmunotherapy by antibody conjugated with radioisotope;
   Therapy by antibody coupled with toxin;
   Therapy by antibody coupled with chemotherapeutic drugs;
   Therapy by antibody combined with conventional therapeutic drugs (or different inhibitors of cancer-related pathways), bioreductive drugs, or radiotherapy to increase treatment efficacy;
   Combined therapy with antibodies to other cancer-related antigens, or with cytokines;
   Gene therapy with plasmid/vector-coupled antibody for targeted delivery; and d) For Anti-Tumor Vaccination
   Production of anti-idiotypic antibodies with internal image of CA IX for use as a vaccine.

The soluble CA IX (s-CA IX) found in vertebrate body fluids, preferably mammalian body fluids, more preferably human body fluids, has a molecular weight of from about 10 kilodaltons (kd) to about 65 kd, preferably from about 15 kd to about 54 kd, more preferably from about 20 kd to about 54 kd; still more preferably said s-CA IX has a molecular weight of either from about 15 kd to about 35 kd or from about 45 kd to about 54 kd, more preferably either from about 20 kd to about 30 kd or from about 50 kd to about 54 kd, and most preferably said s-CA IX has a molecular weight predominantly as a twin protein having a molecular weight of about 50/54 kd as approximated from Western blotting.

The s-CA IX found in body fluids and in the culture medium of tumor cell lines, e.g., HT29, is primarily seen on Western blots as a twin band of 50/54 kd. The other major form of CA IX is the cell associated, transmembrane protein seen on Western blot as a twin bond of 54/58 kd. The s-CAIX found in body fluids and tissue culture (TC) media is considered to be the CA IX extracellular portion released by proteolytic cleavage from the transmembrane (TM) and intracellular (IC) domains.

The s-CA IX is predominantly a twin band of 50/54 kd on Western blot, is considered to represent only the extracellular part of CA IX, comprising the proteoglycan-like (PG) domain and the carbonic anhydrase (CA) domain (see FIG. 4). The complete cell-associated CA IX, predominantly a twin band of 54/58 kd on Western blot, further comprises a transmembrane (TM) region and an intracellular (IC) anchor.

The s-CA IX also exists in other smaller forms, preferably 20-30 kd, which is considered to comprise the CA domain or parts thereof. Higher molecular weight species of the s-CA IX of about 62 kd have been seen in the body fluids of cancer patients, but such species are considered to be rare and perhaps aberrant, as conjoined with other molecular species, in view of the theoretical molecular weight of the CA IX extracellular (EC) domain being about 50/54 kd.

The s-CA IX is considered to be a diagnostic/prognostic marker of many different cancers. A preferred diagnostic/prognostic use for s-CA IX is considered to be to monitor patients after surgical removal of a tumor, and to make decisions about the optimal method for therapy. The CA IX-specific antibodies that are directed to the non-immunodominant epitopes of this invention alone or in combination with CA IX-specific antibodies to the immunodominant epitopes, such as that of the M75 mab or V/18 mab, are considered important to detect all forms of s-CA IX, which are at low concentrations in body fluids.

Preferred samples in which to assay MN antigen by, for example, Western blotting or radioimmunoassay, are tissue and/or cell extracts. However, MN antigen, particularly in a soluble form, as the extracellular domain, can be detected in body fluids, which can include among other fluids: blood, serum, plasma, semen, breast exudate, gastric secretions, fecal suspensions, bile, saliva, tears, sputum, mucous, urine, lymph, cytosols, ascites, pleural effusions, amniotic fluid, bladder washes, bronchioalveolar lavages and cerebrospinal fluid. It is preferred that the MN antigen be concentrated from a larger volume of body fluid before testing. Preferred body fluids to assay would depend on the type of cancer for which one was testing, but in general preferred body fluids would be urine, serum, fecal suspensions, mucous, gastric secretions, bile, breast exudate, pleural effusions and ascites.

A preferred immunoassay format to detect s-CA IX in vertebrate, preferably mammalian, and more preferably human body fluids is a double antibody sandwich assay, using CA IX-specific antibodies directed to different regions of CA IX. A preferred combination of CA IX-specific antibodies would be, for example, the M75 mab to the PG domain and the V/10 mab to the CA domain.

The s-CA IX that can be detected or detected and quantitated can be bound by CA IX-specific antibodies to the EC domain of CA IX, preferably to the PG or CA domains, such as the M75 mab or the V/10 mab, respectively. The smaller form of the s-CA IX with a molecular weight of about 20 to about 30 kd, is considered to lack the PG domain, so that form would preferably be detected and quantitated by CA IX-specific antibodies directed to CA domain, preferably to epitopes that are substantially separated on that domain, which separation may well depend on the conformational nature of the epitopes and the protein/polypeptide 3-D structure, that may differ from that of the full-length CA IX or EC domain thereof.

One method of detecting or detecting and quantifying s-CA IX protein/polypeptide in a vertebrate body fluid comprise the steps of
   (a) contacting said sample with one or more antibodies which specifically bind to CA IX protein or to CA IX polypeptide which comprises at least 16 amino acids; and
   (b) detecting or detecting and quantifying binding of said antibody in said sample. In such a method, one or more of said CA IX-specific antibodies is or are labeled. Such methods can be in standard formats, as for example, Western blots, enzyme-linked immunosorbent assays, radioimmunoassays, competition immunoassays, dual antibody sandwich assays, immunohistochemical staining assays, agglutination assays, and fluorescent immunoassays. Such method can be diagnostic and/or prognostic for cancerous or precancerous diseases, wherein said disease is associated with abnormal expression of CA IX protein, selected from the group consisting of mammary, urinary tract, kidney, ovarian, uterine, bladder cervical, endometrial, vaginal, vulvar, prostate, liver, lung, skin, thyroid, pancreatic, testicular, brain, head and neck, gastrointestinal, and mesodermal precancerous and cancerous diseases.

Such methods might be particularly directed to precancerous and cancerous diseases of breast, colon, rectum and of the urinary tract, as of the kidney, bladder, urethra. Renal cell carcinoma (RCC) and metastatic breast cancer, and precancer leading thereto, are considered particular targets for the diagnostic/prognostic assay methods that detect or detect and quantify s-CA IX in body fluids.

Another aspect of this invention concerns the coexpression of CA IX and HER-2/neu/c-erbB-2 ("HER-2") in precancers and cancers. As reported in Example 11, below, a significant correlation of expression of the two genes has been observed. Trastuzumab® or Herceptin® is a humanized mab to HER-2 used to treat HER-2-positive cancers, particularly breast cancers, more particularly metastastic breast cancer [Horton, M. B., *Cancer Control,* 9(6): 499-507 (2002)]. Herceptin® can be given alone to a patient but can enhance the effectiveness of several chemotherapeutic agents. However, a significant proportion of HER-2-positive cancers do not respond to Herceptin® [Kuter, I. (2001)]. It would be advantageous to test cancer patients for both HER-2 and MN/CA IX expression to enlarge the clinical perspective, therapeutic resources and diagnostic/prognostic parameters to pick the optimal therapeutic combinations for the most promising treatment outcomes.

As explained herein, CA IX is considered to be a hypoxia marker, and hypoxia indicates radiation resistance, and indicates how chemotherapy might progress. For example, drugs like bleomycin have an obligate requirement for oxygen in order to be toxic. When a clinician selects a chemotherapeutic drug or is deciding whether to use radiation with another modality, such as Herceptin®, whether the tumor cells are expressing CA IX indicating hypoxic conditions, should be a factor in the therapeutic decision.

Also disclosed herein are therapeutic methods for targeting CA IX expressing cells. Antibodies, preferably mabs, and often preferably immunoreactive antibody fragments, are well as bispecific, chimeric, humanized variants, intrabodies, among other variants, alone or conjugated to toxic agents, can be used. Further CA inhibitors provide another option to the clinician.

Particularly significant are assays for s-CA IX which are analogous to those for HER-2, which sheds its ectodomain ("p100") into body fluids (See, for example, Carney et al., U.S. Pat. No. 5,401,638). Such tests could be performed on even the same patient body fluid sample with labeling that could be selected for detection by the same automated system.

So, in one aspect, this invention concerns methods of sequentially or simultaneously detecting or detecting and quantitating s-CA IX and the HER-2 ectodomain in patient body fluids, particularly from breast cancer patients. In another aspect, the invention concerns testing the body fluids of a cancer patient particularly a breast cancer patient, that are HER-2 positive but nonresponders to Herceptin®, and treating the subset that are CA IX-positive with CA IX-specific antibodies, preferably mabs or fragments thereof or appropriate antibody variants, preferably fully humanized, alone or conjugated to a toxin, or alternatively with CA inhibitors, or with such CA IX-specific antibodies and/or CA inhibitors with rationally selected conventional therapies, including, for example, appropriate chemotherapeutic agents and in some cases radiation.

Abbreviations

The following abbreviations are used herein:
5-FC—5-flyorocytosine
5-FU—5-fluorouracil
a—predicted target domain
aa—amino acid
ATCC—American Type Culture Collection
bp—base pairs
BLV—bovine leukemia virus
BSA—bovine serum albumin
BRL—Bethesda Research Laboratories
ΔCA—deletion variant of MN/CA IX protein lacking the CA domain expressed in transfected MDCK cells
CA—carbonic anhydrase
CAM—cell adhesion molecule
CARP—carbonic anhydrase related protein
CAT—chloramphenicol acetyltransferase
Ci—curie
CIS—carcinoma in situ
cm—centimeter
CMV—cytomegalovirus
cpm—counts per minute
C-terminus—carboxyl-terminus
CTL—cytotoxic T lymphocytes
° C.—degrees centigrade
DEAE—diethylaminoethyl
DMEM—Dulbecco modified Eagle medium
ds—double-stranded
EDTA—ethylenediaminetetraacetate
EGF—epidermal growth factor
EIA—enzyme immunoassay
ELISA—enzyme-linked immunosorbent assay
EMSA—electrophoretic mobility shift assay
EPO—erythropoietin
ER—estrogen receptor
ex—antigen in cellular extract
F—fibroblasts
FACS—cytofluorometric study
FCS—fetal calf serum
FITC—fluorescein isothiocyanate
fl—full length MN/CA IX expressed in MDCK (madin Darby Canine Kidney) canine renal epithelial cells stably transfected with the wild type cDNA
FTP—DNase 1 footprinting analysis
GST-MN—fusion protein MN glutathione S-transferase
GVC—ganciclovir
H—HeLa cells
HBS—HIF-binding site
H-E—haematoxylin-eosin
HEF—human embryo fibroblasts
HeLa K—standard type of HeLa cells
HeLa S—Stanbridge's mutant HeLa D98/AH.2
H/F-T—hybrid HeLa fibroblast cells that are tumorigenic; derived from HeLa D98/AH.2
H/F—N—hybrid HeLa fibroblast cells that are nontumorigenic; derived from HeLa D98/AH.2
HIF—hypoxia-inducible factor
HPV—Human papilloma virus
HRE—hypoxia response element
HRP—horseradish peroxidase
HSV—Herpes simplex virus
IC—intracytoplasmic or intracellular
IF—immunofluorescence
IFN—interferon
IHC—immunohistochemistry
IL-2-interleukin-2

Inr—initiator
IP—immunoprecipitation with the Protein A Sepharose®
IPTG—isopropyl-beta-D-thiogalacto-pyranoside
kb—kilobase
kbp—kilobase pairs
kd or kDa—kilodaltons
KS—keratan sulphate
KLH—keyhole limpet hemacyanin
LCMV—lymphocytic choriomeningitis virus
LTR—long terminal repeat
M—molar
mA—milliampere
Mab or mab—monoclonal antibody
MCSF—macrophage colony stimulating factor
ME—mercaptoethanol
MEM—minimal essential medium
min.—minute(s)
mg—milligram
ml—milliliter
mM—millimolar
MMC—mitomycin C
mmol—millimole
MLV—murine leukemia virus
N—normal concentration
ND—not done
NEG—negative
ng—nanogram
nm—nanometer
nt—nucleotide
N-terminus—amino-terminus
ODN—oligodeoxynucleotide
ORF—open reading frame
PA—Protein A
PBS—phosphate buffered saline
PCR—polymerase chain reaction
PEST—combination of one-letter abbreviations for proline, glutamic acid, serine, threonine
PG—proteoglycan-like region
PGK—phosphoglycerate kinase
pI—isoelectric point
PMA—phorbol 12-myristate 13-acetate
POS—positive
Py—pyrimidine
RACE—rapid amplification of cDNA ends
RCC—renal cell carcinoma
RIA—radioimmunoassay
RIP—radioimmunoprecipitation
RIPA—radioimmunoprecipitation assay
RNP—RNase protection assay
RT-PCR—reverse transcriptase polymerase chain reaction
SAC—*Staphylococcus aureus* cells
S. aureus—*Staphylococcus aureus*
sc—subcutaneous
SDRE—serum dose response element
SDS—sodium dodecyl sulfate
SDS-PAGE—sodium dodecyl sulfate-polyacrylamide gel electrophoresis
SINE—short interspersed repeated sequence
SP—signal peptide
SP-RIA—solid-phase radioimmunoassay
SSDS—synthetic splice donor site
SSH—subtractive suppressive PCR
SSPE—NaCl (0.18 M), sodium phosphate (0.01 M), EDTA (0.001 M)
SV40—simian virus 40
TBE—Tris-borate/EDTA electrophoresis buffer
TC—tissue culture
TCA—trichloroacetic acid
TC media—tissue culture media
TC—tissue culture
tk—thymidine kinase
TM—transmembrane
TMB—tetramethylbenzidine
Tris—tris (hydroxymethyl)aminomethane
μCi—microcurie
μg—microgram
μl—microliter
μM—micromolar
VEGF—vascular endothelial growth factor
VSV—vesicular stomatitis virus
VV—vaccinia virus
WB—Western blotting
WHO—World Health Organization
X-MLV—xenotropic murine leukemia virus Cell Lines AGS—cell line derived from a primary adenogastric carcinoma [Barranco and Townsend, *Cancer Res.*, 43: 1703 (1983) and *Invest. New Drugs*, 1: 117 (1983)]; available from the ATCC under CRL-1739;
A498—RCC cell line (ATCC HTB-44)
BL-3—bovine B lymphocytes [ATCC CRL-8037; leukemia cell suspension; *J. Natl. Cancer Inst.* (Bethesda) 40: 737 (1968)];
C33—a cell line derived from a human cervical carcinoma biopsy [Auersperg, N., *J. Nat'l. Cancer Inst.* (Bethesda), 32: 135-148 (1964)]; available from the ATCC under HTB-31;
C33A—human cervical carcinoma cells [ATCC HTB-31; *J. Natl. Cancer Inst.* (Bethesda) 32: 135 (1964)];
C4.5—CHO wild-type, parental to Ka13, the same cell line as that described in Wood et al., *J. Biol. Chem.*, 273: 8360-8368 (1998);
COS—simian cell line [Gluzman, Y., Cell, 23: 175 (1981)];
HeLa—from American Type Culture Collection (ATCC)
HeLa K—standard type of HeLa cells; aneuploid, epithelial-like cell line isolated from a human cervical adenocarcinoma [Gey et al., *Cancer Res.*, 12: 264 (1952); Jones et al., *Obstet. Gynecol.*, 38: 945-949 (1971)] obtained from Professor B. Korych, [Institute of Medical Microbiology and Immunology, Charles University; Prague, Czech Republic];
HeLa—Mutant HeLa clone that is hypoxanthine D98/AH.2 guanine phosphoribosyl transferase-deficient (HGPRT⁻) (also HeLa s) kindly provided by Eric J. Stanbridge [Department of Microbiology, College of Medicine, University of California, Irvine, Calif. (USA)] and reported in Stanbridge et al., *Science*, 215: 252-259 (15 Jan. 1982); parent of hybrid cells H/F—N and H/F-T, also obtained from E. J. Stanbridge;
HT29—A cell line derived from colorectal carcinoma. (ATCC No. HBT-38; DSMZ ACC299);
Ka 13—CHO mutant cell functionally defective for the HIF-1∀ subunit, the same cell line as that described in Wood et al. (1998), supra;
KATO III—cell line prepared from a metastatic form of a gastric carcinoma [Sekiguichi et al., *Japan J. Exp. Med.*, 48: 61 (1978)]; available from the ATCC under HTB-103;
MDCK—The MDCK cell line was derived from a kidney from an apparently normal adult female cocker spaniel by S. H. Madin and N. B. Barby in 1958. (ATCC CCL-34);
NIH-3T3—murine fibroblast cell line reported in Aaronson, *Science*, 237: 178 (1987);

QT35—quail fibrosarcoma cells [ECACC: 93120832; *Cell*, 11:95 (1977)];

Raj—human Burkitt's lymphoma cell line [ATCC CCL-86; *Lancet*, 1: 238 (1964)];

Rat2TK⁻—cell line (rat embryo, thymidine kinase mutant) was derived from a subclone of a 5'-bromo-deoxyuridine resistant strain of the Fischer rat fibroblast 3T3-like cell line Rat1; the cells lack appreciable levels of nuclear thymidine kinase [Ahrens, B., *Virology*, 113: 408 (1981)];

SiHa—human cervical squamous carcinoma cell line [ATCC HTB-35; Friedl et al., *Proc. Soc. Exp. Biol. Med.*, 135: 543 (1990)];

XC—cells derived from a rat rhabdomyosarcoma induced with Rous sarcoma virus-induced rat sarcoma [Svoboda, J., *Natl. Cancer Center Institute Monograph No. 17*, IN: "International Conference on Avian Tumor Viruses" (J. W. Beard ed.), pp. 277-298 (1964)], kindly provided by Jan Svoboda [Institute of Molecular Genetics, Czechoslovak Academy of Sciences; Prague, Czech Republic]; and CGL1—H/F—N hybrid cells (HeLa D98/AH.2 derivative);
CGL2—H/F—N hybrid cells (HeLa D98/AH.2 derivative);
CGL3—H/F-T hybrid cells (HeLa D98/AH.2 derivative);
CGL4—H/F-T hybrid cells (HeLa D98/Ah.2 derivative).

Nucleotide and Amino Acid Sequence Symbols

The following symbols are used to represent nucleotides herein:
Base

| Symbol | Meaning |
| --- | --- |
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

| Amino acid name | 3 Ltr. Abbrev. | 1 Ltr. Abbrev. |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |

-continued

| Amino acid name | 3 Ltr. Abbrev. | 1 Ltr. Abbrev. |
| --- | --- | --- |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIGS. 1A-C provides the nucleotide sequence for a MN cDNA [SEQ ID NO: 1] clone isolated as described herein. FIG. 1A-C also sets forth the predicted amino acid sequence [SEQ ID NO: 2] encoded by the cDNA.

FIGS. 2A-F provides a 10,898 by complete genomic sequence of MN [SEQ ID NO: 3]. The base count is as follows: 2654 A; 2739 C; 2645 G; and 2859 T. The 11 exons are in general shown in capital letters, but exon 1 is considered to begin at position 3507 as determined by RNase protection assay.

FIG. 3 provides an exon-intron map of the human MN/CA 1× gene. The positions and sizes of the exons (numbered, cross-hatched boxes), Alu repeat elements (open boxes) and an LTR-related sequence (first unnumbered stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail). Below the map, the alignment of amino acid sequences illustrates the extent of homology between the MN/CA IX protein PG region (aa 53-111) [SEQ ID NO: 8] and the human aggrecan (aa 781-839) [SEQ ID NO: 10].

FIG. 4 schematically represents the MN protein structure. The abbreviations are the same as used in FIG. 3. The scale indicates the number of amino acids.

FIG. 5(A) shows the alignment of amino acid sequences of the human CA IX (HCA IX) (SEQ ID NO: 2) and the mouse CA IX (MCA IX) (SEQ ID NO 90) proteins deduced from the corresponding cDNAs [Pastorek et al. (1994), EMBL Accession No. X66839; Ortova Gut et al. (2002), EMBL Accession No. AJ245857]. Homologous amino acids are written on a grey background. FIG. 5(B) is a schematic illustration of CA IX variants used for immunization and/or immunodetection purposes as described herein. The positions of the amino acids related to CA IX domain composition and to regions involved in variants are indicated below. Arrangement of antigenic sites for the antibodies (Y), assumed from the competitive assay, is shown above the scheme. The percentage of amino acid homology between human and mouse CA IX proteins is written inside the linear model of the full-length human CA IX protein, that is composed of signal peptide (SP), proteoglycan-like region (PG), carbonic anhydrase domain (CA), transmembrane anchor (TM) and intracytoplasmic tail (IC).

FIG. 6 provides a checker board map of antigenic sites delineated on the basis of the competitive binding ELISA.

Figure 7B:
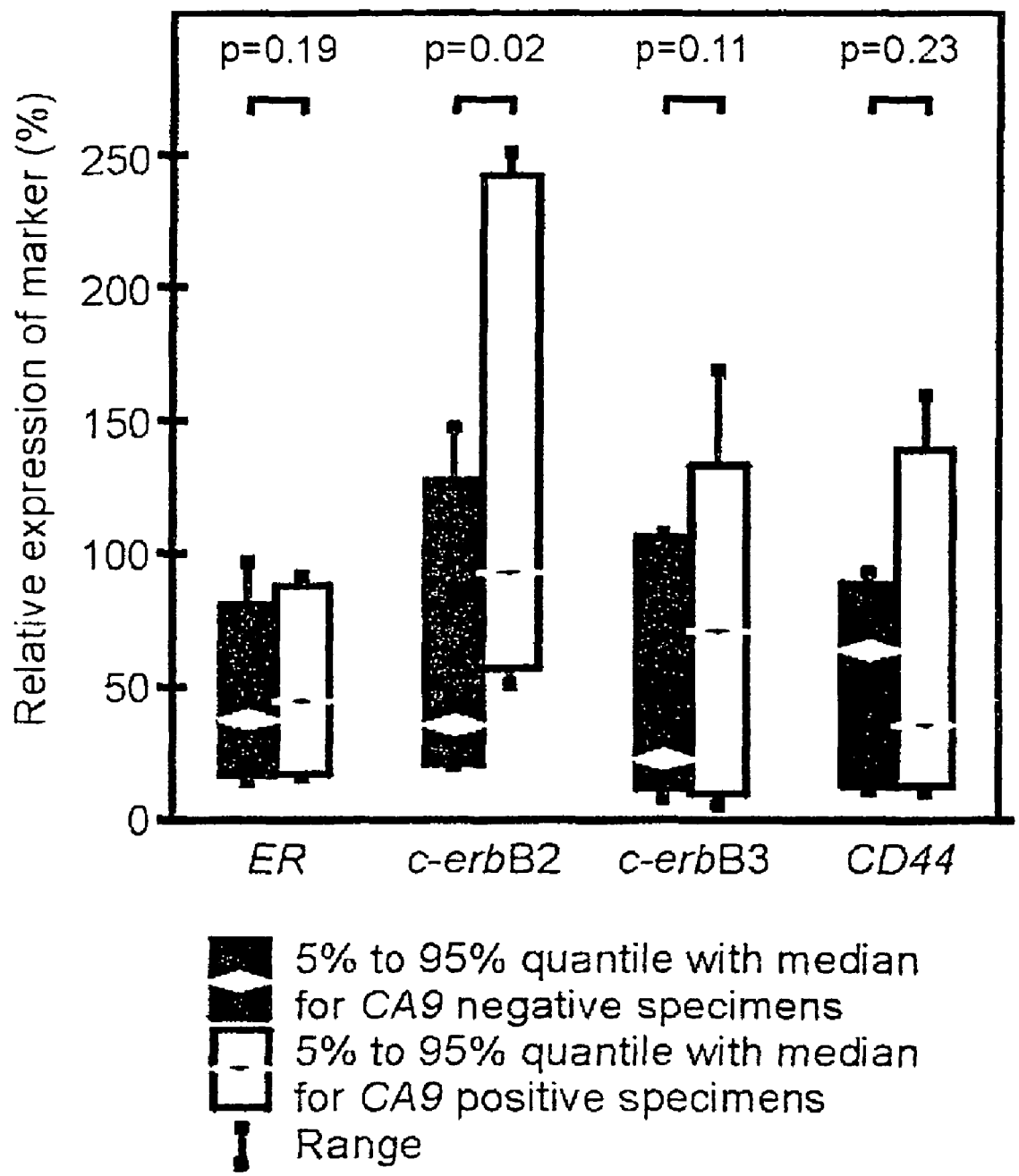

Antigen-coated plates were incubated with fixed amount of biotin-labeled antibody and increasing amount of non-labeled competitor antibody. Results are expressed as a percentage of absorbance measured in the absence of the competitor antibody.

FIG. 7 shows the relationship between CA9 and other breast tumour markers in malignant breast specimens as evaluated by chi-square and Mann-Whitney tests. FIG. 7(A) illustrates the percentage of breast marker-positive tumours in subgroups of CA9-positive versus CA9-negative specimens. The significance of the association between expression of CA9 and individual markers is given above the appropriate columns. Concordance of data corresponds to the percentage of specimens showing equal positivity/negativity for both CA9 and the particular other marker. FIG. 7(B) illustrates the range of 5% to 95% quantile and median of expression of marker-specific PCR products detected in marker-positive tumours from CA9-positive and CA9-negative subgroups, respectively, with values of significance above the relevant columns.

FIG. 8 shows the strategy for the targeted disruption of the mouse Car9 gene. FIG. 8A—Targeting strategy: top, genomic structure of Car9 locus showing exons 1-9; middle, pCar9-neo targeting vector of 6.8 kb with pgk-neo cassette replacing 14 by in exon 1, bottom, structure of the gene after homologous recombination. The 4.0 kb XbaI (X) and 6.5 kb EcoRI (E) fragments present in the wild type allele are shown above, and the 2.0 kb XbaI and 8.3 kb EcoRI fragments present in the mutated allele are shown below. Positions of the restriction sites for BamHI (B), HindIII (H) and the probes used to distinguish between the wild type and the mutant alleles after digestion with EcoRI are indicated. FIG. 8B—The position of the primers on the Car9 genomic locus is schematically illustrated.

FIG. 9 provides a statistical analysis of the numbers of cells in stomachs of $Car9^{+/+}$ versus $Car9^{-/-}$ mice. As quantified by the Mann-Whitney rank test, the mutant mouse stomachs showed significantly increased total numbers of cells on one hand (A) and decreased numbers of $H^+/K^+$-ATPase positive parietal cells (B) and pepsinogen-positive chief cells (C) on the other hand. Regression analysis revealed significant correlation between total cells numbers and numbers of parietal cells in gastric units (D) and significant difference between the slopes of regression lines corresponding to gastric units of $Car9^{+/+}$ and $Car9^{-/-}$ mice, respectively.

FIG. 10 shows the results of ELISAs for CA IX antigen. HT29 cells were grown in 5 cm Petri dish, supplied with 5 ml of media, and exchanged 2 days before harvest. The extract from cell monolayer in this culture contained 5 mg of total protein. Extracts from the tumours were prepared directly from the excisions, without previous cultivation in vitro. Media from the cultures of tumour fragments were harvested after 2 days. A=purified CA IX protein (described in Závada et al, 2000); B=TC media; C=extracts from cells and tumours; O=purified CA IX; ●=A498 cells; ■=HT29 cells; patients No. ▲=38; ▼=50; ♦=59.

DETAILED DESCRIPTION

The following references are cited herein or provide updated information concerning the MN/CA9 gene and the MN/CA IX protein. All the listed references as well as other references cited herein are specifically incorporated by reference.

Aboagye et al., *Anticancer Drug Des.*, 13(6): 703-730 (September 1998)
Airley et al., *Clin. Cancer Res.*, 7: 928-934 (2001)
Airley et al., *Brit. J. Cancer,* 86 (Suppl. 1): S13-S33 (2002)
Arteaga, C. L., *Breast Cancer Res.*, 5(2): 96-100 (2003)
Bartosova et al., *J. Pathol.*, 197: 314-321 (2002)
Beasley et al., *Cancer Research*, 61: 5262-5267 (2001)
Bergstein, I., *Breast Cancer: Molecular Genetics, Pathogenesis, and Therapeutics*, Bowcock A M (ed.), Humana Press: Totowa, pp. 143-169 (1999)
Brizel et al., *Cancer Res.*, 56: 941-943 (1996)
Brizel et al., *Int. J. Radiat. Oncol. Biol. Phys.*, 38: 285-289 (1997)
Carney et al., U.S. Pat. No. 5,401,638
Chapman, J. D., *Radiother. Oncol.*, 20(Suppl. 1): 18-19 (1991)
Chegwidden et al. (eds.), "The Carbonic Anhydrase Inhibitors—New Horizons," *EXS* (Basel) Vol. 90 (2000)
Christianson and Cox, *Annu. Rev. Biochem.*, 68: 33-57 (1999)
EXS (Experientia Supplementa) (Basel) Vol. 90 [Birkhauser; Boston, Mass. (USA): 2000]
Chia et al., *J. Clin. Oncol.*, 19: 3660-3668 (2001)
Chrastina et al., *Int. J. Cancer,* 105(6): 873-881 (Jul. 20, 2003)
Clark M., *Immunol. Today*, 21(8): 397-402 (August 2000)
Dachs et al., *Nature Medicine*, 3: 515-520 (1997)
Dalbadie-McFarland et al., *PNAS* (USA), 79: 6409 (1982)
Davis et al., *Cancer Metastasis Rev.*, 18(4): 421-425 (1999)
Ebert et al., *J. Biol. Chem.*, 270(49): 29083-29089 (1995)
Evans et al., *Cancer Res.*, 56: 405-411 (1996)
Ey et al., *Biochemistry*, 15: 429-436 (1978)
Fleming et al., *J. Clin. Invest.*, 96: 2907-2913 (1995)
Forsythe et al., *Mol. Cell. Biol.*, 16: 4604-4613 (1996)
Fyles et al., *Radiother. Oncol.*, 45: 149-156 (1998)
Gavilondo and Larrick, *Biotechniques*, 29(1): 128-132, 134-136 and 183 passim (July 2000)
Gibadulinova et al., *Acta Virol.*, 42: 369-374 (1999)
Giatromanolaki et al., *Cancer Res.*, 61(21): 7992-7998 (2001)
Glennie et al., *Nature*, 295: 712 (1982)
Goldyne et al., *Adv. Exp. Med. Biol:* 314: 317-327 (1991)
Gray et al., *Br. J. Radiol.*, 26: 638-648 (1953)
Gumbiner, B., *Cell* 84: 345-357 (1996)
Gura, T., *Nature*, 417(6889): 584-586 (Jun. 6, 2002)
Jain and Baxter, *Cancer Res.*, 48: 7022-7032 (1988)
Jain et al., *Nature Med.*, 6(2): 131-132 (2000)
Hall, E. J., *Radiobiology for the Radiologist*, 5$^{th}$ ed., Philadelphia (PA): Lippincott (1998)
Harris, A. L., *Nature Reviews Cancer*, 2: 38-47 (2002)
Heber et al., *Adv. Exp. Med. Biol.*, 399: 41-51 (1996)
Hockel and Vaupel, *Journal of National Cancer Institute*, 93(4): 266-276 (Feb. 21, 2001)
Hockel and Vaupel., *CME J. Gyn. Oncol.*, 6/2: 216-225 (2001)
Hockel and Vaupel, *Seminars in Oncol.*, 28 (Supp. 2): 36-41 (April 2001)
Hockel et al., *Radiother. Oncol.*, 26: 45-50 (1993)
Hocker et al., *Am. J. Physiol.*, 270: G619-633 (1996)
Hodgkiss et al., *Adv. EXP. Med. Biol.*, 428: 61-67 (1997)
Holliger and Bohlen, *Cancer Metastasis Rev.*, 18(4): 411-419 (1999)
Hoogenboom and Chames, *Immunol. Today*, 21(8): 371-378 (August 2000)
Hui et al., *Clinical Cancer Research*, 8: 2595-2604 (2002)
Hunter, W. M., "Radioimmunoassay," In: *Handbook of Experimental Immunology*, pp. 14.1-14.40 (D. W. Weir ed.; Blackwell, Oxford/London/Edinburgh/Melbourne;
Ishikawa et al., *J. Exp. Med.*, 186: 999-1014 (1997)
Ivanov et al., *PNAS* (USA), 95: 12596-12601 (1998)
Ivanov et al., *American Journal of Pathology*, 158: 905-919 (2001)

Kaestner et al., *Genes Dev.*, 11: 1583-1595 (1997)
Kallinowski et al., *Int. J. Radiat Oncol. Biol. Phys.*, 19: 953-961 (1990)
Kaluz et al., *Journal of Biological Chemistry*, 274: 32588-32595 (1999)
Kaluz et al., *Cancer Research*, 62: 4469-4477 (2002)
Karam et al., *Am. J. Physiol.*, 272: G1209-1220 (1997)
Kaufmann et al., *Lancet*, 345: 615-619 (1995)
Kennedy et al., *Int. J. Radiat. Oncol. Biol. Phys.*, 37: 897-905 (1997)
Knowlden et al., *Oncogene*, 17: 1949-1957 (1998)
Koch et al., *Br. J. Cancer*, 72: 869-874 (1995)
Korinek et al., *Nature Genetics*, 19: 379-383 (1998)
Koukarakis et al., *Clin. Cancer Res.* 7(11): 3399-3403 (2001)
Kuter, I., *The Oncologist*, 6: 338-346 (2001)
Lane et al., *Meth. Enzymol.*, 121: 183-192 (1986)
Laughner et al., *Mol. Cell. Biol.*, 21: 3995 (2001)
Lee et al., *J. Clin. Invest.*, 106: 1447-1445 (2000)
Lefebvre et al., *Science*, 274: 259-262 (1996)
Lewis et al., *PNAS* (USA) 85: 1962-1966 (1988)
Li et al., *Mol Cell Biol.*, 20: 697-701 (2000)
Liao and Stanbridge, *Cancer Epidemiol. Biomar. Prev.*, 5: 549-557 (1996)
Liao and Stanbridge, *Cancer*, 88: 1108-1121 (2000)
Liao et al., *Am. J. Pathol.*, 145: 598-609 (1994)
Liao et al., *Cancer Res.*, 57: 2827-2831 (1997)
Lieskovska et al., *Neoplasma*, 46: 17-24 (1999)
Lindmo et al., *J. Immunol. Methods*, 72: 77-89 (1984)
Loncaster et al., *Cancer Res.*, 61: 6394-6399 (2001)
Mandriota et al., *Cancer Cell*, 1: 459-468 (2002)
Marks et al., *BioTechnology*, 10: 779 (1992)
Maren, T. H., *J. Glaucoma*, 4(1): 49-62 (1995)
Maxwell et al., *PNAS* (USA), 90: 2423-2427 (1993)
McKiernan et al., *Cancer Res.*, 57: 2362-2365 (1997)
McKiernan et al., *Cancer*, 86: 492-497 (1999)
Murakami et al., *BJU Int.*, 83: 743-747 (1999)
Moinfar et al., *Cancer Res.*, 60: 2562-2566 (2000)
Nordsmark et al., *Int. J. Radiat. Oncol. Biol. Phys.* 49(2): 581-586 (2001)
Nordsmark et al., *Radiother. Oncol.*, 41: 31-39 (1996)
Olive et al., *Cancer Research*, 61: 8924-8929 (2001)
Opaysky et al., *Genomics*, 33: 480-487 (1996)
Ortova-Gut et al., *Gastroenterology*, 123: 1889-1903 (2002)
Osborne et al., *Science Med:* 32-41 (1996)
Owens and Young, *J. Immunol. Methods*, 168(2): 149-165 (Feb. 10, 1994)
Parkkila and Parkkila, *Scand. J. Gastroenterol.*, 31: 305-317 (1996)
Parkkila et al., *PNAS* (USA), 97: 2220-2224 (2000)
Pastorek et al., *Oncogene*, 9: 2877-2888 (1994)
Pastorekova et al., *Virology*, 187: 620-626 (1992)
Pastorekova et al., *Gastroenterology*, 112: 398-408 (1997)
Peles et al., *Cell*, 82: 251-260 (1995)
Petit et al., *Am. J. Pathol.*, 151: 1523-1530 (1997)
Powell et al., *Radiother. Oncol.* 50(2): 167-171 (February 1999)
Raleigh et al., *Cancer Res.*, 58(17): 3765-3768 (Sep. 1, 1998)
Ramalho-Santos et al., *Development*, 127: 2763-2772 (2000)
Revillion et al., *Euro J. Cancer*, 34: 791-808 (1998)
Saarnio et al., *Gut*, 41(3): 186 (1997)
Saarnio et al., *Am. J. Pathol.*, 153: 279-285 (1998)
Saarnio et al., *J. Histochem Cytochem*, 46: 497-504 (1998)
Saarnio et al., *J. Histochem. Cytochem.*, 47: 517-524 (1999)
Saarnio et al., *Journal of Hepatology*, 35: 643-649 (2001)
Sandhu, J. S., *Crit. Rev. Biotechnol.*, 12(5-6): 437-462 (1992)
Scarff et al., *Gastroenterology*, 117: 605-618 (1999)
Seibert and Chenchik, *Nucleic Acids Res.*, 21: 2019-2020 (1993)
Sharp et al., *Development*, 121: 149-151 (1995)
Spicer et al., *J. Biol. Chem.*, 275: 21555-21565 (2000)
Stratford and Workman, *Anti Cancer Drug Design*, 13: 519-528 (1998)
Sundfor et al., *Br. J. Cancer*, 78: 88822-88827 (1998)
Sundfor et al., *Radiother. Oncol.*, 54: 101-107 (2000)
Supuran and Scozzafava, *Expert Opin. Ther. Patents*, 12(2): 217-242 (2002)
Supuran et al., *Bioorg. Med. Chem.*, 9: 703-714 (2001)
Swinson et al., *Br. J. Cancer*, 86 (Supp. 1): S13 (2002)
Swinson et al., *J. Clin. Oncol.*, 21(3): 473-482 (Feb. 1, 2003)
Teicher et al., *Anticancer Res.*, 13(5A): 1549-1556 (1993)
Trikha et al., *Current Opinion in Biotechnology*, 13(6): 609-614 (2002)
Turner et al., *Hum. Pathol.*, 28: 740-744 (1997)
Turner et al., *Brit. J. Cancer*, 86: 1276-1282 (2002)
Uemura et al., *B. J. Cancer*, 81: 741-746 (1999)
Varia et al., *Gynecol. Oncol.*, 71: 270-277 (1998)
Vaughan et al., *Nat. Biotechnol.*, 16(6): 535-539 (June 1998)
Vaupel and Hoeckel, *Intl. J. Oncol.*, 17(5): 869-879 (November 2000)
Vaupel and Hoeckel, *Adv. Exp. Med. Biol.*, 471: 533-539 (2000)
Vermylen et al., *Eur. Resp. J.*, 14: 806-811 (1999)
Von Mehren et al., *Annu. Rev. Med.*, 54: 343-369 (2003)
Wiesener et al., *Blood*, 92: 2260-2268 (1998)
Wingo et al., *Biochem. Biophys. Res. Comm.*, 288: 666-669 (2001)
World Health Organization. Histological typing of breast tumours. $2^{nd}$ ed. In: International Histological Classification of Tumours, Geneva: World Health Organization, 1981
Wright, N. A., *Int. J. Exp. Pathol.*, 81: 117-143 (2000)
Wykoff et al., *Cancer Res.*, 60: 7075-7083 (2000)
Wykoff et al., *Am. J. Pathol.*, 158(3): 1011-1019 (March 2001)
Young et al., *PNAS* (USA), 85: 9533-9537 (1988)
Zavada et al., *Int. J. Cancer*, 54: 268-274 (1993)
Zavada et al., *Brit. J. Cancer*, 82: 1808-1813 (2000)
Zou and Rajewsky, *Science*, 262(5137): 1271-1274 (Nov. 19, 1993)

Previous attempts to produce CA IX-specific antibodies with specificity different from the M75 monoclonal antibody had been unsuccessful apparently due to the fact that human CA IX differs from the mouse homologue predominantly in the N-terminal amino acid sequence containing the M75 epitope. This sequence appears to be strongly immunogenic possibly because the immunized mice recognize it as non-self, while they do not direct a humoral response to the other, more conserved parts of the human CA IX molecule.

Disclosed herein are detailed methods in Examples 1 and 2 on how to generate from CA IX-deficient mice, hybridoma cell lines producing monoclonal antibodies specific for different extracellular regions of human CA IX protein. Provided herein is detailed characterization of those monoclonal antibodies, assessment of their reactivity in various immuno-detection methods, and the relative position of the epitopes. Further provided are various clinical, diagnostic/prognostic, therapeutic and experimental utilities for those monoclonal antibodies.

Preparation of CA IX Deficient Mice and New CAIX-Specific Antibodies Generated from Said CA IX-Deficient Mice Example 1 details how the MN/CA IX-deficient mice were generated. The knock out mice were used to generate new CA IX-specific monoclonal antibodies (mabs), some of which were directed to other than the CA IX immunodominant epitopes.

It was one object of the inventors to generate monoclonal antibodies (mabs) directed to epitopes different than that to which the M75 mab is directed and/or to generate antibodies with the same epitope specificity as the M75 mab, but with different biological properties. To generate such mabs, the inventors used the knock out mice with the targeted disruption of Car9 gene (coding for mouse MN/CA IX protein), as described herein and in Ortova-Gut et al. (2002) because the knock out mice recognize the entire human MN/CA IX protein as a foreign molecule and may potentially develop humoral responses to epitopes localized in various regions of the human MN/CA IX protein.

In contrast, the wild type mice (wt mice) that express mouse MN/CA IX protein direct the immune response to the N-terminal part of human MN/CA IX because the N-terminal part of the human MN/CA IX protein differs more from the mouse protein than other domains of the human MN/CA IX protein. The wt mice preferentially produce antibodies to epitopes close to or overlapping the epitope to which the M75 mab is directed.

Initial experiments immunizing the MN/CA IX-deficient mice with mouse cells transfected with human MN/CA IX cDNA were not successful, as all the mabs produced were directed to the N-terminal domain of the human MN/CA IX protein, as is the M75 mab. If mabs to epitopes in other regions of the MN/CA IX protein were to be produced, a different immunization protocol was determined to be necessary at about amino acids (aa) 53-111 (SEQ ID NO. 8) or preferably at about aa 52-125 (SEQ ID NO: 98).

There were a number of challenges to overcome. During hybridoma generation, there were several technical problems that required specific solution. First, it was a suitable immunization procedure that had to be invented to assure production of required antibodies. For that purpose, we used different types of immunogens including the recombinant variant of CA IX protein containing the central carbonic anhydrase domain, but lacking N-terminal PG domain (see Example 2 below that shows, which immunization scheme led to production of MN/CA IX-specific antibodies). The other technical problem was development of appropriate screening system that would allow for selection MN/CA IX-specific antibodies and elimination of the non-specific ones, as explained in Example 1.

The inventors produced a recombinant variant of human MN/CA IX protein containing only the central carbonic anhydrase domain of MN/CA IX (the CA IX domain), but lacking the N-terminal PG domain as well as the transmembrane and intracytoplasmic regions. The cDNA coding for the CA IX domain was fused to glutathione-S-transferase (GST), expressed in bacteria and purified by affinity chromatography using glutathione S-Sepharose® (Pharmacia). The GST-CA IX protein was inoculated as a third immunization dose either bound to the Sepharose® or eluted from the matrix. The improved immunization protocols, new fusions, yields of hybridomas and numbers of MN/CA IX specific clones are summarized in the tables of Example 2.

Ten new fusions were made and more than 8000 clones were grown and screened. All MN/CA IX-specific hybridomas were subjected to the freezing-refreezing procedure and consequent subcloning (at least 100 subclones for each clone) in order to select the hybridomas of optimum viability and stable antibody production. That very significant effort resulted in the generation of 11 hybridomas synthesizing MN/CA-IX-specific monoclonal antibodies.

The new MN/CA IX-specific mabs were analyzed to determine their isotype and extensively tested for their reactivity by different immunodetection methods as described in Example 2. Knowledge of the mab isotype is important because the constant region of IgG is closely associated with its biological activity. Various isotypes carry out different effector functions, including complement activation and antibody-dependent cell mediated cytotoxicity. Most of the new antibodies were of IgG2a isotype. Those were able to recognize and bind to the full-length MN/CA IX protein in all tested methods, i.e. ELISA, Western blotting, immunoprecipitation and immunofluorescence. There were also two IgM and two IgG1 antibodies that did not react in immunoprecipitation because of their inability or decreased capacity to bind via Fc fragments to Protein A Sepharose®. However, those antibodies showed MN/CA IX-specific reactivity in ELISA, Western blotting and immunofluorescence. The results indicate that the new antibodies recognize both native and denatured MN/CA IX protein and are potentially useful for different immunodetection approaches.

To determine the domain specificity of the new antibodies, the inventors used the full-length MN/CA IX antigen as well as the antigen lacking the CA domain to test the Mab reactivity in both immunoprecipitation and immunoflourescence. Monoclonal antibodies VII/20, VII/28, VII/32, VII/38, V/10 and V/12 immunoprecipitated the full-length MN/CA IX protein, but failed to react with the ΔCA deletion variant. Similar reactivity was observed in the immunofluorescence experiments, indicating that those antibodies are specific for the CA domain of MN/CA IX.

Mab VII/13 with predicted anti-CA specificity reacted well with the full-length MN/CA IX upon Western blotting. On the other hand, it did not show any reactivity in immunoprecipitation or immunofluorescence. The inventors consider that that mab may be directed to a cryptotope that can be exposed only after the full denaturation of the antigen, whereas it remains hidden in the native or only partially denatured protein.

Among four of the new mabs with the proposed specificity to the N-terminal PG domain of MN/CA IX, three (IV/6, IV/14, IV/11) were of isotypes that are not applicable for immunoprecipitation, because they do not bind to protein A. Antibody IV/18 was able to immunoprecipitate the full-length MN/CA IX protein but not the ΔCA deletion variant. On the other hand, it reacted well with both types of antigen in immunofluorescence. Surprisingly, Mab IV/11 exhibited cytoplasmic reactivity with FL and ΔCA in immunofluorescence experiments. That result might be explained by its specificity to an immature intracytoplasmic form of the protein.

Predicted domain specificity of the new monoclonal antibodies corresponds to their capacity to compete with the M75 mab for binding to MN/CA IX as determined in competitive ELISA using biotinylated M75 mab and individual mabs in samples of hybridoma medium. Preliminary data indicates that the inventors have successfully generated seven new monoclonal antibodies whose epitopes are different from that of the M75 mabs. Another four new mabs seem to be directed to epitopes overlapping the M75 mab's epitope, but have a different isotype than the M75 mab does.

Study of In Vitro Biological Activities of the New Monoclonal Antibodies

The most intriguing and significant feature of the monoclonal antibodies is their ability to interfere with tumor cell growth, which ability can be exploited in anti-tumor therapy. Biological activity of the monoclonal antibodies may be related either to their isotype or to their capacity to engage the receptor molecule and block the signal transduction pathway. Isotype determines the Fc-receptor-dependent mechanisms that contribute substantially to the action of cytotoxic antibodies against tumors (e.g., antibody-dependent cell-mediated cytotoxicity, ADCC and complement-mediated cell lysis). Several mouse monoclonal antibodies of IgG1 and IgG2a isotypes and specificity against different antigens (including HER2/neu, CD20, PSCA) have been shown to stimulate ADCC. Some antibodies may have also a "direct" activity due to receptor-ligand blockade or triggering the pro-apoptotic response (e.g. Trastuzumab®, a humanized IgG1 antibody to HER2/neu, and its "parent" mouse antibody).

As a first step to evaluation of the therapeutic potential of the new monoclonal antibodies specific for MN/CA IX, the inventors are analyzing the effects of the mabs on tumor cell growth and invasion in vitro. The cells are being cultivated in different conditions (including normoxia, hypoxia, serum-starvation, low glucose) and treated with various concentrations of the purified mabs. Proliferation of the treated cells will be measured by MTS assay, and the extent of apoptosis will be determined by TdT labeling and FACS analysis. In addition, the capacity of the new mabs to influence in vitro invasion of the tumor cells through the matrigel membranes will be analysed. The mabs may be combined therapeutically with chemotherapeutic agents. Such a combination has been shown to be effective for Trastuzumab® that was also developed from a typical mouse monoclonal antibody. Therefore, the additive effect of the drugs and MN/CA IX-specific antibody treatment to select mabs with the potential therapeutic efficacy is being investigated. Humanized, partially or completely, versions of such mabs can be prepared.

Those monoclonal antibodies that react with the CA domain of MN/CA IX will be subjected to additional analysis to evaluate their potential capacity to inhibit the enzyme activity of MN/CA IX. The enzyme activity is thought to be highly relevant for the biological role of MN/CA IX. Therefore, the "anti-catalytic" antibodies may become useful tools to elucidate the real significance of CA activity of MN/CA IX in tumor biology and may possibly act in the modulation of tumor growth.

Also, the inventors are evaluating the capacity of the MN/CA IX-specific antibodies to induce ADCC in vitro. Most of the new antibodies are of IgG2a isotype and two of them are IgG1 isotype—both isotypes have been shown to be effective in complement and cell-mediated lysis.

Generation of Monoclonal Antibodies to Mouse MN/CA IX Protein

The inventors perceive that investigators involved in the pre-clinical research of tumor hypoxia and anti-hypoxic therapeutic approaches would like to use specific antibodies for detection of the mouse MN/CA IX as a marker of hypoxia in experimentally induced mouse tumors. The M75 mab is not suitable for that purpose. The M75 mab recognizes the rat and pig proteins, but not the mouse homolog, because its epitope is not preserved in the primary structure of the mouse MN/CA IX.

Availability of the cDNA encoding the mouse MN/CA IX protein allows production of a sufficient amount of a recombinant antigen that can be used for the immunization of the MN/CA IX-deficient mice and generation of corresponding monoclonal antibodies. Such mabs to the mouse MN/CA IX protein may be very useful for future studies of tumor progression utilizing animal models. In addition, the anti-mouse mabs may represent useful tools for pre-clinical examinations of therapeutic targeting of MN/CA IX-positive tumors without the need for immunodeficient animals xenografted with the human tumor cells.

Whether some of the new mabs against human MN/CA IX cross-react with the mouse protein is being investigated. Especially those directed to the CA domain are good candidates because the mouse and human MN/CA IX proteins differ mostly in the N-terminal PG-like regions, but show high sequence homology in the CA domain. Therefore, the reactivity of anti-human mabs to the mouse antigen (both recombinant and extracted from the cells transfected with the mouse cDNA) is being tested.

Example 1 provides the details on how the CA IX-deficient mice (mice with null mutation of Car9) were prepared by targeted gene disruption. Example 1 also reports on the identification of a Car9 cDNA and gene encoding the mouse CA IX, phenotypic consequences of a targeted disruption of Car9 gene and their impact on understanding the physiological significance of CA IX.

CA IX is a highly active enzyme with adhesion, functionally implicated in acid-base balance and intercellular communication. It is normally present in the basolateral membranes of gastrointestinal epithelium and ectopically expressed in many carcinomas. The CA IX deficient mice revealed much about its physiological relevance.

Mice homozygous for the mutation developed gastric hyperplasia of the glandular epithelium with numerous cysts. The first changes were observed in the newborn animals, indicating involvement of CA IX in the development. The hyperplasia of the stomach corpus became prominent at the end of gastric morphogenesis in four-weeks-old mice. Loss of CA IX led to overproduction of mucus-secreting pit cells and reduction of both pepsinogen-positive chief cells and $H^+/K^+$-ATPase-positive parietal cells. It was concluded that phenotypic consequences of the Car9 null mutation demonstrate important and non-redundant role of CA IX in morphogenesis and homeostasis of the glandular gastric epithelium via the control of cell proliferation and differentiation. More detail concerning those points can be found in Example 1 and in Ortova-Gut et al., *Gastroenterology*, 123: 1889-1903 (2002), the latter showing captioned photographs.

One of skill in the art with the instant disclosure enabling the production of CA IX specific antibodies to the CA domain, could analogously make CA IX-specific antibodies to the other CA IX domains. For example, instead of using the recombinant CA domain of CA IX fused to GST as the booster in the protocols of Example 2 below, one of skill in the art would know that using a recombinant TM (SEQ ID NO: 6) domain or a recombinant IC (SEQ ID NO: 7) domain of CA IX would produce antibodies primarily directed to the respective domain used as the booster. Conventional variations of such methods, for example, using synthetic proteins/polypeptides of the selected domain are within the skill of the art.

One of skill in the art could also make antibodies to other regions of CA IX by conventional methods known in the art. For example, peptides from a CA IX region could be conjugated to a carrier, for example, to keyhole limpet hemacyanin (KLH), to prepare antibodies, either polyclonal or monoclonal, to the selected peptide. Such antibodies could be screened by conventional means to determine whether the resulting antibodies are specific to the selected domain. Anti-peptide production services are commercially available, for example, from Ayes Labs, Inc. in Tigard, Oreg. (USA).

Immunodominant Epitopes in PG Domain and In Neighboring Regions

FIG. 4 schematically shows the basic structure of the full-length CA IX. As indicated above, the extracellular domain comprises the PG and CA domains as well as some spacer or perhaps hinge regions. The CA IX immunodominant epitopes are primarily in the PG region at about aa 53-111 (SEQ ID NO: 8) or at about aa 52-125 (SEQ ID NO: 98), preferably now considered to be at about aa 52-125 (SEQ ID NO: 98). The immunodominant epitopes of CA IX may be located in regions neighboring the PG region. For example, the epitope for aa 36-51 (SEQ ID NO: 21) would be considered an immunodominant epitope.

The main CA IX immunodominant epitope is that for the M75 mab. The M75 monoclonal antibody is considered to be directed to an immunodominant epitope in the N-terminal, proteoglycan-like (PG) region of CA IX. The epitope of M75 has been identified as amino acid sequence PGEEDLP (SEQ ID NO: 11), which is 4× identically repeated in the N-terminal PG region of CA IX [Zavada et al. (2000)]. Closely related epitopes to which the M75 mab may also bind, which are also exemplary of immunodominant epitopes include, for example, the immunodominant 6× tandem repeat that can be found at amino acids (aa) 61-96 (SEQ ID NO. 12) of FIGS. 1A-1C, showing the predicted CA IX amino acid sequence. Variations of the immunodominant tandem repeat epitopes within the PG domain include GEEDLP (SEQ ID NO: 13) (aa 61-66, aa 79-84, aa 85-90 and aa 91-96), EEDL (SEQ ID NO: 14) (aa 62-65, aa 80-83, aa 86-89, aa 92-95), EEDLP (SEQ ID NO: 15) (aa 62-66, aa 80-84, aa 86-90, aa 92-96), EDLPSE (SEQ ID NO: 16) (aa 63-68), EEDLPSE (SEQ ID NO: 17) (aa 62-68), DLPGEE (SEQ ID NO: 18) (aa 82-87, aa 88-93), EEDLPS (SEQ ID NO: 19) (aa 62-67) and GEDDPL (SEQ ID NO: 20) (aa 55-60). Other immunodominant epitopes could include, for example, aa 68-91 (SEQ ID NO: 22).

The monoclonal antibodies MN9 and MN12 are considered to be directed to immunodominant epitopes within the N-terminal PG region SEQ ID NOS: 19-20, respectively. The MN7 monoclonal antibody could be directed to an immunodominant epitope neighboring the PG region at aa 127-147 (SEQ ID NO: 23) of FIGS. 1A-1C.

An epitope considered to be preferred within the CA domain (SEQ ID NO: 9) is from about aa 279-291 (SEQ ID NO: 67). An epitope considered to be preferred within the intracellular domain (IC domain) (SEQ ID NO: 7) is from about aa 435-450 (SEQ ID NO: 68).

SEQ ID NO: 69 (aa 166-397 of FIGS. 1A-1C) is considered to be an important antigenic component of the CA domain. There are several antigenic sites within the CA domain. As can be seen in FIG. 6, there are four groups of the CA IX-specific monoclonal antibodies prepared in CA IX-deficient mice such that they are directed to the CA domain; three of those groups are within SEQ ID NO: 69.

S-CA IX

Examples herein show that in addition to its previously described cell-associated form of CA IX (p54/58), there is a soluble form of CA IX. As described below in Examples 3-9 s-CA IX has been observed in tissue culture media from tumor cell lines, such as HT29. Furthermore, we have found s-CA IX in the blood serum and urine of cancer patients.

Preferred soluble forms of CA IX proteins/polypeptides according to this invention are those proteins and/or polypeptides that have substantial homology with the CA IX protein having the deduced amino acid sequence as shown in FIG. 1 [SEQ ID NO: 2]. For example, such substantially homologous soluble CA IX proteins/polypeptides are those homologous that are reactive with the CA IX-specific antibodies of this invention, preferably the Mabs M75, V-10 or their equivalents.

It can also be appreciated that a protein or polypeptide produced by a neoplastic cell in vivo could be altered in sequence from that produced by a tumor cell in cell culture or by a transformed cell. Thus, CA IX proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, soluble CA IX proteins that are significantly truncated and CA IX polypeptides may be found in body fluids, such as, sera. The phrase "CA IX antigen" is used herein to encompass CA IX proteins and/or polypeptides.

Assays

Assays according to this invention are provided to detect and/or quantitate soluble forms of CA IX antigen in vertebrate samples, preferably mammalian samples, more preferably human samples. Soluble forms of CA IX antigen may be detected by immunoassay, for example, Western blotting or radioimmunoassay, among other techniques.

Preferred samples in which to assay soluble forms of CA IX antigen, as the extracellular domain, are body fluids, which can include among other fluids: blood, serum, plasma, semen, breast exudate, gastric secretions, fecal suspensions, bile, saliva, tears, sputum, mucous, urine, lymph, cytosols, ascites, pleural effusions, amniotic fluid, bladder washes, bronchioalveolar lavages and cerebrospinal fluid. It is preferred that the soluble CA IX antigen be concentrated from a larger volume of body fluid before testing. (Examples 3-11 below are representative.) Preferred body fluids to assay would depend on the type of cancer for which one was testing, but in general preferred body fluids would be urine, serum, mucous, gastric secretions, bile, breast exudate, pleural effusions and ascites.

The assays of this invention are both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease.

The present invention is useful for screening for the presence of a wide variety of neoplastic diseases as indicated above. The invention provides methods and compositions for evaluating the probability of the presence of malignant or pre-malignant cells, for example, in a group of cells freshly removed from a host. Such an assay can be used to detect tumors, and help in the diagnosis and prognosis of disease. The assays can also be used to confirm the absence or removal of all tumor tissue following surgery, cancer chemotherapy and/or radiation therapy. It can further be used to monitor cancer chemotherapy and tumor reappearance.

We have used the method of Western blot in experiments reported in the examples below to confirm the presence of soluble CA IX protein in human urine and serum. This method is time-consuming and laborious. However, the presence of soluble forms of CA IX antigen can be detected and/or quantitated using a number of well-defined diagnostic assays. Those in the art can adapt any of the conventional immunoassay formats to detect and/or quantitate soluble CA IX antigen. A preferred diagnostic format for the method of this invention is the dual antibody sandwich assay. Many other formats for detection of CA IX antigen and CA IX-specific antibodies are, of course available. Those can be Western blots, ELISAs (enzyme-linked immunosorbent assays), RIAs (radioimmunoassay), competitive EIA or dual antibody sandwich assays, among other assays all commonly used in the diagnostic industry. In such immunoassays, the interpretation of the results is based on the assumption that the antibody or antibody combination will not cross-react with other proteins and protein fragments present in the sample that are unrelated to CA IX.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Methods to prepare antibodies useful in the assays of the invention are described below. The examples below detail representative assays according to this invention.

Representative of one type of dual antibody sandwich ELISA assay for soluble CA IX antigen is a format wherein a microtiter plate is coated with antibodies made to the extracellular domain of CA IX proteins/polypeptides or antibodies made to whole cells expressing CA IX proteins, and to this is added a patient body fluid sample, for example, serum or urine. After a period of incubation permitting any antigen to bind to the antibodies, the plate is washed and another set of anti-CA IX antibodies which are linked to an enzyme, is added, incubated to allow reaction to take place, and the plate is then rewashed. Thereafter, enzyme substrate is added to the microtiter plate and incubated for a period of time to allow the enzyme to work on the substrate, and the absorbance of the final preparation is measured. A large change in absorbance indicates a positive result. In a preferred embodiment of the invention, the first monoclonal antibody of a dual antibody sandwich assay is selected from the group consisting of the monoclonal antibodies designated M75 which are secreted by the hybridoma VU-M75, and a second enzyme-linked monoclonal antibody is selected from the group consisting of monoclonal antibodies directed to an epitope other than that to which the M75 monoclonal antibody is directed, more preferably to an epitope other than the proteoglycan domain.

It is also apparent to one skilled in the art of immunoassays that CA IX proteins and/or polypeptides can be used to detect and/or quantitate the presence of soluble CA IX antigen in the body fluids of patients. In one such embodiment, a competition immunoassay is used, wherein the CA IX protein/polypeptide is labeled and a body fluid sample is added to compete with the binding of the labeled CA IX protein/polypeptide to antibodies specific to CA IX protein/polypeptide.

In another embodiment, an immunometric assay may be used wherein a labeled antibody made to a CA IX protein or polypeptide comprising the extracellular domain is used. In such an assay, the amount of labeled antibody which complexes with the antigen-bound antibody is directly proportional to the amount of soluble CA IX antigen in the sample.

An exemplary immunoassay method of this invention to detect and/or quantitate soluble CA IX antigen in a vertebrate sample comprises the steps of:

a) incubating said vertebrate sample with one or more sets of antibodies (an antibody or antibodies) that bind to soluble CA IX antigen wherein one set is labeled or otherwise detectable;

b) examining the incubated sample for the presence of immune complexes comprising soluble CA IX antigen and said antibodies.

Another exemplary immunoassay method according to this invention is that wherein a competition immunoassay is used to detect and/or quantitate soluble CA IX antigen in a vertebrate sample and wherein said method comprises the steps of:

a) incubating a vertebrate sample with one or more sets of CA IX-specific antibodies and a certain amount of a labeled or otherwise detectable CA IX protein/polypeptide wherein said CA IX protein/polypeptide competes for binding to said antibodies with soluble CA IX antigen present in the sample;

b) examining the incubated sample to determine the amount of labeled/detectable CA IX protein/polypeptide bound to said antibodies; and c) determining from the results of the examination in step b) whether soluble CA IX antigen is present in said sample and/or the amount of soluble CA IX antigen present in said sample.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,984,533; 3,996,345; 4,034,074; and 4,098,876.

A hybridoma that produces a representative CA IX-specific antibody, the monoclonal antibody M75 (Mab M75), was deposited at the ATCC under Number HB 11128 as indicated above. The M75 antibody was used to discover and identify the CA IX protein and can be used to identify readily CA IX antigen in Western blots, in radioimmunoassays and immunohistochemically, for example, in tissue samples that are fresh, frozen, or formalin-, alcohol-, acetone- or otherwise fixed and/or paraffin-embedded and deparaffinized.

Immunoassay Test Kits

The above outlined assays can be embodied in test kits to detect and/or quantitate soluble CA IX antigen. Kits to detect and/or quantitate soluble CA IX antigen can comprise CA IX protein(s)/polypeptides(s). Such diagnostic/prognostic test kits can comprise one or more sets of antibodies, polyclonal and/or monoclonal, for a sandwich format wherein antibodies recognize epitopes on the soluble CA IX antigen, and one set is appropriately labeled or is otherwise detectable.

Test kits for an assay format wherein there is competition between a labeled (or otherwise detectable) CA IX protein/polypeptide and CA IX antigen in the sample, for binding to an antibody, can comprise the combination of the labeled protein/polypeptide and the antibody in amounts which provide for optimum sensitivity and accuracy.

A kit for use in an enzyme-immunoassay typically includes an enzyme-labelled reagent and a substrate for the enzyme. The enzyme can, for example, bind either a CA IX-specific antibody of this invention or to an antibody to such an CA IX-specific antibody. Test kits may comprise other components as necessary, for example, to perform a preferred assay as outlined in Example 8 below. Such test kits can have other appropriate formats for conventional assays.

Preparation of CA IX-Specific Antibodies

The term "antibodies" is defined herein to include not only whole antibodies but also biologically active fragments of antibodies, preferably fragments containing the antigen binding regions. Descriptions of preparing CA IX-specific antibodies such as M75 suitable for use in immunoassays according to this invention have been described (Zavada et al. U.S. Pat. No. 5,387,676). Such antibodies may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein comprehends polyclonal and monoclonal antibodies and biologically active fragments thereof including among other possibilities "univalent" antibodies [Glennie et al., Nature, 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., PNAS (USA), 79: 6409 (1982)].

There are conventional techniques for making polyclonal and monoclonal antibodies well-known in the immunoassay art. Immunogens to prepare CA IX-specific antibodies include CA IX proteins and/or polypeptides, preferably purified, among others.

Anti-peptide antibodies are also made by conventional methods in the art as described in European Patent Publication No. 44,710 (published Jan. 27, 1982). Briefly, such anti-peptide antibodies are prepared by selecting a peptide from an CA IX amino acid sequence as from FIG. 1, chemically synthesizing it, conjugating it to an appropriate immunogenic protein and injecting it into an appropriate animal, usually a rabbit or a mouse; then, either polyclonal or monoclonal antibodies are made, the latter by the Kohler-Milstein procedure.

Besides conventional hybridoma technology, newer technologies can be used to produce antibodies according to this invention. For example, the use of the polymerase chain reaction (PCR) to clone and express antibody V-genes and phage display technology to select antibody genes encoding fragments with binding activities has resulted in the isolation of antibody fragments from repertoires of PCR amplified V-genes using immunized mice or humans. [Marks et al., BioTechnology, 10: 779 (1992)]. Descriptions of preparing antibodies by recombinant techniques can be found, for example, in U.S. Pat. No. 4,816,567 (issued Mar. 28, 1989).

Preparation of Monoclonal Antibodies

Monoclonal antibodies for use in the assays of this invention may be obtained by methods well known in the art. The production of hybridoma VU-M75 which secretes MAb M75 is exemplary and described below. MAb M75 serves to identify CA IX proteins/polypeptides in various laboratory diagnostic tests, for example, in tumor cell cultures or in clinical samples.

Monoclonal antibodies specific for this invention can be prepared by immunizing appropriate mammals, preferably rodents, more preferably rabbits or mice, with an appropriate immunogen, for example, CA IX proteins/polypeptides attached to a carrier protein if necessary.

One obstacle to overcome in detecting s-CA IX antigen in body fluids was the extremely low concentration of s-CA IX in blood serum and in urine, of the order of 10-100 pg/ml. To detect such an antigen, it is necessary to use two different monoclonal antibodies, directed to non-overlapping epitopes of CA IX. However, until now only one suitable monoclonal antibody, M75, was available for use to detect the CA IX protein. Recently, the inventors overcame this obstacle by using knockout mice with the targeted disruption of Car9 gene to generate a series of monoclonal antibodies specific for various antigenic sites of CA IX protein as described in Example 2. While Mab M75 is specific for the proteoglycan (PG) domain of the CA IX protein, MAb V-10 (one Mab generated by the knockout of Car9) is specific for the carbonic anhydrase (CA) domain. By optimizing combinations and dilutions of two monoclonal antibodies, the inventors were able to obtain extremely sensitive and specific reactions.

MAb M75. Monoclonal antibody M75 (MAb M75) is produced by mouse lymphocytic hybridoma VU-M75, which was initially deposited in the Collection of Hybridomas at the Institute of Virology, Slovak Academy of Sciences (Bratislava, Czechoslovakia) and was deposited under ATCC Designation HB 11128 on Sep. 17, 1992 at the American Type Culture Collection (ATCC). The production of hybridoma VU-M75 is described in Zavada et al., WO 93/18152.

Mab M75 recognizes both the nonglycosylated GST-CA IX fusion protein and native CA IX protein as expressed in CGL3 cells equally well. The M75 MAb recognizes both native and denatured forms of CA IX protein [Pastorekova et al. (1992)].

The monoclonal antibodies useful according to this invention to identify soluble CA IX proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [Hunter, W. M., "Radioimmunoassay," In: Handbook of Experimental Immunology, pp. 14.1-14.40 (D. W. Weir ed.; Blackwell, Oxford/London/Edinburgh/Melbourne; 1978)]. Also preferred is the method of labeling the antibodies using peroxidase.

Described herein is the soluble form of CA IX protein (s-CA IX) shed by tumor cells in tissue culture, and detected in the urine and serum of cancer patients. The s-CA IX shed from tumor cells into culture medium is somewhat shortened. In one embodiment of the invention, the s-CA IX protein is shortened to 50 and 54 kDa, compared with the cell-associated CA IX protein (p54/58). This size corresponds to extracellular part of CA IX molecule, which is composed of PG (proteoglycan-like) and CA (carbonic anhydrase) domains which have been cleaved off from the remainder of the molecule, the TM (transmembrane segment) and IC (intracellular tail) of CA IX (see FIG. 4). The p50/54 form of s-CA IX contains both PG and CA domains, since it reacts with both MAb M75, specific for PG and with MAb V-10, specific for the CA domain.

The high frequency and marked enhancement of CA IX expression in superficial bladder cancer, combined with the relative absence in normal transitional epithelium, and the fact that CA IX is a transmembrane protein found in tumor patient urine, suggests that measurement of shed protein in the urine could be a potential marker of recurrence.

The s-CA IX could be recombinantly, synthetically or otherwise biologically produced, as for example, by proteolytic cleavage or purification from tissue culture medium of an appropriate cell line that expresses MN/CA IX, and could be used therapeutically and/or diagnostically/prognostically. One theory would be that such s-CA IX could be used to sequester the unknown ligand to CA IX, which is considered to activate the signal transduction that results in oncogenic effects. Another therapeutic use for the s-CA IX would be as a vaccine.

The s-CA IX could be used diagnostically/prognostically, for example, to detect MN/CA-IX-specific antibodies in body fluids, or as a calibrator or control in assays to detect comparably sized forms of the naturally occurring s-CA IX in a patient's body fluids. For each of the identified uses, preferably the prepared form of s-CA IX is substantially the CA IX extracellular domain (SEQ ID NO: 5) having a molecular weight of about 50/54 kd.

Since CA IX is known to be expressed on the luminal surface of the bladder when bladder cancer is present [Turner et al., *Br. J. Cancer,* 86: 1276-1282 (2002], and since CA IX is a transmembrane protein, it could be hypothesized that measurement of shed protein in the urine could be a marker of recurrence. Such "shed protein" is now known to be s-CA IX, predominantly as the extracellular domain of CA IX (SEQ ID NO: 5).

Coexpression of C-erbB-2 and CA IX

Example 11 discloses how CA IX was distributed in normal, benign and malignant breast tissues and compared with expression of breast tumour markers including oestrogen receptor (ER), c-erbB2, c-erbB3 and CD44. Tissue specimens were analysed using immunohistochemistry and/or reverse transcriptase-polymerase chain reaction (RT-PCR). CA IX was detected by IHC in 12/26 (46%) malignant tissues, 4/36 (11%) benign lesions, but not in 10 normal breasts. Staining was mostly confined to plasma membranes of abnormal epithelial cells, but in five cases was found in adjacent stroma. Semiquantitative RT-PCR detected CA9 mRNA in 25/39 (64%) malignant tumours, 11/33 (33%) benign lesions, but in none of three normal breasts. Comparative RT-PCR analysis of malignant tissues revealed a relationship between CA9 positivity and c-erbB2 overexpression (p=0.05). Moreover, CA9-positive specimens displayed significantly higher median level of c-erbB2 than CA9-negative ones (p=0.02). No significant association was found with the other markers. The results of this study support possible importance of CA IX for breast carcinogenesis and indicate its usefulness as a breast tumour marker and therapeutic target.

Disclosed herein is the significant association of the ectopic expression of CA IX and the overexpression of HER-2/neu/c-erbB-2. Some of the features associated with high HER-2/neu/c-erbB-2 expression, such as invasion and metastatic capability, may also be mediated by coexpression of CA IX.

A significant proportion of Her-2/neu/c-erbB-2-positive cancers do not respond to treatment by Herceptin®, a humanized monoclonal antibody against Her-2/neu/c-erbB-2 [Kuter, I. 2001]. Inhibitors of the coexpressed CA IX could provide alternative therapeutic approaches. Such inhibitors include, for example, polyclonal and/or monoclonal antibodies, including immunoreactive fragments, and mono- or bi-specific variants, and related anti-anti-idiotype antibodies. Each of those antibody variants and fragments thereof can be used alone and/or conjugated to cytotoxic agents. [See, for example, Zavada et al., U.S. Pat. Nos. 5,955,075 (Sep. 21, 1999) and 6,051,226 (Apr. 18, 2000), and Zavada et al. EP 0 637 836 B1 (Jul. 7, 1999).]

Another class of CA IX inhibitors are the carbonic anhydrase (CA) inhibitors. [See, for example, Chegwidden et al. (2000); Hockel and Vaupel (2001) (April 2001) (Feb. 21, 2001); Supuran and Scozzfava (2002); Teicher et al. (1993) and Maren, T. H. (1995).] Inhibition of CA activity has been shown to reduce invasion of some tumor cell lines [Parkkila et al. (2000)], and CA inhibitor treatment may be beneficial as an adjunct to cancer chemotherapy, synergizing with chemotherapeutic agents in animal models. [Teicher (1993); Parkkila (2000)]. CA inhibitors, e.g., acetozolamide or sulfonamides, have been shown to reduce tumor invasiveness or block tumor growth, respectively [Parkkila et al. (2000); Supuran et al., (2001)]. Further, CA isoenzyme antagonism has been observed to augment the cytotoxic effects of various chemotherapeutic agents, including platinum based drugs [Teicher et al. (1993)].

The classic, clinically important CA inhibitors are aromatic/heterocyclic sulfonamides. Exemplary are acetazalamide, methazolamide, ethoxzolamide, dichlorophenamide, dorzolamide and brinzolamide. A large number of derivatives to enhance desired pharmacological/physicochemical prospective such as water solubility are new being developed [Supuran and Scozzafava (2002)].

Hypoxia and Therapy

Tumor hypoxia occurs as a consequence of an inadequate supply of blood borne oxygen due to the disorganized and chaotic vascular network that develops in tumors [Hockel and Vaupel (2001)]. Tumor hypoxia has been considered to present a therapeutic problem since hypoxic cells are radiation resistant [Gray et al. (1953); Hall, E. J. (1988)], and recent measurements of tumor oxygenation in the clinic have shown clear correlations with outcome of radiotherapy [Höckel et al. (1993); Nordsmark et al. (1996); Brizel et al. (1997); Fyles et al. (1998); Sundfor et al. (2000)]. The role of tumor hypoxia for the outcome of chemotherapy is less clear, but there are a number of reasons why hypoxia may be important. For example, drugs like bleomycin have an obligate requirement for oxygen in order to be toxic. Chronically hypoxic cells tend to be out of cycle and resistant to cell cycle phase specific drugs. Finally, since hypoxic cells lie far from a functional vascular capillary, many chemotherapeutic drugs find it extremely difficult to diffuse that distance in sufficient concentrations to be toxic [Jain et al. (2000)].

Clinical observations have suggested hypoxia can cause cellular changes that result in a more aggressive phenotype [Höckel and Vaupel (2001)]. Such hypoxia-related malignant progression may result in increased potential for local invasiveness and metastatic spread [Brizel et al. (1996), Höckel et al. (1996) Sundfor et al. (1998)]. Results from experimental systems support the notion that these changes are indeed hypoxia-mediated [Young et al. (1988), Graeber et al. (1996)].

There is a need to identify those patients most likely to respond to adjuvant therapy directed towards hypoxic cells. Such therapeutic approaches could include methods to improve tumour oxygenation such as Carbogen® [Powell et al. (1997)], the use of bioreductive drugs [Stratford and Workman (1998)] or hypoxia-mediated gene therapy approaches [Dachs et al. (1997)]. Currently, the method that has received most widespread use to measure tumour oxygenation is the Eppendorf® polarographic oxygen electrode [Kallinowski et al. (1990)]. However, it has limited use in that it is invasive and can only be used on relatively superficial tumours. Nevertheless, this method of $pO_2$ measurement has generated many clinical therapeutic correlations and any subsequent methods of hypoxia measurement must be compared to it.

Bioreductive drug markers provide an alternative approach for assessing the level and extent of tumor hypoxia. This was first articulated by Chapman and colleagues [see Chapman (1991) for review] who used the 2-nitroimidazole, misonidazole. Related compounds such as pimonidazole [Raleigh et al. (1998)], EF-5 [Koch et al. (1995)], NITP [Hodgkiss et al. (1997)] and SR4554 [Aboagye et al. (1998)] have subsequently been developed. They are all structurally similar and will identify intracellular levels of oxygenation at which it is known that cells will be resistant to radiation [see e.g., Evans et al. (1996)]. Pimonidazole is at the most advanced stage of clinical evaluation [Kennedy et al. (1997); Varia et al. (1998)] and recently a clinical comparative study has been made between Eppendorf® measurements of $pO_2$ and the extent of pimonidazole adduct formation in carcinoma of the cervix [Nordsmark et al. (2001)]. In this latter study, there was a trend for tumors with relatively high $pO_2$ readings to show lower pimonidazole binding, however, there was no significant correlation seen between these two assays of hypoxia.

Another method to assess the presence of hypoxia in human tumors is to take advantage of the phenomenon of hypoxia-mediated gene expression. Up regulation of a variety of genes in hypoxia is mediated by activation of the transcription factor HIF-1 (hypoxia-inducible factor-1). The HIF-1 protein is stabilized under hypoxic conditions and binds to genetic enhancer sequences (HREs, hypoxia responsive elements) that exist in the promotor regions of genes including erythropoetin [Maxwell et al. (1993)], VEGF [Forsythe et al. (1996)], GLUT-1 [Ebert et al. (1995)] and CA IX [Wycoff et al. (2000)]. The expression of these genes in human tumours could potentially be determined at the time of tumour biopsy and thus provide an inexpensive, minimally invasive means of measuring tumour hypoxia. If validated, this approach could facilitate the rational selection of patients into various treatment arms of clinical trials and allow appropriate application of therapeutic strategies directed towards hypoxic cells.

Recently the expression of GLUT-1 (glucose transporter-1) and CA IX (carbonic anhydrase IX) has been measured in carcinoma of the cervix and correlated with Eppendorf® measurements of $pO_2$ and these immunohistochemical measurements have in turn also been related to therapeutic outcome [Airley et al. (2001); Loncaster et al. (2001)]. A study was done as reported in Airley et al. (2002) to relate the expression of the hypoxia-regulated genes GLUT-1 and CA9 to the presence of bound pimondazole adducts in carcinoma of the cervix.

CA IX, which, along with CA XII, was initially characterised as a hypoxia-inducible gene due to its overexpression in VHL defective cell lines, catalyses the reversible hydration of carbon dioxide to carbonic acid, providing a means of regulating pH in tumours [Wykoff et al. (2000)]. CA IX may therefore work to help counteract the intracellular acidic conditions found in oxygen deprived regions of tumours. These acidic conditions being promoted, to some extent, by the hypoxia-mediated over-expression of Glut-1, in turn allows increased anaerobic glycolysis. The initial validation of CA IX as a marker of hypoxia in advanced carcinoma of the cervix [Loncaster et al. (2001)], has been accompanied by a range of studies which relate the presence of this enzyme to poor outcome in breast [Chia et al. (2001)] non-small cell lung [Giatromanolaki et al. (2001) and head and neck cancers [Koukourakis et al. (2001)].

The Airley et al. (2002) study concluded that further evidence was provided that hypoxia-regulated membrane proteins such as Glut-1 and CA IX may be used clinically to infer the presence of hypoxia in tumors, which allow the rational use of new modalities, such as bioreductive chemotherapy and/or hypoxia-regulated gene therapy.

Airley et al., *Brit. J. Cancer,* 86 (Suppl. 1): S13-S33 (2002) states: "Hypoxic cells are known to be radioresistant and chemoresistant, thus, a reliable surrogate marker of hypoxia is desirable to ensure that treatment with radiotherapy or hypoxia-directed therapies, such as the use of bioreductive drugs, may be rationally applied. Recently, the HIF-1-regulated proteins Glut-1 and CA IX were validated as intrinsic markers of hypoxia by comparison with $pO_2$ measured using the Eppendorf oxygen electrode, which is believed to measure both acute and chronic hypoxia."

Swinson et al., *Br. J. Cancer,* 86 (Supp. 1): S13 (2002) states: "The presence of activated epidermal growth factor receptor (EGFR) and HER2 reception has been postulated to augment the cellular hypoxic response by increasing synthesis and enhancing the transcriptional activity of HIF-1 . . . [citing to Laughner et al. (2001)]." The HIF-1 transcription factor upregulates CA IX and other enzymes involved in cellular pH homeostatis, as well as vascular endothelial growth factor (VEGF) and enzymes involved in anaerobic metabolism such as glucose transporter-1.

Swinson et al., *J. Clin. Oncol.,* 21(3): 473-82 (Feb. 1, 2003) evaluated CA IX as a hypoxia marker and its prognostic significance in non-small cEll lung cancer (NSCLC). Standard immunohistochemical (IHC) techniques with the M75 mab were used to study tumor sections from 175 resected NSCLC cases. Membranous (m) CA IX (P=0.005), cytoplasmic (c) (p=0.018) and stromal CA IX (p<0.001) expression correlated with the extent of tumor necrosis (TN). Perinuclear (p) CA IX (p=0.035) was associated with poor prognosis. Swinson et al. concluded that mCA IX is a marker of tumor cell hypoxia, and that pCA IX is representative of an aggressive phenotype. The absence of CA IX staining close to microvessels indicates that the tissues are relatively well oxygenated.

Vaupel and Hoeckel, "Predictive power of the tumor oxygenation status," *Advances in Experimental Medicine and Biology,* 471: 533-539 (2000) point out that tumor hypoxia not only indicates decreased radiocurability but is generally associated with malignant progression of disease. So far data indicate that tumor hypoxia and clinical aggressiveness in terms of resistance to therapy and tumor dissemination are interrelated.

Anticancer Drugs and Antibodies that Block Interaction of MN Protein and Receptor Molecules MN protein is considered to be a uniquely suitable target for cancer therapy for a number of reasons including the following. (1) It is localized on the cell surface, rendering it accessible. (2) It is expressed in a high percentage of human carcinomas (e.g., uterine cervical, renal, colon, breast, esophageal, lung, head and neck carcinomas, among others), but is not normally expressed to any significant extent in the normal tissues from which such carcinomas originate.

(3) It is normally expressed only in the stomach mucosa and in some epithelia of the digestive tract (epithelium of gallbladder and small intestine). An anatomic barrier thereby exists between the MN-expressing preneoplastic/neoplastic and MN-expressing normal tissues. Drugs, including antibodies, can thus be administered which can reach tumors without interfering with MN-expressing normal tissues.

(4) MAb M75 has a high affinity and specificity to MN protein. (5) MN cDNA and MN genomic clones which encompass the protein-coding and gene regulatory sequences have been isolated. (6) MN-specific antibodies have been shown to have among the highest tumor uptakes reported in clinical studies with antitumor antibodies in solid tumors, as shown for the MN-specific chimeric antibody G250 in animal studies and in phase I clinical trials with renal carcinoma patients. [Steffens et al., *J. Clin. Oncol.*, 15: 1529 (1997).] Also, MN-specific antibodies have low uptake in normal tissues.

Data as presented in Zavada et al., WO 00/24913 are consistent with the following theory concerning how MN protein acts in normal tissues and in preneoplastic/neoplastic tissues. In normal tissues (e.g., in stomach mucosa), MN protein is considered to be a differentiation factor. It binds with its normal receptor S (for stomach). Stomach carcinomas have been shown not to contain MN protein.

Ectopic expression of MN protein in other tissues causes malignant conversion of cells. Such ectopic expression is considered to be caused by the binding of MN protein with an alternative receptor H (for HeLa cells), coupled to a signal transduction pathway leading to malignancy. Drugs or antibodies which block the binding site of MN protein for receptor H would be expected to cause reversion of prenoplastic/neoplastic cells to normal or induce their death.

Design and Development of MN-Blocking Drugs or Antibodies

A process to design and develop MN-blocking drugs, e.g., peptides with high affinity to MN protein, or antibodies, has several steps. First, is to test for the binding of MN protein to receptors based on the cell adhesion assay as described in Zavada et al., WO 00/24913. That same procedure would also be used to assay for drugs blocking the MN protein binding site. In view of the alternative receptors S and H, stomach epithelial cells or revertants (containing preferentially S receptors), HeLa cells (containing the H receptor and lacking the S receptor) would be used in the cell adhesion assay.

To identify the receptor binding site of MN protein, deletion variants of MN protein lacking different domains can be used to identify region(s) responsible for interaction of MN protein with a receptor. A preferred MN binding site is considered to be closely related or identical to the epitope for MAb M75, as the amino acid sequence PGEEDLP (SEQ ID NO: 11) which is 4× identically repeated in the N-terminal PG region of CA IX, or at least closely related copies within the 6-fold tandem repeat of 6 amino acids (aa) of aa 61-96 (SEQ ID NO: 12) as shown in FIG. 1A-1C in the proteoglycan-like domain of the MN protein. Smaller deletion variants can be prepared within that relevant domain, e.g., fusion proteins with only small segments of MN protein can be prepared. Also, controlled digestion of MN protein with specific proteases followed by separation of the products can be performed.

Further, peptides comprising the expected binding site can be synthesized. All of those products can be tested in cell adhesion assays, as exemplified below. [See, e.g., Pierschbacher and Ruoslahti, *PNAS*, 81:5985 (1984); Ruoslahti and Pierschbacher, *Science*, 238: 491.]

Molecules can be constructed to block the MN receptor binding site. For example, use of a phage display peptide library kit [as Ph.D®-7 Peptide 7-Mer Library Kit from New England Biolabs; Beverly, Mass. (USA)] as exemplified in Examples 2 and 3 of Zavada et al. WO 00/24913, can be used to find peptides with high affinity to the target molecules. Biologic activity of the identified peptides will be tested in vitro by inhibition of cell adhesion to MN protein, by effects on cell morphology and growth characteristics of MN-related tumor cells (HeLa) and of control cells. [Symington, *J. Biol. Chem.*, 267: 25744 (1992).] In vivo screening will be carried out in nude mice that have been injected with HeLa cells.

Peptides containing the binding site of the MN protein will be prepared [e.g. MAPs (multiple antigen peptides); Tam, J. P., *PNAS* (USA) 85: 5409 (1988); Butz et al., *Peptide Res.*, 7: 20 (1994)]. The MAPs will be used to immunize animals to obtain antibodies (polyclonal and/or monoclonal) that recognize and block the binding site. [See, e.g., Brooks et al., *Cell*, 79: 1157 (1994).] "Vaccination" would then be used to test for protection in animals. Antibodies to the MN binding site could potentially be used to block MN protein's interaction(s) with other molecules.

Computer modeling can also be used to design molecules with specific affinity to MN protein that would mediate steric inhibition between MN protein and its receptor. A computer model of the MN binding site for the receptor will contain spatial, electrostatic, hydrophobic and other characteristics of this structure. Organic molecules complementary to the structure, that best fit into the binding site, will be designed. Inorganic molecules can also be similarly tested that could block the MN binding site.

The use of oncoproteins as targets for developing new cancer therapeutics is considered conventional by those of skill in the art. [See, e.g., Mendelsohn and Lippman, "Growth Factors," pp. 114-133, IN: DeVita et al. (eds.), *Cancer: Principles and Practice of Oncology* (4$^{th}$ Ed.; Lippincott; Philadelphia, 1993).] In its broadest sense, the design of blocking drugs can be based in competitive inhibition experiments. Such experiments have been used to invent drugs since the discovery of sulfonamides (competitive inhibitors of para-aminobenzoic acid, a precursor of folic acid). Also, some cytostatics are competitive inhibitors (e.g., halogenated pyrimidines, among others).

However, the application of such approaches to MN is new. In comparison to other tumor-related molecules (e.g. growth factors and their receptors), MN has the unique property of being differentially expressed in preneoplastic/neoplastic and normal tissues, which are separated by an anatomic barrier.

Other CA IX Detection Methods

Diagnostic nucleic acid can be labelled, directly or indirectly, by methods known in the art, and can be used in conventional Southern or Northern hybridization assays. Such assays can be employed in identifying transformants or for in vitro diagnosis, such as to detect MN mRNA in tissues as a measure of oncogenic activity. The presence of MN mRNA or precursors thereto for most tissues being indicative of oncogenic activity, whereas the absence or a reduced level of MN mRNA in stomach and gallbladder tissues in comparison to the levels of mRNA found in the counterpart normal tissues is considered indicative of oncogenic activity. DNA which encodes MN proteins can be obtained by chemical synthesis, by screening reverse transcripts of mRNA from placental or other cells, or by screening genomic libraries from eukaryotic cells, among other methods.

MN-specific antibodies can be bound by serologically active MN proteins/polypeptides in samples of such body fluids as blood, plasma, serum, lymph, mucous, tears, urine, spinal fluid and saliva; however, such antibodies are found most usually in blood, plasma and serum, preferably in serum. Correlation of the results from the assays to detect and/or quantitate MN antigen and MN-specific antibodies reactive therewith, provides a preferred profile of the disease condition of a patient.

The presence of MN antigen or antibodies can be detected and/or quantitated using a number of well-defined diagnostic assays. Those in the art can adapt any of the conventional immunoassay formats to detect and/or quantitate MN antigen and/or antibodies.

Many formats for detection of MN antigen and MN-specific antibodies are, of course available. Those can be Western blots, ELISAs, RIAs, competitive EIA or dual antibody sandwich assays, immunohistochemical staining, among other assays all commonly used in the diagnostic industry. In such immunoassays, the interpretation of the results is based on the assumption that the antibody or antibody combination will not cross-react with other proteins and protein fragments present in the sample that are unrelated to MN.

Representative of one type of ELISA test for MN antigen is a format wherein a microtiter plate is coated with antibodies made to MN proteins/polypeptides or antibodies made to whole cells expressing MN proteins, and to this is added a patient sample, for example, a tissue or cell extract. After a period of incubation permitting any antigen to bind to the antibodies, the plate is washed and another set of anti-MN antibodies which are linked to an enzyme is added, incubated to allow reaction to take place, and the plate is then rewashed. Thereafter, enzyme substrate is added to the microtiter plate and incubated for a period of time to allow the enzyme to work on the substrate, and the absorbance of the final preparation is measured. A large change in absorbance indicates a positive result.

It is also apparent to one skilled in the art of immunoassays that MN proteins and/or polypeptides can be used to detect and/or quantitate the presence of MN antigen in the body fluids, tissues and/or cells of patients. In one such embodiment, a competition immunoassay is used, wherein the MN protein/polypeptide is labeled and a body fluid is added to compete the binding of the labeled MN protein/polypeptide to antibodies specific to MN protein/polypeptide.

In another embodiment, an immunometric assay may be used wherein a labeled antibody made to a MN protein or polypeptide is used. In such an assay, the amount of labeled antibody which complexes with the antigen-bound antibody is directly proportional to the amount of MN antigen in the sample.

A representative assay to detect MN-specific antibodies is a competition assay in which labeled MN protein/polypeptide is precipitated by antibodies in a sample, for example, in combination with monoclonal antibodies recognizing MN proteins/polypeptides. One skilled in the art could adapt any of the conventional immunoassay formats to detect and/or quantitate MN-specific antibodies. Detection of the binding of said antibodies to said MN protein/polypeptide could be by many ways known to those in the art, e.g., in humans with the use of anti-human labeled IgG.

An exemplary immunoassay method of this invention to detect and/or quantitate MN antigen in a vertebrate sample comprises the steps of:

a) incubating said vertebrate sample with one or more sets of antibodies (an antibody or antibodies) that bind to MN antigen wherein one set is labeled or otherwise detectable;

b) examining the incubated sample for the presence of immune complexes comprising MN antigen and said antibodies.

Another exemplary immunoassay method according to this invention is that wherein a competition immunoassay is used to detect and/or quantitate MN antigen in a vertebrate sample and wherein said method comprises the steps of:

a) incubating a vertebrate sample with one or more sets of MN-specific antibodies and a certain amount of a labeled or otherwise detectable MN protein/polypeptide wherein said MN protein/polypeptide competes for binding to said antibodies with MN antigen present in the sample;

b) examining the incubated sample to determine the amount of labeled/detectable MN protein/polypeptide bound to said antibodies; and c) determining from the results of the examination in step b) whether MN antigen is present in said sample and/or the amount of MN antigen present in said sample.

Once antibodies (including biologically active antibody fragments) having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,984,533; 3,996,345; 4,034,074; and 4,098,876.

Antibodies employed in assays may be labeled or unlabeled. Unlabeled antibodies may be employed in agglutination; labeled antibodies may be employed in a wide variety of assays, employing a wide variety of labels.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Immunoassay Test Kits

The above outlined assays can be embodied in test kits to detect and/or quantitate MN antigen and/or MN-specific antibodies (including biologically active antibody fragments). Kits to detect and/or quantitate MN antigen can comprise MN protein(s)/polypeptides(s) and/or MN-specific antibodies, polyclonal and/or monoclonal. Such diagnostic/prognostic test kits can comprise one or more sets of antibodies, polyclonal and/or monoclonal, for a sandwich format wherein antibodies recognize epitopes on the MN antigen, and one set is appropriately labeled or is otherwise detectable.

Test kits for an assay format wherein there is competition between a labeled (or otherwise detectable) MN protein/polypeptide and MN antigen in the sample, for binding to an antibody, can comprise the combination of the labeled protein/polypeptide and the antibody in amounts which provide for optimum sensitivity and accuracy.

Test kits for MN-specific antibodies preferably comprise labeled/detectable MN proteins(s) and/or polypeptides(s), and may comprise other components as necessary, such as, controls, buffers, diluents and detergents. Such test kits can have other appropriate formats for conventional assays.

A kit for use in an enzyme-immunoassay typically includes an enzyme-labelled reagent and a substrate for the enzyme. The enzyme can, for example, bind either an MN-specific antibody of this invention or to an antibody to such an MN-specific antibody.

Preparation of MN-Specific Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen.

Antibodies of the invention may be prepared by conventional methodology and/or by genetic engineering. Chimeric antibodies that are humanized to reduce antigenicity are preferred for in vivo use. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein comprehends polyclonal and monoclonal antibodies and biologically active fragments thereof including among other possibilities "univalent" antibodies [Glennie et al., *Nature*, 295: 712 (1982)]; Fab proteins including Fab' and F(ab')$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of said $V_H$ and $V_L$ regions]; $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., *PNAS (USA)*, 79: 6409 (1982)].

Bispecific Antibodies. Bispecific antibodies can be produced by chemically coupling two antibodies of the desired specificity. Bispecific MAbs can preferably be developed by somatic hybridization of 2 hybridomas. Bispecific MAbs for targeting MN protein and another antigen can be produced by fusing a hybridoma that produces MN-specific MAbs with a hybridoma producing MAbs specific to another antigen. For example, a cell (a quadroma), formed by fusion of a hybridoma producing a MN-specific MAb and a hybridoma producing an anti-cytotoxic cell antibody, will produce hybrid antibody having specificity of the parent antibodies. [See, e.g., *Immunol. Rev.* (1979); *Cold Spring Harbor Symposium Quant. Biol.*, 41: 793 (1977); van Dijk et al., *Int. J. Cancer,* 43: 344-349 (1989).] Thus, a hybridoma producing a MN-specific MAb can be fused with a hybridoma producing, for example, an anti-T3 antibody to yield a cell line which produces a MN/T3 bispecific antibody which can target cytotoxic T cells to MN-expressing tumor cells.

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof. However, for some therapeutic uses bispecific antibodies targeting MN protein and cytotoxic cells would be preferred.

There are conventional techniques for making polyclonal and monoclonal antibodies well-known in the immunoassay art. Immunogens to prepare MN-specific antibodies include MN proteins and/or polypeptides, preferably purified, and MX-infected tumor line cells, for example, MX-infected HeLa cells, among other immunogens.

Anti-peptide antibodies are also made by conventional methods in the art as described in European Patent Publication No. 44,710 (published Jan. 27, 1982). Briefly, such anti-peptide antibodies are prepared by selecting a peptide from an MN amino acid sequence as from FIG. 1, chemically synthesizing it, conjugating it to an appropriate immunogenic protein and injecting it into an appropriate animal, usually a rabbit or a mouse; then, either polyclonal or monoclonal antibodies are made, the latter by a Kohler-Milstein procedure, for example.

Besides conventional hybridoma technology, newer technologies can be used to produce antibodies according to this invention. For example, the use of the PCR to clone and express antibody V-genes and phage display technology to select antibody genes encoding fragments with binding activities has resulted in the isolation of antibody fragments from repertoires of PCR amplified V-genes using immunized mice or humans. [Marks et al., *BioTechnology*, 10: 779 (July 1992) for references; Chiang et al., *BioTechniques*, 7(4): 360 (1989); Ward et al., *Nature*, 341: 544 (Oct. 12, 1989); Marks et al., *J. Mol. Biol.*, 222: 581 (1991); Clackson et al., *Nature*, 352: (15 Aug. 1991); and Mullinax et al., *PNAS (USA)*, 87: 8095 (October 1990).]

Descriptions of preparing antibodies, which term is herein defined to include biologically active antibody fragments, by recombinant techniques can be found in U.S. Pat. No. 4,816, 567 (issued Mar. 28, 1989); European Patent Application Publication Number (EP) 338,745 (published Oct. 25, 1989); EP 368,684 (published Jun. 16, 1990); EP 239,400 (published Sep. 30, 1987); WO 90/14424 (published Nov. 29, 1990); WO 90/14430 (published May 16, 1990); Huse et al., *Science*, 246: 1275 (Dec. 8, 1989); Marks et al., *BioTechnology*, 10: 779 (July 1992); La Sastry et al., PNAS (USA), 86: 5728 (August 1989); Chiang et al., *BioTechniques*, 7(40): 360 (1989); Orlandi et al., *PNAS (USA)*, 86: 3833 (May 1989); Ward et al. *Nature*, 341: 544 (Oct. 12, 1989); Marks et al., *J. Mol. Biol.*, 222: 581 (1991); and Hoogenboom et al., *Nucleic Acids Res.*, 19(15): 4133 (1991).

Representative Mabs

Monoclonal antibodies for use in the assays of this invention may be obtained by methods well known in the art for example, Galfre and Milstein, "Preparation of Monoclonal Antibodies: Strategies and Procedures," in *Methods in Enzymology: Immunochemical Techniques*, 73: 1-46 [Langone and Vanatis (eds); Academic Press (1981)]; and in the classic reference, Milstein and Kohler, *Nature*, 256: 495-497 (1975).]

Although representative hybridomas of this invention are formed by the fusion of murine cell lines, human/human hybridomas [Olsson et al., *PNAS (USA)*, 77: 5429 (1980)] and human/murine hybridomas [Schlom et al., PNAS (USA), 77: 6841 (1980); Shearman et al. *J. Immunol.*, 146: 928-935 (1991); and Gorman et al., PNAS (USA), 88: 4181-4185 (1991)] can also be prepared among other possibilities. Such humanized monoclonal antibodies would be preferred monoclonal antibodies for therapeutic and imaging uses.

Monoclonal antibodies specific for this invention can be prepared by immunizing appropriate mammals, preferably rodents, more preferably rabbits or mice, with an appropriate immunogen, for example, MaTu-infected HeLa cells, MN fusion proteins, or MN proteins/polypeptides attached to a carrier protein if necessary. Exemplary methods of producing antibodies of this invention are described below.

The monoclonal antibodies useful according to this invention to identify MN proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [Hunter, W. M., "Radioimmunoassay," In: Handbook of Experimental Immunology, pp. 14.1-14.40 (D. W. Weir ed.; Blackwell, Oxford/London/Edinburgh/Melbourne; 1978)].

Representative mabs of this invention include Mabs M75, MN9, MN12 and MN7 described below. Monoclonal antibodies of this invention serve to identify MN proteins/polypeptides in various laboratory diagnostic tests, for example, in tumor cell cultures or in clinical samples.

Epitopes

The affinity of a MAb to peptides containing an epitope depends on the context, e.g. on whether the peptide is a short sequence (4-6 aa), or whether such a short peptide is flanked by longer aa sequences on one or both sides, or whether in testing for an epitope, the peptides are in solution or immobilized on a surface. Therefore, it would be expected by ones of skill in the art that the representative epitopes described herein for the MN-specific MAbs would vary in the context of the use of those MAbs.

Epitope Mapping

Epitope mapping was performed by the Novatope® system, a kit for which is commercially available from Novagen, Inc. [See, for analogous example, Li et al., Nature, 363: 85-88 (6 May 1993).] In brief, the MN cDNA was cut into overlapping short fragments of approximately 60 base pairs. The fragments were expressed in E. coli, and the E. coli colonies were transferred onto nitrocellulose paper, lysed and probed with the mab of interest. The MN cDNA of clones reactive with the mab of interest was sequenced, and the epitopes of the mabs were deduced from the overlapping polypeptides found to be reactive with each mab.

Therapeutic Use of MN-Specific Antibodies

The MN-specific antibodies of this invention, monoclonal and/or polyclonal, preferably monoclonal, and as outlined above, may be used therapeutically in the treatment of neoplastic and/or pre-neoplastic disease, either alone or in combination with chemotherapeutic drugs or toxic agents, such as ricin A. Further preferred for therapeutic use would be biologically active antibody fragments as described herein. Also preferred MN-specific antibodies for such therapeutic uses would be humanized monoclonal antibodies and/or bispecific antibodies.

MN-specific antibodies can be administered in a therapeutically effective amount, preferably dispersed in a physiologically acceptable, nontoxic liquid vehicle, to patients afflicted with preneoplastic/neoplastic disease. The MN-specific antibody can be given alone or as a carrier of an anti-tumor drug. Among the various antiproliferative, antineoplastic or cytotoxic agents that may be linked to the MN-specific antibodies are antimetabolites, such as the antifolate, methotrexate, or the purine or pyrimidine analogs mercaptopurine and fluorouracil. Others include antibiotics, lectins such as ricin and abrin, toxins such as the subunit of diphtheria toxin, radionuclides such as $^{211}$Astatine and $^{131}$Iodine, radiosensitizers such as misanidazole or neutron sensitizers such as boron containing organics. Such agents may be attached to the antibody by conventional techniques such as glutaraldehyde cross-linking.

MN-specific antibodies can be used to target cytoxic cells (e.g. human T cells, monocytes or NK cells). Cytotoxic cells can be attached to MN-expressing tumor cells through Fc receptors on the cytotoxic cells, which bind the Fc portion of a MN-specific antibody, or via a bridging antibody of dual specificity, that is, a bispecific antibody specific for MN protein and for the cytotoxic cell.

The cytotoxic cell can be targeted by allowing the bispecific antibody to bind the cell. After targeting, the cells can be administered to the patient. Therapy with targeted cells can be used as an adjunct to surgical therapy, radiation therapy, or chemotherapy.

Anti-Idiotype MN-Specific Antibodies as Tumor Vaccines and Anti-Anti-Idiotype Antibody Sera as Immunotherapeutic MN-specific anti-idiotype antibodies have therapeutic utility as a vaccine for neoplastic disease associated with abnormal MN expression. MN-specific anti-anti-idiotype sera also have therapeutic anti-tumor efficacy. Those therapeutic utilities are demonstrated by research done with the MN-specific G250 MAb, and anti-idiotype antibodies thereto (Ab2), and further anti-anti-idiotype sera (Ab3) as demonstrated by the studies described below.

Uemura et al., Biotherapy (Japan) 10(3): 241-244 (1996) (English summary) define an anti-idiotype antibody (Ab2) as "an antibody directed against an antigenic determinant located within a variable region of the immunoglobulin molecule. Ab2 mimicking the normal antigen (so-called internal image Ab2) may be used as a surrogate antigen for vaccination to trigger the host's immune system specifically against the nominal antigen."

Uemura et al., id., having previously isolated six internal image murine Ab2s directed against the G250 MAb— NUH31, 51, 71, 82 (IgG1) and NUH44 (IgG2a), explores the application of monoclonal Ab2 as tumor vaccines. Uemura et al. investigated in view of "previous results that RCC tumor-associated-antigen-related idiotype vaccination induced antigen-specific humoral as well as cellular responses, the anti-tumor efficacy of anti-anti-idiotype antibody (Ab3) sera obtained from mice immunized with different internal image Ab2 that . . . mimic the RCC-associated antigen . . . G250 [MN] . . . Nu/nu BALB/c mice carrying small established NU12 human RCC xenografts (G250+, 20 mm$^3$) rr receiving an s.c. injection of 2×10$^5$ SK-RC-52 (G250+) RCC cells were treated by i.p. injection of 0.2 ml Ab3 sera. This treatment resulted in complete tumor rejection and significant tumor growth inhibition as compared to control groups (p<0.01)." Uemura et al. concluded that "immunization with Ab2s elicits powerful anti-tumor effects in immunocompetent animals."

Uemura et al., J. Urol., 159(5) (Suppl.): Abstract 724 (May 1998), describe MN as an immunotherapeutic target for renal cell carcinoma (RCC). The therapeutic potential of the MN-specific MAb G250 was evaluated in combination with IFN/IL-2/MCSF (interferon, interleukin-2, macrophage colony stimulating factor) and Ab2 (NUH82)-induced mouse serum (Ab3-82). Ab2s are monoclonal anti-idiotype antibodies raised against MAbG250 which have been shown to be useful as tumor vaccines for RCC.

Uemura et al., id. reported that mice with NUR-2 RCC xenografts were treated by peri-tumor injection of MAbG250 and/or cytokines or 0.2 ml of Ab3 sera with/without MCSF. The tumor volume in MAbG250 treated animals was significantly lower than in the controls. IFN or IL-2 treatments was similarly effective, but MCSF resulted in no significant tumor inhibition. The IFN/IL-2/MAbG250 therapy increased significantly the anti-tumor effects as compared to MAbG250 or cytokine monotherapy. Further, Ab3-based (Ab2-induced) immunotherapy resulted in tremendous tumor monotherapy growth inhibition as compared to MAbG250 or the other cytokine combination therapies.

MN-Specific Intrabodies—Targeted Tumor Killing Via Intracellular Expression of MN-Specific Antibodies to Block Transport of MN Protein to Cell Surface The gene encoding antibodies can be manipulated so that the antigen-binding domain can be expressed intracellularly. Such "intrabodies" that are targeted to the lumen of the endoplasmic reticulum provide a simple and effective mechanism for inhibiting the transport of plasma membrane proteins to the cell surface. [Marasco, W. A., "Review—Intrabodies: turning the humoral immune system outside in or intracellular immunization," *Gene Therapy*, 4: 11-15 (1997); Chen et al., "Intracellular antibodies as a new class of therapeutic molecules for gene therapy," *Hum. Gene Ther.,* 5(5): 595-601 (1994); Mhashilkar et al., *EMBO J.,* 14: 1542-1551 (1995); Mhashilkar et al., *J. Virol.,* 71: 6486-6494 (1997); Marasco (Ed.), *Intrabodies: Basic Research and Clinical Gene Therapy Applications*, (Springer Life Sciences 1998; ISBN 3-540-64151-3) (summarizes preclinical studies from laboratories worldwide that have used intrabodies); Zanetti and Capra (Eds.), "Intrabodies: From Antibody Genes to Intracellular Communication," *The Antibodies: Volume* 4, [Harwood Academic Publishers; ISBN 90-5702-559-0 (December 1997)]; Jones and Marasco, *Advanced Drug Delivery Reviews,* 31 (1-2): 153-170 (1998); Pumphrey and Marasco, *Biodrugs,* 9(3): 179-185 (1998); Dachs et al., *Oncology Res.,* 9(6-7); 313-325 (1997); Rondon and Marasco, *Ann. Rev. Microbiol.,* 51: 257-283 (1997)]; Marasco, W. A., *Immunotechnology,* 1(1): 1-19 (1995); and Richardson and Marasco, *Trends in Biotechnology,* 13(8): 306-310 (1995).]

MN-specific intrabodies may prevent the maturation and transport of MN protein to the cell surface and thereby prevent the MN protein from functioning in an oncogenic process. Antibodies directed to MN's EC, TM or IC domains may be useful in this regard. MN protein is considered to mediate signal transduction by transferring signals from the EC domain to the IC tail and then by associating with other intracellular proteins within the cell's interior. MN-specific intrabodies could disrupt that association and perturb that MN function.

Inactivating the function of the MN protein could result in reversion of tumor cells to a non-transformed phenotype. [Marasco et al. (1997), supra.] Antisense expression of MN cDNA in cervical carcinoma cells, as demonstrated herein, has shown that loss of MN protein has led to growth suppression of the transfected cells. It is similarly expected that inhibition of MN protein transport to the cell surface would have similar effects. Cloning and intracellular expression of the M75 MAb's variable region is to be studied to confirm that expectation.

Preferably, the intracellularly produced MN-specific antibodies are single-chain antibodies, specifically single-chain variable region fragments or sFv, in which the heavy- and light-chain variable domains are synthesized as a single polypeptide and are separated by a flexible linker peptide, preferably $(Gly_4\text{-}Ser)_3$ [SEQ ID NO: 116].

MN-specific intracellularly produced antibodies can be used therapeutically to treat preneoplastic/neoplastic disease by transfecting preneoplastic/neoplastic cells that are abnormally expressing MN protein with a vector comprising a nucleic acid encoding MN-specific antibody variable region fragments, operatively linked to an expression control sequence. Preferably said expression control sequence would comprise the MN gene promoter.

Antibody-Mediated Gene Transfer Using MN-Specific Antibodies or Peptides for Targeting MN-Expressing Tumor Cells An MN-specific antibody or peptide covalently linked to polylysine, a polycation able to compact DNA and neutralize its negative charges, would be expected to deliver efficiently biologically active DNA into an MN-expressing tumor cell. If the packed DNA contains the HSVtk gene under control of the MN promoter, the system would have double specificity for recognition and expression only in MN-expressing tumor cells. The packed DNA could also code for cytokines to induce CTL activity, or for other biologically active molecules.

The M75 MAb (or, for example, as a single chain antibody, or as its variable region) is exemplary of such a MN-specific antibody. Example 5 discloses heptapeptides (SEQ ID NOS: 107-109) that bind to the enzymatic center of the CA domain of the MN protein and, selected peptides or proteins comprising such heptapeptides would also be expected to bind to a binding side on the extracellular domain of the MN protein.

Imaging Use of Antibodies

Further, the MN-specific antibodies of this invention when linked to an imaging agent, such as a radionuclide, can be used for imaging. Biologically active antibody fragments or humanized monoclonal antibodies, may be preferred for imaging use.

A patient's neoplastic tissue can be identified as, for example, sites of transformed stem cells, of tumors and locations of any metastases. Antibodies, appropriately labeled or linked to an imaging agent, can be injected in a physiologically acceptable carrier into a patient, and the binding of the antibodies can be detected by a method appropriate to the label or imaging agent, for example, by scintigraphy. Exemplary are studies with the G250 Mab.

Steffens et al., *J. Urol.,* 159(5) (Suppl.): Abstract 562 (May 1998), describe a Phase I/II study with $^{131}$I-cG250 MAb in patients with metastasized RCC. MAb cG250 is a chimeric MAb in which constant regions of the mouse immunoglobulin have been exchanged for human immunoglobulin regions. [Oosterwijk and Debruyne, *World J. Urol.,* 13: 186 (1995).] Uptake of the cG250 MAb in primary RCC was shown to be as high as 0.52 percent of the injected dose per gram of tumor tissue (% ID/g). The study concluded that "$^{131}$I-cG250 is a promising candidate for radioimmunotherapy and a phase I/II activity dose escalation study was initiated to determine the safety, maximum tolerable dose (MTD) and therapeutic potential of $^{131}$I-cG250."

Bander et al., *Proceedings Am. Urol. Assoc.,* 155 (Suppl.): 583A (Abstract 1088) (May 1996), describes renal cancer imaging with the MN-specific MAb G250, which detects MN present in 85-90% of renal cancers but does not detect MN on normal kidney cells. Bander et al. reports that 48 patients were entered in clinical trials with $^{131}$I-G250 MAb.

MN Gene—Cloning and Sequencing

FIGS. 1A-C provides the nucleotide sequence for a full-length MN cDNA clone [SEQ ID NO: 1]. FIGS. 2A-F provides a complete MN genomic sequence [SEQ ID NO: 3]. The nucleotide sequence for a proposed MN promoter is shown in FIGS. 2A-F at nts 3001 to 3540 [SEQ ID NO: 24].

It is understood that because of the degeneracy of the genetic code, that is, that more than one codon will code for one amino acid [for example, the codons TTA, TTG, CTT, CTC, CTA and CTG each code for the amino acid leucine (leu)], that variations of the nucleotide sequences in, for example, SEQ ID NOS: 1 and 3 wherein one codon is substituted for another, would produce a substantially equivalent protein or polypeptide according to this invention. All such variations in the nucleotide sequences of the MN cDNA and complementary nucleic acid sequences are included within the scope of this invention.

It is further understood that the nucleotide sequences herein described and shown in FIGS. 1 and 2 represent only the precise structures of the cDNA, genomic and promoter nucleotide sequences isolated and described herein. It is expected that slightly modified nucleotide sequences will be found or can be modified by techniques known in the art to code for substantially similar or homologous MN proteins and polypeptides, for example, those having similar epitopes, and such nucleotide sequences and proteins/polypeptides are considered to be equivalents for the purpose of this invention. DNA or RNA having equivalent codons is considered within the scope of the invention, as are synthetic nucleic acid sequences that encode proteins/polypeptides homologous or substantially homologous to MN proteins/polypeptides, as well as those nucleic acid sequences that would hybridize to said exemplary sequences [SEQ. ID. NOS. 1, 3 and 24] under stringent conditions, or that, but for the degeneracy of the genetic code would hybridize to said cDNA nucleotide sequences under stringent hybridization conditions. Modifications and variations of nucleic acid sequences as indicated herein are considered to result in sequences that are substantially the same as the exemplary MN sequences and fragments thereof.

Stringent hybridization conditions are considered herein to conform to standard hybridization conditions understood in the art to be stringent. For example, it is generally understood that stringent conditions encompass relatively low salt and/or high temperature conditions, such as provided by 0.02 M to 0.15 M NaCl at temperatures of 50° C. to 70° C. Less stringent conditions, such as, 0.15 M to 0.9 M salt at temperatures ranging from 20° C. to 55° C. can be made more stringent by adding increasing amounts of formamide, which serves to destabilize hybrid duplexes as does increased temperature.

Exemplary stringent hybridization conditions are described in Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982); Tsuchiya et al., *Oral Surgery, Oral Medicine, Oral Pathology*, 71(6): 721-725 (June 1991).

Plasmids containing the MN genomic sequence (SEQ ID NO: 3)—the A4a clone and the XE1 and XE3 subclones—were deposited at the American Type Culture Collection (ATCC) on Jun. 6, 1995, respectively under ATCC Deposit Nos. 97199, 97200, and 97198.

Exon-Intron Structure of Complete MN Genomic Region

The complete sequence of the overlapping clones contains 10,898 by (SEQ ID NO: 3). FIG. 3 depicts the organization of the human MN gene, showing the location of all 11 exons as well as the 2 upstream and 6 intronic Alu repeat elements. All the exons are small, ranging from 27 to 191 bp, with the exception of the first exon which is 445 bp. The intron sizes range from 89 to 1400 bp. The CA domain is encoded by exons 2-8, while the exons 1, 10 and 11 correspond respectively to the proteoglycan-like domain, the transmembrane anchor and cytoplasmic tail of the MN/CA IX protein. Table 1 below lists the splice donor and acceptor sequences that conform to consensus splice sequences including the AG-GT motif [Mount, *Nucleic Acids Res.* 10: 459-472 (1982)].

TABLE 1

Exon-Intron Structure of the Human MN Gene

| Exon | Size | Genomic Position** | SEQ ID NO | 5' splice acceptor | SEQ ID NO |
|---|---|---|---|---|---|
| 1 | 445 | *3507-3951 | 25 | AGAAG gtaagt | 46 |
| 2 | 30 | 5126-5155 | 26 | TGGAG gtgaga | 47 |
| 3 | 171 | 5349-5519 | 27 | CAGTC gtgagg | 48 |
| 4 | 143 | 5651-5793 | 28 | CCGAG gtgagc | 49 |
| 5 | 93 | 5883-5975 | 29 | TGGAG gtacca | 50 |
| 6 | 67 | 7376-7442 | 30 | GGAAG gtcagt | 51 |
| 7 | 158 | 8777-8934 | 31 | AGCAG gtgggc | 52 |
| 8 | 145 | 9447-9591 | 32 | GCCAG gtacag | 53 |
| 9 | 27 | 9706-9732 | 33 | TGCTG gtgagt | 54 |
| 10 | 82 | 10350-10431 | 34 | CACAG gtatta | 55 |
| 11 | 191 | 10562-10752 | 35 | ATAAT end | |

| Intron | Size | Genomic Position** | SEQ ID NO | 3' splice acceptor | SEQ ID NO |
|---|---|---|---|---|---|
| 1 | 1174 | 3952-5125 | 36 | atacag GGGAT | 56 |
| 2 | 193 | 5156-5348 | 37 | ccccag GCGAC | 57 |
| 3 | 131 | 5520-5650 | 38 | acgcag TGCAA | 58 |
| 4 | 89 | 5794-5882 | 39 | tttcag ATCCA | 59 |
| 5 | 1400 | 5976-7375 | 40 | ccccag GAGGG | 60 |
| 6 | 1334 | 7443-8776 | 41 | tcacag GCTCA | 61 |
| 7 | 512 | 8935-9446 | 42 | ccctag CTCCA | 62 |
| 8 | 114 | 9592-9705 | 43 | ctccag TCCAG | 63 |
| 9 | 617 | 9733-10349 | 44 | tcgcag GTGACA | 64 |
| 10 | 130 | 10432-10561 | 45 | acacag AAGGG | 65 |

**positions are related to nt numbering in whole genomic sequence including the 5' flanking region [FIG. 2A-F]
*number corresponds to transcription initiation site determined below by RNase protection assay

Mapping of MN Gene Transcription Initiation and Termination Sites

Zavada et al., WO 95/34650 describes the process of mapping the MN gene transcription initiation and termination sites. A RNase protection assay was used for fine mapping of the 5' end of the MN gene. The probe was a uniformly labeled 470 nucleotide copy RNA (nt −205 to +265) [SEQ ID NO: 66], which was hybridized to total RNA from MN-expressing HeLa and CGL3 cells and analyzed on a sequencing gel. That analysis has shown that the MN gene transcription initiates at multiple sites, the 5' end of the longest MN transcript being 30 nt longer than that previously characterized by RACE.

MN Proteins and/or Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies of this invention, preferably the Mabs M75, V/10, MN12, MN9 and MN7 or their equivalents.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

MN proteins exhibit several interesting features: cell membrane localization, cell density dependent expression in HeLa cells, correlation with the tumorigenic phenotype of HeLa× fibroblast somatic cell hybrids, and expression in many human carcinomas among other tissues. MN protein can be found directly in tumor tissue sections but not in general in counterpart normal tissues (exceptions noted above as in normal gastric mucosa and gallbladder tissues). MN is also expressed sometimes in morphologically normal appearing areas of tissue specimens exhibiting dysplasia and/or malignancy. Taken together, these features suggest a possible involvement of MN in the regulation of cell proliferation, differentiation and/or transformation.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means.

Recombinant Production of MN Proteins and Polypeptides

A representative method to prepare the MN proteins shown in FIG. 1 or fragments thereof would be to insert the full-length or an appropriate fragment of MN cDNA into an appropriate expression vector. In Zavada et al., WO 93/18152, supra, production of a fusion protein GEX-3×-MN (now termed GST-MN) using a partial cDNA in the vector pGEX-3×(Pharmacia) is described. Nonglycosylated GST-MN (the MN fusion protein MN glutathione S-transferase) from XL1-Blue cells.

Zavada et al., WO 95/34650 describes the recombinant production of both a glycosylated MN protein expressed from insect cells and a nonglycosylated MN protein expressed from *E. coli* using the expression plasmid pEt-22b [Novagen Inc.; Madison, Wis. (USA)]. Recombinant baculovirus express vectors were used to infect insect cells. The glycosylated MN 20-19 protein was recombinantly produced in baculovirus-infected sf9 cells [Clontech; Palo Alto, Calif. (USA)].

Preparation of MN-Specific Antibodies

The term "antibodies" is defined herein to include not only whole antibodies but also biologically active fragments of antibodies, preferably fragments containing the antigen binding regions. Monoclonal and polyclonal antibodies use encompassed by that term as the context indicates. Further included in the definition of antibodies are bispecific antibodies that are specific for MN protein and to another tissue-specific antigen. Von Mehren et al., *Annu. Rev. Med.*, 54: 343-369 (2003) explains the use of mabs for cancer therapy and clearly delineates preferred fragments thereof.

Size is critical to the design of antibody fragments used for tumor therapy; smaller fragments often have diminished affinity and antigen specificity. A class of molecules of about 25 kDa, single-chain FV (scFv) molecules, composed of peptide-linked $V_H$ and $V_L$ domains, are large enough to be effective targeting vehicles while providing the basis for the construction of larger antibody-based reagents. However, the scFv molecules are small enough to allow their rapid renal elimination, and therefore are attractive candidates for radiolabelling. They can also be dimerized into larger molecules for slower systemic clearance and greater avidity for target cells, making them potentially useful in tumor therapy.

Zavada et al., WO 93/18152 and WO 95/34650 describe in detail methods to produce MN-specific antibodies, and detail steps of preparing representative MN-specific antibodies as the M75, MN7, MN9, and MN12 monoclonal antibodies. *Bispecific Antibodies*. Bispecific antibodies can be produced by chemically coupling two antibodies of the desired specificity. Bispecific MAbs can preferably be developed by somatic hybridization of 2 hybridomas. Bispecific MAbs for targeting MN protein and another antigen can be produced by fusing a hybridoma that produces MN-specific MAbs with a hybridoma producing MAbs specific to another antigen. For example, a cell (a quadroma), formed by fusion of a hybridoma producing a MN-specific MAb and a hybridoma producing an anti-cytotoxic cell antibody, will produce hybrid antibody having specificity of the parent antibodies. [See, e.g., *Immunol. Rev.* (1979); Cold Spring Harbor Symposium Quant. Biol., 41: 793 (1977); van Dijk et al., *Int. J. Cancer,* 43: 344-349 (1989).] Thus, a hybridoma producing a MN-specific MAb can be fused with a hybridoma producing, for example, an anti-T3 antibody to yield a cell line which produces a MN/T3 bispecific antibody which can target cytotoxic T cells to MN-expressing tumor cells.

It may be preferred for therapeutic and/or imaging uses that the antibodies be biologically active antibody fragments, preferably genetically engineered fragments, more preferably genetically engineered fragments from the $V_H$ and/or $V_L$ regions, and still more preferably comprising the hypervariable regions thereof. However, for some therapeutic uses bispecific antibodies targeting MN protein and cytotoxic cells would be preferred.

Humanized or Fully Human Antibodies to Various CA IX Domains

For clinical use, whether diagnostic/prognostic or therapeutic, but preferably for therapeutic use, it is preferable to use humanized or more preferably fully human CA IX specific antibodies. Such antibodies could be made to any of the CA IX domains, the extracellular domain, including the PG and CA regions, the TM and/or IC domains. It may be preferred to downregulate CA IX abnormally expressing cells by contacting them with CA IX-specific antibodies directed to the extracellular domain, and more specifically to either the PG and/or CA regions. One might also interfere with the signal transduction of CA IX by contacting the IC domain with antibodies specific thereto.

References that are representative of those explaining how one of skill in the art can prepare humanized and fully human antibodies by antibody engineering, including the use of transgenic mice include the following: Clark M., *Immunol. Today,* 21(8): 397-402 (August 2000); Davis et al., *Cancer Metastasis Rev.,* 18(4): 421-425 (1999); Gavilondo and Larrick, *Biotechniques,* 29(1): 128-132 and 134-136, 138 passim (July 2000); Zou and Rajewsky, *Science,* 262(5137): 1271-1274 (Nov. 19, 1993); Sandhu, J. S., *Crit. Rev. Biotechnol.,* 12(5-6): 437-462 (1992); Vaughan et al., *Nat. Biotechnol.,* 16(6): 535-539 (June 1998); Hoogenboom and Chames, *Immunol. Today,* 21(8): 371-378 (August 2000); Holliger and Bohlen, *Cancer Metastasis Rev.,* 18(4): 411-419 (1999); Owens and Young, *J. Immunol. Methods,* 168(2): 149-165 (Feb. 10, 1994); and Gura, T., *Nature,* 417(6889): 584-586 (Jun. 6, 2002).

Epitopes

The affinity of a MAb to peptides containing an epitope depends on the context, e.g. on whether the peptide is a short sequence (4-6 aa), or whether such a short peptide is flanked by longer aa sequences on one or both sides, or whether in testing for an epitope, the peptides are in solution or immobilized on a surface. Therefore, it would be expected by ones of skill in the art that the representative epitopes described herein for the MN-specific MAbs would vary in the context of the use of those MAbs.

The term "corresponding to an epitope of an MN protein/polypeptide" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the protein or polypeptide containing them is immunogenic and antibodies elicited by such a polypeptide or protein cross-react with naturally occurring MN proteins and polypeptides to a sufficient extent to provide protective immunity and/or anti-tumorigenic activity when administered as a vaccine.

MN-Specific Intrabodies—Targeted Tumor Killing Via Intracellular Expression of MN-Specific Antibodies to Block Transport of MN Protein to Cell Surface The gene encoding antibodies can be manipulated so that the antigen-binding domain can be expressed intracellularly. Such "intrabodies" that are targeted to the lumen of the endoplasmic reticulum provide a simple and effective mechanism for inhibiting the transport of plasma membrane proteins to the cell surface. [Marasco, W. A., "Review—Intrabodies: turning the humoral immune system outside in or intracellular immunization," *Gene Therapy,* 4: 11-15 (1997); Chen et al., "Intracellular antibodies as a new class of therapeutic molecules for gene therapy," *Hum. Gene Ther.,* 5(5): 595-601 (1994); Mhashilkar et al., *EMBO J.,* 14: 1542-1551 (1995); Mhashilkar et al., *J. Virol.,* 71: 6486-6494 (1997); Marasco (Ed.), *Intrabodies: Basic Research and Clinical Gene Therapy Applications*, (Springer Life Sciences 1998; ISBN 3-540-64151-3) (summarizes preclinical studies from laboratories worldwide that have used intrabodies); Zanetti and Capra (Eds.), "Intrabodies: From Antibody Genes to Intracellular Communication," *The Antibodies: Volume* 4, [Harwood Academic Publishers; ISBN 90-5702-559-0 (December 1997)]; Jones and Marasco, *Advanced Drug Delivery Reviews,* 31 (1-2): 153-170 (1998); Pumphrey and Marasco, *Biodrugs,* 9(3): 179-185 (1998); Dachs et al., *Oncology Res.,* 9(6-7); 313-325 (1997); Rondon and Marasco, *Ann. Rev. Microbiol.,* 51: 257-283 (1997)]; Marasco, W. A., *Immunotechnology,* 1(1): 1-19 (1995); and Richardson and Marasco, *Trends in Biotechnology,* 13(8): 306-310 (1995).]

MN-specific intrabodies may prevent the maturation and transport of MN protein to the cell surface and thereby prevent the MN protein from functioning in an oncogenic process. Antibodies directed to MN's EC, TM or IC domains may be useful in this regard. MN protein is considered to mediate signal transduction by transferring signals from the EC domain to the IC tail and then by associating with other intracellular proteins within the cell's interior. MN-specific intrabodies could disrupt that association and perturb that MN function.

Inactivating the function of the MN protein could result in reversion of tumor cells to a non-transformed phenotype. [Marasco et al. (1997), supra.] Antisense expression of MN cDNA in cervical carcinoma cells has shown that loss of MN protein has led to growth suppression of the transfected cells. It is similarly expected that inhibition of MN protein transport to the cell surface would have similar effects. Cloning and intracellular expression of the M75 MAb's variable region is to be studied to confirm that expectation.

Preferably, the intracellularly produced MN-specific antibodies are single-chain antibodies, specifically single-chain variable region fragments or scFv, in which the heavy- and light-chain variable domains are synthesized as a single polypeptide and are separated by a flexible linker peptide, preferably $(Gly_4\text{-}Ser)_3$.

MN-specific intracellularly produced antibodies can be used therapeutically to treat preneoplastic/neoplastic disease by transfecting preneoplastic/neoplastic cells that are abnormally expressing MN protein with a vector comprising a nucleic acid encoding MN-specific antibody variable region fragments, operatively linked to an expression control sequence. Preferably said expression control sequence would comprise the MN gene promoter.

Antibody-Mediated Gene Transfer Using
MN-Specific Antibodies or Peptides for Targeting
MN-Expressing Tumor Cells An MN-specific antibody or peptide covalently linked to polylysine, a polycation able to compact DNA and neutralize its negative charges, would be expected to deliver efficiently biologically active DNA into an MN-expressing tumor cell. If the packed DNA contains the HSVtk gene under control of the MN promoter, the system would have double specificity for recognition and expression only in MN-expressing tumor cells. The packed DNA could also code for cytokines to induce CTL activity, or for other biologically active molecules. The M75 MAb (or, for example, as a single chain antibody, or as its variable region) is exemplary of such a MN-specific antibody.

The following examples are for purposes of illustration only and are not meant to limit the invention in any way.

EXAMPLE 1

Preparation of Ca IX-Deficient Mice

Materials and Methods

Cloning of mouse Car9 cDNA

Mouse cDNA was obtained by RT PCR using primers derived from a human Car9 cDNA (EMBL Accession No. X66839; SEQ ID NO: 70). The template total RNA was prepared from C57BL/6J mouse stomach by acid guanidium thiocyanate-phenol/chloroform isolation [Siebert et al. (1993)]. First strand synthesis was carried out under standard conditions using SuperScript® II reverse transcriptase (Life Technologies, Germany). The set of the human primers was as follows: sense ATC CAC GTG GTT CAC CTC AG (SEQ ID NO: 71) and antisense CTT TGG TTC CCC TTC TGT GC (SEQ ID NO: 72); corresponding to the human cDNA fragment 760-1345 [SEQ ID NO: 73] of FIGS. 1A-1C. PCR reactions were carried out in 30 cycles (94° C., 30 sec, 55° C., 40 sec, and 72° C., 60 sec). Entire cDNA including open reading frame, 3'- and 5'-untranslated regions, was obtained by the 3' and 5' RACE (rapid amplification of cDNA ends). The 3' and 5' RACE kits (Life Technologies) were used as recommended by the manufacturer. Two gene-specific primers were used in 3' RACE: sense S1—CAG GAG AGC CCA GAA GAA AA (SEQ ID NO: 74); sense S2—TGA AGG GTC TCT GAO CAC AC (SEQ ID NO: 75). Three gene-specific primers were used in 5' RACE: antisense A1—AGC TGT AGG AGG AAG GCG AT (SEQ ID NO: 76); antisense A2—TGA CAG CAA AGA GAA GGC CA (SEQ ID NO: 77); antisense A3—CAG GGA AGG AAG CCT CAA TC (SEQ ID NO: 78). All resulting amplicons were cloned with the TA Cloning® KIT (Invitrogen, Netherlands) and sequenced on Applied Biosystems™ automatic sequencer. The cDNA sequence was deposited in EMBL (Accession No. AJ245857; SEQ ID NO: 79).

Cloning of Mouse Car9 Gene

A mouse embryonic stem (ES) cell 129/Sv BAC library (Genome Systems, USA) was screened with the full size Car9 cDNA. BAC DNA was analyzed with various restriction endonucleases and hybridized with the murine Car9 cDNA. Selected positive clones resulting from EcoRI (6.5 kb) and KpnI (1.4 kb) digestion were subcloned into pBluescript® KS and analyzed by automatic sequencing. The genomic sequence was deposited in the Gen Bank® (Accession No. AY049077; SEQ ID NO: 80).

Generation of Car9 Deficient Mouse

The EcoRI-HindIII fragment (5.9 kb) derived from the subcloned genomic EcoRI fragment and encompassing the first 6 exons of the Car9 gene was used for the construction of the pCar9-neo targeting vector. The pCar9-neo vector was constructed by standard recombinant techniques in a pBluescript® KS lacking BamHI restriction site. EcoRI-BamHI restriction fragment (1.5 kb) was used as a 5' genomic arm containing the promoter and a part of the first exon. BamHI-HindIII restriction fragment (4.5 kb) was used as a 3' genomic arm extending from the end of the first exon to the exon 6. Using this approach, the sequence of 14 bp region situated between the two BamHI sites was deleted from the first exon and replaced by the phosphoglycerate kinase-neomycin phosphotransferase (pgk-neo) cassette. Linearized targeting vector was introduced into E14 ES 129/Ola cell line by electroporation. Targeted ES cell clones were enriched by selection with G418 (400 µg/ml) and identified by Southern blot analysis using EcoRI-XbaI fragment as an external 5' probe and HindIII-EcoRI fragment as an external 3' probe (see FIG. 8). Cloned ES cell lines were injected into C57BL/6J blastocysts to produce C57BL/6]-129/Ola chimeric mice. Chimeras were created from two different ES clones possessing the pCar9-neo inserted by homologous recombination. The 129/Ola contribution in adult chimeric offspring was determined by coat color. Southern blotting with the above-described probes was used to recognize those mice that carried the targeted allele. Animal experiments were approved by the government office LAGETSI, Berlin, under the license number G 0224/00.

Analysis of the Car9 mRNA Expressed from the Targeted Gene

Isolation of RNA from $Car9^{+/+}$ and $Car9^{-/-}$ mouse stomach, RT PCR and 5' RACE were performed and analyzed as described above using the following primers: (i) primers for the 5'RACE: 900A antisense—GAT ACA TCC AAA CCT GGG ATC TCA A (SEQ ID NO: 81); 800A antisense—TCC TGC AGA AAG GCA GCC AAA ACT G (SEQ ID NO: 82); 700A antisense—CAG GGA AAC GGT GAC CAT TGA CTG T (SEQ ID NO: 83); (ii) primers for RT PCR: A (MNG sense)—GAC ACC CCA GTC AGC TGC ATG GCC T (SEQ ID NO: 84); B (NeoV)—CAT TCT CAG TAT TGT TTT GCC AAG TT (SEQ ID NO: 85); C (Neo sense)—CGA AGG AGC AAA GCT GCT ATT GGC C (SEQ ID NO: 86); D (MNA antisense)—TGT GCT CAG GAG CCT CGG GAG TCG A (SEQ ID NO: 87); E (EXS1 sense)—AGT CAA GGT TCC CAC GGG GAT GAA (SEQ ID NO: 88); F (1403A antisense)—AAG GAG GCT GTA TAA CAG GCA GGA C (SEQ ID NO: 89).

Preparation of the Rabbit Anti-Mouse CA IX Polyclonal Antibody

Full length Car9 cDNA was subcloned into the bacterial expression vector pGEX-4T-1. GST-mCAIX bacterial recombinant protein was produced in transformed E. coli strain DH5[[alpha]] cells following induction with 1 mM IPTG for 5 hrs and isolated from the bacterial cell lysate by affinity chromatography using Glutathione Sepharose® 4B (Amersham Pharmacia, Sweden). Rabbits were inoculated intramuscularly with 1 mg of the GST-mCAIX fusion protein and complete Freund's adjuvant. The next three injections at monthly intervals were given with 0.25 mg of the protein and incomplete adjuvant. To remove GST-specific antibodies, immune sera were purified using Glutathione Sepharose®-bound GST protein and tested for the reactivity to mouse CA IX. Selected serum was employed in 1:500 dilution in immunohistochemical analysis described below and in immunoblotting. Briefly, protein extracts were prepared from the stomach mucosa of Car9$^{+/+}$ and Car9$^{-/-}$ mice as well as from the mock-transfected and Car9 cDNA-transfected NIH3T3 cells using Lipofectamine™ (Life Technologies). Total protein concentrations were determined using BCA kit (Pierce, USA) in all samples and aliquots containing equal amount of total proteins were analyzed as described elsewhere [Pastorekova et al. (1997)].

Analysis of Blood Gases, Electrolytes and Serum Gastrin

Awakened mice were gently warmed for 10 min under a red light lamp to increase peripheral blood circulation. Blood (1.5-5.5 ml) from the tail vein was collected from several animals in heparin-, EDTA-treated tubes or non-treated tubes and analyzed for gases, electrolytes and pH using automated laboratory analyzers (Boehringer Mannheim, Germany) according to manufacturer's recommendations. The gastrin levels were measured using a specific antibody raised against human gastrin 17 as described [Hocker et al. (1996)].

Histochemical and Immunohistochemical Analyses

Tissue specimens from Car9$^{+/+}$ and Car9$^{-/-}$ mice were cut from stomach, duodenum, jejunum, ileum, colon, liver, pancreas, kidney and lung. The specimens were fixed in Carnoy's fluid (absolute ethanol+chloroform+glacial acetic acid in 6:3:1 ratio) for 24 hr at 4° C. or in 4% neutral-buffered formaldehyde for 24-48 hr at room temperature. The samples were then dehydrated, embedded in paraffin wax in a vacuum oven at 58° C., and sections of 5 µm were placed on gelatin-coated microscope slides. For the histochemical analysis, the sections were stained with hematoxylin/eosin and with diastase-resistant periodic acid Schiff® (PAS). The immunohistochemical analysis was carried out using the following primary antibodies: anti-CA IX rabbit polyclonal serum (described above, diluted 1:500), anti-PCNA rabbit polyclonal antibody, anti-E-cadherin rabbit polyclonal antibody, anti-α catenin rabbit polyclonal antibody and anti-β catenin rabbit polyclonal antibody (all from Santa Cruz Biotechnology, Santa Cruz, Calif., final concentration 5 µg/100µ), polyclonal sheep anti-human pepsinogen II antibody (Binding Site, UK, diluted 1:2000), and polyclonal rabbit anti-α subunit of porcine gastric H$^+$/K$^+$-ATPase (Calbiochem-Novabiochem, Germany, diluted 1:50). The immunostaining of tissue sections was performed by the biotin-streptavidin complex method, employing the following steps: (1) Pre-treatment of the sections with undiluted cow colostral whey for 40 min and rinsing in phosphate-buffered saline (PBS). (2) Incubation for 1 hr with the first antibody (except overnight incubation with anti-H$^+$/K$^+$-ATPase antibody) in PBS containing 1% bovine serum albumin (BSA). (3) Treatment with cow colostral whey for 40 min and rinsing in PBS. (4) Incubation for 1 hr with biotinylated swine anti-rabbit IgG (Dakopatts, Copenhagen, Denmark) or donkey anti-sheep/goat IgG (Binding Site) diluted 1:300 in 1% BSA-PBS. (5) Incubation for 30 min with peroxidase-conjugated streptavidin (Dakopatts) diluted 1:500 in PBS. (6) Incubation for 2 min in DAB solution containing 9 mg 3,3'-diaminobenzidine tetrahydrochloride (Fluka, Buchs, Switzerland) in 15 ml PBS+5µ 30% H$_2$O$_2$. The sections were washed three times for 10 min in PBS after incubation steps 2, 4, and 5. All the incubations and washings were carried out at room temperature and the sections were finally mounted in Permount® (Fisher Scientific, Fair Lawn, N.J.). The stained sections were examined and photographed with Nikon® Eclipse E600 (Tokyo, Japan) microscope.

Morphometric Analysis and Statistical Evaluation of Data

Stomach specimens from 10 wild type and 10 CA IX-deficient mice at the age of 26 and 35 weeks were stained for pepsinogen C and α subunit of H$^+$/K$^+$-ATPase. Both total and immunostained cells were counted in 50 longitudinally cut glands per mouse. Mann-Whitney rank test was applied to compare the numbers of cells in the Car9$^{+/+}$ versus Car9$^{-/-}$ mice. Relationship between the total numbers of cells and the numbers of parietal cells within the gastric units was analyzed in both groups of animals by regression analysis and the strength of the linear relationship was estimated by the Pearson's correlation coefficient R. Slopes of regression lines were compared by T test. P values of <0.05 and <0.01 were considered as significant and highly significant, respectively, for each of two tests.

Results

Identification of Car9 cDNA

Cloning and characterization of the cDNA and gene encoding the mouse CA IX was the first step towards generation of CA IX-deficient mice. Mouse Car9 cDNA fragment was isolated by RT PCR using primers derived from the human cDNA [Pastorek et al. (1994)] and the template RNA isolated from the stomach of C57 BL/6J mouse. The full-length cDNA was obtained by rapid amplification of cDNA ends in both 5'/3' directions. It encompasses 1965 by composed of 32 by 5' untranslated region, 1311 by open reading frame and 622 by 3' untranslated sequence (deposited in EMBL database under the Accession No. AJ245857; SEQ ID NO: 79).

The Car9 cDNA has a coding capacity for a 437 amino acid protein (deposited in EMBL database under the Accession No. CAC80975 (Q8VDE4); SEQ ID NO: 90) with a theoretical molecular mass of 47.3 kDa. The mouse protein shows 69.5% sequence identity with its human homologue and has a similar predicted domain arrangement [Opaysky et al. (1996)]. Amino acids (aa) 1-31 (SEQ ID NO: 91) correspond to a signal peptide. The N-terminal extracellular region of the mature protein (aa 32-389) (SEQ ID NO: 92) is composed of a proteoglycan-like region (aa 48-107) (SEQ ID NO: 93), and a carbonic anhydrase domain (aa 112-369) (SEQ ID NO: 94). The C-terminal region (aa 390-437) (SEQ ID NO: 95) consists of the transmembrane anchor (aa 390-411) (SEQ ID NO: 96) and a short cytoplasmic tail (aa 412-437) (SEQ ID NO: 97). Most of the sequence differences between the mouse and human CA IX were found within the proteoglycan-like (PG) region, while the CA domain revealed the highest conservation. However, out of the five key amino acids involved in the enzyme active site (His$^{94}$, His$^{96}$, Glu$^{106}$, His$^{119}$, Thr$^{199}$) [Christianson and Cox (1999)] all are preserved in human CA IX, but one is altered in the mouse isoenzyme (Thr$^{199}$→Ser). Despite this substitution, the mouse CA IX bound to a sulfonamide agarose suggesting that it may possess an enzyme activity.

Availability of Car9 cDNA allowed the analysis of the expression pattern of Car9 mRNA in mouse tissues. A ribonuclease protection assay (RNP) was carried out with a riboprobe of 170 by designed to detect the 3' part of the region encoding the CA domain. As expected on the basis of the distribution in human and rat tissues, the highest level of Car9 mRNA was detected in the mouse stomach. Medium level of Car9 mRNA was found in the small intestine and colon, while the kidney and brain showed very weak expression. The liver and spleen were negative. Noteworthy, the RNP signal was also present in the mouse embryo at the age of embryonic day E18.5, but not in embryonic stem cells and in the E10.5 embryo. This may suggest a role for CA IX in the development of the mouse gastrointestinal tract.

Organization of Car9 Gene

In order to isolate the Car9 gene and determine its organization, the full-length Car9 cDNA was used for screening of a mouse embryonic stem cell 129/Ola genomic library in pBAC108L. Obtained was one BACM-355(G13) clone that contained complete Car9 genomic sequence as confirmed by restriction mapping and Southern blot analysis of a mouse wild type genomic DNA. Three overlapping genomic fragments derived from this clone were subcloned into pBluescript® II KS.

Analysis of the genomic sequence (GenBank® Accession No. AY049077; SEQ ID NO: 80) revealed that the Car9 gene covers 8.7 kb of the mouse genome and consists of 11 exons and 10 introns. Distribution of introns and exon-to-protein domain relationships are similar to the human counterpart [Opaysky et al. (1996)]. The Southern hybridization pattern indicated that Car9 is a single copy gene. The EcoRI-HindIII fragment encompassing 5.9 kb and spanning the promoter region and exons 1-6 was used for a construction of the targeting vector.

Targeting of the Car9 Gene and Generation of Car9$^{-/-}$ Mice

To disrupt the Car9 gene in the mouse embryonic stem cells, a pCar9-neo targeting vector was constructed using the above-described genomic fragment. The first exon was interrupted by a replacement of a 14 by region (at position 268-282) with a pgk-neo cassette in a reverse orientation (FIG. 8A). Since the deleted region corresponded to a part of the PG domain of CA IX, insertion of a pgk-neo cassette caused a disruption of this domain and a separation of the sequence encoding the signal peptide from the rest of the protein. Moreover, deletion of the 14 by was designed to cause a shift of the reading frame in the murine Car9 mRNA and prevent its correct translation.

After electroporation and selection of E14 embryonic stem cells by G418, eight clones that had undergone homologous recombination were identified. Two of them were chosen for further manipulations. As confirmed by the Southern blotting with the 3' and 5' external probes, both targeted clones were shown to be without unintended rearrangements at the Car9 locus. Using these two lines of mutant ES cells, chimeric and Car9$^{+/-}$ mice that were healthy and fertile were generated. The intercrossing of the heterozygous mice resulted in all three genotypes with Mendelian distribution among the offspring, as demonstrated by Southern blot analysis from the tail genomic DNA samples. [Southern blot showed the genotyping of the offspring from a heterozygous mating. DNA from tails of 3-weeks old mice was digested with EcoRI and hybridized with the 3' probe. The bands corresponded to wild type (6.5 kb) and mutated (8.3 kb) allele, respectively.]

RT PCR analysis with the gene specific primers revealed that homozygous Car9$^{-/-}$ mice expressed mRNA that was lacking exon 1. In contrast, both mutated and wild type transcripts contained exons 2-11. Furthermore, pgk-neo-derived primers in combination with exon 1-specific primers allowed for PCR amplification of the genomic DNA from Car9$^{-/-}$ mice confirming that the cassette was successfully introduced into the Car9 locus. Corresponding RT PCR amplicons from mutated RNA were absent, bringing additional evidence that the 5' end of Car9 mRNA is missing. It was deduced from the 5' mRNA sequence obtained by RACE analysis that this was due to unexpected splicing of mutated Car9 transcript leading to deletion of the 5' untranslated region as well as the sequences coding for signal peptide, large part of PG-like domain and majority of pgk-neo cassette. Thus, the Car9$^{-/-}$ mice expressed chimeric mRNA that contained 77 nucleotides derived from the pgk-neo cassette linked via the 3' part of PG domain-related sequence (starting from nt 283) to the rest of Car9 cDNA. There were two potential translation initiation codons. The first AUG codon was out of frame. The second one would potentially lead to translation of the truncated protein that could not be properly processed due to the lack of signal peptide. Absence of this putative translation product in the mutant stomach was demonstrated by Western blotting analysis performed with the rabbit polyclonal antiserum raised against the full-length recombinant mouse CA IX protein. [Western blot analysis of the protein extracts from the wild type Car9$^{+/+}$ and mutant Car9$^{-/-}$ mouse stomach epithelium were performed. Extracts from NIH3T3 cells transfected with the full length Car9 cDNA and from mock-transfected NIH3T3 cells served as controls. The blot was processed with anti-CA IX rabbit antiserum raised against a full-length recombinant GST-mCA IX protein.]

The CA IX-deficient mice showed no deviations from their wild type litter mates in growth, behavior, reproductive potential, health and life span. No morphological and histological abnormalities were observed in their lung, spleen, liver, kidney, jejunum, ileum and colon.

Gastric Phenotype of CA IX Mutant Mice

Histopathological examination of stomach specimens from Car9$^{-/-}$ mice regularly revealed remarkable hyperplastic changes when compared to stomachs of their heterozygous and wild type litter mates. While no changes were visible in mutant mice during embryonic development, an increase in mucosal thickness was seen at postnatal day P0.5. The hyperplasia became prominent in 4 weeks-old animals, but it did not progress with the age and remained similar in 1.5 years old mice.

In adult Car9$^{-/-}$ mice, the hyperplastic changes affected only the glandular stomach epithelium, while the squamous epithelium of the non-glandular forestomach remained normal. The most pronounced hyperplasia concerned the corpus region. Mucosal folds were more prominent in the homozygous mutant mice than in their wild type littermates, and the pit-to-gland ratio increased to 1:3 or even 1:2 from the usual 1:4 in the wild type and heterozygous animals. These hyperplastic changes in the Car9$^{-/-}$ mouse mucosa were accompanied with numerous pathological cysts lined with a single layer of low cuboidal epithelial cells. No morphological signs of dysplasia were observed in any of the stomach sections from 2 to 3 mice checked at monthly intervals up till 1.5 years of age and normal structure of the subepithelial lamina propria was seen at all age points.

Presence of hyperplasia in Car9$^{-/-}$ mouse mucosa was confirmed by the morphometric analysis of stomach sections that revealed a highly significant (P=0.0007) difference between the total numbers of cells counted per 50 gastric units in 10 Car9$^{+/+}$ mice compared to 10 Car9$^{-/-}$ mice (see FIG. 9A). Based on median values, the mucosa of CA IX deficient mouse contained approximately by 30% more cells than the control epithelium.

Interestingly, small duodenal adenomas with slight to moderate dysplasia were observed in three of 15 Car9$^{-/-}$ mice. It cannot be excluded that their appearance was also associated with loss of CA IX, which is normally expressed in the proximal small intestine.

Cell Proliferation, Death and Adhesion in Hyperplastic Mucosa

To explore possible mechanisms that underlie gastric hyperplasia in Car9$^{-/-}$ mice, performed were immunohistochemical analyses of the stomach sections obtained from both mutant and wild type mice. First, an antibody raised against the mouse CA IX to analyze its distribution in the wild type stomach was employed. Strong CA IX-specific staining occurred in the corpus but not in the forestomach of adult Car9$^{+/+}$ mice, consistent with the reversible presence of phenotypic changes only in the corpus, but not in the forestomach of the Car9$^{-/-}$ mice. Positive staining of the Car9$^{+/+}$ stomach corpus was distributed in all epithelial cells, but its intensity was strongest at the basolateral surfaces of mature glandular and superficial pit cells. Noteworthy, immunohistochemical staining revealed lack of CA IX in stomachs of E15.5 and E17.5 embryos, but showed that it is weakly expressed in the stomach of the newborn mice.

Because hyperplasia may involve an increase in cellular proliferation and/or decrease in apoptosis, the determination of whether one of these two processes, or both were responsible for the observed gastric phenotype was considered important. Studied was the expression of PCNA, a marker of proliferating cells and observed characteristic staining pattern restricted to the proliferative zone in the $Car9^{+/+}$ mouse mucosa. In contrast, the proliferative compartment was considerably expanded in $Car9^{-/-}$ mice as suggested by the widely spread staining signal. Total number of PCNA-positive cells in mutant epithelium was markedly increased. On the other hand, annexin V staining and TUNEL DNA fragmentation analysis performed to assess the extent of apoptosis did not reveal any differences between the $Car9^{-/-}$ and $Car9^{+/+}$ mouse stomachs in proportion of apoptotic cells, thus indicating that hyperplasia could not be attributed to an impaired cell death.

Further immunohistochemical stainings were carried out to analyze possible relationship between gastric epithelial hyperplasia and expression of adhesion-related molecules, including E-cadherin, β-catenin and α-catenin. These analyses were based on the importance of cadherin/catenin-mediated pathways for proper development and organization of epithelial tissues [Gumbiner, B. (1996)] and on the observations supporting possible role of CA IX in cell adhesion and communication [Zavada et al. (2000), Pastorekova et al. (1997)]. We found that gastric mucosa of the wild type animals expressed E-cadherin predominantly at the basolateral surfaces of mature epithelial cells located in the deep glands and surface pits, in a fashion reminiscent of normal CA IX distribution. In contrast, E-cadherin-positive staining of $Car9^{-/-}$ mouse stomach was slightly weaker throughout the mucosa and its regional arrangement was less apparent. However, total E-cadherin level determined by Western blotting in mutant stomach did not differ from the wild type control. Expression of α- and β-catenins showed similar pattern: both catenins were mostly present in mature epithelial cells of $Car9^{+/+}$ mice, while their staining signal in $Car9^{-/-}$ mice was weaker and disorganized. The data indicate that loss of CA IX may result in perturbation of normal cell-cell adhesion albeit without pronounced effect on the expression level of the studied adhesion molecules.

Aberrant Cell Lineage Distribution in the Corpus of $Car9^{-/-}$ Mouse Stomach

The above observations led us to examine the spatial distribution and proportion of the major cell types in the stomach epithelium of the $Car9^{-/-}$ mice in comparison with the $Car9^{+/+}$ controls. To detect the mucus-producing pit cells, sections of the glandular stomachs were stained with a diastase-resistant periodic acid of Schiff® (PAS). PAS staining of the wild type stomach corpus was strongly positive in the surface pit region. In contrast, $Car9^{-/-}$ mice showed a markedly different staining pattern, with the intense PAS signal mostly expanded from the surface to the base of the corpus mucosa, although there was some inter-individual variation in the extent of the PAS positive area. This could probably occur as a result of abundant production and aberrant migration of the mucous cells that consequently populated inappropriate areas of the gastric epithelium.

Numbers of parietal cells were assessed by the morphometric analysis following immunohistochemical detection of α subunit of $H^+/K^+$-ATPase that served as a parietal cell lineage marker. As it is shown on FIG. 9B, stomachs of $Car9^{-/-}$ mice contained significantly reduced proportion of parietal cells when compared to the wild type controls (P=0.0051). Regression analysis revealed significant positive correlation between the numbers of parietal cells and the total numbers of cells in gastric units from both wild type and CA IX-deficient mouse stomachs (Pearson's correlation coefficients $R^2=0.68$ and $R^2=0.61$, respectively). Slopes of the regression lines of gastric units from $Car9^{-/-}$ and $Car9^{+/+}$ mice, respectively, were significantly different (P<0.0005) and CA IX-deficient gastric units showed clear tendency toward diminished production of parietal cells with increasing hyperplasia (FIG. 9D). Altogether, these data support the view that loss of CA IX resulted in the perturbed differentiation of parietal cells.

To determine the position and number of functional chief cells, we performed an immunohistochemical staining for a pepsinogen C, a chief cell lineage-specific marker [Karam et al. (1997)]. Cells containing pepsinogen granules were confined to the basal area in both normal and CA IX-deficient mouse gastric epithelia. However, morphometric analysis has revealed a marked depletion of chief cells in corpus mucosa of $Car9^{-/-}$ mice. As demonstrated on FIG. 9C, decrease in percentage of chief cells was highly significant (P=0.0001).

Abnormal composition of the $Car9^{-/-}$ mouse gastric epithelium suggests that loss of CA IX has affected a cell-lineage allocation by redirecting the differentiation program towards the formation of pit cells at the expense of parietal and chief cells.

Systemic Acid-Base and Electrolyte Status

Based on the abundant expression in normal gastric mucosa and relationship to other carbonic anhydrases acting in alimentary tract, CA IX has been proposed to participate in maintenance of acid-base balance. Its basolateral localization indicated that it could be involved in electrolyte exchange within the mucosa and/or with the submucosal region rather than in production of gastric acid that is directly linked to the catalytic properties of highly active CA II isoenzyme [Parkkila et al. (1996)]. Therefore, systemic acid/base and electrolyte status of the $Car9^{-/-}$ mice were examined. Blood samples taken from the adult mutant mice were compared to the samples from the age-matched wild type controls with respect to blood pH and content of plasma electrolytes. We have also measured the serum level of gastrin, as it may predict changes in gastric acid secretion. However, no statistically significant differences were found in any of the examined parameters (Table 2), suggesting that elimination of CA IX resulting in gastric hyperplasia did not lead to any gross physiological defects.

TABLE 2

Plasma electrolytes, blood pH and serum gastrin were measured in two separate measurements from the blood of $Car9^{+/+}$ and $Car9^{-/-}$ animals.

| Genotype | pH | $HCO_3^-$ (mM) | $Cl^-$ (mM) | $K^+$ (mM) | $Na^+$ (mM) | Serum gastrin (pg/ml) |
|---|---|---|---|---|---|---|
| $Car9^{+/+}$ | 7.30 ± 0.035 | 24.35 ± 1.95 | 119 ± 2 | 3.8 ± 0.6 | 139.5 ± 4.5 | 60 ± 4 |
| $Car9^{-/-}$ | 7.32 ± 0.015 | 24.15 ± 0.55 | 118 ± 6 | 4.9 ± 0.4 | 141.5 ± 3.5 | 59 ± 12 |

Discussion

Morphogenesis of gastric mucosa in mouse is a complex process initiated during late gestation by a series of events. These include formation of primordial buds around embryonic day E18, precursor cell differentiation from postnatal day P1 to P7, elongation of buds due to increase in number of precursors and their progeny from P7 to P15 and finally, assembly of gastric units and compartmentalization of cellular migration-differentiation programs between P15 and P21 [Karam et al. (1997)]. Accomplishment of this complex process results in self-renewing epithelium in which cell proliferation is confined to the stem and precursor cells in the middle portion of the unit. Their progenitors bi-directionally migrate and simultaneously differentiate to supply the surface and the base of the unit by functional mature cells [Wright, N. A. (2000)]. Maintenance of a dynamic equilibrium between cell differentiation and proliferation ensures the proper mucosal functioning and integrity.

Expression of CA IX is firstly detectable at low level in mouse newborn stomach at day P0.5, during the early phase of gastric unit morphogenesis, and its abundance increases towards the adult age. The protein occupies membranes of epithelial cells throughout the adult mucosa of gastric body, but its level is higher in mature superficial pit cells and deep glandular cells.

Consistently with expression pattern and coincidentally with the course of gastric unit morphogenesis, targeted disruption of a Car9 gene encoding CA IX leads to manifestation of the gastric hyperplasia. First mild changes in the thickness of the gastric mucosa appear in the newborn $Car9^{-/-}$ mice as early as at day P0.5. This is the time when expression of CA IX initiates in the wild type stomach. Absence of CA IX results in partial elongation of buds probably as a consequence of excessive cell proliferation, while the normal bud elongation occurs later, between days P7 and P15. Hyperplastic changes are clearly visible in the 4-weeks' mutant mouse mucosa, when the unit morphogenesis is finished, but do not progress with the age. Deregulated proliferation affects the mucosa without any evident morphological alterations of the cells and without any significant changes in the cell death.

Interestingly, no additional phenotypic changes were observed in other tissues that normally do express CA IX, except the rare cases of duodenal adenoma. This could be due to redundancy provided by related carbonic anhydrase isozymes [Parkkila et al. [1996]] similarly as it has been suggested for disruption of Tcf-7/2 gene resulting in changes only in the small intestine but not in the colon, where this gene is highly expressed [Korinek et al. (1998)].

The hyperplasia of $Car9^{-/-}$ gastric corpus mucosa is accompanied with increased pit-to-gland ratio and aberrant distribution of mucus-producing pit cells as well as significant reduction of parietal and chief cells. These alterations indicate that loss of CA IX may directly affect lineage repertoire and partially disturb positional instructions that normally direct upward migration of pit cell precursors and their descendants. Alternatively, elimination of CA IX may affect differentiation of parietal cells that are the important source of instructions affecting other cells lineages [Karam et al. (1997)]. Hence, disbalance in production of pit and chief cells may be secondary to changes in parietal cell population.

Phenotype of mice with the targeted disruption of Car9 gene is reminiscent of other genetically modified models, including the mice lacking α/β subunits of $H^+/K^+$-ATPase [Spicer et al. (2000), Scarff et al. (1999)], Kvlq1 voltage-gated potassium channel [Lee et al. (2000)], and the mice overexpressing TGFα [(Sharp et al. (1995)]. These models show some similarities, but differ from $Car9^{-/-}$ model in specific aspects. Mice lacking either of two subunits of $H^+/K^+$-ATPase are hypergastrinemic and achlorhydric, consistently with the established role of $H^+/K^+$-ATPase in production of gastric acid. Both models contain normal numbers of parietal cells but these have aberrant secretory membranes. Number of chief cells is reduced in mice deficient in β subunit but not in α subunit. The Kvlq1-deficient mice display mucous neck cell hyperplasia and production of vacuolated, nonfunctional parietal cells leading to hypergastrinemia and hypochlorhydria.

In contrast, there are no significant changes in serum gastrin levels in mice overexpressing TGF α despite expanded mucous pit cell population and depletion of mature parietal and chief cells. These findings are in accord with our observations. Because changes in levels of serum gastrin usually reflect perturbed gastric acid secretion, both studies indicate that CA IX and TGF α may not be directly involved in the production of gastric acid but may have other important functions within the gastric mucosa.

Based on all available facts, CA IX appears to contribute to balance between differentiation and proliferation in gastric mucosa via negative control of cell proliferation and as a possible regulatory component of migration-associated differentiation program. Loss of CA IX therefore leads to uncoupling of proliferation control from differentiation and migration signals and, consequently, to disruption of normal mucosal integrity and architecture.

Molecular pathways underlying the proposed CA IX function are not known. As a cell surface molecule, CA IX may be involved in reception and/or processing of maturation signals impeding the proliferation. In addition, it may serve as an acceptor of instructions that direct differentiation, spatial assignment and allocation of cell lineages. Taking into account phenotypic similarities with additional transgenic models, list of possible candidates acting in the CA IX-related putative signal transduction pathway may involve mesenchymal transcription factor Fkh6 [Kaestner et al. (1997)], Shh protein expressed in the epithelium of glandular stomach [Ramalho-Samos et al. (2000)], pS2 trefoil protein [Lefebvre et al. (1996)], NF-κ B2 transcription factor [Ishikawa et al. (1997)], and/or modulator of cadherin function IQGAP1 [Li et al. (2000)]. However, genetic modifications of these genes lead to phenotypic changes beyond that observed with CA IX, involving more distinct alterations in differentiation program and/or physiological defects, such as development of dysplasia, or systemic changes in electrolyte status. Therefore, it is possible that they act upstream of CA IX or occupy independent signaling traits.

In fact, CA IX possesses several features predisposing it to function in a signal transduction. The PG-like region located at the N-terminus of human CA IX homologue was shown to possess the cell adhesion capacity in vitro [Zavada et al. (2000)]. Via this region, CA IX located at the basolateral membranes may influence transmission of adhesion signals between mucosal cells and/or between mucosal and mesenchymal cells. In support of this view, stomach mucosa of mice lacking CA IX shows disorganized distribution of critical adhesion-related molecules E-cadherin, α-catenin and β-catenin, although their levels are not markedly altered. Moreover, assuming from the homology with other carbonic anhydrases, large enzyme core of CA IX forms wide and deep pocket that may potentially serve as a receptor site. This idea is quite plausible given the capability of CA domain present in RPTP [β and γ to bind contactin, a neural cell-specific regulator of adhesion and differentiation [Peles et al. (1995)].

Functional involvement of the carbonic anhydrase activity of mouse CA IX in stomach mucosa is unclear, first due to lack of precise knowledge concerning its efficiency in catalyzing reversible conversion between carbon dioxide and carbonic acid and second because of absence of any systemic acid-base and gastrin imbalance in Car9$^{-/-}$ mice. The latter may be also related to the presence of other CA isoenzymes whose activity may compensate for deficiency of CA IX. A highly active cytosolic CA II is present in surface epithelial cells where it produces bicarbonate and in parietal cells where it provides protons for secretion of gastric acid [Parkkila et al. (2000)]. Another isoenzyme, salivary CA VI, is swallowed into the stomach in order to buffer mucosal surface by removal of excessive acid in the form of carbon dioxide [Id]. In addition, CA IV is expressed in the endothelial cells of the submucosal capillaries and mitochondrial CA V in parietal cells and G cells [Fleming et al (1995), Saarnio et al, (1999)]. However, significance of individual isoenzymes and their interplay in gastric morphogenesis and physiology is largely unknown also because the corresponding animal models are not available. The only exception is heritable CA II deficiency induced in mouse by chemical mutagenesis. Those mutant mice suffer from renal acidification, growth retardation and calcification of blood vessels, but no gastric phenotype has been reported [Lewis et al. (1998)].

Thus, Car9$^{-/-}$ mice represent the first animal model of carbonic anhydrase deficiency constructed by the gene targeting. Moreover, phenotypic consequences of the targeted disruption of Car9 gene demonstrate important and nonredundant role of CA IX in control of cell proliferation/differentiation and protection of integrity of the stomach mucosa. CA IX is clearly required for the normal gastric morphogenesis and coordination of the dynamic homeostasis within the gastric epithelium. These conclusions are in accord with the high level of CA IX in normal human stomach mucosa and its diminished expression observed in gastric tumor cell lines and tumors in vivo [Pastorekova et al. (1997)].

In summary, the analysis of CA IX null-mutation in mice revealed the biological importance of this protein and provided a useful model for clarifying its role in the morphogenesis of stomach mucosa. As can be seen in Example 2, the CA IX-deficient mice were also integral to the aspects of the invention herein concerning a new series of monoclonal antibodies.

EXAMPLE 2

CA IX-Specific Monoclonal Antibodies Generated from CA IX-Deficient Mice

Materials and Methods
Cell Culture

Hybridoma cell lines were grown in DMEM medium supplemented with 10% FCS (BioWhittaker, Verviers, Belgium), 2 mM glutamine and 40 μg/ml gentamicin (Lek, Slovenia) at 37° C. in 5% $CO_2$ in air. The same cultivation conditions were applied to following cell lines that were used either as a source of CA IX antigen or as negative controls: mouse NIH 3T3 fibroblasts permanently transfected with the full-length human CA9 cDNA (NIH 3T3-flCA IX) and corresponding mock transfected NIH 3T3-neo controls [Pastorek et al. (1994)], MDCK cells transfected with the full-length CA9 cDNA (MDCK-flCA IX) and corresponding MDCK-neo controls, human HT 29 colon carcinoma cells as well as human HeLa cervical carcinoma cells naturally expressing CA IX, and C33a cervical carcinoma cells negative for CA IX.

For the immunization purposes, the cells grown for 24-48 h were washed twice in PBS, scraped, collected by centrifugation and re-suspended in appropriate volume of PBS. For the final booster, NIH 3T3-flCA IX cells were extracted with OCG extraction buffer composed of 0.5M NaCl, 0.5% octyl-beta-D-glucopyranoside (Chemical Institute SAV, Bratislava, Slovakia), 0.1 mM PMSF) for 30 min at 4° C., scraped, centrifuged for 5 min at 13 000 rpm and dialyzed against PBS for 48 h at 4° C.

Cloning and Preparation of Recombinant GST-CA IX Proteins

The cDNA fragments encoding PG and CA extracellular domains of CA IX (see FIG. 5) were either individually or together amplified by specific primers using a full-length CA9 cDNA as a template. The fragment coding for PG domain (aa 52-125) (SEQ ID NO: 98) was obtained with PG3 (sense) 5'-TAG AAT TCG GCT CTT CTG GGG AAG AT-3' (SEQ ID NO: 99) and PG4 (antisense) 5'-ATA CTC GAG GGG TTC TTG AGG ATC TCC-3' (SEQ ID NO: 100) primers, and the fragment coding for CA domain (aa 121-397) (SEQ ID NO: 101) was obtained with CA5 (sense) 5'-TAG AAT TCG ATC CTC AAG AAC CCC AG-3' (SEQ ID NO: 102) and CA6 (antisense) 5'-AAT CTC GAG ACT GCT GTC CAC TCC AGC-3' (SEQ ID NO: 103) primers. The combination of primers PG3 and CA6 was employed to produce cDNA fragment encoding PG+CA domains (aa 52-397) (SEQ ID NO: 104).

The resulting PCR products were cloned into pGEX 4T-1 bacterial plasmid via EcoRI and XhoI restriction sites inserted in the primer sequences. Fusion proteins GST-PG, GST-CA, GST-PG+CA were expressed in *E. coli* strain DH5α using the standard procedure [Gibadulinova et al. (1999)]. The full-length fusion GST-flCA IX protein generated earlier was produced in parallel. The proteins were purified by affinity chromatography using Glutathion-S Sepharose® (Amersham Pharmacia) and eluted with 10 mM GSH (reduced glutathion). Obtained proteins were utilized either as antigens for MAb testing or as immunogen (GST-CA) for immunization.

Immunization

For immunization, CA IX-deficient mice generated and characterized by Ortova Gut et al. (2002) were used at the age of eight to ten weeks. The mice were injected intraperitoneally (i.p.) with $5 \times 10^6$ NIH 3T3-flCA IX cells in 0.5 ml PBS. Three weeks later, the mice received either the same i.p. injection of NIH 3T3-flCA IX cells or i.p. injection of $5 \times 10^6$ HT-29 cells in 0.5 ml PBS. After another three weeks, mice were boosted alternatively as follows: (i) i.p. with 100 μg of GST-CA protein bound to Glutathion-S Sepharose® in 0.5 ml PBS, (ii) intravenously (i.v.) with 100 μg of eluted GST-CA protein in 200 μl PBS, (iii) i.p. with $5 \times 10^6$ NIH 3T3-flCA IX cells in 0.5 ml PBS, (iv) i.v. with 200 μl OCG extract of NIH 3T3-CA IX cells. Splenocytes were harvested three days later and fused with the Sp2/0 myeloma cells.

Production of Mabs

The fusion of splenocytes from immunized mice with Sp2/0 cells was carried out according to Lane et al. (1986). Hybridomas were selected in DMEM-HAT medium. The supernatants were screened for the specific reactivity towards CA IX by ELISA as described below. Positive hybridoma cultures were cloned by limiting dilution using Terasaki microplates. Clonal hybridoma cells lines were expanded, subjected to freezing-refreezing and repeatedly tested for reactivity to CA IX. Large quantities of antibodies were purified from hybridoma culture medium using affinity chromatography on Protein A Sepharose® Cl-4B (Amersham Biosciences AB, Upsala, Sweden) as described by Ey et al. (1978).

ELISA Screening

Screening of positive hybridomas was performed by a sandwich ELISA. Microplate wells were coated overnight at 37° C. with RIPA extract (specified below) of NIH 3T3-fICA IX cells, diluted 1:10 in PBS, and in parallel with analogous extract of NIH 3T3-neo cells as a negative control. Then the coated wells were incubated with undiluted culture media from individual hybridomas. Peroxidase-labeled pig anti-mouse IgG (Sevapharma, Praha, Czech Republic) was used as detector. M75 MAb was employed as positive control.

For the differential ELISA screening, the wells were coated with the following antigens: 10 ng/well of GST-fICA IX, 10 ng/well of GST-CA IX, RIPA extract of HeLa cells diluted 1:10 in PBS, RIPA extract of HT-29 cells diluted 1:10 in PBS, and then assayed as above.

Determination of Isotypes

MAb isotypes were determined by ELISA using affinity purified rabbit anti-mouse IgG1, IgG2a, IgG2b, IgG3, IgM and IgA antibodies (Mouse Monoclonal Antibody Isotyping Reagents, Sigma, St. Louis, USA) according to instructions of the manufacturer.

Immunofluorescence

Cells grown on glass coverslips were fixed in ice-cold methanol at −20° C. for 5 min. Non-specific binding was blocked by incubation with PBS containing 1% BSA for 30 min at 37° C. Then, the cells were sequentially incubated with primary antibodies diluted in PBS with 0.5% BSA (PBS-BSA) for 1 h at 37° C., washed three times with PBS-BSA for 10 min, incubated with anti-mouse FITC-conjugated horse antibody (Vector Laboratories, Burlingame, USA.) diluted 1:300 in PBS-BSA for 1 h at 37° C. and washed as before. Finally, the cells were mounted onto slides in mounting medium with Citifluor (Agar), analyzed by a Nikon® E400 epifluorescence microscope equipped with objectives Plan-Fluor™ 20×, 40× and photographed. Images were acquired by Nikon® Coolpix® 990.

Immunoblotting

Cells grown in confluent monolayer were rinsed twice with cold PBS and solubilized in ice-cold RIPA buffer (1% Triton X-100, 1% deoxycholate, 0.15 M NaCl, pH 7.2) containing COMPLETE™ cocktail of protease inhibitors (Roche Diagnostics GmbH, Mannheim, Germany) for 30 min on ice. The extracts were collected, cleared by centrifugation at 15 000 rpm for 10 min at 4° C. and stored at −80° C. Protein concentration in extracts was quantified by BCA protein assay reagent (Pierce, Rockford, Ill., USA).

Total cellular extracts (50 μg of proteins/lane) were resolved in 10 SDS-PAGE gel. The proteins were then transferred onto PVDF membrane (Amersham Pharmacia Biotech, Little Chalfont Buckinghamshire, England). After blocking in 5% nonfat dry milk with 0.2% Nonidet P40 in PBS, the membrane was probed with MAbs (undiluted hybridoma medium), washed and treated with secondary anti-mouse HRP-conjugated swine antibody diluted 1:5000 (SEVAPHARMA, Prague, Czech Republic). The protein bands were visualized by enhanced chemiluminiscence using ECL kit (Amersham Pharmacia Biotech).

Cell Biotinylation

Cells in monolayer of 70%-80% confluence grown in a 10 cm dish were washed with ice-cold buffer A (20 mM sodium hydrogen carbonate, 0.15 M NaCl, pH 8.0). Immediately before use, 1 mg of NHS-LC-Biotin (Pierce) was dissolved in 50 μl DMSO, mixed with 4 ml buffer A, added to cells and incubated for 60 minutes at 4° C. After the biotinylation, the cells were washed 5 times with buffer A and extracted as described above.

Immunoprecipitation.

Tested MAb in a volume of 1 ml culture medium was bound to 25 μl 50% suspension of protein-A Sepharose® (Pharmacia, Uppsala, Sweden) in RIPA buffer for 2 hrs at RT. Biotinylated cell extract (200 μl) was pre-cleared with 20 μl of 50% suspension of protein-A Sepharose® and then added to bound MAb. Immunocomplexes collected on protein-A Sepharose® were washed according to Williams et al. (1985), boiled 5 minutes in Laemmli loading buffer and separated by SDS-PAGE gel (10%) electrophoresis. Afterwards, the proteins were transferred onto PVDF membrane and revealed with peroxidase-conjugated streptavidin (1:1000, Pierce) followed by ECL.

Biotinylation of MAbs

Purified MAbs were labeled with NHS-LC-Biotin (Pierce) according to the instructions of the manufacturer. Briefly, 2 mg purified IgG dissolved in PBS, pH 8.0 were incubated with 100 μg NHS-LC-Biotin for 2 h on ice. Free biotin was removed using microconcentrator (PALL Gelman Lab., Wien, Austria) or gel filtration.

Competitive Antibody-Binding ELISA

Extract of NIH 3T3-fICA IX cells was adsorbed on microplate wells at a concentration corresponding to 50% of maximal binding of labeled MAbs. Coated plates were washed and saturated with 10% FCS in PBS. Serial tenfold dilutions of purified MAbs in 30 μl and a constant amount of biotinylated MAb in 30 μl were added and incubated overnight at 4° C. The plates were washed and peroxidase-labeled streptavidin (Pierce) was used as a detector.

Results

Generation and Basic Characterization of Monoclonal Antibodies to CA IX

To avoid an epitope preference caused by the significant difference in the N-terminal sequences of the mouse and human CA IX proteins and produce monoclonal antibodies directed also to other protein regions (FIG. 5), we prepared the new CA IX-specific monoclonal antibodies with the CA IX-deficient mice constructed in Example 1 [Ortova Gut (2002)]. It was hypothesized that those mice that do not express their own CA IX protein would recognize the entire human CA IX molecule as non-self and direct their humoral response to different portions of the protein.

We examined five immunization protocols based on different combinations of human cells that naturally express high level of CA IX (HT 29), mouse cells with ectopic overexpression of CA IX (NIH 3T3-fICA IX) and finally, recombinant protein composed of glutathion-S transferase fused to CA domain of CA IX (GST-CA). Three protocols led to successful production of CA IX-specific MAbs (Table 3).

TABLE 3

Overview of immunization protocols, fusions and yields of CA IX-specific hybridomas.

| Fusion No. | Immunization Scheme[a] | Total No. Of clones | Non-Specific[b] | MN-specific hybridomas | | |
|---|---|---|---|---|---|---|
| | | | | Initial No.[c] | Subcloned[d] | Stable |
| I | 1. NIH 3T3-fICA IX i.p. 2. NIH 3T3-fICA IX i.p. 3. NIH 3T3-fICA IX i.p. | 50 | 0 | 1 | 0 | 0 |
| II, III | 1. NIH 3T3-fICA IX i.p. 2. NIH 3T3-fICA IX i.p. 3. HT-29 i.p. | 1700 | 50 | 60 | 6 | 0 |

TABLE 3-continued

Overview of immunization protocols, fusions and yields of CA IX-specific hybridomas.

| Fu-sion No. | Immunization Scheme[a] | Total No. Of clones | Non-Specific[b] | MN-specific hybridomas | | |
|---|---|---|---|---|---|---|
| | | | | Initial No.[c] | Subcloned[d] | Stable |
| IV | 1. NIH 3T3-fICA IX i.p.<br>2. NIH 3T3-fICA IX i.p.<br>3. OCGexNIH-CA IX i.v. | 800 | 40 | 5 | 5 | 4 |
| V, VI | 1. NIH 3T3-fICA IX i.p.<br>2. NIH 3T3-fICA IX i.p.<br>3. GST-CA IX i.p. | 1220 | 17 | 9 | 6 | 2 |
| VII, VIII, IX, X | 1. NIH 3T3-fICA IX i.p.<br>2. HT-29 i.p.<br>3. GST-CA IX i.p. | 4400 | 16 | 83 | 12 | 5 |
| | Altogether | 8170 | 123 | 158 | 29 | 11 |

[a]Brief description of the immunization scheme including order of injections, type of immunogen and route of administration (i.p. - intraperitoneal, i.v. - intravenous) Immunogens: NIH 3T3-fICA IX - mouse NIH3T3 fibroblasts stably transfected with the wild type CA9 cDNA OCGexNIH-CA IX - extract from NIH 3T3-fICA IX cells obtained using OCG detergent HT-29 - human colorectal carcinoma cells naturally expressing MN/CA IX GST-CA IX - recombinant bacterial CA domain of MN/CA IX fused to GST
[b]Non-specific hybridomas producing the MAbs against non-CA IX mouse or human cellular proteins of unknown identity
[c]MN-specific hybridomas that were successfully subcloned
[d]Hybridomas with optimum viability and stable productivity of MN-specific Mabs Altogether, we performed 10 fusions and screened 8170 hybridomas. Initially selected 158 hybridomas producing CA-IX reactive antibodies in ELISA screening were reduced to 29 hybridomas after subcloning and finally to 11 viable and stable clones after freezing-refreezing. Seven of these antibodies were of IgG2a isotype, two antibodies were IgG1 and two were of IgM isotype (Table 4).

TABLE 4

Summary of the isotypes and reactivity of the new CA IX-specific monoclonal antibodies in comparison with M75

| | | Antigen | | | |
|---|---|---|---|---|---|
| | | N, HT, G | HT, HL, M | HT, HL, M? | M, HT |
| Mab | Isotype | ELISA | Blotting | Precipitation | Fluorescence |
| M75 | IgG2b | + | + | + | + |
| IV/6 | IgM | + | + | nd | + |
| IV/18 | IgG2a | + | + | + | + |
| IV/14 | IgM | + | − | nd | nd |
| IV/11 | IgG1 | + | − | − | + |
| V/10 | IgG2a | + | − | + | + |
| V/12 | IgG2a | + | − | + | + |
| VII/13 | IgG1 | + | − | − | − |
| VII/20 | IgG2a | + | − | + | + |
| VII/28 | IgG2a | + | − | + | + |
| VII/32 | IgG2a | + | − | + | + |
| VII/38 | IgG2a | + | − | + | + |

Reactivity of the new Mabs including M75 for comparison was examined using the following antigens:
N - extract from transfected mouse NIH 3T3-fICA IX cells expressing human CA IX protein in parallel with corresponding NIH 3T3-neo as negative control
HT - extract from human HT-29 cells naturally expressing high level of CA IX
HL - extract from human HeLa cells naturally expressing CA IX in dense culture
G - recombinant GST-fICA IX fusion protein
M - transfected MDCK-fICA IX cells compared to MDCK-neo controls The antibodies were first tested in ELISA against the full-length CA IX antigen expressed in mouse and human cell lines. All antibodies bound to extracts of NIH 3T3-CA IX cells and HT-29 cells, but not to control NIH 3T3-neo cells and C33a CA IX-negative human cervical carcinoma cells. They also recognized GST-CA IX protein, but not the GST only, supporting their specificity for CA IX (Table 5).

TABLE 5

Target domains of the CA IX-specific monoclonal antibodies based on the reactivity to truncated forms of CA IX

| Antigen Mab | PGCA (G) ELISA | PG (G) | ΔCA (M) Precipitation | ΔCA (M) Fluorescence | ΔPG (M) | Target domain |
|---|---|---|---|---|---|---|
| M75 | + | + | Nd | + | − | PG |
| IV/18 | + | + | Nd | + | − | PG |
| V/10 | + | − | − | − | + | CA |
| V/12 | + | − | − | − | + | CA |
| VII/20 | + | − | − | − | + | CA |
| VII/28 | + | − | − | − | + | CA |
| VII/32 | + | − | − | − | + | CA |
| VII/38 | + | − | − | − | + | CA |

Domain-specificity of the monoclonal antibodies was determined with the following antigens:
PGCA (G) - N-terminal portion of CA IX molecule containing both PG and CA domains expressed as GST-PGCA fusion protein
PG (G) - PG domain expressed as GST-PG fusion protein
CA (G) - CA domain expressed as GST-CA fusion protein
ΔCA (M) - truncated variant of CA IX protein expressed in MDCK cells from transfected cDNA with deletion in a region encoding CA domain
ΔPG (M) - truncated variant of CA IX protein expressed in MDCK cells from transfected cDNA with deletion in a region encoding PG domain Indirect immunofluorescence demonstrated that all the examined antibodies bound to an antigen localized at the cell surface of transfected polarized epithelial cells MDCK as well as of HT-29 human colon carcinoma cells that naturally express CA IX. [The cells were grown to confluence, fixed by methanol and incubated with representative monoclonal antibodies followed by FITC-conjugated anti-mouse antibodies. All the antibodies revealed plasma membrane CA IX-specific staining in both cell lines used. Cells with omitted primary antibody and treated only by the secondary antibody served as a negative control.] Distribution of the staining signal was identical to distribution of CA IX visualized by M75.

Noteworthy, only two of the new Mabs, namely IV/6 and IV/18, and the old Mab M75 reacted in immunoblotting with naturally expressed CA IX derived from HT-29 and HeLa cells, respectively, and with CA IX ectopically expressed in MDCK cells. The antibodies of IgG2 isotype were all able to immunoprecipitate CA IX from the extract of both HT-29 and HeLa human cells labeled by biotinylation. [The cells were grown to confluence, labeled by biotin, and extracted with RIPA buffer. CA IX was immunoprecipitated from the cell extracts as described in Materials and Methods, separated by SDS-PAGE, and blotted. Blots were incubated with peroxidase-conjugated streptavidin and developed by ECL.] They also immunoprecipitated the CA IX protein ectopically expressed in MDCK cells.

Determination of Target Domains by Antibody Binding to Recombinant Variants of CA IX The initial tests proved the reactivity of the new monoclonal antibodies towards human CA IX. To reveal the target protein domains, we selected the antibodies with the best properties and performed additional series of analyses using recombinant variants of CA IX protein produced in bacteria and variants of CA IX protein expressed from truncated cDNAs transfected to NIH 3T3 and MDCK cells, respectively. [Immunofluorescence detection of CA IX and its deletion variants ΔPG and ΔCA expressed in transfected MDCK cells was used. The cells were grown to confluence, fixed by methanol and incubated with new monoclonal antibodies followed by FITC-conjugated anti-mouse antibodies. The antibodies revealed plasma membrane CA IX-specific staining only in the cells expressing CA IX variant containing their target domain.] The results summarized in Table 5 indicate that one of the newly produced antibodies, namely IV/18, is directed to PG domain, similar to M75.

The other six antibodies (i.e. V/10, V/12, VII/20, VII/28, VII/32 and VII/38) target the CA domain, as also confirmed by their capacity to immunoprecipitate the full-length CA IX protein, but not its deletion variant lacking a large portion of CA domain. [CA IX was immunoprecipitated from extracts of MDCK cells expressing the full length CA IX protein and its ΔCA variant, respectively. The cells were grown to confluence, labeled by biotin, and extracted with RIPA buffer. CA IX was immunoprecipitated from the cell extracts as described in Materials and Methods, separated by SDS-PAGE, and blotted. Blots were incubated with peroxidase-conjugated streptavidin and developed by ECL.] In fact, these reagents represent a proof-of-concept that CA IX-deficient mice are suitable for generation of monoclonal antibodies that recognize the regions outside the immunodominant PG domain.

Mapping of Antigenic Sites by Competitive Binding

In order to determine relative positions of the antigenic sites, recognized by the monoclonal antibodies within their target domains, we performed a competitive-binding assay. Biotin-labeled purified antibodies were allowed to bind in the concurrent presence of increasing amount of the non-labeled competitive antibodies. Extent of binding of the labeled antibody in the presence of the non-labeled competitor was expressed as percent of the binding in the absence of the competitor. Examination of all different pairs of the MAbs including the homologous ones and their classification according to the extent of competition allowed for elaboration of a basic map indicating principal relationships between the antibodies, their clustering and relationships between the clusters (FIG. 6). The map shows that the M75 and IV/18 antibodies recognize overlapping antigenic sites in a separate region, consistent with their proven specificity for the PG domain of CA IX protein. The antibodies targeting CA domain form three clusters. Two pairs of the MAbs, namely V/12 versus VII/20 and V/10 versus VII/32, respectively, showed significant mutual competitions indicating their overlapping epitopes within two separable antigenic sites. However, strong one-sided competition between one member of each of two antigenic site-related clusters, i.e. V/10 (label) and V/12 (competitor), indicated that the two sites partially extend over each other via the epitopes corresponding to V/10 and V/12 MAbs. MAb VII/38 belongs to a distinct site within a CA domain of CA IX.

The map of antigenic sites provides important information that can be further utilized to propose non-competing pairs of antibodies that would be suitable for sensitive immunodetection of CA IX antigen using capture-detection approaches.

Discussion

Due to a strong association with cancer tissues and proposed functional involvement in tumor progression, carbonic anhydrase IX has become an interesting object for both basic and clinical research, as evidenced by the growing number of CA IX-related papers [summarized in Pastorek and Pastorekova (2003)]. Most of these papers were based on the utilization of a CA IX-specific monoclonal antibody M75 [Pastorekova et al. (1992)]. The M75 MAb has facilitated acquisition of many important data, but certain aspects of CA IX could not be touched without additional detection tools, including the monoclonal antibodies directed to M75-independent antigenic sites.

We describe herein the generation of such antibodies using a mice deficient for CA IX as donors of immune splenocytes for fusion and hybridoma production. This strategy has been chosen in order to eliminate the epitope preference possibly related to a high regional homology between the mouse and human proteins particularly in the sequences outside the M75 target domain [Ortova Gut et al. (2002)]. Our assumption that the mice lacking CA IX would recognise also these regions as a non-self has been approved by the production of six monoclonal antibodies directed to CA domain of CA IX. Interestingly, the immunization protocol that led to successful generation of the anti-CA antibodies involved the injection of a recombinant CA IX variant containing only the CA domain as a key third dose component. Instead, injection with the full-length CA IX antigen extracted from the transfected NIH 3T3 cells resulted in production of antibodies out of which MAb IV/18 competes with M75, and two other antibodies (IV/6 and IV/14) also appear to bind to the PG region, similar to M75. This experience suggests that even in the absence of endogenous mouse CA IX protein that would normally compromise the immune recognition of highly homologous regions of human CA IX (including the CA domain) by the immunized mice, the M75 MAb-binding PG domain behaves as strongly immunodominant. The reason for the apparent immunodominance could reside in both N-terminal exposition and the amino acid sequence of the PG domain that is highly acidic and composed of four perfect and two imperfect hexameric repeats [Opaysky et al. (1996)]. These repetitions potentially offer multiple binding sites (and may influence also relative affinity of MAbs) and the very N-terminal position of this region may allow for its spatial protrusion from the presumably globular CA domain in the extracellular portion of CA IX [Pastorek et al. (1994)].

These attributes of PG domain may also explain the finding that anti-PG MAbs recognize denatured CA IX protein in immunoblotting, while anti-CA MAbs fail to do so. It is possible to speculate, that relatively short PG domain with repetitive motifs constitutes a linear antigenic region that does not suffer from denaturing, while a presumably globular structure of the large CA domain carrying putative conformational epitopes can be completely disrupted. This idea is consistent with the finding that both anti-PG and anti-CA are able to immunoprecipitate native CA IX antigen extracted with mild detergents as well as the antigen on the surface of transfected MDCK cells that were fixed by methanol. Such antigen apparently possesses intact epitopes irrespective of whether they are linear or conformational.

As delineated by the competitive immunoassay performed with the repertoire of the new MAbs, CA domain contains three distinct antigenic sites, two of which partially overlap. While it is possible to propose relative mutual positions of these sites, it is difficult to predict their localization on CA domain. Based on the extent of the deletion that was associated with the loss of binding of these MAbs we can at least conclude that the CA antigenic region spans the amino acids 166-397 (SEQ ID NO: 105) of CA IX. However, it cannot be excluded, that the deletion lead to disconnection of the antigenic site(s) partly located also on the amino acids 135-166 (SEQ ID NO: 106) that remained preserved in the ΔCA deletion variant.

Characteristics of the new CA IX-specific monoclonal antibodies allow us to foresee their clinical applications. In the basic research, these antibodies represent important specific reagents for study of functional contribution of PG and CA domains, respectively. Each of these two extracellular domains of CA IX has been associated with different aspects of tumor progression: enzymatically active CA domain is thought to contribute to acidification of tumor microenvironment and PG domain (absent from other CA isoforms) is believed to determine its participation in adhesion-related processes. Using the MAbs generated as disclosed herein in CA IX-deficient mice, it will be possible to differentiate between biological effects exerted by these domains expressed separately in the form of deletion variants or mutants of CA IX.

Nevertheless, the main potential of the new MAbs is in their clinical applications. Many clinical studies of different tumor tissues have recently demonstrated predictive and prognostic value of CA IX, especially related to its tight connection with tumor hypoxia [Loncaster et al. (2001); Chia et al. (2001); Giatromanolaki et al. (2001); Koukourakis et al. (2001); Hui et al. (2002)]. In this respect, it is obvious that the new MAbs can be utilized for detection and/or targeting of CA IX-expressing cancer cells in different settings (as reviewed in von Mehren et al, 2003). Future experiments designed to examine the biological activity of these MAbs will also show, whether they could be of any significance for antibody-mediated anti-cancer therapy, analogously to well-known MAbs directed to HER-2/neu/c-erbB2 and EGFR oncoproteins. Also importantly, the availability of non-competing antibodies specific for distinct antigenic sites on two separate extracellular domains offers an opportunity to elaborate a sensitive assay that could be particularly important for detection of CA IX in body fluids of cancer patients. As disclosed herein and detailed in Example 3 below the extracellular portion of CA IX is shed from tumor cell surfaces and can be detected in body fluids, particularly blood and urine of cancer carriers by immunoprecipitation. Development of a fast and reliable micro-assay based on combination of the antibodies described in this work could potentially allow for non-invasive monitoring of cancer patients.

In summary, the anti-human CA IX monoclonal antibodies generated using CA IX-deficient mice and characterized in this paper, represent important tools for improvement of our knowledge on structure-function relationship in CA IX molecule, for better understanding of CA IX role in cancer development, for elucidating its clinical implications and for clinically relevant detection of CA IX in biological materials.

EXAMPLES 3-10

The following materials and methods were used in the Examples 3-10 below.

Materials and Methods

Cell and Tumor Cultures and Media

The cell line HT29 (DSMZ ACC299), derived from colorectal carcinoma, and A498 (ATCC No. HTB-44) from renal clear cell carcinoma, were grown in D-MEM supplied with 10% FCS (Gibco), unless otherwise stated. In Example 8, the HT29 cells were cultivated in Dulbecco's MEM medium BioWhittaker, Verviers, Belgium) supplemented with 10% FCS (BioWhittaker) and 160 g/ml gentamicin (Lek, Slovenia). The A549 lung carcinoma cells were grown in DMEM (Sigma) supplemented with 10% FCS (Globepharm), L-glutamine (2 µM), penicillin (50 IU/ml), and streptomycin sulphate (50 µg/ml). Cell cultures were maintained in a humidified atmosphere with 5% $CO_2$ at 37° C. For short-term cultures of tumors, fresh tumor excisions were cut in 1 mm pieces, rinsed with PBS, suspended in D-MEM with 10% FCS (about 50-100 mg of fresh weight of tumor fragments in 5 ml of the medium) and incubated in 5 cm Petri dishes at 37° C. in a 5% $CO_2$ incubator. Cell lysis buffer: PBS with 1% Igepal CA-630 (Sigma), 0.25% deoxicholate and proteinase inhibitors [Zavada et al. (2000)].

Effect of Reoxygenation of Hypoxically Induced CA IX Protein Tissue Culture

Studies of gene expression were performed on A549 lung carcinoma cells approaching confluence in normal growth medium. Parallel incubations were performed on aliquots of cells in normoxia (humidified air with 5% $CO_2$) and hypoxia. Hypoxic conditions were generated in a Napco® 7001 incubator (Precision Scientific) with 0.1% $O_2$, 5% $CO_2$, and balance $N_2$. Reoxygenation experiments were performed by exposure of cells to hypoxia for 16 h followed by a return to normoxia for the indicated time.

Patient Serum and Urine

All patients routinely underwent ultrasound and CT before surgery to obtain information for the standard staging protocol. Serum and urine from these patients were obtained before surgery and 5 days after it. In some patients a sample of tumour tissue after nephrectomy was used for short-term RCC cultures. In all these patients the diagnosis was confirmed by the histological finding of RCC. 18 patients acted as controls, these had been admitted to the hospital for other urological conditions than RCC (infectious disease, urinary stones, other urological tumours, etc.). The study was approved by the Departmental Ethics Committee. Sera of healthy blood donors were kindly provided by Dr. Eva Hamšíková, Institute of Haematology and Blood Transfusion, Prague.

Blood Plasma from Nude Mice with Xenograft of HT29 Cells

Male nude mice CD-1 nu/nu (Charles River, Germany) were injected subcutaneously in the flank with 5×105 HT29 cells at 6-8 weeks of age. Approximately 2-3 weeks after injection, heparinized plasma samples were prepared; blood was drawn from either the eye or by heart puncture prior to mouse dissection and xenograft removal.

Immunological Reagents and Methods

Monoclonal antibodies: M75 specific for PG region of CA IX has been produced by Pastorekova et al. (1992); V-10 specific for CA domain generated as described in Example 2. The isotype of MAb M75 is IgG 2b and of V-10 is IgG 2a. The IgG was purified from hybridoma TC fluid by affinity chromatography as before protein A Sepharose® CL-4B column (Amersham Pharmacia Biotech, Uppsala, Sweden). Purity of the M75 was checked by SDS-PAGE [(Zavada et al. (2000)].

M75 was labeled by $^{125}I$ using chloramines T method as described by Hunter (1978). Free $^{125}I$ was removed by the size exclusion chromatography on Sephadex® G50 column (Amersham Pharmacia Biotech). Specific activity of the radiolabeled antibody was determined after the precipitation of the antibody together with BSA carrier protein by trichloroacetic acid.

To determine the immunoreactive fraction, $10^4$ cpm of $^{125}I$-M75 in 100 µl of PBS containing 3% BSA and 0.05% Tween®-20 were added to wells of 96-well plates coated with increasing amounts of antigen extracted from HT29 cells and incubated for 2 hours at 37° C. The bound radioactivity was measured after washings and lysis with 2M NaOH, using the Clinigamma counter from Pharmacia LKB (Uppsala, Sweden). Nonspecific binding was determined in the presence of 100-fold molar excess of unlabeled M75 and subtracted from the total binding. The results were analyzed as described by Lindmo et al. (1984).

For the concentration of immune complexes formed by the MAbs with CA IX antigen from TC media or cell extracts Protein A-Sepharose® (Sigma #P-9424) was used; the MAb-CA IX complexes from human sera or urine were adsorbed to anti-mouse IgG-Agarose (Sigma #A-6531). Alternatively, we used Magnetic beads anti-mouse IgG (Immunotech-Coulter #1181). The immunoperoxidase conjugate M75-Px was prepared using the Peroxidase labeling kit (Roche Diagnostics #1829696, GmBH, Mannheim, Germany).

Immunoprecipitation of s-CA IX from mouse blood plasma and cell culture medium was performed as follows: A confluent monolayer of HT29 cells was washed with PBS and fresh medium was applied (15 ml per 10 cm dish). After 18 h incubation, the medium was harvested and filtered through a 0.22 μm-pore-size filter. Samples of cell culture medium and heparinized plasma were preincubated with protein A-Sepharose® CL-4B (Pharmacia Biotech) to remove potentially competing calf and mouse IgG prior to immunoprecipitation with M75. Immunoprecipitation was performed from 1 ml of heparinized plasma (diluted 1:2 with PBS) and from 3 ml of cell culture media by incubation with 50 μl of suspension of protein A-Sepharose® with bound M75 Mab for 2 h at room temperature with gentle rotation.

Immunoprecipitation of s-CA IX from human sera and urine was carried out as follows: to 0.75 ml of serum or 10 ml of urine (both clarified by centrifugation) was added 2 μg of M75 IgG for 60 min. at room temperature. Following this, each sample was supplied with 50 μl of 50% pre-washed anti-mouse IgG Agarose beads and the suspension was agitated on a rotator for 4 hours or overnight at +4° C. Then the beads with bound mouse IgG and immune complexes were centrifuged (1200 rpm/2 min.), the pellet was resuspended in 1 ml PBS-T (phosphate buffered saline with 0.05% Tween®-20, Sigma) centrifuged as above and the beads were heated in 60 μl of Laemmli sample buffer at 100° C. for 5 min. blood sera. The precipitates, when analysed by Western blots developed with M75-peroxidase conjugate and ECL, in addition to s-CA IX p50/54 were showing strong non-specific bands of 92 and 125 kDa. These cross-reactive proteins were present also in control human sera.

We were able to eliminate the non-specific bands by using two different monoclonal antibodies. For immunoprecipitation MAb V-10 specific for the CA domain was employed, while M75-peroxidase conjugate, specific for PG domain, was used for developing the blots. Only the lanes loaded with precipitate obtained with M75 show, in addition to CA IX bands at 50 and 54 kD, also the cross-reaction with human serum proteins of 92 and 128 kDa. The lanes employing new non-M75 MAbs for immunopreciipitation showed no cross-reaction visible on the scan or the film.

A second problem encountered with CA IX immunoprecipitated from human sera was that Western blots looked dirty or obscured by smears and clouds. We suspected that this was due to a partial denaturation of M75-IgG during conjugation with peroxidase, using HPLC we found that M75 IgG which had been conjugated with activated peroxidase under conditions recommended by the manufacturer formed oligomers several times larger than corresponding to 5 Px molecules for 1 IgG. Therefore, we reduced the Px:IgG ratio 3× and obtained the conjugate yielding a clear background on Western blots with immunoprecipitate from human sera.

Immunohistochemistry

CA IX immunostaining using monoclonal antibody M75 in Example 9 was as described [for example in Wykoff et al. (2000)]. Slides were viewed by two observers. The CA IX score was derived from the product of (i) the percentage of tumor cells staining for CA IX and (ii) the average intensity of that staining on a scale of 1 (least intense) to 3.

ELISA

The "sandwich" was composed of these layers in Max-iSorp™ strips or plates (NUNC, Denmark): (1) immobilized phase: MAb V-10 IgG, 5 μg/ml in 50 mM carbonate buffer pH 9.6, was adsorbed 3 h at room temperature; (2) test antigen dilutions in PBS with 1% FCS were adsorbed overnight at +4° C.; (3) M75-Px conjugate 1:5000 in PBS with 1% FCS, was allowed to bind for 2 hr. at room temperature; (4) orthophenylene diamine (OPD, Sigma) 1 mg/ml in 100 mM phosphate/citrate buffer pH 5.0+1 μl/ml of 30% $H_2O_2$ (Sigma), was allowed to react 30 min. in the dark at room temperature. After each step the strips or plates were washed 4× with PBS-T.

Immunoblots

SDS-PAGE and Western blotting were as described before [Zavada et al. (2000)]. Whole cell protein extracts were prepared from tissue culture cells by 10 homogenization in denaturing conditions [Wiesener et al. (1998)]. Aliquots were separated by SDS-polyacrylamide gel electrophoresis and transferred to Immobilon™-P membranes (Immobilon™-P, Millipore, Bedford, UK). CA IX was detected using the mouse monoclonal anti-human CA IX antibody M75 (1:50) as described [(Pastorekova et al. (1992)]. For Examples 3-7 and 10, HRP-conjugated goat-anti-mouse immunoglobulin (DAKO) (1:2000) was applied for 1 h at room temperature (RT). ECL Plus (Amersham Pharmacia) was used for visualization. For Example 8, the cells (cell monolayer and sediment of tumor homogenates, respectively) were extracted by RIPA buffer (1% Triton X-100, 0.1% sodium deoxycholate, 1 mM PMSF, 20 μg/ml trypsin inhibitor, 1 mM ethylenediaminetetraacetic acid in PBS) for 30 min at room temperature. The extracts were then centrifuged (15 min at 13,000 rpm) and concentration of proteins was determined by BCA assay (Pierce) according to the manufacturer's instruction. The extracts (aliquots containing 30 g of proteins) were directly analyzed. Culture medium and plasma were first concentrated by immunoprecipitation with M75 Mab as described above. Samples were separated by electrophoresis on a 10% SDS-PAGE gel, blotted onto the membrane as described above. The membrane was incubated with $^{125}$I-labeled M75 Mab and then exposed to X-ray film.

EXAMPLE 3

Cell-Associated and Soluble CA IX in Cell Cultures

Western blot analysis was performed to determine CA IX in culture media (soluble CA IX) or in cell extracts (cell-associated CA IX), as described above. As previously described, various human tumor cell lines, when grown to a high density, produce CA IX seen on Western blots as a "twin" protein p54/58 [Pastorekova et al. (1992); Zavada et al., (1993)]. Present results are consistent with these reports: cell extracts from the colorectal carcinoma cell line HT29 show 54 and 58 kDa bands of CA IX on the Western blot. Media from these cell cultures also contain CA IX, but the soluble form is somewhat shorter, with 2 bands of 50 and 54 kDa. The total content of CA IX in cell extracts is about 10× higher than in the medium, as determined by ELISA (FIG. 10).

EXAMPLE 4

CA IX in Tumor Extracts and in Media of Short-Term Cultures of RCC

The study included 50 patients (28 men and 22 women, mean age 63.2, range 36-79) with newly diagnosed RCC. Western blots of the extracts from RCC tumors resemble blots of tumor cell cultures. They also contain two bands of 54 and 58 kDa, and the proportion of CA IX per total protein is somewhat lower than in HT29 cells (FIG. 10). All of the 6 RCC tumor extracts were strongly CA IX positive. Control kidneys and a non-RCC tumor, an angiolipoma, do not contain any CA IX.

Shedding of s-CA IX was examined in short-term cultures: fresh tumor excisions from the patients were cut in 1 mm pieces and grown in short-term cultures in DMEM with 10% FCS, as described above. The medium from a suspension culture of tumor fragments was harvested after 2 days and analysed by Western blotting and ELISA (FIG. 10). Again, both the concentration and $M_r$ of s-CA IX were comparable (two bands of 50 and 54 kDa) with cultures of the tumor cell line HT29.

EXAMPLE 5

Recovery of CA IX 50 and 58 kDa Bands from Diluted HT29 Cell Extract or TC Medium The concentration of CA IX in blood serum and in urine of RCC patients is too low to be detected without previous concentration. Therefore, we first tested how efficiently CA IX can be immunoprecipitated from cell extracts or TC media of HT29 cells.

Immunoprecipitation was performed as described above. The result was somewhat puzzling. Original HT29 cell extract or TC medium contained 2 bands of CA IX. However, after addition of M75 antibody followed by PA-Sepharose® beads and a low speed centrifugation, no CA IX was detected in the supernatant and all of the CA IX antigen was present in the pellet. Surprisingly, it was seen only as a single band of 54 kDa, no matter whether it was from cell extract (cell-associated CA IX) or from the medium (soluble CA IX). The other band disappeared. When the pellets were mixed with corresponding supernatants, the lost bands appeared again in their original intensity. For the re-appearance of the lost band, it was sufficient to add FCS to a final concentration of 1-2%. This observation suggests that FCS (or various other proteins) is providing some sort of steric support for CA IX on Western blots. In this experiment, the p54 band did not disappear after adding the MAb and Protein A-Sepharose® and centrifugation, most likely because on migration in PAGE it overlaps with denatured heavy chain of M75 IgG. Since this observation, we have added 1.5% FCS to Laemmli sample buffer for extracting of CA IX from the immunoprecipitates and for diluting the samples before gel electrophoresis and Western blotting. We conclude that the sensitive detection of CA IX antigens on Western blots requires the presence of other "contaminating" proteins which do not cross-react with CA IX.

EXAMPLE 6

CA IX in Blood Serum of RCC Patients

As described in Examples 3-5, there were no problems with detection and quantitation of CA IX protein in extracts from cells or tumors and in culture media. The concentration of CA IX was sufficient for direct analysis by Western blotting or by ELISA. Control cell extracts or media showed no false positivity or non-specific bands.

The difficulties emerged when we started to test human blood sera. The concentration of CA IX was too low and the concentration of normal blood serum proteins was too high to allow direct gel separation. Therefore, we prepared immunoprecipitates from control and patients' sera using M75, followed by anti-mouse IgG agarose beads. The precipitates, when analysed by Western blots developed with M75-peroxidase conjugate and ECL, in addition to the s-CA IX p50/54 bands showed strong non-specific bands of 92 and 125 kDa. These cross-reactive proteins were present also in control human sera.

Fortunately, we were able to eliminate the non-specific bands by using two different monoclonal antibodies, as described above. For immunoprecipitation MAb V-10 specific for the CA domain was employed, while M75-peroxidase conjugate, specific for PG domain, was used for developing the blots.

We tested 30 samples of sera from RCC patients, 14 sera of patients with tumors other than RCC, 6 sera of non-tumor patients suffering from various urological diseases and 42 sera of healthy blood donors. Sera evaluated as positive were found mainly in the RCC group. Out of total 30 RCC sera, 12 scored as "positive" (40%). The RCC group included 1 sarcomatous RCC, which was CA IX positive. Among 14 non-RCC tumor patients, 1 was positive (papillary carcinoma).

There does not seem to be a clear correlation between tumor size and the presence or concentration of CA IX in the serum. All sera evaluated as "negative," including sera of healthy blood donors, did in fact show an extremely weak 50 kDa band of s-CA IX, which became well visible only after prolonged exposure of the blots.

For Western blot analysis of soluble CA IX protein in blood sera of RCC patients and of control individuals, each lane was loaded with immunoprecipitate corresponding to the original 0.6 ml of the serum. Sera samples were from three healthy blood donors: a patient (100) who had stones in the urether; patients with non-RCC tumors: (39) papillary carcinoma from renal cells, (103) urothelial tumor of renal pelvis, (121) sarcomatoid renal carcinoma; all other samples, RCC (the largest are No. 68, 2350 cm$^3$; No. 36, 1466 cm$^3$; No. 50, 725 cm$^3$; and the smallest, No. 102, 9 cm$^3$; No. 112, 14 cm$^3$).

To obtain more support for presumed origin of blood s-CA IX from the tumors, we tested several paired sera from RCC patients before and after nephrectomy. Indeed, in 3 cases the sera after operation contained much less of s-CA IX than corresponding pre-operation sera. One exception was patient No. 68, showing an increase of s-CA IX level—but this patient underwent only a palliative operation. Only a moderate decrease of s-CA IX was seen in the patient No. 104; in his case the post-operative sample was taken only 1 day after nephrectomy, whereas in all other patients the post-operative samples were obtained 7 days after operation.

EXAMPLE 7

CA IX in Urine of RCC Patients

The RCC patients (see Example 6 above) excrete s-CA IX protein in urine. For obvious reasons, we could afford to concentrate the antigen from 10 ml of urine (or from larger volumes if needed), and load 1 lane on the gel with an aliquot corresponding to 8 ml. For the Western blot analysis, the non-tumor patients Nos. 45 and 48 had stones in the urether; non-RCC tumor patients No. 28 and 57 had angiolipoma and No. 39 had a papillary carcinoma. All other samples were from patients with RCC (largest tumors were No. 36, 1466 cm³; No. 50, 725 cm³; the smallest, No. 44, 1 cm³; No. 60, 12 cm³; and No. 38, 14 cm³).

Our results show that a relatively high percentage (19/27=70%) of the patients excrete CA IX in urine. The $M_r$ of the s-CA IX protein is about the same as in blood (see Example 6). In some of the urine samples, there is an additional band of intermediate size. In two strongly positive samples (No. 50 and 54) there is an additional band of 62 kDa. Control specimens of urine from 25 healthy persons, 2 non-tumor and from 3 non-RCC tumor urology patients were all CA IX negative.

As shown in Examples 3 and 4, shedding of CA IX is moderately efficient. Two days after media exchange, the medium contains about 10% of the total amount of CA IX compared with the cell monolayer (FIG. 10). On the other hand, the concentration of s-CA IX in the blood of RCC patients, even if they carry very large tumors, is approximately 1000× lower than in TC media (Table 6). This shows that s-CA IX is rapidly cleared from the blood. There may be several mechanisms of clearance. We have demonstrated one of them: excretion in the urine without any major degradation. Concentration of the s-CA IX in urine corresponds approximately to the antigen in blood. Possibly, some of CA IX could be degraded to smaller fragments; we are aware of the existence of CA IX-related polypeptides of 20-30 kDa lacking the PG domain. But their sensitive detection and quantification will require optimizing the conditions of assays, probably double antibody sandwich assays using CA IX-specific mabs to the CA domain. Two urine samples—Nos. 50 and 54 contain a larger protein of 62 kDa, reacting with MAb M75. Significance of this larger protein is not clear; it was not found in the blood or in tumor extract from the same patient.

The data on CA IX concentration in biological materials tested in Examples 3-7 are summarized in Table 6 below.

TABLE 6

Concentration of CA IX in biological materials

| | |
|---|---|
| HT29 cell extract* | 4 mg/g total protein |
| Fresh RCC extract | 0.5-2 mg/g total protein |
| Normal kidney extract | not detectable |
| HT29 TC medium* | 100 ng/ml |
| RCC TC media | 100 ng/ml |
| Sera of RCC patients | 20 pg-3.6 ng/ml |
| Control sera | 5-25 pg/ml |
| Urine of RCC patients | 20 pg-3 ng/ml |
| Control urine | 0-2 pg/ml |

*5 cm Petri dish corresponds to 5 ml of medium or to 0.5 mg total protein ectracted from cell monolayer.

There is a wide range of concentrations observed. The results for cell and tumor extracts and for TC media are based on ELISA. The CA IX concentration in blood sera and in urine was determined by densitometric reading of films exposed with Western blots and calculated by a comparison with included calibration with HT29 medium, titrated in ELISA. All the blots must be taken only as approximate, due to high biological variability (density-dependent expression of CA IX in cell cultures, volume of fluids consumed by the patients before providing the urine for CA IX determination). Western blots are only a semi-quantitative method and there exists no clear-cut borderline between "normal" and "elevated" concentrations of the antigen.

EXAMPLE 8

Soluble Form of CA IX in Medium of HT29 Culture and in Serum of Nude Mice with a Xenograft of HT29 Cells The appearance of soluble CA IX in the medium of HT29 culture and in the serum of nude mice with a xenograft of HT29 cells were compared [Chrastina et al. in press (2003)]. In this experiment, we used athymic nude mice xenografted with HT29 human colorectal carcinoma, as described above. Western blotting using $^{125}$I -M75 mab showed the level of CA IX in xenograft and in HT29 culture in vitro. Soluble CA IX shedded to culture medium and to blood plasma was first concentrated by immunoprecipitation and then subjected to Western blotting analysis.

Western blot analysis showed that in vivo expression of CA IX in the HT29 xenograft was lower than in culture, possibly due to presence of CA IX-negative stroma surrounding the tumor parenchyma as well as to in situ heterogeneity of expression in the tumor cells as mentioned above. In addition, a subpopulation of CA IX molecules with the size corresponding to the extracellular portion of the protein (s-CA IX) was detectable in both culture medium and blood circulation as a result of antigen shedding from the cell membrane.

EXAMPLE 9

Expression of CA IX in Bladder Cancer Sections

The expression pattern of CA IX in superficial and invasive bladder cancers has been compared by immunohistochemical methods [Turner et al., Br. J. Cancer, 86:1276-1282 (2002)]. The expression of CA IX was enhanced in bladder cancer specimens, greater in superficial than invasive tumors, confirming CA IX as a possible marker to detect urinary tract tumors.

Formalin-fixed, paraffin-embedded tissue specimens collected by standard surgical oncology procedures were obtained from the Pathology Department, John Radcliffe Hospital, Oxford, UK. Samples of normal bladder were taken from cadaveric organ donors at the time of nephroureterectomy.

CA IX expression was evaluated by immunochemistry in 22 cases on serial sections (Table 7), as described above. These 22 cases were selected to represent the range of stage and grade in human bladder tumors, and in two samples of normal bladder. In 17 cases, CA IX was expressed maximally on the luminal surface of tumors and around regions of necrosis in invasive tumors. In addition, while both superficial and invasive tumors showed luminal enhancement, this was much more marked in superficial tumors. CA IX was not detected in normal bladder specimens, nor was it detected in samples from the patient with isolated CIS.

The high frequency and marked enhancement of CA IX expression in superficial bladder cancer in this experiment, combined with the relative absence in normal transitional epithelium, and the fact that CA IX is a transmembrane protein, suggests that measurement of shed protein in the urine could be a potential marker of recurrence.

TABLE 7

Expression of CA IX protein in human bladder cancer

| Patient | Tumor stage/grade | CA IX immunostaining |
|---|---|---|
| 1 | CIS | −ve |
| 2 | Ta G1 | luminal |
| 3 | Ta G1 | luminal |
| 4 | Ta G2 | luminal |
| 5 | T1 G1 | luminal |
| 6 | T1 G2 | luminal |
| 7 | T1 G2 | luminal |
| 8 | T1 G2 | luminal |
| 9 | T1 G2 | luminal |
| 10 | T2 G2 | luminal and perinecrotic |
| 11 | T2 G2 | luminal and invasive tumor |
| 12 | T2 G3 | luminal |
| 13 | T2 G3 | luminal |
| 14 | T2 G3 | luminal but sparse |
| 15 | T2 G2, CIS in separate biopsy | perinecrotic CIS−ve |
| 16 | T2 G2, CIS in separate biopsy | perinecrotic CIS weakly positive |
| 17 | T2 G2 | luminal and perinecrotic |
| 18 | T2 G3 | luminal and perinecrotic |
| 19 | T2 G3 | invasive tumor |
| 20 | T2 G3, CIS in separate biopsy | luminal and perinecrotic CIS −ve |
| 21 | T3 G3 | −ve |
| 22 | T4 G3, CIS in separate biopsy | luminal, CIS weakly positive |

In serial sections expression of CA IX was assessed by immunochemistry using monoclonal antibody M75.

EXAMPLE 10

Temporal Relationship of CA IX Expression to Hypoxia and Reoxygenation

Hypoxically-induced CA IX protein was shown to be present in tissue culture for 72 hours, even after reoxygenation, further supporting its potential usefulness as a biomarker [Turner et al., (2002)]. Previously hypoxic induction of CA IX in invasive bladder cancer cell lines had not been detected [Wykoff et al. (2000)], which is consistent with the observation of the low level of CA IX expression in invasive tumors. There appears to be no currently available cell lines derived from superficial human bladder tumors. For those reasons, the A549 lung carcinoma cell line, which shows marked hypoxic induction of the CA9 gene, was chosen for this experiment. Western blot analysis of expression of CA IX protein in A549 lung carcinoma cells was performed after growth under hypoxic conditions and then subsequent reoxygenation. Levels of CA IX protein detected remained constant for at least 72 h, indicating that the protein may persist in tissues for a relatively long period of time.

EXAMPLE 11

Comparison of CA IX Expression in Normal, Benign and Malignant Breast Tissues with ER, C-erbB-2 (HER-2/neu), C-erbB3 and CD44 Expression Materials and Methods Tissue Specimens Breast tissue specimens were obtained from 111 patients (mean age 50.4 years, ranging from 19 to 82) during surgical treatment (KP) at the Department of Obstetrics and Gynaecology II, School of Medicine, Comenius University, Bratislava, in 1998-1999. The patients had not received anti-tumour treatment before surgery. Portions of all tissues were fixed in formaldehyde, embedded in paraffin wax and processed for routine histopathology. The specimens were divided into two overlapping groups, so that the tissues of 36 patients were analysed by IHC only, the tissues of 36 patients were subjected to both IHC and RT-PCR, and the tissues of 39 patients were used for RT-PCR only. IHC was performed using the paraffin-embedded specimens. For RT-PCR, fresh tissues were snap-frozen in liquid nitrogen and stored at −80° C. until used for RNA extraction.

Histopathology

Histopathological evaluation of tissues was performed independently. The diagnosis was assessed separately for the sections subjected to IHC and for the specimens corresponding to tissues analysed by RT-PCR. The tissues were classified according to the WHO classification (World Health Organization 1981) and categorized as normal (derived from distant areas of surgical tumour specimens), benign (fibrocystic change, fibroadenoma and other types) and malignant (carcinomas in situ and invasive carcinomas).

Immunohistochemistry

The tissue sections were immunostained by the biotin-streptavidin complex method using the monoclonal antibody M75 to the N-terminal domain of CA IX and applied in 1:10 dilution for 1 h at room temperature, as described previously [Pastorekova et al. 1997]. Briefly, the procedure was performed as follows: (1) Pre-treatment with undiluted cow colostral whey for 40 min and rinsing in phosphate-buffered saline (PBS). (2) Incubation for 1 h with M75 monoclonal antibody in PBS containing 1% bovine serum albumin (BSA). (3) Incubation for 1 h with biotinylated goat anti-mouse IgG (Dakopatts, Copenhagen, Denmark) diluted 1:300 in 1% BSA-PBS. (4) Incubation for 30 min with peroxidase-conjugated streptavidin (Dakopatts) diluted 1:500 in PBS. (5) Visualization for 2 min in diaminobenzidine solution (Fluka, Buchs, Switzerland). The sections were washed three times for 10 min in PBS after steps 2, 3, and 4. All the incubations and washings were carried out at room temperature. The sections were counterstained with haematoxylin, mounted in Permount® [Fisher Scientific, Fair Lawn, N.J. (USA)], examined and photographed with a Nikon® Eclipse E600 (Tokyo, Japan) microscope. The level of staining was scored in a blinded manner, taking into account intensity of signal, pattern and extent of staining under low and high magnification. Sections of normal human intestine were used as positive controls. For the negative control, M75 antibody was substituted with PBS. The staining intensity was scored using a scale of 0-3 as follows: 0, no reaction; 1, weak reaction; 2, moderate reaction; 3, strong reaction. The staining pattern was evaluated as cytoplasmic or membranous and positivity was assigned only to those specimens that showed the plasma membrane staining. The extent of staining was evaluated as focal if occasional single cells or small groups of cells were positive, or diffuse, if continuous or extensive areas were stained.

RNA Extraction and Reverse Transcription of cDNA

Extraction of total RNA from the frozen breast specimens was done by disrupting the tissues in Trizol solution (GIBCO, Life Technologies). RNA was precipitated by ethanol, dissolved in water treated with diethylpyrocarbonate (DEPC, Sigma) and reverse transcribed with SuperScript® II reverse transcriptase (GIBCO, Life Technologies) using oligo(dT)$_{12-18}$ (500 µg/ml). 5 µl RNase-free sterile water containing 1 µg of total RNA was added to a reaction mixture composed of dNTPs, each at 0.5 mM concentration (Pharmacia), and reverse transcriptase buffer containing 6 mM MgCl$_2$, 40 mM KCl, 1 mM DTT, 0.1 mg/ml BSA and 50 mM Tris-HCl, pH 8.3. The mixture in a final volume of 20 µl was heated for 10 min at 70° C., cooled quickly on ice, supplemented with 200 U of reverse transcriptase, incubated for 1 h at 42° C., heated for 15 min at 70° C. and stored at −80° C. until used.

PCR Amplification

PCR reaction was performed with an automatic DNA thermal cycler (BIORAD) using the cDNA-specific primers for CA9 as well as for β$_2$-microglobulin (β$_2$-m) which served as an internal standard. The nucleotide sequences of the primers, with relevant positions and database accession numbers in parentheses, were as follows:

CA9 (X66839): MN1 5' CCGAGCGACGCAGCCTTTGA 3' (1188-1207) (SEQ ID NO: 107), MN2 5' TAGTCGACTAG-GCTCCAGTCTCGGCTACCT 3' (1443-1414) (SEQ ID NO: 108); β$_2$-microglobulin (AF072097): B2M1 5' CATC-CAGCGTACTCCAAAGA 3' (860-879) (SEQ ID NO: 109), B2M2 5' GACAAGTCTGAATGCTCCAC 3' (1024-1005) (SEQ ID NO: 110).

To compare the expression of CA9 with breast tumour markers ER, c-erbB2, c-erbB3 and CD44, we used the same templates for parallel semi-quantitative RT-PCR reactions using the following primers:

Oestrogen receptor (M12674): ER1 5' ACTCGCTACTGTG-CAGTGTGCAATG 3' (776-800) (SEQ ID NO: 111), ER2 5' CCTCTTCGGTCTTTTCGTATCCCAC 3' (1014-990) (SEQ ID NO: 112); c-erbB-2 (M11730): EB2-1 5' AGTTTCCA-GATGAGGAGGG CGCATGCC 3' (1994-2020) (SEQ ID NO: 113), EB2-2 5' TTCTCCCCATCAGGGAT CCAGAT-GCCC 3' (2384-2358) (SEQ ID NO: 114); c-erbB-3 (M34309): EB3-1 5' GGTGCTGGGCTTGCTTTTCAGC-CTGG 3' (222-247) (SEQ ID NO: 115), EB3-2 5' ACCACGCGGAGGTTGGGCAATGGTAG 3' (512-487) (SEQ ID NO: 116); CD44 (M59040.1): CD44-1 5' GGGTC-CCATACCACTCATGGA TCT 3' (725-748) (SEQ ID NO: 117), CD44-2 5' GGGAAAGGTTGGCGATCAGGAA TA 3' (1444-1421) (SEQ ID NO: 118).

The reaction mixture was composed of 1/40 of cDNA template obtained from 1 µg of RNA, 15 pmol of each upstream and downstream primers for both the analysed gene and β$_2$-m, 0.2 mM of each dNTP (Pharmacia), 1 U of Taq DNA polymerase (Boehringer Mannheim) and PCR buffer (10 mM Tris-HCl pH 8.3, 50 mM KCl and 1.5 mM MgCl$_2$) in a total volume of 25 µl. Following an initial denaturation at 95° C. for 1 min, the amplification program was set as follows: denaturation at 95° C. for 20 s, annealing at 65° C. for 30 s, and extension at 72° C. during 40 s for a total of 30 cycles, and finally 5 min at 72° C. In these conditions, amplified products were obtained in the exponential phase for the two sets of primers, and the yield of PCR products obtained by co-amplification was similar to those obtained by individual amplifications in separate tubes. In addition to tumour samples, negative and positive controls were systematically processed in parallel.

Semi-quantitation of RT-PCR products

20 µl of RT-PCR products were run on a 1.8% agarose gel. Quantification of PCR products was done using Scion Image software. The amount of CA9-specific PCR product was expressed as a percentage of the internal standard. The specimens were classified as 0 when amount of CA9 product was less than or equal to 10% of internal standard, as 1 for 11-50%, 2 for 51-80% and 3 for more than 80% of β$_2$-m. Similar semi-quantitation in relative percentages of gene-specific products was used for the other markers without further categorization of data.

Statistical Evaluation

Association between expression of CA9 and expression of ER, c-erbB2, c-erbB3 and CD44 in breast tumours was evaluated by chi-square test of independence (or by Fisher's exact test) using data obtained in a parallel RT-PCR analysis of the same specimens. Mann-Whitney rank test applied to positive specimens was used to compare expression levels of individual markers in CA9-positive versus CA9-negative subgroups of malignant tissues. A significance level of p 0.05 was used in both tests.

Results

Immunohistochemical Analysis of Breast Tissues

The set of 72 breast specimens subjected to IHC analysis of CA IX expression consisted of 10 normal tissues, 36 benign lesions and 26 malignant tumours (Table 8). The benign lesions included 20 specimens with fibrocystic changes, six fibroadenomas and 10 specimens of other type (two hyperplasias, two adenoses, four fibroses, one adenoma, one benign phylodes tumour). The malignant tumours included five ductal carcinomas in situ, two lobular carcinomas in situ, 13 invasive ductal carcinomas, two invasive lobular carcinomas, three tubular carcinomas and one mucinous carcinoma.

All 10 normal breast tissues were negative for membrane CA IX, with only few occasional cells with weak cytoplasmic staining found in one specimen of lactating breast. In benign lesions, a positive membrane signal ranging from weak to strong was detected in four of 36 (11%) specimens (Table 8). All positive lesions were classified as fibrocystic changes. Among negative specimens, one fibroadenoma and three lesions with fibrocystic changes showed weak cytoplasmic staining in a few epithelial cells, while other benign lesions did not stain at all.

In sections with fibrocystic changes, the staining signal was mainly confined to abnormal epithelium, mostly in areas of apocrine metaplasia. [E.g., weak diffuse cytoplasmic staining seen in apocrine metaplastic epithelium.] Weak signal of a diffuse cytoplasmic pattern was observed in three specimens. The four moderately to strongly positive specimens showed focal membrane staining. [E.g., strong focal membrane staining of epithelial cells seen in benign hyperplastic epithelium.] In one case with fibrocystic change and sclerosing adenosis, strong CA IX-specific staining was detected in sub-epithelial fibroblasts and endothelium.

TABLE 8

Summary of the immunohistochemical staining of CA IX in the normal, benign, and malignant breast tissues

| Type of tissue | Total No. | Positive specimens* | | Expression Level | |
|---|---|---|---|---|---|
| | | No. | % | Mean | Range |
| Normal breast | 10 | 1 | 10 | 0.10 | 0-1 |
| Benign lesions | 36 | 4 | 11 | 0.39 | 0-3 |
| Fibroadenomas | 6 | 0 | 0 | 0.17 | 0-1 |
| Fibrocystic changes | 20 | 4 | 20 | 0.65 | 0-3 |
| Other types | 10 | 0 | 0 | 0.00 | |
| Malignant tumours | 26 | 12 | 46 | 1.42 | 0-3 |
| In situ | 7 | 4 | 57 | 1.28 | 1-2 |
| Invasive | 19 | 8 | 42 | 1.47 | 0-3 |

*Positivity was assigned only to specimens with membrane staining

Out of 26 malignant breast tissue specimens, plasma membrane expression of CA IX protein was detectable in 12 carcinomas (46%) (Table 8). The positivity was observed mainly in the abnormal epithelium. The majority of weakly stained specimens showed a focal cytoplasmic pattern, while moderate to strong staining was mainly of focal membrane type. Interestingly, in four invasive ductal carcinomas out of six strongly positive malignant cases, staining was observed in stromal fibroblasts and occasionally also in endothelial cells. Indeed, there were two specimens with strongly positive stroma and negative carcinoma cells. [E.g., strong specific positivity was present in stromal fibroblasts and endothelial cells, but absent in the area of invasive ductal carcinoma in a tumour specimen.] In one specimen of ductal in situ carcinoma with sclerosing adenosis, strong positivity was found in adenosis, whereas the in situ area was negative. The last strongly positive tumour tissue specimen was classified as mucinous carcinoma and was found to express CA IX focally in membranes of abnormal epithelial cells. On the other hand, both lobular carcinomas in situ and one of two invasive lobular carcinomas showed only weak cytoplasmic staining, while the other lobular carcinoma specimen was completely negative.

Comparison of CA IX expression with basic clinicopathological parameters of the analysed malignant tumors did not reveal any significant relationship with the age, nodal status, tumor size and grade.

TABLE 9

Summary of the RT-PCR analysis of CA9 gene expression in the normal, benign and malignant breast tissues

| Type of tissue | Total No. | Positive specimens No. | Positive specimens % | Expression level Mean | Expression level Range |
|---|---|---|---|---|---|
| Normal breast | 3 | 0 | 0 | 0.0 | |
| Benign lesions | 33 | 11 | 33 | 0.39 | 0-3 |
| Fibroadenomas | 9 | 5 | 56 | 0.56 | 0-3 |
| Fibrocystic changes | 20 | 6 | 30 | 0.40 | 0-1 |
| Other types | 4 | 0 | 0 | 0.00 | |
| Malignant tumours | 39 | 25 | 64 | 1.03 | 0-3 |
| In situ | 3 | 1 | 33 | 0.33 | 1-3 |
| Invasive | 36 | 24 | 67 | 1.08 | 0-3 |

RT-PCR Analysis of Breast Tissues

The specimens utilized for RT-PCR analysis included three normal tissues, 33 benign lesions and 39 malignant tumours (Table 9). The benign tissue specimens consisted of 20 lesions with fibrocystic changes, nine fibroadenomas and four lesions of other types (one adenosis, one epitheliosis, one intraductal papilloma and one non-specific autoimmune alveolitis). The malignant tissues involved three ductal carcinomas in situ, 32 invasive ductal carcinomas, two invasive lobular carcinomas, one tubular carcinoma and one mucinous carcinoma.

All three normal tissue specimens were negative for CA9 transcript, while the specific RT-PCR product was detected in 33% of benign lesions. Nine benign lesions were evaluated as weakly positive, one lesion showed moderate positivity and only one benign lesion showed strong positivity. On the other hand, 64% of malignant tumours expressed CA9, of which 14 tissues were weakly positive, nine were moderately positive and three were strongly positive (Table 9). [The CA9 specific PCR product of 255 by was detected using $\beta_2$-microglobulin-related PCR product of 165 by as a standard.] As above, there was no significant association between CA9 expression and any of the clinicopathological parameters.

Concordance of IHC and RT-PCR Data

Comparison of IHC and RT-PCR data obtained from specimens of 36 patients analysed simultaneously by both methods revealed 69.4% concordance of the results. There were 19 IHC-negative/RT-PCR-negative, six IHC-positive/RT-PCR-positive, 10 IHC-negative/RT-PCR positive patients, and one IHC-positive/RT-PCR-negative. The discrepancies could partially result from differences in methodology, which accounted for at least some RT-PCR-positive/IHC-negative data. Indeed, weak cytoplasmic staining was observed in six specimens evaluated as negative in IHC, but found to be positive in RT-PCR. In addition, there was an objective problem connected with breast tumour heterogeneity and related to the fact that the two methods were performed using different portions of tissue obtained from the same patient. This problem could be relevant especially in the cases with focal CA IX expression in a small area, present in the first portion of the breast specimen but lacking from the second. In support of this assumption was differential histological evaluation of five paired specimens, in which CA IX negativity was observed in the portion of tissue containing less severe morphological changes such as hyperplasia, while the positivity was associated with the presence of more striking abnormalities such as carcinoma in situ.

Relationship of CA9 to Breast Tumour Markers

In order to understand the molecular context of CA9 gene expression and to learn more about its possible significance in breast cancer, we have performed simultaneous semi-quantitative RT-PCR analyses of four additional markers. They included the genes encoding: (1) oestrogen receptor (ER), a known predictor of response to endocrine therapy; (2) type 1 receptor tyrosine kinase c-erbB2 (HER-2/neu), associated with lack of endocrine response, aggressive phenotype and poor prognosis; (3) c-erbB3, a catalytically-inactive ligand-binding c-erbB2 homologue, proposed as a favourable predictor of endocrine response in ER positive tumours; and (4) an adhesion molecule CD44, a promising indicator of metastatic potential [Osborne et al. (1996); Revillion et al. (1998); Knowlden et al. (1998); Kaufmann et al. (1995)].

For the statistical analysis, 39 malignant specimens were divided into two groups. The CA9-negative group contained 14 specimens with expression of CA9 below 10% of internal control and the CA9-positive group consisted of 25 specimens expressing CA9 mRNA at any level above 10%. In both groups, specimens were categorized as either positive or negative for expression of each of the four markers. The cut-off value of 10% of internal control was used for ER, c-erbB3 and CD44. The cut-off value of 100% of internal control was estimated for the overexpression of c-erbB2 as a value corresponding to the mean expression level in c-erbB2-positive benign lesions multiplied by two. Using this criterion, 25.6% of malignant breast tissues in our collection were found to overexpress c-erbB2, in agreement with the data from literature [Revillion (1998)]. Association between CA9 and each marker was tested by the Chi-square test (or the Fisher's exact test in the case of c-erbB2) and concordance in negativity/positivity evaluation was calculated (FIG. 7A).

Expression of CA9 in malignant breast tissues showed no significant relationship with ER (p=0.86), c-erbB3 (p=0.35) and CD44 (p=0.15), but there was a positive association between CA9 and c-erbB2 (p=0.05). Nine of 25 (36%) specimens positive for CA9 mRNA overexpressed c-erbB2, while only 1/14 (7%) CA9 negative tissues were classified as positive for c-erbB2 overexpression.

To test whether expression levels of the markers differ between CA9-negative tissues and CA9-positive tissues, Mann-Whitney rank test was performed including only the marker-positive specimens. In the group of 14 CA9-negative cases, there were eight ER-, one c-erbB2-, eight erbB3- and eight CD44-positive specimens. On the other hand, there were 15 ER-, nine c-erbB2-, 18 erbB3- and 19 CD44-positive specimens among 25 CA9-positive cases. The distribution of expression values for individual markers was of similar shape and differed between CA9-positive and -negative tissues. Although three of the markers, namely ER, c-erbB2 and c-erbB3, showed a higher median of expression in the CA9-positive group of specimens, a significant difference (p=0.02) was found only for c-erbB2 (FIG. 7B). Median expression of c-erbB2 was 57% higher in the CA9-positive than the CA9-negative group of tissues. This result further supported the association between CA9 and c-erbB2.

Discussion

Development of breast cancer is driven by accumulation of numerous molecular changes. This process does not follow a linear progression model, but is highly complex and variable [Bergstein, I. (1999)]. Its understanding and identification of relevant components is essential not only for better stratification of patients for treatment, but also to allow for the development of more effective therapeutic strategies targeted to aberrant cellular pathways.

According to Example 11, ectopic activation of a cell surface carbonic anhydrase IX appears to be one of the molecular alterations contributing to breast tumourigenesis. Neither mRNA nor the protein was found in normal breast tissues. CA IX expression was observed in relatively low percentage of benign lesions, while the incidence and level of CA IX in the malignant tumours were considerably higher, as documented by both IHC and RT-PCR analyses performed on two partially independent series of specimens. A similar scenario, with relatively early onset and increased CA IX expression in malignant tissues, was earlier observed in other types of carcinomas derived from the uterine cervix, oesophagus and colon [Liao et al (1994), Turner et al. (1997), Saarnio et al. (1998)]. On the other hand, lack of expression in preneoplastic disease and its association with malignant conversion was demonstrated in renal cell carcinomas and lung carcinomas [McKiernan et al. (1997), Vermylen et al. (1999), Liao et al (1997)]. The cause of a different timing of activation in different tissues is unclear, but it may be connected with regulatory pathways involved in the development of diverse type of tumours. For example, high and homogeneous expression of CA IX in renal cell carcinomas appears to be linked to inactivation of von Hippel Lindau tumour suppressor protein, leading to elimination of its negative control over CA IX [Ivanov et al. (1998)].

Present immunohistochemical analysis revealed that the majority of CA IX-positive breast lesions contained staining signal in abnormal epithelial cells. The expression pattern was very variable, most probably reflecting the heterogeneity of breast tumour cells: the protein was localized in the plasma membrane and/or cytoplasm, and the stained area varied from focal to diffuse. Noteworthy, there were two cases, in which strong specific positivity was detected also in stromal cells and two cases with strong staining present in stroma but absent from the area of carcinoma. Such a distribution of CA IX has been observed before in malignant colorectal tumours, where desmoplastic connective tissue occasionally showed prominent immunostaining [Saarnio et al. (1998)]. These peculiar findings are difficult to explain but suggest existence of microenvironmental factors influencing CA IX expression. It is well known that mutual cross-talk between epithelium and adjacent stroma plays an important role in modulating the process of neoplastic transformation [Heber et al (1996), Goldyne et al. (1991)]. Activation of CA IX in stroma may therefore represent a consequence of aberrant paracrine communication between abnormal epithelial cells and surrounding fibroblasts. Alternatively, expression of CA IX in the tumour stroma might be connected with genetic aberrations recently observed in stromal cells in mammary carcinoma [Moinfar et al. (2000)].

The expression pattern of CA IX may be also affected by microenvironmental stresses, whose critical contribution to the development of tumour phenotype has become an increasingly accepted phenomenon [Blancher and Harris (1998)]. Indeed, Wykoff et al. 2000 have recently demonstrated an intimate connection between hypoxic stress and induction of CA IX. They have shown that upregulation of CA IX occurs at the level of transcriptional activation via HIF-1 transcriptional complex, the critical mediator of hypoxic responses, and they have proposed that CA IX may be a useful marker for tumour hypoxia.

Hypoxia is one of the major drives to tumour progression [Blancher and Harris (1998)]. It leads to activation of genes involved in the development of tumour metabolic pathways including aerobic glycolysis and neovascularization. CA IX appears to participate in hypoxia-induced oncogenic metabolism via extracellular acidification and maintenance of normal intracellular pH, thus contributing to conditions required for the spread and survival of tumor cells [Wykoff et al. (2000)]. From the clinical point of view, hypoxia is associated with poor prognosis, aggressive phenotype and resistance to anti-cancer therapy [Blancher and Harris (1998)]. This may explain our finding of an association between ectopic expression of CA IX and overexpression of c-erbB2, an oncogene encoding a receptor tyrosine kinase that serves as a marker of aggressive breast tumours with poor outcome [Revillion et al. (1998)].

Signal transduction mediated by activated oncogenes may induce the expression of a tumour metabolic phenotype independently of hypoxia, or may amplify the hypoxic response [Blancher and Harris (1998)]. It was shown that inactivation of c-erbB2 was associated with decreased expression of an important hypoxic target vascular endothelial growth factor [Petit et al. (1997)]. By analogy, this observation may offer clues to a functional link between c-erbB2 and CA IX. It is possible that some of the features associated with high c-erbB2 expression, such as invasion and metastatic capability, are also mediated by coexpression of CA IX. In fact, a significant proportion of c-erbB2-positive cancers does not respond to treatment by Herceptin®, a humanized monoclonal antibody against c-erbB2 Kuter, I. (2001)]. Thus it is conceivable that inhibitors of the associated expression of CA IX could be of further therapeutic value. This assumption is supported by the evidence that inhibition of CA activity reduces invasion of some tumour cells lines [Parkkila et al. (2000)] and that treatment by CA inhibitor may be beneficial as an adjunct to cancer chemotherapy [Teicher et al. (1993)].

In conclusion, this example has shown that expression of CA9 gene is associated with breast cancer in a manner similar to some other types of carcinomas, with respect to both incidence and/or expression pattern. The data shown here highlight the need for further large-scale analyses, specifically directed to a possible prognostic/predictive value of CA9 in breast cancer and a significance of its relationship with c-erbB2. In general, our work adds to accumulating evidence supporting the view that CA9 activation is a common event in carcinogenesis and is a new therapeutic target.

EXAMPLE 12

Accessibility In Vivo of MN Protein Expressed in Tumor Cells and in Stomach

Lewis rats (384 g) carrying a BP6 subcutaneous tumor (about 1 cm in diameter) expressing rat MN protein were injected intraperitoneally (i.p.) with $^{125}$I-M75 Mab ($2.5 \times 10^6$ cpm). Five days later, 0.5-1 g pieces of the tumor and organs were weighed and their radioactivity was measured by a gamma counter.

Table 10 summarizes the results. The highest radioactivity was present in the tumor. Relatively high radioactivity was found in the liver and kidney, apparently reflecting the clearance of mouse IgG from the blood. The stomach continued a relatively low level of radioactivity, indicating that the M75 Mab had only limited access to MN protein exposed in the gastric mucosa.

TABLE 10

Distribution of radioactivity of $^{125}$I-M75 in rat organs and in the tumor

| Organ | cpm/g | | | | |
|---|---|---|---|---|---|
| Kidney | 2153 | 2184 | | | |
| Spleen | 653 | 555 | | | |
| Liver | 1993 | 1880 | | | |
| Lung | 1183 | 1025 | | | |
| Blood | 1449 | | | | |
| Heart | 568 | 477 | | | |
| Stomach | 1184 | 1170 | | | |
| Testis | 812 | 779 | | | |
| Tail | 647 | | | | |
| Tumor | 3646 | 4058 | 3333 | 8653 | 3839 |

Budapest Treaty Deposits

The materials listed below were deposited with the American Type Culture Collection (ATCC) now at 10810 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

| | Deposit Date | ATCC # |
|---|---|---|
| Hybridoma | | |
| VU-M75 | Sep. 17, 1992 | HB 11128 |
| MN 12.2.2 | Jun. 9, 1994 | HB 11647 |
| Plasmid | | |
| A4a | Jun. 6, 1995 | 97199 |
| XE1 | Jun. 6, 1995 | 97200 |
| XE3 | Jun. 6, 1995 | 97198 |

Similarly, the hybridoma cell line V/10-VU which produces the V/10 monoclonal antibodies was deposited on Feb. 19, 2003 under the Budapest Treaty at the International Depository Authority (IDA) of the Belgian Coordinated Collections of Microorganisms (BCCM™) at the Laboratorium voor Moleculaire Biologie-Plasmidencollectie (LMBP) at the Universeit Gent, K. L. Ledeganckstraat 35, B-9000 Gent, Belgium [BCCM™/LMBP] under the Accession No. LMBP 6009CB.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method of screening for a disease associated with abnormal expression of CA IX in a human subject, wherein said disease associated with abnormal expression of CA IX is a cancerous disease and/or a disease associated with hypoxia, comprising:
   (a) measuring human soluble CA IX in a type of body fluid sample of said subject;
   (b) comparing the measured human soluble CA IX in said subject's body fluid sample with that measured in a sample of the same type of body fluid of a human control known to be unaffected with said disease associated with CA IX abnormal expression; and
   (c) determining that there is an indication that said subject is afflicted with said disease associated with CA IX abnormal expression when there is an elevated level of human soluble CA IX in said subject's body fluid sample relative to said control's body fluid sample;
   wherein said human soluble CA IX is a protein having a molecular weight of from about 15 kilodaltons (kD) to about 54 kD found in human body fluids which is specifically bound by the V/10 monoclonal antibody that is secreted from the hybridoma V/10-VU, which was deposited under the Budapest Treaty at the 14 International Depository Authority of the Belgian Coordinated Collection of Miccroorganisms (BCCM) at the Laboratorium voor Moleculaire Biologie-Plasmidencollectie (LMBP) at the Universeit Gent in Gent, Belgium, under Accession No. LMBP 6009CB.

2. The method according to claim 1 wherein said measuring step (a) is performed by immunoassay, comprising the use of one or more antibodies or antigen binding fragments thereof which specifically bind human CA IX's extracellular domain having the amino acid sequence SEQ ID NO: 5.

3. The method according to claim 2 wherein said method is in a format that is selected from the group consisting of Western blots, enzyme-linked immunosorbent assays, radioimmunoassays, competition immunoassays, dual antibody sandwich assays, agglutination assays, and fluorescent immunoassays.

4. The method according to claim 2 wherein said one or more antibodies is or are monoclonal.

5. The method according to claim 4 wherein said one or more monoclonal antibodies are selected from the group consisting of the monoclonal antibody designated M75 which is secreted by the hybridoma VU-M75, which is deposited at the American Type Culture Collection in Manassas, Va. (USA) under ATCC Number HB 11128, and a monoclonal antibody that specifically binds to an epitope of human CA IX's extracellular domain having the amino acid sequence of SEQ ID NO: 5 but which does not bind to a peptide consisting of SEQ ID NO: 11.

6. The method according to claim 1, wherein said cancerous disease associated with CA IX abnormal expression is a cancerous disease of a tissue selected from the group consisting of mammary, urinary tract, kidney, ovarian, uterine, bladder, cervical, endometrial, vaginal, vulvar, prostate, liver, lung, skin, thyroid, pancreatic, testicular, brain, head and neck, gastrointestinal, and mesodermal tissues.

7. The method according to claim 1, wherein said cancerous disease is selected from the group consisting of renal cell carcinoma, breast cancer, or colorectal cancer.

8. The method according to claim 2 wherein a sandwich immunoassay is used to quantify the human soluble CA IX.

9. The method according to claim 8 wherein said sandwich immunoassay uses one monoclonal antibody specific for the carbonic anhydrase (CA) domain of CA IX having the amino acid sequence of SEQ ID NO: 101, and another monoclonal antibody of said sandwich assay is directed to the proteoglycan-like (PG) domain of CA IX having the amino acid sequence of SEQ ID NO: 98.

10. The method according to claim 9 wherein the antibody directed to the CA domain is the V/10 monoclonal antibody, which is secreted by the hybridoma V/10-VU, which is deposited at the Belgian Coordinated Collections of Microorganisms at the Laboratorium voor Moleculaire Biologie-Plasmidencollectie at the Universeit Gent in Gent, Belgium, under Accession Number LMBP 6009CB, and wherein the antibody directed to the PG domain is the M75 monoclonal antibody, which is secreted by the hybridoma VU-M75, which is deposited at the American Type Culture Collection, Manassas, Va. (USA) under ATCC Number HB 11128.

11. The method according to claim 2 wherein one of the antibodies is specific to the CA IX carbonic anhydrase (CA) domain and one of the antibodies is specific to a CA IX immunodominant epitope, wherein said carbonic anhydrase (CA) domain has the amino acid sequence of SEQ ID NO: 101, and wherein said CA IX immunodominant epitope is contained within CA IX's proteoglycan-like (PG) domain having the amino acid sequence of SEQ ID NO: 98 or within a region neighboring the PG domain.

12. The method according to claim 2, further comprising using antibodies specific to the HER-2 ectodomain to detect or to detect and quantify HER-2 ectodomain having a molecular weight of from about 97 to about 115 kilodaltons, and wherein said HER-2 ectodomain is otherwise known as p100 as defined in U.S. Pat. No. 5,401,638.

13. The method according to claim 1 wherein the sample of body fluid is from a cancer patient who received, or is currently receiving, treatment with a monoclonal antibody specific to HER-2 protein/polypeptide.

14. The method according to claim 13 wherein the sample of body fluid is from a cancer patient, further comprising deciding to treat said cancer patient with a CA IX-targeted therapy if both the human soluble CA IX and HER-2 ectodomain are at elevated levels in said body fluid.

15. The method according to claim 1 wherein said body fluid is selected from the group consisting of blood, serum, plasma, semen, breast exudate, saliva, tears, sputum, mucous, urine, gastric secretions, fecal suspensions, bile, lymph, ascites, pleural effusions, amniotic fluid, bladder washes, bronchioalveolar lavages and cerebrospinal fluid.

16. The method according to claim 1 wherein said body fluid is selected from the group consisting of urine, serum, mucous, gastric secretions, bile, breast exudate, pleural effusions and ascites.

17. The method according to claim 1 wherein said body fluid is selected from the group consisting of serum and urine.

18. The method according to claim 1 wherein said human soluble CA IX has a molecular weight of from about 20 kilodaltons to about 54 kilodaltons.

19. The method according to claim 1 wherein said human soluble CA IX has a molecular weight of about 50 to 54 kilodaltons.

20. The method according to claim 1 wherein said human soluble CA IX has a molecular weight of either about 50 or about 54 kDa as approximated by Western blotting.

21. The method according to claim 2 wherein one of said antibodies is a monoclonal antibody specific to CA IX's carbonic anhydrase (CA) domain, wherein said carbonic anhydrase (CA) domain has the amino acid sequence of SEQ ID NO: 101, and wherein said monoclonal antibody specific to CA IX's CA domain was generated from CA IX-deficient mice and screened for specific binding to said CA domain.

22. The method according to claim 21 wherein said CA IX-deficient mice have a null mutation in Car9.

23. The method according to claim 1, wherein said disease associated with abnormal expression of CA IX is a cancerous disease.

24. The method according to claim 14, wherein said cancer is breast cancer.

25. The method according to claim 1, wherein if said human soluble CA IX is present in said body fluid sample at an elevated level, further comprising deciding to treat said patient with a CA IX-targeted therapy.

26. The method according to claim 2 wherein at least one of said antibodies is a polyclonal antibody.

27. The method according to claim 2 wherein said antibodies are a monoclonal antibody and a polyclonal antibody.

28. The method according to claim 8 wherein at least one of the antibodies used in the immunoassay is a polyclonal antibody.

29. The method according to claim 8 wherein the antibodies used in the immunoassay are a monoclonal antibody and a polyclonal antibody, wherein if the monoclonal antibody is specific for the carbonic anhydrase (CA) domain of CA IX, then the polyclonal antibody is directed to the proteoglycan-like (PG) domain of CA IX, but if the monoclonal antibody is specific for the proteoglycan-like (PG) domain of CA IX, then the polyclonal antibody is directed to the carbonic anhydrase (CA) domain of CA IX.

30. The method according to claim 2 wherein said antibodies which specifically bind human CA IX's extracellular domain bind to non-overlapping epitopes of CA IX's carbonic anhydrase domain.

31. The method according to claim 1, wherein said disease associated with of CA IX abnormal expression is a cancerous disease of the urinary tract.

32. The method according to claim 2 wherein at least one of said one or more antibodies is labeled.

33. The method of claim 2, wherein said soluble form of CA IX is a protein having an amino acid sequence from or of SEQ ID NO: 5, or a protein having an amino acid sequence from or of CA IX's extracellular domain, wherein CA IX is encoded by a nucleotide sequence selected from:
  i) SEQ ID NO: 1;
  ii) nucleotide sequences which hybridize under stringent hybridization conditions of 0.02 M to 0.15 M NaCl at temperatures of 50° C. to 70° C. to the complement of SEQ I D NO: 1; and
  iii) nucleotide sequences encoding said soluble form of CA IX that differ from SEQ ID NO: 1 due to the degeneracy of the genetic code.

34. The method according to claim 11, wherein the antibody specific to a CA IX immunodominant epitope contained within a region neighboring CA IX's proteoglycan-like (PG) domain having the amino acid sequence of SEQ ID NO: 98 is an antibody that binds to an epitope contained within a region of CA IX having the amino acid sequence of SEQ ID NO: 21.

\* \* \* \* \*